US006331427B1

(12) United States Patent
Robison

(10) Patent No.: US 6,331,427 B1
(45) Date of Patent: Dec. 18, 2001

(54) PROTEASE HOMOLOGS

(75) Inventor: Keith E. Robison, Wilmington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/280,116

(22) Filed: Mar. 26, 1999

(51) Int. Cl.$^7$ .............................. C12N 9/64; C12N 15/57; C12N 15/79; C12Q 1/37; C12Q 1/38
(52) U.S. Cl. ................... 435/226; 435/6; 435/7.1; 435/23; 435/69.1; 435/252.3; 536/23.2
(58) Field of Search .................. 435/6, 23, 7.4, 435/69.1, 226, 7.1, 252.3; 436/86, 94; 536/23.5, 23.2

(56) References Cited

U.S. PATENT DOCUMENTS 5,700,676 * 12/1997 Bott et al. ............................ 435/221

OTHER PUBLICATIONS

Adams, M.D., et al., 1995, Nature, vol. 377 (Supp.), and GenBank EST Accession No. AA305106, "Initial assessment of human gene diversity and expression patterns based upon 83 million nucleotides of cDNA sequence", pp. 3–174.*

Franz, T., et al., 1999, Mammalian Genome, vol. 10, "Capn7: A highly divergent vertebrate calpain with a novel C–terminal domain", pp. 318–321.*

Marra, M., et al., murine EST sequence having GenBank Accession No. 238915, cDNA similar to caplain thiol protease, 494nt.*

Futai, E., et al., SPTREMBL translation of human EST having GenBank accession No. AB028639, "Human and mouse homologues of fungus calpain–like protease, PalB", EC 3.4.22.17, 813aa.*

Prosite Database Search.

* cited by examiner

*Primary Examiner*—Ponnathapu Achuta Murthy
*Assistant Examiner*—William W. Moore
(74) *Attorney, Agent, or Firm*—Alston & Bird LLP

(57) ABSTRACT

The invention relates to polynucleotides encoding newly identified protease homologs belonging to the superfamily of G-protein-coupled proteases. The invention also relates to the proteases. The invention further relates to methods using the protease polypeptides and polynucleotides as a target for diagnosis and treatment in protease-mediated disorders. The invention further relates to drug-screening methods using the protease polypeptides and polynucleotides to identify agonists and antagonists for diagnosis and treatment. The invention further encompasses agonists and antagonists based on the protease polypeptides and polynucleotides. The invention further relates to procedures for producing the protease polypeptides and polynucleotides.

7 Claims, No Drawings

SEQUENCE LISTING

<160> NUMBER OF SEQ ID NOS: 268

<210> SEQ ID NO 1
<211> LENGTH: 1504
<212> TYPE: DNA
<213> ORGANISM: Homo sapiens
<220> FEATURE:
<223> OTHER INFORMATION: trypsin-like serine proteases

<400> SEQUENCE: 1

```
tcatttaggg atcgacgccc gcgtccgcgg acgcgtgggc ggacgcgtgg gcggacgcgt      60
gggtggttat aactcaggcc cggtgcccag agcccaggag gaggcagtgg ccaggaaggc     120
acaggcctga gaagtctgcg gctgagctgg gagcaaatcc cccacccct acctggggga      180
caggtgcctg ggtctcagcg cagtgccgat ggtgcccgt ccttgtggtt cctctctacc      240
tgggggacag ggcaagtgag acctggtgca gcggccatgg ctacagcaag acccccctgg    300
atgtgggtgc tctgtgctct gatcacagcc ttgcttctgg gggtcacaga gcatgttttc     360
gccaaacaat gatgtttcct gtgaccaccc ctctaacacc cgtgccctct gggagcaaac    420
caggacttgg ggaactgggg cccggggaag aacgcccggt cggatgacag cagcagcccg    480
catcatcaat ggatccgaac tgcgatatgc acacccagcc gtggcaggcc cgcgctgttg    540
ttaaaggccc caaccaagtt cttattgcgg ggcggtgttg gtgcatccac agtggtggtt    600
cacggccgcc ccactgcagg aagaaagttt tcagagtccg tctcggccac tattccctgt   660
caccagttta tgaatctggg cagcaagatg ttccaggggg tcaaatccat ccccccaccct  720
ggctactccc accctggcca ctctaacgac ctcatgctca tcaaactgaa cagaagaatt   780
cgtcccacta aagatgtcag acccatcaac gtctcctctc attgtccctc tgctgggaca   840
aagtgcttgg tgtctggctg ggggacaacc aagagccccc aagtgcactt ccctaaggtc   900
ctccagtgct tgaatatcag cgtgctaagt cagaaaaggt gcgaggatgc ttacccgaga   960
cagatagatg acaccatgtt ctgcgccggt gacaaagcag gtagagactc ctgccaggg   1020
gattctgggg ggcctgtggt ctgcaatggc tccctgcagg gactcgtgtc ctgggggaga  1080
ttaccctttgt gcccggccca acagaccggg tgtctacacg aacctctgca agttcaccaa  1140
gtggatccag gaaaccatcc aggccaactc ctgagtcatc ccaggactca gcacaccggc  1200
atccccacct gctgcaggga cagccctgac actcctttca gaccctcatt ccttcccaga  1260
gatgttgaga atgttcatct ctccagcccc tgacccatg tctcctggac tcagggtctg   1320
cttccccccac attgggctga ccgtgtctct ctagttgaac cctgggaaca atttccaaaa   1380
ctgtccaggg cggggttgc gtctcaatct ccctggggca ctttcatcct caagctcagg   1440
```

-continued

```
gcccatccct tctctgcagc tctgacccaa atttagtccc cagaaataaa ctgagaagtg    1500
gaat                                                                  1504
```

<210> SEQ ID NO 2
<211> LENGTH: 328
<212> TYPE: DNA
<213> ORGANISM: Homo sapiens
<220> FEATURE:
<223> OTHER INFORMATION: trypsin-like serine proteases

<400> SEQUENCE: 2

```
cttatctccc catgcccaaa gtttgcctgt tccataacac tcactccctt cccccttgct     60
aatcagaagc catctcctct cagtgtctga tctctgctct tcatacatga ttacagtcat    120
ggggtagaga gtgcttgcta aattatgcag ttaatcctat ggtgctttaa ttttcaggcc    180
ttcaaaaaac acttgtacag tgatgtgcag atttttaaac agttgaactt ccttgtacta    240
cagtttttgt attgacagcc aaatttgtct ttcattcttc agattgtgaa taaagtgatt    300
tttacagggc ttccagcaaa gttttttcc                                      328
```

<210> SEQ ID NO 3
<211> LENGTH: 618
<212> TYPE: DNA
<213> ORGANISM: Homo sapiens
<220> FEATURE:
<223> OTHER INFORMATION: trypsin-like serine proteases

<400> SEQUENCE: 3

```
gcggctactc tgtggggcga cctcatcgcc tcagatggct cctgacagca gcccactgcc     60
tcaagccccg ctacatagtt cacctggggc agcacaacct ccagaaggag gagggctgtg    120
agcagacccg gacagccact gagtccttcc cccaccccgg cttcaacaac agcctcccca    180
acaaagacca ccgcaatgac atcatgctgg tgaagatggc atcgccagtg ctccatcacc    240
tgggctgtgc gaccccctcac cctctcctca tgctgtgtca ctgctggcac cagctgcctc    300
atttccggct ggggcagcac gtccagcccc cagttacgcc tgcctcacac cttgcgatgc    360
gccaacatca ccatcattga gcaccagaag tgtgagaacg cctacccccgg caacatcaca    420 gacaccatgt gtgtgccag cgtgaaggaa ggggggcaagg actcctgcca agtctcttca    480
aaggcattat ctcctggggg ccaggactcc gtgtgcgatc acccgaaagc ctggtgtcta    540
cacgaaagtc tgcaaatatg tggactggat ccaggaagac gattgaagaa caattagact    600
ggacccaacc aacaaagg                                                  618
```

<210> SEQ ID NO 4
<211> LENGTH: 840
<212> TYPE: DNA
<213> ORGANISM: Homo sapiens
<220> FEATURE:
<223> OTHER INFORMATION: trypsin-like serine proteases

<400> SEQUENCE: 4

```
actactatag ggagtcgacc ccgcgtccgc ggacgcgtgg gctagaacac tcagctgctt     60
ctttggtcat ccttgttttc taactttatg aactccctct gtgtcactgt atgtgaaagg    120
aaatgcacca acaaccgaaa actgaacgtg ttcttttgtg ctcttttata acttgcatta    180
catgttgtaa gcatggtccg ttctataccct ttttctggtc ataatgaaca ctcatttttgt   240 tagcgagggt ggtaaaagtt gaacaaaaag gggaagtatc aaactactgc catttcagtg    300
agaaaatcct aggtgctact ttataataag acatttgtta ggccattctt gcattgatat    360
```

```
aaagaaatac ctgagactgg gtaatttata aagaaaagag gtttaattgg ctcacaagtt      420
ctgcaggctg tacaggaaac atggctgggg aggcctcagg aaacttacac tcatggcaga      480
aggggaagca aacacatcct tcttcacagg gtggcaggag agaaagaat gagagtgagg       540 ggggtgaaag ccctttataa aatcgtcaga tttcatgaga actcattccc tgtcatgagt      600
acagcatgag ggtaaccgcc cccatgattc agttacttcc ctccaggtcc ctcccataac      660
acatggggat tatgggaact acagttcaat atgagatttg gatggggaca cacccaaacc      720
acatcaccgc cttatctggt gattttgctt tctgcagttt cagttaccct tggtcaaccg      780
ttggttcaaa atattcaat gggaaaattc cagaaacaat ttcctaagtt ctaaatttca       840
```

<210> SEQ ID NO 5
<211> LENGTH: 559
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(559)
<223> OTHER INFORMATION: n = a,t,c or g

<400> SEQUENCE: 5

```
tttttttttt ttttcaaaaa ggcaactttt ttttttttct tggcatcaat gaatatgcac       60
ttcanaaatc tacagagaac tttttcact tnggntttgt tccacagcat tctagccagg       120
agtacaaaat aggagctctt caagcagcac atgaagatgg cccaggagcc ttcagccatc      180
cagagcagca nagcagcacc taatctcca cacacttccc agtntaacca ctaanaacac       240
actagaccct tggcattagg ggatttatca tttccagttc tattatctgg gaatgactcc      300
aagggtttgt gacaagcttt tgaaacgtaa gtgctaanac gagtgtggac aagtcactga     360
gctaatgaan aatagaccca ctgtctgctt ggctctgcta ttttgtacct gtcttcacat     420
gtggggaaac ttcataactg tgcccacaaa tcagagaaat tcgcaaagga ctagacaatg     480
tattgcctgt gaacttcaga ggcaactgga aatagtgcaa ctggaaatca actagcttca     540
tacataggcg gatttgttt                                                    559
```

<210> SEQ ID NO 6
<211> LENGTH: 216
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(216)
<223> OTHER INFORMATION: n = a,t,c or g

<400> SEQUENCE: 6

```
tcgcagctgc agccaaatca taaacggcga ggactgcagc ccgcactcgc agccctggca       60
ggcggcactg gtcatggaaa acgaattntt ctgctcgggc gtcctggtgc atccgcagtg      120
ggtgctgtna gccgcacact gtttccagaa ctcctacacc atcgggctgg gcctncacag      180
tnttnaggcc gaccaagagc cagggagcca gatggt                                 216
```

<210> SEQ ID NO 7
<211> LENGTH: 576
<212> TYPE: DNA
<213> ORGANISM: Homo sapiens
<220> FEATURE:

<223> OTHER INFORMATION: trypsin-like serine proteases
<220> FEATURE:
<221> NAME/KEY: misc_feature
<222> LOCATION: (1)..(576)
<223> OTHER INFORMATION: n = a, t, c, or g

<400> SEQUENCE: 7

| | | | | | |
|---|---|---|---|---|---|
| gccgactact | actactacta | ctactaaatt | cgcggccggt | cgaccagaag | gactcctgca | 60 |
| acggtgactc | ctgtggggcc | cctgatctgc | aacgggtact | tgcagggcct | tgtgtctttc | 120 |
| ggaaaagccc | cgtgtggcca | agttggcgtg | ccaggtgtct | acaccaacct | ctgcaaattc | 180 |
| actgagtgga | tagagaaaac | cgtccaggcc | agttaactct | ggggactggg | aacccatgaa | 240 |
| attgaccccc | aaatacatcc | tgcggaagga | attcaggaat | atctgttccc | agcccctcct | 300 |
| ccctcaggcc | caggagtcca | gatccccaga | aactacttcc | ttcaacccag | gttacagatt | 360 |
| cccaaaggac | acttacatca | ggaccaagga | gtacacgatc | aanaaacana | nnnnnggcca | 420 |
| aagaacacag | taaggacaaa | gtcacgaaat | ggccgatgta | cgcagtaaag | aaaattttgc | 480 |
| gccactctcg | nnaggagcaa | ggagcgaaac | acagaggaga | gatgagtcca | gcgcgccagg | 540 |
| agacaccgta | tggcntgaga | gaacaatatt | acgaga | | | 576 |

<210> SEQ ID NO 8
<211> LENGTH: 428
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(428)
<223> OTHER INFORMATION: n = a, t, c, or g

<400> SEQUENCE: 8

| | | | | | |
|---|---|---|---|---|---|
| ccgggtnttg | gggaagggtg | ggantgggga | ccanagtgct | gtacggtgct | gtgggatctg | 60 |
| cagatgaagc | ggtgggggct | aaggaaaggt | cccctggccg | ccacttccca | gcagcgcctc | 120 |
| tcccaggtcc | cccagtcctg | ctccctgctg | agacccacct | ctgatccatg | attcccctc | 180 |
| attgccccca | tactttgcat | ctcacnaaag | gccaggggag | cacatacatc | ccgaaaaggg | 240 |
| cnngtccctn | ttnaaatgaa | caacctanaa | cccggtcacg | cctggcacca | tgtccctcan | 300 |
| attactnccc | cacnattatt | cagggacttg | cccatnactg | gctctncctt | ttattcnact | 360 |
| cccnnatcan | atcttgagac | catnngacct | ggaatcaccc | cacnaaacan | tttcctgaaa | 420 |
| tattccac | | | | | | 428 |

<210> SEQ ID NO 9
<211> LENGTH: 678
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(678)
<223> OTHER INFORMATION: n = a, t, c, or g

<400> SEQUENCE: 9

| | | | | | |
|---|---|---|---|---|---|
| cggggaanga | gtcnaagttc | aacnggagcg | cccancttg | gggccgnnag | caggtnaang | 60 |
| natggtttcc | agcnccggtc | ggcagttttn | gtttcgcccn | aatttnggga | ntggtnactt | 120 |
| cagcaacaat | tcagtttgca | cccgngccag | tttttccaag | agtttnggca | gnacttggcg | 180 |
| gtcaaacagg | tnttcttcna | gtgcttaaca | atgatcttnt | cntccaccga | gtgtgtcttt | 240 |

-continued

| | |
|---|---|
| aacatttatt gacggggttt cccacaggtc cgcagtcaaa gaatcgctga accgcgtttc | 300 |
| ctcgagagac ggtgtgtggc atgggcgcct tgctgctgcc ccagtcccag agcttctcct | 360 |
| gtagggtgt cggctacagg aaccttatcc cagctccaaa ctggacgcca tcacatatcc | 420 |
| tgtcgcctgt ctgtactccc atggggacgc agtaattaag ttccaaccga gcgatgttgc | 480 |
| caagcctgag gacaatcccg gccccgtacg accagcggat gaactcagcc agcttaccga | 540 |
| atatgagctt tgggcccct ccccataagt tgaggtttca gaggtttcct gcgttgagaa | 600 |
| agaagtgtgt tcgaaaaag ttctcccaaa gccaccctgg gctggccgga aaangtaatg | 660 |
| ggggtgtaga aggtgcan | 678 |

<210> SEQ ID NO 10
<211> LENGTH: 1553
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(1553)
<223> OTHER INFORMATION: n = a, t, c, or g

<400> SEQUENCE: 10

| | |
|---|---|
| tccgatgnga agtgcctntc gaaaagccag cagtgcaatg ggaaggacga ctgtggggac | 60 |
| ggctccgacg aggcctnctg ccccaaggtg aacgtcgtca cttgtaccaa acacaccctac | 120 |
| cgctgcctca atgggctctg cttgagcaag ggcaaccctg agtgtgacgg gaaggaggac | 180 |
| tgtagcgacg gctcagatga aaggactgc gactgtgggc tgcggtcatt cacgagacag | 240 |
| gctcgtgttg ttgggggcac ggatgccgga tgagggacga gtggccctgg caggtaagcc | 300 |
| tgcatgctct gggccagggc cacatctgcg gtgcttccct catctctccc aactggctgg | 360 |
| tctctgccgc acactgctac atcgatgaca gaggattcag gtactcagac cccacgcagt | 420 |
| gaacggcctt cctgggcttg cacgaccaga gccagcgcag cccccttggg gtgcaggagc | 480 |
| gcaggctcaa gcgcatcatc tcccacccct tcttcaatga cttcaccttc gactatgaca | 540 |
| tcgcgctgct ggagctggag aaaccggcag agtacagctc catggtgcgg cccatctgcc | 600 |
| tgccggacgc ctcccatgtc ttccctgccg gcaaggccat ctgggtcacg ggctgggac | 660 |
| acacccagta tggaggcact ggcgcgctga tcctgcaaaa gggtgagatc cgcgtcatca | 720 |
| accagaccac ctgcgagaac ctcctgccgc agcagactca cgccgcgcat gatgtgcgtg | 780 |
| ggcttcctca gcggcggcgt ggactcctgc caggtgtgatt ccgggggacc cctgtccagc | 840 |
| gtggaggcgg atggcggat cttccaggcc ggtgtggtga ctggggaga cggctgcgct | 900 |
| cagaggaaca agccaggcgt gtacacaagg ctccctctgt ttcgggactg gatcaaagag | 960 |
| aacactgggg tataggggcc ggggccaccc aaatgtgtac acctgcgggg ccacccatcg | 1020 |
| tccacccag tgtgcacgcc tgcaggctgg agactggacc gctgactgca ccagcgcccc | 1080 |
| cagaacatac actgtgaact caatctccag ggctccaaat ctgcctagaa aacctctcgc | 1140 |
| ttcctcagcc tccaaagtgg agctgggagg tagaagggga ggacactggt ggttctactg | 1200 |
| acccaactgg gggcaaaggt ttgaagacac agcctccccc gccagcccca agctgggccg | 1260 |
| aggcgcgttt gtgcatatct gcctcccctg tctctaagga gcagcgggaa cggagcttcg | 1320 |
| gggcctcctc agtgaaggtg gtggggctgc cggatctggg ctgtgggccc ttgggccacg | 1380 |
| ctcttgagga agcccaggct cggaggaccc tggaaaacag acgggtctga gactgaaatt | 1440 |

```
gttttaccag ctcccagggt ggacttcagt gtgtgtattt gtgtaaatga gtaaacatt    1500 ttatttcttt ttaaaaaaaa aaaaaaaaaa aaaaaaaaaa aaaaaaaaaa aan          1553

<210> SEQ ID NO 11
<211> LENGTH: 2128
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(2128)
<223> OTHER INFORMATION: n = a, t, c, or g

<400> SEQUENCE: 11
ccgcctgcga gcccgtgagc ttctacacgc agcccttctc gcactatggc caggccctgt     60
gcgtgtcctt cccgcagccc tgccgcgccg ccnaccccg cgtccgctgc tcacctaccg    120
cgtcggggag ggacccgggg tttgctggtt ggctcccgag cagacagcag gaaagaagaa    180
gcccttcgtg tacacccagg ccaggctgt cctaaaccgg gccttcttcc cttgcttcga    240
cacgcctgct gttaaataca agtattcagc tcttattgag gtcccagatg gcttcacagc    300
tgtgatgagt gctagcacct gggagaagag aggtccaaat aagttcttct tccagatgtg    360
tcagcccatc ccctcctatc tgatagcttt ggccatcgga gatctggttt cggctgaagt    420
tggacccagg agccgggtgt gggctgagcc ctgcctgatt gatgctgcca aggaggagta    480
caacgggtgt atagaagaat ttttggcaac aggagagaag ctttttggac cttatgtttg    540
gggaaggtat gacttgctct tcatgccacc gtccttttcca tttggaggaa tggagaaccc    600
ttgtctgacc tttgtcaccc cctgcctgct agctggggac cgctccttgg cagatgtcat    660
catccatgag atctcccaca gttggtttgg gaacctggtc accaacgcca actggggtga    720
attctggctc aatgaaggtt tcaccatgta cgccagagg aggatctcca ccatcctctt    780
tggcgctgcg tacacctgct tggaggctgc aacggggcgg gctctgctgc gtcaacacat    840
ggacatcact ggagaggaaa acccactcaa caagctccgg tggaagattg aaccaggcgt    900
tgacccggac gacacctata atgagacccc ctacgagaaa ggtttctgct tgtctcata    960 cctggcccac ttggtgggtg atcaggatca gtttgacagt tttctcaagg cctatgtgca    1020
tgaattcaaa ttccgaagca tcttagccga tgactttctg gacttctact ggaatatttt    1080
ccctgagctt aagaaaaaga gagtggatat cattccaggt tttgagtttg atcgatggct    1140 gaatacccc ggctggcccc cgtacctccc tgatctctcc cctggggact cactcatgaa    1200
gcctgctgaa gagctagccc aactgtgggc agccgaggag ctggacatga aggccattga    1260
agccgtggcc atctctcct ggaagaccta ccagctggtc tacttcctgg ataagatcct    1320
ccagaaatcc cctctccctc ctgggaatgt gaaaaaactt ggagacacat acccaagtat    1380
ctcaaatgcc cggaatgcag agctccggct gcgatggggc caaatcgtcc ttaagaacga    1440
ccaccaggaa gatttctgga agtgaagga gttcctgcat aaccagggga agcagaagta    1500
tacacttccg ctgtaccacg caatgatggg tggcagtgag gtggcccaga ccctcgccaa    1560
ggagactttt gcatccaccg cctcccagct ccacagcaat gttgtcaact atgtccagca    1620
gatcgtggca cccaagggca gttagaggct cgtgtgcatg gcccctgcct cttcaggctc    1680
tccaggcttt cagaataatt gttgttccc aaattcctgt tccctgatca acttcctgga    1740
gtttatatcc cctcaggata atctattctc tagcttaggt atctgtgact cttgggcctc    1800
tgctctggtg ggaacttact tctctatagc ccactgagcc ccgagacaga gaacctgccc    1860
```

-continued

```
acagctctcc ccgctacagg ctgcaggcac tgcagggcag cgggtattct cctccccacc    1920
taagtctctg ggaagaagtg gagaggactg atgctcttct tttttctctt tctgtccttt    1980
ttcttgctga ttttatgcaa agggctggca ttctgattgt tcttttttca ggtttaatcc    2040
ttattttaat aaagttttca agcaaaaatt aaaaaaaaaa aaaaaaaga gcggccgctc    2100 gcgatntaga actagnggac gggggtcn                                       2128
```

<210> SEQ ID NO 12
<211> LENGTH: 594
<212> TYPE: DNA
<213> ORGANISM: Homo sapiens
<220> FEATURE:
<223> OTHER INFORMATION: thimet oligopeptidase
<220> FEATURE:
<221> NAME/KEY: misc_feature
<222> LOCATION: (1)..(594)
<223> OTHER INFORMATION: n = a, t, c, or g

<400> SEQUENCE: 12

```
cccccgcgtc cgtaaatatt gaaaactcca ggcatcgaaa acaagagcag aagcaccttc      60
agccacagcc ttataaaagg gaaggtaaat ggcataaata tggtcgcact aatggaagac     120
aaatggcaaa tcttgaaata gaattggggc aattaccttt tgatcctcaa tactgattca     180
caattgagtt aaattagaca actgtaagag aaaaatttat gctttgtata atgtttggta     240
ttgaaactaa tgaaattacc aagatgacaa tgtcttttct tttgtttcta agtatcagtt     300
tgataacttt atattattcc tcagaagcat tagttaaaag tctactaacc tgcattttcc     360
tgtagtttag cttcgttgaa tttttttttga cactggaaat gttcaactgt agttttatta    420
aggaagccag gcatgcaaca gattttgtgc atgaaatgag acttcctttc agtgtaagag     480
cttaaagcaa gctcagtcat acatgacaaa gtgtaattaa cactgatgtt ttgtgttaaa     540
tttgcagcag agcttgagaa aagtcatttg gtctggaatt catcattaac attn           594
```

<210> SEQ ID NO 13
<211> LENGTH: 540
<212> TYPE: DNA
<213> ORGANISM: Homo sapiens
<220> FEATURE:
<223> OTHER INFORMATION: thimet oligopeptidase
<220> FEATURE:
<221> NAME/KEY: misc_feature
<222> LOCATION: (1)..(540)
<223> OTHER INFORMATION: n = a, t, c, or g

<400> SEQUENCE: 13

```
aatacaatca tgcggcctgc ttcggtctcc agcctggctg ccttctgcct gatggaagcc      60
ggatgatggc agtggctgcc ctcgtggtga acttctcaca gccagtggca ggtcgtccct     120
ctctcctgag acacgacgag gtgaggactt actttcatga gtttggtcac gtgatgcatc     180
agatttgtgc acagactgat tttgcacgat ttagcggaac aaatgtggaa actgactttg     240
tagaggtgcc atcgcaaatg cttgaaaatt gggtgtggga cgtcgattcc ctccgaagat     300
tgtcaaaaca ttataaagat ggaagcccta tttgcagacg atctgcttga aaaacttgtt    360
gcttctaggc tgggtcaaca caggtcttct gaccctgcgc cagaattgtt ttgaagcaag     420
ttgatcagtc tcttcatacc aacacatcgc tggatgctgc aagtgaatat gccaaatact     480
gctcanaaat nttanggagt tgcagctact ccaggcacaa atatgccagc tacctttggn     540
```

<210> SEQ ID NO 14

<211> LENGTH: 466
<212> TYPE: DNA
<213> ORGANISM: Homo sapiens
<220> FEATURE:
<223> OTHER INFORMATION: thimet oligopeptidase

<400> SEQUENCE: 14

| | | | | | |
|---|---|---|---|---|---|
| ttatcctgtc | ttggtttcct | tattgaatag | atttccacag | gaaaaatact | gtgagtttac | 60 |
| tgatctgctg | cagaattgga | atttagactc | acaataaaga | gagttaaaga | tagatccaaa | 120 |
| ggttcactta | aaataaaaat | caccagacag | aacaggctac | tgaagagtct | cttccccgtg | 180 |
| gttaagtttc | atcatacaca | taaggctttg | gagcagctgt | cctcaaatgc | ttctatccaa | 240 |
| aacccactcc | tcttctggag | tttctgaacc | ctttatgttc | cacatccacc | tcctctctct | 300 |
| tcccatggct | ctctacagag | ccatttgtga | catgtctacc | tgacactttt | ggggacgtgg | 360 |
| taagtaaaag | aggcaaagtc | cctaacactt | attagaaacg | tgagaagaga | aaaatggtgc | 420 |
| ttgggacttg | ctttagtatt | ctaattgggc | acacatgcca | aaagac | | 466 |

<210> SEQ ID NO 15
<211> LENGTH: 1477
<212> TYPE: DNA
<213> ORGANISM: Homo sapiens
<220> FEATURE:
<223> OTHER INFORMATION: cathepsin
<220> FEATURE:
<221> NAME/KEY: misc_feature
<222> LOCATION: (1)..(1477)
<223> OTHER INFORMATION: n = a, t, c or g

<400> SEQUENCE: 15

| | | | | | |
|---|---|---|---|---|---|
| cctctttttcc | cccgatccaa | ggatgtatgc | atggaggtcg | tatctatcca | gtcttgggaa | 60 |
| cgtactggga | caactgtaac | cgttgcacct | gccaggagaa | caggcagtgg | cagtgtgacc | 120 |
| aagaaccatg | cctggtggat | ccagacatga | tcaaagccat | caaccagggc | aactatggct | 180 |
| ggcaggctgg | gaaccacagc | gccttctggg | gcatgaccct | ggatgagggc | attcgctacc | 240 |
| gcctgggcac | catccgccca | tcttcctcgg | tcatgaacat | gcatgaaatt | tatacagtgc | 300 |
| tgaacccagg | ggaggtgctt | cccacagcct | tcgaggcctc | tgagaagtgg | cccaacctga | 360 |
| ttcatgagcc | tcttgaccaa | ggcaactgtg | caggctcctg | ggccttctcc | acagcagctg | 420 |
| tggcatccga | tcgtgtctca | atccattctc | tgggacacat | gacgcctgtc | ctgtcgcccc | 480 |
| agaacctgct | gtcttgtgac | acccaccagc | agcaggctg | ccgcgtggg | cgtctcgatg | 540 |
| gtgcctggtg | gttcctgcgt | cgccgagggg | tggtgtctga | ccactgctac | cccttctcgg | 600 |
| gccgtgaacg | agacgaggct | ggccctgcgc | ccccctgtat | gatgcacagc | cgagccatgg | 660 |
| gtcgggcaa | gcgccaggcc | actgcccact | gccccaacag | ctatgttaat | aacaatgaca | 720 |
| tctaccaggt | cactcctgtc | taccgcctcg | gctccaacga | caaggagatc | atgaaggagc | 780 |
| tgatggagaa | tggccctgtc | caagccctca | tggaggtgca | tgaggacttc | ttcctataca | 840 |
| agggaggcat | ctacagccac | acgccagtga | gccttgggag | gccagagaga | taccgccggc | 900 |
| atgggaccca | ctcagtcaag | atcacaggat | ggggagagga | gacgctgcca | gatggaagga | 960 |
| cgctcaaata | ctggactgcg | gccaactcct | ggggcccagc | ctggggcgag | aggggccact | 1020 |
| tccgcatcgt | gcgcggcgtc | aatgagtgcg | acatcgagag | cttcgtgctg | ggcgtctggg | 1080 |
| gccgcgtggg | catggaggac | atgggtcatc | actgagctg | cgggcaccac | gcgggtccg | 1140 |
| gcctgggatc | caggctaagg | gccggcggaa | gaggcccaa | tggggcggtg | accccagcct | 1200 |
| cgcccgacag | agcccggggc | gcaggcgggc | gccagggcgc | taatcccggc | gcgggttccg | 1260 |

```
ctgacgcagc gccccgcctg ggagccgcgg gcaggcgaga ctggcggagc ccccagacct    1320
tccagtgggg acggggcaag ggcctggcct gggaagagca cagctgcaga tcccaggcct    1380
ntggcgcccc cactcaagac taccaaaagc caggacacct caagtcttca gccccactac    1440 cccacccccac tcctgtattc ttttttttt ttttaan                             1477
```

<210> SEQ ID NO 16
<211> LENGTH: 331
<212> TYPE: DNA
<213> ORGANISM: Homo sapiens
<220> FEATURE:
<223> OTHER INFORMATION: cathepsin
<220> FEATURE:
<221> NAME/KEY: misc_feature
<222> LOCATION: (1)..(331)
<223> OTHER INFORMATION: n = a, t, c or g

<400> SEQUENCE: 16

```
atttaaaaac agtgaaaaga aaanaaata ncngangaat aagaatacag ggctgggngc      60
agnggctcag gcctgcaatc ccagcacttn gggaggcgga ggcaggngga ccgcttgagc    120
ccaggngttc gagaccagcc tgggcaacac agtgagaccc ccctctttac aaaaaataca    180
aaantnagcc aggngtggng gngcacctgt agnccagct acttgagagg ctgaggnggg     240
agggtcactt ganccccaggn ntcggaggtt acagtgagcc ctganggnca ctgcactcca    300
acctggggca acggagcaag nccctgtcta a                                    331
```

<210> SEQ ID NO 17
<211> LENGTH: 474
<212> TYPE: DNA
<213> ORGANISM: Homo sapiens
<220> FEATURE:
<223> OTHER INFORMATION: trypsin-like serine proteases

<400> SEQUENCE: 17

```
gaattcggga acgatgggga gcaccaggca ggtggtcctc gctgtgacac tgaggtgctg      60
agccagtgag ctagggtgga ggggctgtgt ttattggaac aaagggtggt accaaaatgc    120
atccccatga cccacagccc ccccacaccc gtccttgggt agggtacggt ggggtggggt    180
gttgggtggc ctgctgctcc tgttgctttc acgtagagtc tcggcctggg cagtcacgtg    240
gtggtcactc ctggatgtgc tgtcctatcc agcctctcac agctgccacc cgggtataga    300
cacctgggaa gtggggccgg ccacagccat agccccagct agtgacccca gttagcaccc    360
accgtccaga gggctccctg caggccaggg gtcccccagc gtcaccctgt tggggagaga    420 agaaagggg ttcagaggcc ggtacctccc ctacagcagc ccttgggtca ttgg            474
```

<210> SEQ ID NO 18
<211> LENGTH: 147
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(147)
<223> OTHER INFORMATION: n = a, t, c, or g

<400> SEQUENCE: 18

```
ttcctcttgg ttgcaaccng nggctgtaga ggccgnggtt tggggaagnc ggngcttggt      60
tcggcccaat ngttttggtt ccgggttaag ncaatctccc ggcntccaag ngcccncngt    120
```

```
tttccgccga ccccggttcn cttggtt                                        147

<210> SEQ ID NO 19
<211> LENGTH: 611
<212> TYPE: DNA
<213> ORGANISM: Homo sapiens
<220> FEATURE:
<223> OTHER INFORMATION: trpsin-like serine proteases
<220> FEATURE:
<221> NAME/KEY: misc_feature
<222> LOCATION: (1)..(611)
<223> OTHER INFORMATION: n = a, t, c, or g

<400> SEQUENCE: 19
tcgtccgtaa tttttttttt tttgtgatca aagatgttta tttaaatgca gattttacaa    60
cctcaacttg tccctttaca acaggtcttc ccagagcttt taatgtgcag acaggcatgt   120
gaacctctga taaagagagg gaaaatggag aggcatcttc ctctgactta atacaaccct   180
ttttactttt ggtagaaaat cataaggcat gagtgtttaa ggagcacact ttgggaaatg   240
tggttctact agccttacta ggcaaatatg ctcggaagcg tgataactaa cacatgtaaa   300
gcactaatta tattaataat gccatgagtc cttttttctt tttctgtcta cttctatgat   360
agtttaatac catgctttct tttattatca ctaaaaagat ggacatgttg aattatttta   420 taatttctt ttacagttct gtgagttaag ctgtatatag catatgggtg tatcattctt    480
tagtaaatta catctacttg tgaactaaac attgatttca ttttgacttt gtgccattgt   540
ctaactttgc aaaaaatcaa aatcaaggaa tcaagggtct tcncaaaang aacatctatt   600
tttttaaaaa n                                                        611

<210> SEQ ID NO 20
<211> LENGTH: 1364
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(1364)
<223> OTHER INFORMATION: n = a, t, c, or g

<400> SEQUENCE: 20
tttttttttt ttttacattt ctcaactttt attgtgggcc cttcaaccat ttttgctgct    60
gggtttcata ttttcggatt gtttcacgga tccacaggac gtatcttgag cacgggtgt    120 agacaccagg ccggtcaggt tgcccacatg ggaagtctcc ccaggagacg atgccataca   180
gtgttctgtt acagaccagg ggcccccag agtcaccctc acaggagtct tgccaccct    240 cttttgtgcc ggcacacaac atgttgtcag tgatctttcc tgggtagact tgacgacact   300
cctcatctga gcgaagttgg atgttggcac attgtagagt tttggggtaa ttcactcaga   360
ccttccctcc catctctgcc cctgtttccc cagccactcc tatgggcct caggcacctg    420 tgtgggtgca tacccgggg gctggtggtg gtgcccagc cagacacccg acaggtggtg    480 ccagggtta ggcggttgtt gtgggaaagg ggcagggttt ggatgtagcc tgtgagctgg    540
accggggact gcagctccag aagcatgatg tcatggtngt ggttcaggtg ggtgggctt    600 ctccggtatt cagggtgggg gatagagtgg acaacttccc tcacctgctc accagcttcc   660
acacgcccta gggcgtgctt gcctaggtaa actttgagcc cctcctttag acagtgtgcg   720
gcagtgagga cccatttggg gtggaccagg acttcccca cagagtagcc gcccttgcac   780
tagtagggca gcctgccagg gctgagagtg ggggaagcag gtgtagccac ctgggagaaa   840
```

```
cccactggtc ccattggtgt tgagaacctt ggaagactcc tgggagacac ctgagtgagg      900
ggcccacgag gagcgtcacg gaggtccagg gggcagagga gccctgggtt tgtggtttct      960
gggtttgggg taagggtcgg attattgccc tgggtgacca ggaactgaag atgaatttgc     1020
cgacctatgg cagttgctat tcttgaccaa gtggagatga attagggcaa aggggtgaca     1080
ttattttctc aggaagtacc aaatcctcca ctggggtta acagaagagt tcacaaaatg      1140
aggatgttgc tgataggtaa gcaggagcct gactttctct ccacatgcat tttttatatc     1200
attctaccag aagatggatt tcaggaggta gaagtgagac tgacctacac atccacctag     1260
gcaatatcta tccatcaatc tatccaatca tccatccccc attcatccta ttgatttgtc     1320
catccgtcta ctcatccatc tatccattca tccatttagg tagn                      1364

<210> SEQ ID NO 21
<211> LENGTH: 416
<212> TYPE: DNA
<213> ORGANISM: Homo sapiens
<220> FEATURE:
<223> OTHER INFORMATION: trypsin-like serine proteases

<400> SEQUENCE: 21
tttttttttt tttggtcgtc ttggtgtatt ttatttctat ttgcaactgt actatagggc       60
tggccatata gtatttgata agtgaacaaa tgagtgaatg gatgaatgat gagtgaatga      120
atgaatgaat gaatgaatga agtcttcttt gacgtcccct gtccacagtg atcttctgag      180
aacctctgca gcatttcctt tgtgtagcct cctttggtcc ttagcaacaa cgttgtagca      240
attagttgtt tgaatgtgta ctcagcttaa gttctcgact gcagggtaag caatttgcca      300
gtctagagcc aggtggggag acattgcttg ggaatcagat cgacctggtt ccaatcccag      360
agctaccacc tattacttgt ggcctcaggt aattatctct ctgtaaagct ccattt          416

<210> SEQ ID NO 22
<211> LENGTH: 610
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(610)
<223> OTHER INFORMATION: n = a, t, c, or g

<400> SEQUENCE: 22
aatgcccttc ccagcggtat atctccctcc agtgttccca ctgcggactg agggccatga       60
ccgggcggat cgtgggaggg gcgctggcct cggatagcaa gtggccttgg caagtgagcc      120
tgcacttcgg caccacccac atctgtggag gcacgctcat tgacgcccag tgggtgctaa      180
ttgcggccca ctgcttcttc gtgacccggg agaaggtcct ggagggctgg aagtgtacg       240 cgggcaccca gnaacctgca cccagttgcc tgaggcagcc tccattgccg agatcatcat      300
caacagcaat tacaccgatg aggaggacga ctatgacatc gccctcatgc ggctgttcaa      360
gccccttgac cctgttccgg tgagggaatc tgcactcccc gctctcctgc cccccagccc      420 cagcacccctc tgcagccctc gcacttgtca gcatctgtca actcatatcc gggccccaaa      480
gcttctgcag ggcagaagtc aaagactctt aaagatcctt acatggaaca cttctgtttt      540
ataattaggg aaactgaagc ccaagggtta taaataagtt tgctccaaat gacacatctc      600
acattacaaa                                                            610
```

<210> SEQ ID NO 23
<211> LENGTH: 481
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(481)
<223> OTHER INFORMATION: n = a, t, c or g

<400> SEQUENCE: 23

```
gcgtccggtt tttaactcct gcctcccaca tgttcttgac tgataactga ctcatgtccc      60
tgaattaaaa tgactgacct atgacagcat caagcattct ttgtaagcag agtgatatat     120
ctgagagggc gttgacctgt tgtgtagaat acatatcctt tcccccttca gaatcctgtc     180
tcgcctcgta actgggagag aggctgtgcc tgaaactagg ggcgatgtca aggaagctag     240
aggcctcgat gcaattatta ctgactctgg ggaggaagac agagaataag gggacaccaa     300
ctgcccagtc cactggccat ttttaagggt cccccaccc  caagccaaag tttggtttgt     360
tgctgttaag acaattttg ttgtatgtat ataaatattt tanttagagg agccggggaa      420
tgggatgccg gctttcacag ttctanggaa tggggcagg  gagggatttt gcttttgct      480
t                                                                     481
```

<210> SEQ ID NO 24
<211> LENGTH: 2234
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(2234)
<223> OTHER INFORMATION: n = a, t, c or g

<400> SEQUENCE: 24

```
cccgcgtccg ggcggggcgg gcgggcctcg ggtggcgcgg ggggcggacc cgccagctgc      60
ctgcgctgct cgccagcttg ctcgcactcg gctgtgcggc ggggcaggca tgggagccgc     120
gcgctctctc ccggcgccca cacctgtctg agcggcgcag cgaagccgcg gcccgggcgg     180
gctgctcggc gcggaaacaa tgctcggcat ggcatgggat tcctgggctc ctcttccttc     240
tcttcttttct gctctgtgct gttgggcaaa gtgagccctt acagtgcccc ctggaaaccc     300
acttggcctg cataccgcct ccctgtcgtc ttgccccagt ctaccctcaa tttagccaag     360
ccagactttg gagcccgaaa gccaaattag aaagtatctt cttcatgtgg accccagtgt     420
cataagggaa ctccactgcc cacttacgaa gaggccaagc aatatctgtc ttatgaaacg     480
ctctatgcca atggcagccg cacagagacg ccaggtgggg catctacatc ctcagcaagt     540
agtggagatg gggcccaaca ccgagatcaa gggtcttagg gaaagtctcg aaggaagcgg     600
cagatttatg gctatgacag gcaggttcaa gcatttttgg ggaaggactt cctgctcaac     660
taccctttct caacatcagt tgaaatttat ccacgggctt gcaccggcac cctggtggca     720
gagaagcatg tcctcacagc tgcccactgc atacacggat ggaaaaaccc tatgtgaaag     780
ggacccagaa gctttcgagt gggcttccta agcccaagt ttaaagatgg gtggtcgagg      840
ggccaacgac tccacttcag ccatgcccga gcagatgaaa tttcagtggg atccgggtga     900
aacgcaccca tgtgcccaag ggtttggatc aagggcaatg ccaatgacat cggcatggat     960
tatgattatg ccctcctgga actcaaaaag cccccacaag agaaaattta tgaaagattt    1020
```

-continued

```
ggggtgaccc tccctgcata agccagcttg ccaaggggc aagaattcca cttctctggt    1080
tatgacaaat gaccgaccca ggcaatttgg tgtatcgctt ctgtgacgtc aaagacgaga    1140
cctatgactt gctctaccaa gcaatgcgat gcccaaccag gggccagcgg tcttggggt     1200 ctatgtgagg gatgtggaaa gagacagcag cagaagttgg gaccgaaaaa ttattggcat    1260
tttttcaggg caccagtggg tggacatgaa tggttcccca caggatttca acgtggctgt    1320
cagaatcact cctctcaaat atgcccagat ttgctattgg attaaaggaa actacctgga    1380
ttgtagggag gggtgacaca agtgttccct cctggcagca attaagggt cttcatgttc      1440 ttattttagg agaggccaaa ttgttttttg tcattggcgt gcacacgtgt gtgtgtgtgt    1500
gtgtgtgtgt gnaangtgnc ntataatctt ttacctattt cttacaattg caagatgact    1560
ggctttacta tttgaaaact gctttgtgta tcatatcata tatcatttaa gcngttngaa    1620
cgcatacttt tgcatagaaa tananaaaat ctgatttggg gcaatgagga atatttgaca    1680
attaagttaa tcttcacagt ttttgcaaac tttgattttt atttcatctg aacttgtttc    1740
aaagatttat attaaatatt tggcatacaa gagatatgaa ttcttatatg tgtgcatgtg    1800
tgttttcttc tgagattcat cttggtggtg ggttntttg ttttttttaat tcagtgcctg    1860 atctttaatg cttccataag gcagtgttcc catttaggaa ctttgacagc atttgttagg    1920
cagaatattt tggatttgga ggcatttgca tggtagtctt tgaacagtaa aatgatgtgt    1980
tgactatact gatacacata ttaaactata ccttatagta aaccagtatc ccaagctgct    2040
tttagttcca aaaatagttt cttttccaaa ggttgttgct ctactttgta ggaagtcttt    2100
gcatatggcc ctcccaactt taagtcata ccagagtggc caagagtgtt tatcccaacc     2160
cttccattta acaggatttc actcacattt ctggaactag ctattttcca gaagacaata    2220
atcagggctt aatt                                                      2234
```

<210> SEQ ID NO 25
<211> LENGTH: 373
<212> TYPE: DNA
<213> ORGANISM: Homo sapiens
<220> FEATURE:
<223> OTHER INFORMATION: trypsin-like serine proteases

<400> SEQUENCE: 25

```
tcgctcggtg aggacgttcc cggacagtgc ctcactcacc tgggcactgg tatccctcc      60 cagggtccac caagggctcc tgcttttcag acacccatc atcctcgcgc gtcctcaccc     120
tgtctctacc agggggaagtt gcctagcttg gtgaggttac tcctgctcct ccaacctttt    180
tttgccaagg tttgtacacg actcccatct aggctgaaaa cctagcaagt ggaccttgtg    240
tgtgtgcatg gtgtcagccc aaagccaggc tgagacagtc ctcatatcct cttgagccaa    300
actgtttggg tctcgttgct ttatggtatg gtctggattt gtgggaatgg ctttgcgtga    360 gaaagggag gag                                                         373
```

<210> SEQ ID NO 26
<211> LENGTH: 1619
<212> TYPE: DNA
<213> ORGANISM: Homo sapiens
<220> FEATURE:
<223> OTHER INFORMATION: trypsin-like serine proteases

<400> SEQUENCE: 26

```
ccgcgtccgg aaatatgaag aactgaggag gaaaaaaaaa aaaaagaaa agaaccaaca      60
```

-continued

| | |
|---|---|
| acctcaactg cctactccaa aatgttggtc attttatgtt aagggaagaa ttccagggtt | 120 |
| atggccatgg agtgtacaag tatgtgggca gattttcagc aaactctttt cccactgttt | 180 |
| aaggagttag tggattactg ccattcactt cataatccag taggatccag tgatccttac | 240 |
| aagttatgaa acataatct tctgccttct catgatccaa ctaatgcctt actcttcttg | 300 |
| aaatttaac ctatgatatt ttctgtgcct gaatatttgt tatgtaaata caagacctc | 360 |
| agtgccttcc tgtttttcac attttccttt tcaaataggg tctaactcag caactcgctt | 420 |
| taggtcagca gcctccctga agaccaaaat tagaatatcc atgacctagt tttccatgcg | 480 |
| tgtttctgac tctgagctac agagtctggt gaagctcact tctgggcttc atcttggcaa | 540 |
| catctttatc ccgtaatggg tatggttgac actagcccaa tgaaatgaat taaagtggac | 600 |
| caatagggct gagctctctg tgggctggca gtcctggaag ccagctttcc ctgcctctca | 660 |
| tcaactgaat gaggtcagca tgtctattca gcttcgttta ttttcaagaa taatcacgct | 720 |
| ttcctgaatc caaactaatc catcaccagg gtggtttagt ggctcaacat tgtgttccca | 780 |
| tttcagctga tcagtgggcc tccaaggagg ggctgtaaaa tggaggccat tgtgtgagcc | 840 |
| tatcagagtt gctgcaaacc tgacccctgc tcagtaaagc acttgcaacc gtctgttatg | 900 |
| ctgtgacaca tggcccctcc ccctgccagg agctttggac ctaatccaag catcccttttg | 960 |
| cccagaaaga agatggggga ggaggcagta ataaaaagat tgaagtattt tgctggaata | 1020 |
| agttcaaatt cttctgaact caaactgagg aatttcacct gtaaacctga gtcgtacaga | 1080 |
| aagctgcctg gtatatccaa aagctttta ttcctcctgc tcatattgtg attctgcctt | 1140 |
| tgggacttt tcttaaacct tcagttatga ttttttttc atacacttat tggaactctg | 1200 |
| cttgattttt gcctcttcca gtcttcctga cactttaatt accaacctgt tacctacttt | 1260 |
| gacttttgc atttaaaaca gacagtggcg tggatatagt tttactttta aactgtgtac | 1320 |
| ataactgaaa atgtgctata ctgcatactt tttaaatgta aagatatttt tatctttata | 1380 |
| tgaagaaaat cacttaggaa atggctttgt gattcaatct gtaaactgtg tattccaaaa | 1440 |
| catgtctgtt ctacatagat gcttagtccc tcatgcaaat caattactgg tccaaaagat | 1500 |
| tgctgaaatt ttatatgctt actgatatat tttacaattt tttatcatgc atgtcctgta | 1560 |
| aaggttacaa gcctgcacaa taaaaatgtt taaccggtta aaaaaaaaaa aaaaaaagg | 1619 |

<210> SEQ ID NO 27
<211> LENGTH: 216
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(216)
<223> OTHER INFORMATION: n = a, t, c or g

<400> SEQUENCE: 27

| | |
|---|---|
| cgatgcctgt tctncaaaag cagtggtttc tttacgctgt ntagcctgcg gggtcaactt | 60 |
| gaactcaagc cgccagagna ggatcgtggg cggcgagagc gcgctcccgg gggcctggcc | 120 |
| ctggnaggtc agcctgcacg cccagaacgt ccacgtgtgc ggaggntcca tcatcacccc | 180 |
| cgagtggatc gtgacagccg cccactgcgt ggaaaa | 216 |

<210> SEQ ID NO 28
<211> LENGTH: 340
<212> TYPE: DNA
<213> ORGANISM: Homo sapiens
<220> FEATURE:
<223> OTHER INFORMATION: trypsin-like serine proteases

<400> SEQUENCE: 28

```
ctggggtctg atcacagggt caccaggatg cccaggggca tcaccagaca caggactagg      60
atgaggaagt cttttgaattc aaacaggaag cttgtctcag gtgatcaata atccatttct    120
tgtagaaact aacttctgtg taaactccag ggtatccttt gcgaccgcag ccaatgcccc     180
agctcacaat ccccacctgg acccatgtgc catttaattc acagaccagg ggccccccag     240
aatctccctg gaaaagaaa gacagtcact gtaggaaaga aataggatcc acatcagagc      300
aggctaattg cactgcaatg cgctacagag ctaagcacta                           340
```

<210> SEQ ID NO 29
<211> LENGTH: 340
<212> TYPE: DNA
<213> ORGANISM: Homo sapiens
<220> FEATURE:
<223> OTHER INFORMATION: trypsin-like serine proteases

<400> SEQUENCE: 29

```
ctggggtctg atcacagggt caccaggatg cccaggggca tcaccagaca caggactagg      60
atgaggaagt ctttgaattc aaacaggaag cttgtctcag gtgatcaata atccatttct     120
tgtagaaact aacttctgtg taaactccag ggtatccttt gcgaccgcag ccaatgcccc     180
agctcacaat ccccacctgg acccatgtgc catttaattc acagaccagg ggccccccag     240
aatctccctg gaaaagaaa gacagtcact gtaggaaaga aataggatcc acatcagagc      300
aggctaattg cactgcaatg cgctacagag ctaagcacta                           340
```

<210> SEQ ID NO 30
<211> LENGTH: 511
<212> TYPE: DNA
<213> ORGANISM: Homo sapiens
<220> FEATURE:
<223> OTHER INFORMATION: aspartyl proteases

<400> SEQUENCE: 30

```
catcacagtc atccacgggc actgttatgg gagctgttat catggagggc ttctacgttg      60
tctttgatcg ggcccgaaaa cgaattggct ttgctgtcag cgcttgccat gtgcacgatg    120
agttcaggac ggcagcggtg gaaggcccctt ttgtcacctt ggacatggaa gactgtggct    180
acaacattcc acagacagat tagtcaaccc tcatgaccat agcctatgtc atggctgcca    240
tctgcgccct cttcatgctg ccactctgcc tcatggtgtg gtcagtggcg ctgcctccgc    300
tgcctgcgcc agcagcatgg aatgactttg ctgatgacat ctccctgctt gaagtgaagg    360
aggcccatgg gaagaaagat agagattccc ctggaccaca ccttccgtgg ttcactttgg    420
tcacaagtag gagacacaga tggcacctgt ggccagagca cctcaggacc cttcccacca    480
ccaaatgcct ctgccttgat ggagaaggaa a                                    511
```

<210> SEQ ID NO 31
<211> LENGTH: 434
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(434)
<223> OTHER INFORMATION: n = a, t, c or g

```
<400> SEQUENCE: 31
aattcaagag gcaatctttg caccaatgtt aggcttgttt atacagtccc tgtctctaaa      60
gcaaatagca aactgtgcat cctctcctac tgactttggc cagcagggaa acaagcttgg     120
tctcttctct gccagggtac cacagggaca cacgccaagg taacctgcgt gtgatgccag     180
tacttctgaa actaagaaaa gaagaatact ttgggttgga gaatttaaag gaatggtgga     240
caaaggttca gggctgaaag tttcaagcag cagaatttcc cgacttaaat ttgaggtgac     300
caagagtaat tcccgccagc aggagttgct tcttttcttc tcttttttct ggttttccta     360
acanggtaca agttccctgg gaaccccacc ctttggccaa gccttttttcc cttcttccat    420 ccaagggcna gagg                                                       434

<210> SEQ ID NO 32
<211> LENGTH: 2514
<212> TYPE: DNA
<213> ORGANISM: Homo sapiens
<220> FEATURE:
<223> OTHER INFORMATION: aspartyl proteases

<400> SEQUENCE: 32
acaagttgca cttaagaagc tatgctaaga aaacaaacac acagaagcct acatcattac      60
atgtatagaa tgttcaagaa ctgatgaaac cagtccgtgg tcacaaaagc cagaaagtgg     120
ttgcttctgg ggaccagaag ggaaagggc ataaggaac cttttgaggt gaatagaagt       180
ttctgcatct tggtttggca cacatgccaa aactcaccag ctacagattc tcgttgacac     240
tggaagcagt aactttgccg tggaggaacc ccgcactcct acatagacac gtactttgac     300
acagagaggt ctagcacata ccgctccaag ggctttgacg tcacagtgaa gtacacacaa     360
ggaagctgga cgggcttcgt tggggaagac ctcgtcacca tccccaaagg cttcaaatac     420
ttcttttctt gtcaacattg ccactatttt tgaatcagag gaatttcttt ttgcctggga     480
ttaaatggaa tggaatactt ggcctagctt atgccacact tgccaagcca tcaagttctc     540
tggagacctt cttcgactcc ctggtgaaca caagcaaaac atcccaaac gttttctcca      600 tgcagatgtg tggagccggg cttgcccgtt ggctgggatt ctggggaacc aacggaggta     660
gtcttgtctt gggtggaatt gaaccaagtt tgtataaagg agacatctgg tatacccta      720 ttaaggaaga gtggtactac cagatagaaa ttcttgaaat tgggaaattg ggaggccaaa     780
gctttaattc ttgggactgc aggaggagta ttaacgcaga caagggccat cgttggacag     840
tgggcaccac gctgctgcgc cttgccccca gaaggtgttt gatgcggtgg tgggaagctg     900
tggcccgcgc atctctgatt ccagaattct ctgatgttt ctggactggg tcccagctgg      960
cgtgctggac gaattcggaa acaccttggt cttacttccc taaaatctcc atctacctga    1020
gagacgagaa ctccagcagg tcattccgta tcacaatcct gcctcagctt tacattcagc    1080
ccatgatggg ggccggcctg aattatgaat gttaccgatt cggcatttcc ccatccacaa    1140
atgcgctggt gatcggtgcc acggtgatgg agggcttcta cgtcatcttc gacagagccc    1200
agaagagggt gggcttcgca gcgagcccct gtgcagaaat tgcacggtgc tgcaagtgtc    1260
tgaaatttcc gggcctttct caaacagagg atgtagccag ccaactgtgt ccccgctcaa    1320
gtctttgagc gacgcccatt tgtggattg tgtccctatg ccgctcaatg aagcgtctgt     1380
ggaagccatc ctccttgtcg ttaattcagt cgctgctgct gcttgccgtt ccggtgtcag    1440
cgtcgccccc gtgaccctga ggtcgtcaat gatgagtcct ctctgggtca gacatcgctg    1500
gaaatgaata gccaggcctg acctcaagca accatgaact cagctattaa gaaaatcaca    1560
```

```
tttccagggc agcagccggg atcgatggtg gcgctttctc ctgtgcccac ccgtcttcaa    1620
tctctgttct gctcccagat gccttctaga ttcactgtct tttgattctt gattttcaag    1680
cttttcaaat cctccctact tccaagaaaa ataattaaaa aaaaaacttc attctaaacc    1740
aaaacagagt ggattgggct gcaggctcta tggggttcgt tatgccaaag tgtctacatg    1800
tgccaccaac ataaaacaaa accaagcctt ggctcgttct cttctctctt caatctctgg    1860
aaaaataagt acatatagtt gataacccct cttagcttac aggaagcttt ttgtattaat    1920
tgcctttgag gttatttttcc gccagacctt caacctgggc aaaagtggt acaggaaggc    1980 ttgcagtatg atggcaggag aatcagcctg gggcctgggg atgtaaccaa gctgtaccct    2040
tgagacctgg aaccagagcc acaggcccct tttgtgggtt tctctgtgct ctgaatggga    2100
gccagaattc aactaggagg tccatcaaac cgatggtcct cacaagcctc ttctgaagat    2160
gggaaggcct tttgcccgtt gaggtagagg ggaaggaaat ctcctctttt gtacccaata    2220
cttatgttgt attgttggtg cgaaagtaaa aacactacct cttttgagac tttgcccagg    2280
gtcctgtgcc tggatggggg tgcaggcagc ctttgaccac cgctgttccc ctcacccaaa    2340
agaattatca tcccaacagc caagacccaa caggtgctga actgtgcatc aaccaggaag    2400
agttctatcc ccaagctggc cactatcaca tatgcttact cttgcttaaa attaataaat    2460
catgttttga tgagaaaaaa ctaaaaaaac ccacgcgtcc gcggacgcgg ggcg          2514

<210> SEQ ID NO 33
<211> LENGTH: 265
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(265)
<223> OTHER INFORMATION: n = a, t, c, or g

<400> SEQUENCE: 33
cttcctantg cagttaaagg gccattgcca gtcagctgaa gaaggaaatg tttgcttctc     60
cctttaaggt gttaaagtaa tgcacagaaa ataaaaatag cagcctcata aatctgcacg    120
gcattgcatt caagcaaagg acaatatgag taacttngag anatatccac attcnatgca    180
cttaatgaaa tcctgttttc nttggagtta catgaggcag cagtactagc tagtgtctaa    240
tattgcactt ttatagcata aacac                                          265

<210> SEQ ID NO 34
<211> LENGTH: 393
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(393)
<223> OTHER INFORMATION: n = a, t, c or g

<400> SEQUENCE: 34
ccacgcgtcc gcgccggccg agtcgctgag ccgcggctgc cggacgggac gggaccggct     60
aggctgggcg cgcccccccgg gccccgccgt gggcatgggc gcactggccc gggcgctgct    120
gctgcctctg ctggcccagt ggctcctgcg cgccgccccg gagctggccc ccgcgccctt    180
cacgctgccc ctccgggtgg ccgcggccac naaccgcgta gttgcgccca ccccgggacc    240
```

-continued

```
cgggacccct gccgagcgcc acgccgacgg cttggcgctc gccctggagc ctgccctggc      300 gtccccgcg ggcgccgcaa cttcttggcc atggtagaca acctgcaggg ggactctggc       360
cgcggctact acctggagat gctgatcggg acc                                   393
```

<210> SEQ ID NO 35
<211> LENGTH: 727
<212> TYPE: DNA
<213> ORGANISM: Homo sapiens
<220> FEATURE:
<223> OTHER INFORMATION: aspartyl proteases

<400> SEQUENCE: 35

```
ttcagcctcc gctggatgcg attggtggag caagggctgc tggagaaacc cgtcttctcc      60
ttttacctca acaggattc tgaagggtct gatgggggag agctggtcct aggggctca       120 gaccccgcct cactacgtac ctcccctcac cttcatacca gtcaccatcc ctgccctact     180
ggagggtcca catggagaag tgtgaaaggt cgggcacaag ggcttaagcc tctgtgccca     240
agggctgcag tgccatccta gacacaggca catccctcat cacaggacct agtgaggaga     300
tccgggcctt gaataaagcc attggggggat atcccttcct gaatcgggca gtacttcatt     360
cagtgttcca agacgccaac gcttccccct gtctccttcc accttggtga agtctggttt     420
aacctcacag gccaggacta tgtcatcaag attcttcaga gcgatgttgg cctctgcctg     480
ttgggcttcc aagctttgga tatccccaaa gcctgcggga cccctcttgg aatccttggg     540
gacgtctttt tggggcccta tgtggctgtc tttgaccgtg gggacaaaaa cgtcgggccc     600
gcgcgtggga ctggcgcgtg ctcagtctcg ttcaacagac cgggcagaaa gaaggactac     660
gcaggcgcag ttcttcaaaa gacgccctgg ttagggtaca agctcaccgg gccacagcag     720
ctatgct                                                              727
```

<210> SEQ ID NO 36
<211> LENGTH: 693
<212> TYPE: DNA
<213> ORGANISM: Homo sapiens
<220> FEATURE:
<223> OTHER INFORMATION: aspartyl proteases

<400> SEQUENCE: 36

```
agggaccctg aagagcctga tggaggagag ctggtcctgg ggggctcgga cccggcacac      60
tacatcccac ccctcacctt cgtgccagtc acggtccctg cctactggca gatccacatg     120
gagcgtgtga aggtgggccc agggctgact ctctgtgccc agggctgtgc tgccatcctg     180
gatacaggca cacctgtcat cgtaggaccc cactgaggaa atccggggccc tgcatgcagc     240 cattggggga atcgccgtgc tgactgggga gtacatcatc ctgtgctcgg aaaatcccaa     300
aagctccccc gcaagtctcc ctttccttct tggggggggtc tggtttaaac ttcacggccc     360
atgattacgt catccagatt acttcgaaat ggcgtccgcc tctgcttgtc cggtttccag     420
gccctggatg tccctccgcc tgcagggccc ttctggatcc tcggtgacgt cttcttgggg     480
gcctatgtga acctcttcga ccgcggggac attaaagacc ggcgcacgag tgggactggc     540
gcgcgctcgc cctccggagc ggacctggga agcgcgagac cggcaggcgc agttccccgg     600
gtgccgccca ggttgatgca tgcgcagcgg gtggtcgcgg aggtcctgct acccagtaaa     660
aatccactat ttccattgaa aaaaaaaaaa aaa                                   693
```

<210> SEQ ID NO 37
<211> LENGTH: 69

```
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(69)
<223> OTHER INFORMATION: n = a, t, c or g

<400> SEQUENCE: 37
ggaattgtng taccncgcca gaacacangg gtcanngaaa acnaccccta aaagccanaa      60
tgggaaagg                                                             69

<210> SEQ ID NO 38
<211> LENGTH: 91
<212> TYPE: DNA
<213> ORGANISM: Homo sapiens
<220> FEATURE:
<223> OTHER INFORMATION: ADAM family of metalloprotease

<400> SEQUENCE: 38
gatttagtac agagctcttt tttgaaatga aggctggaga tgtgcatttt tcacggtgtt      60
aactggttgt acttataaca agaaatgggg t                                    91

<210> SEQ ID NO 39
<211> LENGTH: 485
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(485)
<223> OTHER INFORMATION: n = a, t, c or g

<400> SEQUENCE: 39
ctcataaaaa atgctgtaat cctgcagatt gtactctagt tagatctgca gaatgtggca      60
ctggatcatg ctgtaacaat aaaacttgta cgatccacga aagaggccat gtctgcagaa     120
aaagtgtaga tatgtgtgat tttccagaat attgcaatgg aacatctgag ttttgtgtac     180
ctgatgtgaa agctgctgat ttagaatact gcagtaataa gactagctat tgctttaaag     240
gagtatgcag agaaagggat agacagtgtt cacagttatt tggaaaattt gctaagtctg     300
ctaatcttct gtgtacagaa gaagtgaatt tcaaaatga caaatttgga aactgtggtt      360
cccgttgtga tttttttgat atcctttgtg gaaagattgt ttgtcactgg atacattcag     420
aactagtacc aatgacagac ttagacatac aatatactta ccttagaggt cacgtatngt     480
tgtcg                                                                 485

<210> SEQ ID NO 40
<211> LENGTH: 2350
<212> TYPE: DNA
<213> ORGANISM: Homo sapiens
<220> FEATURE:
<223> OTHER INFORMATION: angiotensin-converting enzyme

<400> SEQUENCE: 40
cctctagact acttgtcgtc gtcgtccttg tagtcggaaa caggggggctg gttaggaggt      60 ccaagtgttg gctgtatccc cagaaactct aggctgttgt cattcagacg gaaagcatca    120
ttgatacggc tccgggacat cctgatggcc ttttcaactt cagttctagg aatgatatca    180
gacacatttt tagggggcagt gaccaaagaa attaaaggag attcttggtt tcaaattagc    240
```

-continued

```
cactcgcaca tccttcctcc ccaaaaagaa tcatgctgat ttttttacttt taaaaagtac      300
tgcctcatag catatgcaac agatgatcgg aacaggtaca tttcattgtc gttccattca      360
tatgctttat ctccaagagc tgattttagg ctttatcctc actttgatgc ttttggtctg      420
catatggact ccagtcggta ctccatccca caaaagaatt cttgttctgg tctttcagcc      480
aggtaaataa cgggctcaaa gtacgttgag cagtggcctt acattcatgt tcctttgctc      540
ctacaacatt ttccaatgct agggtccagg gttctgattt ccaagcctc agcatattga      600
acagtttctg tccagcttct gtagagttac gagatgtcac atttgtgcag agggccttca      660
tgtttagctg gttggacaaa gtgcttcttg aaactgggaa ttgggtaaag ggtccttgtg      720
taatatcgaa tgaatggagt aatcattaga acatggaac agagatgcgg ggtcacagta      780
tgtttcatca tgggggcaca aggttcccaa ccaccccaac tatctctcgc ttcatctccc      840
accactttgt tcatccactg gtctttggga atttcccctt taaagaccat ccacctccac      900
ttctctaaca tgtaagtaaa tggcaggagt cccaacaatc gtgagtgctt tgtttgagca      960
ggaagtttat ttctgtttca ttgtcttctt gaaaattcgg gtgacaaaaa aaccaatggg     1020
atttttaaatg cttaaggtgt ggctgcagaa agtgacatga tttccccaac agcttcatgg     1080
aatccttcat tagctccatt tcttaccaga aaaggttgtg cagcatatgc catatcatac     1140
tggatatgcc ccatctcatg atgagctgtc aggaagtcgt ccattgtcac ctttgtgcac     1200
attaaggatc ctgaaagtcg cccttccccc aggtcccaag ctgtgggatg gcagactgct     1260
ttctgaacat ttcctgggtc ccgttagcat ggaattttcc ccagaatcct tgagtcatat     1320
taggaagacc aacagataca aagaacttct cgggcctcct tgaatattct ctggtgcatc     1380
ccaggcctgg tccaccattg gcatcagtaa catcgtatgt ttggtttcct gtccaaaggg     1440
acactgtcaa agagtacaga tttgtcccaa atctaaccc cacatatcac caagcgaaat     1500
gagcagggag gcatccaatt ggactgatat aggaaggata ggcattcatc aactttgccc     1560
tcacataggc atgaagatgt tcatataatg gtttaatctc ttcaaaaggt atgttccaca     1620
tcttcaatca actggccgcg gcatgtagtc atagccatct tacccccattt actttcatag     1680
tctcctctcc aataatcccc atagtcctca taatgatttg ctcttgccat ctcatttttc     1740
aagaccacat actcttcata taatggcctc agctgcttgc cgacctcaga tctccagctt     1800
tcccaagccc agagcctctc attgtagtct aaactgtttg ccattatttc attcaaacct     1860
ggttcaagta ataagcattc ttgtggatta tctgggttac aaacttttttc cagtactgta     1920
tgatggtgct cattgtattt agaattgtgt tcaaccgttt gctcttgtct tctgagagca     1980
ctgaagaccc attttgttga agagcctgca gatgaagctt gactgtgaga ttctgaattt     2040
cttgtagtgg atacatttgg gcaagtgtgg actgttcctt taaaaaggca cgaccatttt     2100
gtccccagca ttattcatgt tttggacatt ctcttcagta atattgggtg ttataattcc     2160
aagaagcaag tgaactttga tagaacaggt cttcggcttt cgtggttaaa cttgtccaaa     2220
aaatgtcttg gcctgttcct caatggtgga ctgagcagca gtctacagca acaaggctga     2280
gaaggagcca ggaagagctt gacatcgtcc cctgtgagcc aagataccctg ccccgggcgg     2340
cccgctcgag                                                             2350
```

<210> SEQ ID NO 41
<211> LENGTH: 387
<212> TYPE: DNA
<213> ORGANISM: Homo sapiens
<220> FEATURE:
<223> OTHER INFORMATION: trypsin-like serine proteases

```
<220> FEATURE:
<221> NAME/KEY: misc_feature
<222> LOCATION: (1)..(387)
<223> OTHER INFORMATION: n = a, t, c or g

<400> SEQUENCE: 41
actgcagtac cggtncggnt tcccgggtcg acccacgngt ccggcccgct tctcccagan      60
agtgtccgnc gtgtgcctgn ccagcgccga cgacgacttc cccgcgggga cactgtgtgc    120
caccacaggc tggggcaaga ccaagtacaa cgggtgactc tggaggcccc ctggtctgcc    180
agaaggacgg agcctggacc ctggtgggca ttgtgtcctg gggcagccgc acctgctcta    240
ccaccacgcc cgctgtgtac gcccgtntca ccaagctcat accctgggtg cagaagatcc    300
tggccgccaa ctgagcccgc agctcctgcc acccctgcct taagatttcc cattaaatgc    360
atctgtttag aaaaaaaaaa aaaaaaa                                         387

<210> SEQ ID NO 42
<211> LENGTH: 637
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(637)
<223> OTHER INFORMATION: n = a, t, c or g

<400> SEQUENCE: 42
gccccgcgtc cgtccacctc aggttttaca ggtgctccca ccccagttga cggctcccac      60
ccacagggct gtctgtcaca aacccacctc tgttgggagc tattgagcca cctgggatga    120
gatgacacaa ggcactccta ccactgagcg cctttgccag gtccagcctg ggctcaggtt    180
ccaagactca gctgcctaat cccagggttg agccttgtgc tcgtggcgga ccccaaacca    240
ctgccctcct gggtaccagc cctcagtgtg gaggctgagc tggtgcctgg ccccagtctt    300
atctgtgcct ttactgcttt gcgcatctca gatgctaact tggttctttt tccagaagcc    360
tttgtattgg ttaaaaatta ttttccattg cagaagcagc tggactatgc aaaaagtatt    420
tctctgtcag ttccccactc tataccaagg atattattaa aactagaaat gactgcattg    480
aaggggagtt gtgggaaata agaagaatga aaagcctttt ttctgtccgc agatcctgac    540 tttttccaaag tgccttaaaa gaaataaaca aatgccctga gtggnaacta tgggtattta    600
ctttaaaacc aacttacctt tctggttttt tttttttt                             637

<210> SEQ ID NO 43
<211> LENGTH: 505
<212> TYPE: DNA
<213> ORGANISM: Homo sapiens
<220> FEATURE:
<223> OTHER INFORMATION: trypsin-like serine proteases

<400> SEQUENCE: 43 ttttttttttt tctaaacaga tgcatttaat gggaaatctt aaggcagggg tggcaggagc      60
tgcgggctca gttggcggcc aggatcttct gcacccaggg tatgagcttg cgacacggg     120 cgtacacagc gggcgtggtg gtagagcagg tgcggctgcc ccaggacaca atgcccacca    180
gggtccaggc tccgtccttc tggcagacca ggggcctcc agagtcaccc atgcaggagg    240
agacgccact ggccccggca cagatcatca cgtcggtgat cccctgccc caggacttct    300 tgcattcggc attggacagg aggggcaagg ctgcctgctg cagcttggtc aggggtcttg    360
```

```
ttggcgttgt acttggtctt gccccagccc tgtgtgggac aaagtgttcc ccgcgggaaa      420
agtcgtcgtt ggcgactggg aaggcacacg ggggacactg tcctgggaaa accggtcagg      480
tgttggccag cttcaacagg gtgat                                            505
```

<210> SEQ ID NO 44
<211> LENGTH: 522
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(522)
<223> OTHER INFORMATION: n = a, t, c or g

<400> SEQUENCE: 44

```
gaccacgcgt ccgccacncc cgncctnctg cngagacncn anaaggaatn cntgntcgct       60
nctnatgatg gatncnaaan tntcnanagt ttgacgaagt ggggctcggc ttccctgtaa      120
ccctctactc ctntagttcn tggtactgat anacaaaccc antctggatt ctgangaggg      180
cttaaaaaac ataggctata taaacatatn gttggagata tggttnacag ganaatccga      240
tgncaggntg tgcgaattag aaaatcccat naancctgac canattccct aatctntgtc      300
tgaaatctcc atagtnatcn ctgcacaagn tnttgnactc ctctgagact agnnatcngg      360
agctgatcca acacatttta ccctgacctn cttgaacctc gggccctaaa ctactggnat      420 cccggttta atagnaaaac nccccggtcc cctanggtnc catntagggc cttctttaaa       480
aagngnnnnn aaatttgggt tnntttattt tttnccccc cc                          522
```

<210> SEQ ID NO 45
<211> LENGTH: 351
<212> TYPE: DNA
<213> ORGANISM: Homo sapiens
<220> FEATURE:
<223> OTHER INFORMATION: zinc carboxypeptidases

<400> SEQUENCE: 45

```
ccacgcgtcc ccggacgcgt gggcggacgc gtgggctgag ccagtgcgag actgaacttg       60
tgcagcctta gccaagacaa agcagtgttt ttcagcagac ggctgatggg acaggaattg      120
aagaagagaa ttgactcgta tgaacaggac agggtgaaaa tgctgggaat tataatggga      180
aacaaaacta tctatgttca tattttgtaa tatttcattt gttaagttta tatctggata      240
taatgttctt tttaaacaag tataatcata tcgtcggagg ttaagattat gaaattttaa      300
aatctctatt caagatgatg ttcactccaa atacactaca gaaatttagt c               351
```

<210> SEQ ID NO 46
<211> LENGTH: 554
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(554)
<223> OTHER INFORMATION: n = a, t, c or g

<400> SEQUENCE: 46

```
gtccgccgac gcgtgggcgg acgcgtgggt tttttcatt tccactgacc aataaacaga       60
actacaggtg cacccaacca cggacatgca ttaactcgtc atgagaaatc taggtaggct      120
aagtaggatg agagaatgtt tgtcactccc aaaaaatatc tggagaggaa gaatggagga     180
```

```
ttggcattga gatccatgtg acaagctaa gtgggctctg tctgaaagct ggcattcatc    240
cacaacatta aaaaaatatc aaataagaa aggctgtaaa ttaaaaagaa aacacagaaa    300
atactgctct cataaagatc tgattgcctt ggcacaggcc ctgtgggcag aatcaaacgc    360
atcactccca actcccattg cagaagaaaa gctattcaac tctcagcggt ggaggagtgc    420
atgtggcggg cagtttcagg tacaaaccga tgtactgcac tttcagacgc ggatcttgga    480
aatccaggac tttcttggtn aagttgactg aaggtatatt aggatatttc cccacaaaaa    540
tactatttgg gatt                                                     554
```

<210> SEQ ID NO 47
<211> LENGTH: 508
<212> TYPE: DNA
<213> ORGANISM: Homo sapiens
<220> FEATURE:
<223> OTHER INFORMATION: zinc carboxypeptidases

<400> SEQUENCE: 47

```
gacccgcgtc cgcggacgcg tgggcggacg cgtgggggaa cccaacacca gagctttgct    60
aataattagt gtggtcaaga gccgtctgag cctaatgagt cccagctgca ttaggttaag    120
agactcttcc agagccagcg ccaggtcttg aatggcacct ctccctagga tacacagcct    180
gcaggtcccc aggacctgga tgacacccgc ctcactgtgg cagtgtattg cctgttaatt    240
gctgctaatt ctaattctga tgatgactcc tactccattg tttaccccaa agcatcagct    300
aggctggagt gatttgttac aaatgagcaa aagatgagtc cttgcttccc tcagaaataa    360
aaggagctca gctgcagccg ttgcattggg cttcttggcc tcccaactct tcccactccc    420
agaatccaga agtaagctct gcatgttccc cttcctggga ggaaaccaat tgtcagaagg    480
atgtatgatg accccctccc tcccatcc                                      508
```

<210> SEQ ID NO 48
<211> LENGTH: 546
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(546)
<223> OTHER INFORMATION: n = a, t, c or g

<400> SEQUENCE: 48

```
gagtccccc acgcttccgc ccacgcgtcc gcccacgcgt ccgttttttt tttttttttt    60 ttttatttt tacaaagttt tattgaaact tgtccatcaa ggtgacagta attcactgtt    120
ttgaaaagtc acaaaaaagg gtaccccaa actcaggtat accaagtaaa tactggaacc    180
cagggagctc actcctccct ctcccaccag gagcaaaggg cataacggga gcttccgctg    240
actcacagca acctgggcta gtgggtacat ctgtggcgac tcccgggaaa ctgagctgcg    300
tataaagaag tctgctttgg tccaaaggac atcttcctga cccagactca gaaggctgct    360
gtcaagttct acattccttt cagaataagc aacagcaact gctgcantct tgctaactaa    420
gggcanaagt cctgaacaag gtgccacggg aacttgttaa atcacgctgt gtgatttttat    480 agggaaaaag gcanaatgct ctcaantttt cacggttaac actgtcncta ttatgantgg    540
aataaa                                                              546
```

<210> SEQ ID NO 49

```
<211> LENGTH: 191
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(191)
<223> OTHER INFORMATION: n = a, t, c or g

<400> SEQUENCE: 49
accacgcgtc cgcngacgcg tgggcggang cgtgggtttg cttctcggtt atcctgtgct    60
tcagaagaac cnaaacaaat cnattnncan atgtcttact nnaccangtg tgtcacccaa   120
gatncnntan nccacnanaa atcaacnanc accncacnag tngtngtnan ancnntacat   180
aggtgggaat g                                                        191

<210> SEQ ID NO 50
<211> LENGTH: 212
<212> TYPE: DNA
<213> ORGANISM: Homo sapiens
<220> FEATURE:
<223> OTHER INFORMATION: zinc carboxypeptidases

<400> SEQUENCE: 50
ccggaattcc cggggtcgac ccacgcgtcc gcccacgcgt ccgctgatga cctggatttt    60
aagcaccaca attataagga aatgcgccag ttgatgaaag ttgtgaatga aatgtgtccc   120
aatatcacca gaatttacaa cattggaaaa agccaccagg gcctgaagct gtatgctgtg   180
gagatctcag atcaccctgg ggagcatgaa tc                                 212

<210> SEQ ID NO 51
<211> LENGTH: 71
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(71)
<223> OTHER INFORMATION: n = a, t, c or g

<400> SEQUENCE: 51
aatacccggg tcgacccacg cgtccgccca attggaccaa tctatcaccc tatanaagaa    60
ctaatgttag t                                                         71

<210> SEQ ID NO 52
<211> LENGTH: 306
<212> TYPE: DNA
<213> ORGANISM: Homo sapiens
<220> FEATURE:
<223> OTHER INFORMATION: aspartyl proteases

<400> SEQUENCE: 52
ctggcgtgct ggacgaattc ggaaacacct tggtcttact tccctaaaat ctccatctac    60
ctgagagatg agaactccag caggtcattc cgtatcacaa tcctgcctca gctttacatt   120
cagcccatga tgggggccgg cctgaattat gaatgttacc gattcggcat tccccatcc   180 acaaatgcgc tggtgatcgg tgccacggtg atggagggct tctacgtcat cttcgacaga   240
gcccagaaga gggtgggctt cgcagcgagc ccctgtgcag aaattgcagg tgcttgcagt   300
gtctga                                                              306
```

<210> SEQ ID NO 53
<211> LENGTH: 262
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(262)
<223> OTHER INFORMATION: n = a, t, c or g

<400> SEQUENCE: 53

| | | | | |
|---|---|---|---|---|
| gtctccacca | ccgctgctgc | aaccctgct | gctgctnctg | cctctgctga atgtggagcc | 60 |
| ttccggggcc | acactgatcc | gnatccctct | tnatcgagtc | caacctggac gcaggatcct | 120 |
| gaacctactg | aggggatgga | gagaaccagc | agagctcccc | aagttggggg ncccatcccc | 180 |
| tgggacaag | cccatcttcg | tacctntntc | gaactacagg | gatgtgcagt attttgggga | 240 |
| aattgggctg | gggacggctt | ca | | | 262 |

<210> SEQ ID NO 54
<211> LENGTH: 205
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(205)
<223> OTHER INFORMATION: n = a, t, c or g

<400> SEQUENCE: 54

| | | | | |
|---|---|---|---|---|
| tgcnttccan | ttgttggttg | ttccaacncc | cccatgttcc | taaccnntnc ngattcccgg | 60 |
| ttnccaaccc | naaataatcc | ccctccggtt | ccncctncan | taaatccccn ggcnccgggc | 120 |
| nttcggtggc | gggaaaacgg | ttttnctccc | tccaaagggg | ggtatncgg tttnccccaa | 180 |
| aaccggggaa | aaccccngaa | aaaaa | | | 205 |

<210> SEQ ID NO 55
<211> LENGTH: 1363
<212> TYPE: DNA
<213> ORGANISM: Homo sapiens
<220> FEATURE:
<223> OTHER INFORMATION: cathepsin

<400> SEQUENCE: 55

| | | | | |
|---|---|---|---|---|
| gcatcttggg | aagaacccgc | cggcgattga | ctgtctttgc | aagaaatatg atacgagcac | 60 |
| agaagattca | ggccctggac | cgcggcacag | ctcagtatgg | gatcaccaag ttcagtgacc | 120 |
| tcacagagga | ggaattccac | accatctacc | tgaatcccct | cttacagaag gagtctggca | 180 |
| ggaagatgag | tccagccaag | tccataaatg | atcttgcccc | gcctgaatgg gactggagga | 240 |
| agaaaggggc | tgtcactgaa | gtgaagaacc | agggcatgtg | tggctcctgc tgggcctttt | 300 |
| ctgtcacagg | caacgtggag | ggccagtggt | tcctgaaccg | ggggactctg ctctccctgt | 360 |
| cagagcagga | gctcttggat | tgtgacaagg | tggacaaggc | ctgcttgggt ggattgcccc | 420 |
| ccaacgccta | tgcagccata | aagaatttgg | gagggctgga | gacagaggat gactacggct | 480 |
| accagggcca | tgttcagacc | tgcaacttct | cagcacagat | ggcaaaagtc tacatcaatg | 540 |
| attcagtgga | gctgagccgg | aatgaaaata | agatagcagc | ctggctggcc cagaaaggac | 600 |
| ctatctcagt | tgccattaac | gccttcggca | tgcaagttct | atcgcagggg attgttcaa | 660 |
| cccattccgg | cccttctgca | gcccttggtt | catcgaccat | gctgtgttgc tggtgggcta | 720 |

```
tggcaaccgc tctaacattc cttactgggc catcaagaac agctggggca gtgactgggg      780
tgaggagggt tactactact tgtaccgtgg atctggagcc tgtggtgtga ataccatggc      840
cagctcggcg gtggtggact gaagaggggc ccccagctcg ggacctggtg ctgatcagaa      900
gtggctgctg ccccagcctg acatgtgtcc aggcccctcc ccgggaggta cagctggcag      960
agggaaaggc actgggtacc tcaggatgag cagagggcac tgggctgggg cacagccect      1020 gcttccctgc accccattcc caccctgaag ttctgcacct gcacctttgt tgaattgtgg      1080
tagcttagga ggatgtcagg gtgaagggtg gtatcttggc agttgaagct ggggcaagaa      1140
ctctgggctt gggtaatgag caggaagaaa attttctgat cttaagccca gctctgttct      1200
gcccccgctt tcctctgttt gatactataa attttctggt tcccttggat ttaaggatag      1260 tgtcccctc catgtccagg aaacttgtaa caacccttt ctaacagcaa aaaaaagatg      1320
tccttataaa aaaataaaa aaaaaagaa aaaaaaaaa aaa                         1363
```

<210> SEQ ID NO 56  
<211> LENGTH: 418  
<212> TYPE: DNA  
<213> ORGANISM: Homo sapiens  
<220> FEATURE:  
<223> OTHER INFORMATION: trypsin-like serine proteases  
<220> FEATURE:  
<221> NAME/KEY: misc_feature  
<222> LOCATION: (1)..(418)  
<223> OTHER INFORMATION: n = a, t, c or g

<400> SEQUENCE: 56

```
ttttcaatgt gaggagttaa tttatattta attctaaagg tgaacgatgg ggacaagctg       60
tgtcatatgg tccacaactg ccacagctca gttattttgg attacatttt caatccaggg      120
tatatagtaa aaaatttttgg catagatgcc aacatcagct ctcaaaacac atccatccgc      180
aaaagacagg attccttgaa gcatcccatt gcagattgcc ggggcagcag aaacttcctt      240
gcagggctgc ctccttcctg gcacaatgcc cacacacagc atattttccg tgatgttgta      300
ggttttatat gcatcgcgac actgaggctt ggagattaca gagatgttca cagtttgcag      360
tgaatcgggc tctttgtaga tatcacacac attgtagctc caggtagaga cagagcan       418
```

<210> SEQ ID NO 57  
<211> LENGTH: 654  
<212> TYPE: DNA  
<213> ORGANISM: Homo sapiens  
<220> FEATURE:  
<223> OTHER INFORMATION: trypsin-like serine proteases

<400> SEQUENCE: 57

```
ccctgcgccc cagccaggcc tgaggacatg aggcggccgg cggcggtgcc gctcctgctg       60
ctgctgtgtt ttgggtctca gagggccaag gcagcaacag cctgtggtcg ccccaggatg      120
ctgaaccgaa tggtgggcgg gcaggacacg caggagggcg agtggccctg caagtcagc      180 atccagcgca acgaagcca cttctgcggg ggcagcctca tcgcggagca gtgggtcctg      240
acggctgcgc actgcttccg caacacctct gagacgtccc tgtaccaggt cctgctgggg      300
gcaaggcagc tagtgcagcc gggaccacac gctatgtatg cccgggtgag gcaggtggag      360 agcaacccc tgtaccaggg cacggcctcc agcgctgacg tggccctggt ggagctggag      420
gcaccagtgc ccttcaccaa ttacatcctc ccgtgtgcc tgcctgaccc ctcggtgatc      480
tttgagacgg gcatgaactg ctgggtcact ggctgggca gccccagtga ggaagacctc      540
ctgcccgaac cgcggatcct gcagaaactc gctgtgccca tcatcgacac acccaagtgc      600
```
aacctgctct acagcaaaga caccgagttt ggctaccaac ccaaaaccat caag      654

<210> SEQ ID NO 58
<211> LENGTH: 421
<212> TYPE: DNA
<213> ORGANISM: Homo sapiens
<220> FEATURE:
<223> OTHER INFORMATION: trypsin-like serine proteases

<400> SEQUENCE: 58
gcgtccgctt ggcttcagtt cagatttcaa gctgtgttgg tgttgggacc agcagaaggc      60
aaacgtccag ccaacacaca ggactgtaag aggactctga gctacgtgcc ctgtgaagac     120
ccccaggctt tgtcatagga ggtcgttcag cttccccaaa gtcagaggtg atttgatttg     180
gggaagactg aatattcaca cctaagtcgt gagcatatcc tgagttttac ttccttatgg     240
cttgccctcc aagttctctc tctcatacac acacacaccc ttgctccaga atcaccagac     300
acctccatgg ctccagctat gggaacagct gcattggggc tgcctttctg tttggcttag     360
gaacttctgt gcttcttgtg gctccactcg cgaggcagct cggaggtgtg gactccgatt     420
g                                                                    421

<210> SEQ ID NO 59
<211> LENGTH: 865
<212> TYPE: DNA
<213> ORGANISM: Homo sapiens
<220> FEATURE:
<223> OTHER INFORMATION: trypsin-like serine proteases

<400> SEQUENCE: 59
gtccgttttc ttttagaaat aatgtattgt gtctgtgcag aaaaaaaaaa accaaaaagg      60
attgctttac tccaagagga gagattgtct taggataaac ctccaagctc acatttaata     120
taacagactg aagtaaacat tagaatcctg tttagagcta ttctgcacag ttaactactg     180
atctttagaa tctaaaattg tatatgaact tattcttaaa taattgaacc gttttatatt     240
caaatgactt atgatcgtgg ttagtttggg aaaaataaga tggttaaatt ttgatttatt     300
gaaatgtaat tgtattattt tcataaaata gcattttcat ttgtaatgtg gtttaacatc     360
cttgttgttt gccaaagaaa tttcatttgg ctgtgaatat tctatttgct tgcagtatct     420
gtttctcttc ctaggctcaa gttggtgacc caagcctatt gtaaacaagt gattatctca     480
aagggagatg ccaatggagt aacaatttgt taaccttacg ttttctgtct gtatattttt     540
ttaaaaatct ggtagtttct ggaaaaaaaa gagaaggggg tttgtagtac ttaaccctat     600
ttatttccgt atattttagt taattagttt ttggaataaa tggatttcag tatagctttg     660
tggttaaatt gcattgcctt tattttatgt ttaggcttat ttttaaatta acatttaaca     720
gaaacatttg aaatagaatt tgcatgtctg ccttaattaa cttaaagact gattttaatc     780
tgactatgac actgagcata ttctttaaat tactcataat ttataatgct taatataatc     840
ttaattaaat taagcagttt tagtt                                           865

<210> SEQ ID NO 60
<211> LENGTH: 388
<212> TYPE: DNA
<213> ORGANISM: Homo sapiens
<220> FEATURE:
<223> OTHER INFORMATION: trypsin-like serine proteases

<400> SEQUENCE: 60

-continued

| | |
|---|---|
| agtgagcaga caccactcga cttcctttct gcgtcaccag tgtcgtcagc agagagagga | 60 |
| cagcacaggc tcaaggttgg tagtgaagtc aggttcgggg tgcatgggct gtggtggtgt | 120 |
| tgatcagttg ctccagtgtt tgaaataaga agactcatgt ttatgtctgg aataagttct | 180 |
| gtttgtgctg acaggtggcc taggtcctgg agatgagcac cctctctctg gcctttaggg | 240 |
| agtcccctct taggacaggc actgcccagc agcaagggca gcagagttgg gtgctaagat | 300 |
| cctgaggagc tcgaggtttc gagctggctt tagacattgg tgggaccaag gatgtttttg | 360 |
| caggatgccc tgatcctaag aaggggggc | 388 |

<210> SEQ ID NO 61
<211> LENGTH: 549
<212> TYPE: DNA
<213> ORGANISM: Homo sapiens
<220> FEATURE:
<223> OTHER INFORMATION: trypsin-like serine proteases

<400> SEQUENCE: 61

| | |
|---|---|
| gaccacgcgt ccgaagccca gcacgctgca ggtcgatcta ttgcaggaat atttccattg | 60 |
| gtggtgtgct tgtcccactg gaactgaagt ctaaagagcc tgatggggac agagttgttt | 120 |
| atacgggtac atatgacaca gaaggtgtga ccccaacgaa gagtggagaa cggcaaccca | 180 |
| tccagatcac catgccgttc acagacattg ggaccttcga gacagtgtgg caagtcaagt | 240 |
| tctacaatta ccacaagcgg gatcactgcc agtggggaag ccccttctct gtcattgagt | 300 |
| atgaatgcaa gcccaacgag acaccgcagt ctgatgtggg tgaacaagga gtccttcctc | 360 |
| tgaaagtggc tctttctgat gctactggac aatcttttca gaaatctact tttagataaa | 420 |
| ccagcgcagg cctaaacaa ggcatgccac accattgctt tccccatct ggtactaatg | 480 |
| acctactagc cctggttatt ttgaaagtgt aattcccctc tgacacaata tccctcacat | 540 |
| acaagatgg | 549 |

<210> SEQ ID NO 62
<211> LENGTH: 230
<212> TYPE: DNA
<213> ORGANISM: Homo sapiens
<220> FEATURE:
<223> OTHER INFORMATION: trypsin-like serine proteases

<400> SEQUENCE: 62

| | |
|---|---|
| ggggccgagg ctgctccaac cctctgtacc ctggagtgta tgccagtgtt tcctatttct | 60 |
| caaaatggat atgtgataac atagaaatca cgcccactcc tgctcagcca gcccctgctc | 120 |
| tctctccagc tctggggccc actctcagcg gcctaatggc catgctggct ggctggtcag | 180 |
| tgctgtgagg tcaggatacc cactctagga ttctcatggc tgcacaccct | 230 |

<210> SEQ ID NO 63
<211> LENGTH: 865
<212> TYPE: DNA
<213> ORGANISM: Homo sapiens
<220> FEATURE:
<223> OTHER INFORMATION: trypsin-like serine proteases

<400> SEQUENCE: 63

| | |
|---|---|
| ttttttgcta cattcccaaa ttttcatttg gagatttat tttgaataga gggaaaatta | 60 |
| tctgcttgta tagtccatgg cagagcacgt ggaatgcaga gggagaagta gggtctcact | 120 |
| tgtccttagc agtgttctca atccaggata catatttgta aacattggtg tagatgccga | 180 |
| cgtcccctcc catgaagtgc cccacctcga ttccctggag cttgtctttg cagatgacag | 240 |

```
tagcaacggc cacctcccca aaaattcggc tgaatacttt cacaaatttc acacataagg      300
aattcctgtg gcttttttcct tgttctgttt tttggcattc tcgatcagac atcacggggg     360
cctccaggtt ctgccgcaag tcagggtgtc ggccactgtt ttccttggct cagtccaaac     420
ctgagagtag acagacagtg cccggcctga cattggtggt ggcgaagggt aaggggctgg     480
actttgggat tgagcatggc aggcttagcc agcttgatga gcatgaggtc atcctgtggg     540
gcgctatgac tgtagttcca gtagcggacg atctgaatgg ggttaattgt ctgttcagta     600
ccgtctctga ctctgctctt gaaatttccc agcatcactt tcagatttgg taaatagcag     660
tgagctgggg ccagcaccca gctgggtttg atgaggacgc ccacacaggg gttgaagtga     720
gacttgaggt acaccaaata gggagcaggg tcttctttct gaacagatga gtcagcaaag     780
aaaaatgtcc cagcgaggac acccaaatag aagacatatt tcatggtgat ccagctcttc     840
ccccttagct cagggagtaa gtgcc                                            865

<210> SEQ ID NO 64
<211> LENGTH: 452
<212> TYPE: DNA
<213> ORGANISM: Homo sapiens
<220> FEATURE:
<223> OTHER INFORMATION: trypsin-like serine proteases

<400> SEQUENCE: 64
caaaaaggag accagacagg aggcgtctgt agagatatca tgaacttcaa cttagctttg      60
ttttccagag actggagcta aactgggctt tcaacatcat catgaagttt atcctcctct     120
gggccctctt gaatctgact gttgctttgg cctttaatcc agattacaca gtcagctcca     180
ctccccctta cttggtctat ttgaaatctg actacttgcc ctgcgctgga gtcctgatcc     240
acccgctttg ggtgatcaca gctgcacact gcaatttacc aaagcttcgg gtgatattgg     300
gggttacaat cccagcagac tctaatgaaa agcatctgca agtgattggc tatgagaaga     360
tgattcatca tccacacttc tcagtcactt ctattgatca tgacatcatg ctaatcaagc     420
tgaaaacaga ggctgaactc aatgactatg tg                                    452

<210> SEQ ID NO 65
<211> LENGTH: 197
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(197)
<223> OTHER INFORMATION: n = a, t, c or g

<400> SEQUENCE: 65
ttntgtttaa atatatttac aatgtnttct gctctattct ttagtagact tttcctcacg      60
tggtcntacg catttctttc taagtttatt ttcatatagc ctatccctgt ctacaattta     120
aattgggatc ttctatattc tagttattat ttgtaaataa gaaaactact gactttttc     180 tagtatatnn tctcaga                                                     197

<210> SEQ ID NO 66
<211> LENGTH: 492
<212> TYPE: DNA
<213> ORGANISM: Homo sapiens
<220> FEATURE:
<223> OTHER INFORMATION: trypsin-like serine proteases
```

```
<400> SEQUENCE: 66
tttttttttt tttgggggga aggaaacata ttatttggaa tcaaggaca ataatacgtc      60 aagcaccaaa tgctacaaag aaatcatgaa aataggcctt aaacgagtca ttcctagatt    120
aacctcccca catgtgaaaa taagtcttgg aagtagaaag ggtgggtttg gttctggtcc    180
ctagagatga caacgtgcag tgactgcagt tctgcacttc tcccctggtg cgtcttttct    240
gagtggctgt tggtggcttt gcacgtgagg tcacataact gcttatctcg tcaggaattt    300
tgcaagaccc ctggagagaa aaccagatgg accagtggga aaggccgccc ttgcaagttg    360
ctgcttcttt tgttcttagt gaagatcaga aacgaaggag gtgacaccgg tgtacacccc    420
aggcttgttc acctctgcgc agcgaatgcc aaagctggtc ggtcccacta acttccacag    480
gctcctctct tg                                                        492

<210> SEQ ID NO 67
<211> LENGTH: 460
<212> TYPE: DNA
<213> ORGANISM: Homo sapiens
<220> FEATURE:
<223> OTHER INFORMATION: trypsin-like serine proteases

<400> SEQUENCE: 67
gtccgcggac gcgtgggatt ttttgaagta ttttgccaa ctaaaatgaa gtctgtaaat      60
tctgttaata aacaaggagt tcatccgttg ctcacatctt tcattggtgc cctctgaact    120
ctgtgggttg ctaggatgta attttaatgc ttccctgcag tccaaagatg attttttcac    180
cacaaatggt aagggatgcc cacctacttt tataaacacc actgcaactt aacaagttta    240
tttatctatg tccagatttc tgtttctgtc ctaaattgat ctggtgtttt taggtggatc    300
aacttggatc tttagacctc atctataaat tgaaattata ttttagtca taagccaagt    360 acaatctaac tcagaatggg attaaaaatt ttagaagcag aagctaatat ataaatgaag    420
tttgggattt ggaactttct gtatctctta agaagaacaa                          460

<210> SEQ ID NO 68
<211> LENGTH: 700
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(700)
<223> OTHER INFORMATION: n = a, t, c or g

<400> SEQUENCE: 68
ttgagcccgc actcgcagcc ctggcaggcg gcactggtca tggaaaacga attgttctgc      60
tcgggcgtcc tggtgcatcc gcagtgggtg ctgtcagccg cacactgttt ccagaagtga    120
gtgcagagct cctacaccat cgggctgggc ctgcacagtc ttgaggccga ccaagagcca    180
gggagccaga tggtggaang ccagcctct ccgtacggca cccagagtac aacagaccct    240
tgctcgctaa cgacctcatg ctcatcaagt tggacgaatc cgtgtccgag tctgacacca    300
tccggagcat cagcattgct tcgcagtgcc ctaccgcggg gaactcttgc ctcgtttctg    360
gcttggggtc tgctggcgaa cggcagaatg cctaccgtgc tgcagtgcgt gaacgtgtcg    420
gtggtgtctg agggaggtct gcagtaagct tctatgaccc gctgtaccac ccaagcatg    480 ttctgcgccc ggcggagggc aagaccagaa ggacttctgc aacggtgact ctgggggcc    540 cctgatctgc aacgggtact tgcagggcct tgtgtctttc ggaaaagccc cgtgtggcca    600
```
agttggcgtg caggtgtcta caccaacctc tgcaaattca ctgagtggat agagaaaacc     660
gtccaggcca gttaactctg gggactggga acccatgaaa                           700

<210> SEQ ID NO 69
<211> LENGTH: 417
<212> TYPE: DNA
<213> ORGANISM: Homo sapiens
<220> FEATURE:
<223> OTHER INFORMATION: trypsin-like serine proteases

<400> SEQUENCE: 69
ttttcaggtt ttcaaagctt tatttctcca gcaccacctt tatccagaag gtggttcata     60 gcccctgca aattgtaaac caatattgct cttttaaatt taatagaaag tcttctgcat     120
tgtttatgta tataagtgca gaaatttagg attattttgg accatcaaca aggaagttgc    180
tggattcttt gactttctta cgttgtaatt tgcttacttg ccaccgatac aggtgagaag    240
ggccaaacac ataatagtgc atgaagactt taacacacta agttatgact ctgacattgc    300
cctaatacaa ctaagctttc ctctggagta caactcggtg gtgaggccag tatgtctccc    360
acacagcgca gagcctctat tttcctcgga gatctgtgct gtgaccggat ggggaag       417

<210> SEQ ID NO 70
<211> LENGTH: 502
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(502)
<223> OTHER INFORMATION: n = a, t, c or g

<400> SEQUENCE: 70
cgcgtccgca aagactgtga ggagaggaga gtaagtataa gaatgagcat tgaactacaa     60
tcagtttcta atccagttca cagaaaggac ttagttattc gtctgactga tgacacggat    120
ccattttttt ttatataacc ttgttatatc tgaggaagat tttcaaagtt taaaattcca    180
gcaaggtctt ctggtagact tnttagcttt cccacaaaaa tttatagatc tccttcagca    240
atgtactcaa gaacatgcca agaaattcc aaggttttg ctacagttag tttctccagc     300
agctattttg gataactcac ctgcattttt aaatgtggta gagacaaatc cttttaagca    360
tcttacacac ctctcactaa aacttttacc tggaaatgat gtggagataa agaaatttct    420
cgcaggctgt ttgaaatgta gcaaggaaga aaaattatca ttgatgcaat cctagatgat    480
gctactaagc aactggactt ta                                             502

<210> SEQ ID NO 71
<211> LENGTH: 614
<212> TYPE: DNA
<213> ORGANISM: Homo sapiens
<220> FEATURE:
<223> OTHER INFORMATION: trypsin-like serine proteases

<400> SEQUENCE: 71 ttttttttt aatcaaaacc atctttatta tttaaagagc attccatcat gcacgggca      60 cctagacagg agtcccccac tagcacagca atattaacat gggggtcagg aggggaggt    120 tgggtggcct cggggcttag tggacccgcc actgtggaat acaggaccct ggagggaggg    180
tgtccttcaa cctgtggacc gggcccaata ataaaaactt tccatcctcc gccctatcgt    240

-continued

```
ggatcccacc accgggatca ccttgggccc tggagggtgc gcagcgagaa aaccacccgg    300
tccagagctg tgtcattatt gtcgctggct tctggatttt attctttatg gtctggaata    360
ttcactcccg gaagtcactg actttggtgt agacgcctgg cttctgggcc aaggcacagc    420
cagtgcaacc aactcacaat gccacacagc cgcaaacgtg gcgtccgaga gatgctgtcc    480
tcacacgcaa agggaccacc gctgtcgccc tggcaggcat acaatgccac ctgcgggtag    540
gccagcacag aacatcttgg ggcttgatct ggttgtccat agaagtcagc gccattgcgg    600
acatcaatgc tgat                                                     614
```

<210> SEQ ID NO 72
<211> LENGTH: 506
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(506)
<223> OTHER INFORMATION: n = a, t, c or g

<400> SEQUENCE: 72

```
tttcagcatt ttcaaagcac tttattgagt tcctgcgcca tcctggcann gctggccgca    60
ctgggggaat gggacacaat cttgccttcc atgcccagc cactctctca ctgcggaatc     120
accaaggagg gaaagatgag tccctgagca atcaggaaac ggtgtgctcc cggatccagg    180
ccaggtagta gggcacatcg gtgtagacgc ctggcttgtt gcggtcacca cagcccgatc    240
ccccagctga tgatgccttg cagggttgag ccggcgctct gcaactttgg ttcctcacac    300
accagcgggc ctccggaatc accctggcaa ggcatcggtg cgcccctcga ggaacccctgc    360 gcagagcatg ccggggaaga tggaggatcc gtgcacgtcc ggggctgagc agcgcccagg    420
ggagaggaag gttacctgcg cttcctgcag gaagctggca tattccttcg cccccttcgga    480 ctggttggcc ccagcgggcc aactgg                                          506
```

<210> SEQ ID NO 73
<211> LENGTH: 463
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(463)
<223> OTHER INFORMATION: n = a, t, c or g

<400> SEQUENCE: 73

```
tatacaacac gaccctacga gaagcagaga cctaccgcat gagggtccga gcctcatcct    60
acagtgccaa tgggaccatt gaatatcaga ccacattcat agtttatata gctgtgtccg    120
cctatccata ctaaggaact ctccaaagcc tattccacat atttaaaccg cattaatcat    180
ggcaatcaag cccccttcca gattactgtc tcttgaacag ttgcaatctt ggcagcttga    240
aaatggtgct acactctgtt ttgtgtgcct tccttggtac ttctgaggta ttttcatgat    300
cccaccatgg tcatatcttg aagtatggtc tagaaaagtc ccttattatt ttatttatta    360
cactggagca gttacttcca aagattattc tgaacatcta acaggacata tcaagtggat    420
gggttacagn agtggtagga cctaaagaac attttcctga agg                      463
```

<210> SEQ ID NO 74
<211> LENGTH: 126

<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(126)
<223> OTHER INFORMATION: n = a, t, c or g

<400> SEQUENCE: 74

```
taaatgaata ttatgtgtaa ttgtttcaaa catccatttt ctttgtgaac atattagtga      60
ttgaagtatt tcgactttng agattgaatg taaaatattt tannttttggg atcatcgcct    120 gttctg                                                                126
```

<210> SEQ ID NO 75
<211> LENGTH: 249
<212> TYPE: DNA
<213> ORGANISM: Homo sapiens
<220> FEATURE:
<223> OTHER INFORMATION: trypsin-like serine proteases

<400> SEQUENCE: 75

```
gagtgggatc tcactttaat ggagaggacg ttatgacctc cggggcatgg ctcttggcgt      60
tgggaagccc ctggttttca tggacctgtc gatccacttg aggaaggcgg tgaccttggt    120
gtagatcccg tacttcccct tacgggcaca gcctctcccc agctgaagaa gcctgtcacg    180
aagtagggtg tcctttaagc ggggacgtg tgggcccccc ttgttccccc tggagggta     240 ctcctcctt                                                              249
```

<210> SEQ ID NO 76
<211> LENGTH: 487
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(487)
<223> OTHER INFORMATION: n = a, t, c or g

<400> SEQUENCE: 76

```
cactttaggg agtcgaccca cgcntccgcg gacgcgtggg ttttcaaact gacaatgttt      60
aggttttaag caaataaagt tccagttaat gtgaaactca gtcacaaaga gttgagattt    120
ttcctttatg aaatagaatt gacattcttt tatgctataa atgtgcattc aggtcccatt    180
aaccatgctc tgctttattt tggggataga acattttctt tttcatatcc cgatcttccc    240
atttcttcat agaaatgtga taagaagtac atccctgtga tcctgctgct tcgtagagca    300
ccactgcaca ccctaccccg agtgccaacc acctctgcta taggacacta ttttcctggc    360
cctattcttc acttacttcc catcctgtcc ttgactagga atatgttaaa tgctgctccc    420
atacaattca gttagctctt gtctttttat ttggtccaac ccctgcttta ctgctcatgc    480
tgcttaa                                                                487
```

<210> SEQ ID NO 77
<211> LENGTH: 474
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature
<222> LOCATION: (1)..(474)

<223> OTHER INFORMATION: n = a, t, c or g

<400> SEQUENCE: 77

```
tcaccagatt taaaggggat tgcagacatc atgattgcct ttaggactcg aggattcaac      60
ttgtttcttg tggctgctca tgaatttggt catgcactgg ggctctctca ctccaatgat     120
caaacagcct tgatgttccc aaattatgtc tccctggatc ccagaaaata cccactttct     180
caggatgata tcaatggaat ccagtccatc tatggaggtc tgcctaaggt acctgctaag     240
ccaaaggaac ccactatacc ccatgcctgt gaccctgact tgactttttga cgctatcaca     300
actttccgca gagaagtaat gttctttaaa ggcaggcacc tatggaggat ctattatgat     360
atcacggatg ttgagtttga attaattgct tcattctggc catctctgcc agctgatctg     420
caagctgcat acgagaaccc cagagataag attctggttt taaagatga aaan            474
```

<210> SEQ ID NO 78
<211> LENGTH: 1687
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature
<222> LOCATION: (1)..(1687)
<223> OTHER INFORMATION: n = a, t, c or g

<400> SEQUENCE: 78

```
gtctnnnnnn nnnnnnnnnt tnttttttnt agaattgcta aagattggtt taataaatgt      60
ttcagtattc agttataaga catgtcttct ccaagtccac aaagcatgaa ataggcttaa     120
agtacagtca gagattttttg tttctacata taacttcct attaaaagaa tcaggcagct     180
caaaatggcc attgaatttg gatatttaga actaggacca gcaacttgtt gttaaagaat     240
ggttttattc tattttgaag cagaatttat attaaaagac ctgttgaggt ttattttagg     300
tctatgaatt tattgataaa tagaagtgtt tttcagcaaa tgaacaatac caaaaataaa     360
caagcttaaa ctcttatgat acaatatctt tatgcctcct gaatgtgctt tttccttgtt     420
gatatcaaaa ccaaatgagg agttcttttgg ttctttgcat gaaaccaag tattagttct     480
catgattcgg gtaatattct ttgtcttaat gttgtattca aattgctttg atccacggct     540
gaaaaagaag aatcctttgt actggaaagc agcatcaaca cggatactga ttccaggaaa     600
gtgttttacc actctctgcg ggaatccttt gtccatggtt tgggtcattt catcaaacct     660
ccagcaccaa atgcccacaa agaagtaggt ttttcttgtg gtcttatcac agacggctgc     720
atctattttc ttcacacggt cctggaaaac ctaatgtatg gatggatttg ggataatctg     780
gcaagacagc atatcctctg atcatccaga agttttcatc tttaaaaacc agaatcttat     840
ctctggggtt tcgtatgca gcttgcagat cagctggcag agatggccag aatgaagcaa     900
ttaattcaaa ctcaacatcc gtgatatcat aatagatcct ccataggtgc ctgcctttaa     960
agaacattac ttctctgcgg aaagttgtga tagcgtcaaa agtcaagtca gggtcacagg    1020
catggggtat agtgggttcc tttggcttag caggtacctt aggcagacct ccatagatgg    1080
actggattcc attgatatca tcctgagaaa gtgggtattt tctgggatcc agggagacat    1140
aatttgggaa catcaaggct gtttgatcat tggagtgaga gagccccagt gcatgaccaa    1200
attcatgagc agccacaaga aacaagttga atcctgctcc atccttggtc cagtttttcat    1260
cctcatcaaa atgagtgtca ccacccagac ccggaccagg aggaaaggca tggccaagca    1320
ctcccaaggg accatcaaaa tagcgaggac accgaccatg gactcgagtc ctaaaggcaa    1380
```

```
tcatgatgtc tgcaatcccc tttgaaatct tggtgaattt tagtggagtg actttgctcc    1440
acacttctaa accttcttgg atagcctcat ccacagcagc tcgtgccata tccggagtat    1500
agtttattat tctgtaggtg aggttgtatt ttctccaccc agggagggtg tagccatact    1560
ggcccacatc aggcacccca cacctgggtg tcttcatgat ctcaagggtg tttgagtcca    1620
gttttccagt cactgtcaat ccaaaaaatg cttgcatttc ccgaattttg tcatctcgga    1680 cgcgtgn                                                              1687
```

<210> SEQ ID NO 79
<211> LENGTH: 542
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(542)
<223> OTHER INFORMATION: n = a, t, c or g

<400> SEQUENCE: 79

```
gttgatgata aaaacttaaa accaggacct ccattctgtc atgactgaca ccatggtagt      60
ctgtcagctt gaccagtgga gagtcattca tttagcacaa gcagctggag atttaaactg     120
ccagtactat gtatttggtg tataatgcaa ggaagaaact ttatccttga atttgagggt     180 gatgggtgg gtcaggaaag gatggcgcca gaattctaca tgataatgaa ctaaaaaatg      240
ttgcttttca gaggaagata aagcatcttc ttttgggagg gggggtatct catgtctaag     300
taagtaaaag aaagaagtag ctactgtctc ttttaaaaac cacgtacaaa acagaacaag     360
tctcagtttt cagtgcaaca tttcaaaaaa tatatatgct gcaatctaat aattaaaagg     420
aattttacct attatgaaac ttattacatt tnttaaggta ggataatcag nttcaaagga    480
gtattcaggg tatttaactt ggttttaaat ggctgctcaa aaaaaaatgn ctattttttt     540 tn                                                                     542
```

<210> SEQ ID NO 80
<211> LENGTH: 265
<212> TYPE: DNA
<213> ORGANISM: Homo sapiens
<220> FEATURE:
<223> OTHER INFORMATION: angiotensin-converting enzyme

<400> SEQUENCE: 80

```
ctggtcctgg atgcaccgca cccgcatagc aggtggctgc tgcactacca aggcatacgc      60
tgcgtggaag ccaccctaag ccacagacag cggatcttcg gagtccgcca gcgcggcctc     120
caacggcact cccacagacc caagatcgga tccgaggtgg aactgtagac actcctgagg     180
tgacccggct agatcggccc tgcccaaggc taaccaccag agactgcgat gggcacactg     240
gtgggcagct gagggcactc cgcca                                            265
```

<210> SEQ ID NO 81
<211> LENGTH: 510
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(510)
<223> OTHER INFORMATION: n = a, t, c or g

<400> SEQUENCE: 81

```
atgtattcac caagcatttt acggatttga cttttcact aaccagttga cgaagcagtg      60
catttacaag gcactgccaa acaagatgcc cttgggagct gtgagggaaa gaggacctgc    120
gggcttagat caatctcaat tccttttcat gccctcctgc attgctgctg cgtgggtatt    180
tgtctcctta gccatcaggt acagtttaca ctacaatgta agctataggt ggagcatcag    240
cagtgagtga ggccattctt catccttagg atgtggcaat gaaatgatgg tgcaagttcc    300
tttctctttt gtgaatcttt cccccatt cctgtttaca tgtaacccaa caaaatgcaa      360
tttctagtgc cttctgtcca atcagttctt tcctctgagt gagacgtact tggctacaga    420
tttctgcctt gttttgcgac attgtcccat tcacacagat attttgggat antaaaggaa    480
aataagctnc aaaaaaaaaa aaaaaaaagg                                     510
```

<210> SEQ ID NO 82
<211> LENGTH: 798
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature
<222> LOCATION: (1)..(798)
<223> OTHER INFORMATION: n = a, t, c or g

<400> SEQUENCE: 82

```
tccgggnccc cctnaaggag cangcttac aggaggactg gagccagtgc accctgccan      60
nctcccggac tcctctctgg caaccagtgc ccgctgtgc tgcaccctct gccacgaagc    120
ggctggagga cacccntttn gtgcattgcc cgtccgtccc ttcncacaat tnctgctncc    180
ctngctccaa acaaancntc aancaccagg nanctattga aaagntctnt tntcccattg    240
gggaaaaatg ccctcttgtg ggctccaatg tcccctgggc ctttatgcaa ggggaaattg    300
caaccatcct tgctggagat gtgaaagtga aaaagagag agactcgtga cttttccggt      360
ttcaaaaaaa acccaatgat taccccttaa ttaaaactgc tttgaaattg tatatatatc    420
tccatatata tatatatcca agacaaggga aatgtagact tcataaacat ggctgtataa    480
ttttgatttt ttttgaatac attgtgtttc tatatttttt ttgacgacaa aaggtatgta    540
cttataaaga cattttttc ttttgttaac gttattagca tatctttgtg ctttattatc      600
ctggtgacag ttaccgttct atgtaggctg tgacttgcgc tgcttttta gagcacttgg    660
caaatcagaa atgcttctag ctgtatttgt atgcacttat tttaaaaga aaaaaaagc      720
caaatacatt ttctgacatt gtaaaaaaaa aaaaaaaggg cggccgctcg cgcccacgcg    780
tccgcggacg gggggcgn                                                  798
```

<210> SEQ ID NO 83
<211> LENGTH: 712
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature
<222> LOCATION: (1)..(712)
<223> OTHER INFORMATION: n = a, t, c or g

<400> SEQUENCE: 83

```
naaaggcttc tgtagaganc atgctgggtc tgcatctcct ctcgtctcct ccatggtggt      60
cactgcccct ggcaggtctc tgaaagggaa atgctttttc ccagaggccc ctgcttgggc    120
```

-continued

```
agttcacagt gagaccgacc ccctctgaat atgataacag cctgtttcac atgaggagat    180
gttaccaatc ccgttcgctc tgacccttgc tggctgatca ccttgagcaa cttacttaac    240
atctgtgttc ctcagtttct catgggtaat atagggataa ttactggcac ctgcctccca    300
ggccattctg acgtgtaacc gcatatagga gcccactggc tgagtagcta ccatcatcgc    360
tggtggggaa actggtggta ggggtgtagg tatttggggg gggttgttca gcccccagg     420 tgtttcagaa caaggcctcg ggcactccca agtctgcctt ttggctccca ccctcaaagc    480
ccatgttctg tgaggcccaa gaaaacacac tggagttctt agccaaatgc actaatgtat    540
tcccggggga actgtcacct tggccaccac ctggggccac tcctgcttgg ctacaactcc    600
atacttcctg ttggttggca ttgggaanaa tttcccccca tgaatgaang gcccaagaa     660 atanaaatct tgttaccact ccanttgcta ccaatccccc caccccctac an            712

<210> SEQ ID NO 84
<211> LENGTH: 317
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature
<222> LOCATION: (1)..(317)
<223> OTHER INFORMATION: n = a, t, c or g

<400> SEQUENCE: 84
tgaaggagct gaaggaggcc ctgcagctga acagtactca cttcctcaac atctactttg    60
ccagctcagt gcgggaagac cttgcaggtg ctgccacctg gccttgggac aaggacgctg    120
tcactcacct gggtggcatt gtcctcagcc cagcatatta tgggatgcct ggccacaccg    180
acaccatgat ccatgaagtg ggacatgttc tgggactcta ccatgtcttt aaaggagtca    240
gtgaaagaga atcntgcaat gacccctgca agagacagtg ccatccatgg aaacgggaga    300
cctctgtgcc gacaccg                                                   317

<210> SEQ ID NO 85
<211> LENGTH: 1021
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(1021)
<223> OTHER INFORMATION: n = a, t, c or g

<400> SEQUENCE: 85
gcggacgcgt gggcggacgc gtgggcggac gcgtgggtcc gggtggccgc ggccacgaac    60
cgcgtagttg cgcccacccc gggacccggg agccctgccg agcgccacgc cgacggctng    120
gcgctcgccc tggagcctgc cctggcgtcc cccgcgggcg ccgccaactt cttggccatg    180
gtagacaacc tgcaggggga ctctggccgc ggctactacc tggagatgct gatcgggacc    240
cccccgcaga agctacagat tctcgttgac actggaagca gtaactttgc cgtggcagga    300
accccgcact cctacataga cacgtacttt gacacagaga ggtctagcac ataccgctcc    360
aagggctttg acgtcacagt gaagtacaca caaggaagct ggacgggctt cgttggggaa    420
gacctcgtca ccatccccaa aggcttcaat acttcttttc ttgtcaacat tgccactatt    480
tttgaatcag agaatttctt tttgcctggg attaaatgga atggaatact tggcctagct    540
```

-continued

| | |
|---|---|
| tatgccacac ttgccaagcc atcaagttct ctggagacct tcttcgactc cctggtgaca | 600 |
| caagcaaaca tccccaacgt tttctccatg cagatgtgtg gagccggctt gcccgttgct | 660 |
| ggatctggga ccaacggagg tagtcttgtc ttgggtggaa ttgaaccaag tttgtataaa | 720 |
| ggagacatct ggtatacccc tattaaggaa gagtggtact accagataga aattctgaaa | 780 |
| ttggaaattg gaggccaaag ccttaatctg gactgcagag agtataacgc agacaaggcc | 840 |
| atcgtggaca gtggcaccac gctgctgcgc ctgccccaga aggtgtttga tgccggtggt | 900 |
| ggaaagctgt ggcccgcgca tctctgattc cagaattctc tgatggtttc tggactgggt | 960 |
| cccacttggc gtgctggacg aattcggaaa caccttggtc ttacttccct aaaatcttca | 1020 |
| n | 1021 |

<210> SEQ ID NO 86
<211> LENGTH: 751
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(751)
<223> OTHER INFORMATION: n = a, t, c, or g

<400> SEQUENCE: 86

| | |
|---|---|
| cattataaat aaataaaang caaaatctgt tgtacatata tttgtacatc tatgcatttg | 60 |
| ccttgcntcc tccttattgt aaatggcata tttatgactc tttgcatatt gtaatcacaa | 120 |
| ttntggaaaa tggatatcat agtaaaaaat acagtcttct atatttgctt ggggttacag | 180 |
| gtgccccgcg tccggctcca ttattaaacg ggctgaaaat tgttgtgtgc taataatttt | 240 |
| aaaaatcaaa atcatgaaac aaagaaaaa aagaaagac aatgttacaa acaattaatc | 300 |
| tacaaaaata tttcagtgat tcccataatt tacctttag taatgtatac tatgttttca | 360 |
| atgagtttaa atgaattaac aaagaaaaaa acagaaaaaa gaaaacaagt ttgaatgttt | 420 |
| taggcaagtt gtagcgtaac tacattgtta tagttgagaa aattacaaat atcaataata | 480 |
| cataaagatg aaactaccaa agtaatacaa gttagataca atacttttcc acaaattaaa | 540 |
| acaaatgcaa cgatacaagc actatgtaag aatacattta gccgtgtgac tttctttaa | 600 |
| tagggttatc agatctacga tataagataa atagatagta attcgacttt gccaacatga | 660 |
| attaaaatgc agatttcttt ttttctcaaa caaataatga tacgggtggt gcatctagtt | 720 |
| ttcaagacag gcgatgatcc ccaatttaaa n | 751 |

<210> SEQ ID NO 87
<211> LENGTH: 895
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(895)
<223> OTHER INFORMATION: n = a, t, c or g

<400> SEQUENCE: 87

| | |
|---|---|
| ccgccccgcg tccggataag ccatttatta aaggagtat ttactagaat tttttgtcat | 60 |
| ataaacttg aatcaggatt ttatgcccca catactctgg aacttgaagt ataatatact | 120 |
| taatataaca taaaaagcca gttgggttct aaattgtagt tgaaacacag aaaatgccac | 180 |
| ttttctgttc ctgaagaggc tcttttgtgc ataatattct aaaatgaaga catttcaagc | 240 |

```
tatacaaatt acttccaagt tttcatgatg tatgggaaga ttttcagtag gtgtattata    300
ttcacggtac caaatgctga ccagtgttgc tccatttttt aaatcttgaa aagggtttct    360
gtacttacct ggtttgccaa gtatgccagt gtaatgaaac tgcccttatt ttaaaagcca    420
gtcaaagatt ccactgattg acatttgata ataaacatc aggattatgt ttattgtttg     480
ttttcagtct ttgcactata ttaccagtat atggtttccg aggaagatta tctactgcaa    540
aacaccactg ttggaaaaat aggtattttt aaattgtttt taatcttttt tggtgctttt    600
aaacatgttt agcaaaaacc aattcagttc cattccccgc aaaaaacccc taactttact    660
ctgaactttt tttgtttttg cattccatga ggttctgtat tcagtcattc tctaggtaat    720 gtcattttg tacacatata tttatataat cactgatttg agatttatga aaaagcattt     780
ctaaagaata tttgcttccc ttagaactac agactcgaaa tctttaaaga tggtgcctaa    840
gcatctatgt attttttta agttccacag atttttctgt tgggcagcca aggan          895

<210> SEQ ID NO 88
<211> LENGTH: 172
<212> TYPE: DNA
<213> ORGANISM: Homo sapiens
<220> FEATURE:
<223> OTHER INFORMATION: zinc carboxypeptidases

<400> SEQUENCE: 88
tggatataca tctaaactgc cacttaatca tgaggacttg gcgcaagttg tatagagtgg    60
taatgatgtg ctattaactt ggtatgtcat gagctacatc tgtaggctta tagtatcaca   120
gagttatgag atatcaggtt agtcgttaga gtgtggctat gacctgggga tc           172

<210> SEQ ID NO 89
<211> LENGTH: 467
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(467)
<223> OTHER INFORMATION: n = a, t, c or g

<400> SEQUENCE: 89
gtgtactcta tctgccacta aaggagagtc aaaggtataa ccagccctaa acttcgcagc    60
aatctattca aagttgctta acaggctctc tagaacgttc tagtaataat cctccagaat   120
ggagccatgt ttgtcctccg agcactctat ttcaaagcat tcagtcactc accctcgagc   180
agatgctgtg atttttataag ttcctggaac caagagacgc cagtaatctc cagttttgta   240
agtagtcact gggtgattaa tctcagcaac actaatggtg gcatttaata taccccctgcc  300 atctgtggca tctagaacaa atcctctgac gccctgatga acctggatta agtacaagga   360
caccagattt caataataaa catcatcatc taattatctt gggaggtcat attcaaaata   420
acagattgtc aacacaaata aatggaacaa acagggattt aggagtn                  467

<210> SEQ ID NO 90
<211> LENGTH: 488
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(488)
```

```
<223> OTHER INFORMATION: n = a, t, c or g

<400> SEQUENCE: 90
gtctggaaat acaaggttct aaanttcgga agagtttaga atttattagg agtttcccaa      60
gttgggatgt tagtctttaa ataaacttca tgcacctatt ccacttaagg ttttgcacct     120
cctttttatt agtgcagtgc catttcttct gcttgatttt aggtatgtta atattccagc     180
cttgctagtt agcataaagt gacaggtgtg agccatgagg aaattttctg acttaatttg     240
tacacaacta catataagag ttttagtgga ggaaaaaaat tagtcccttg tgcgtataca     300
gtagttaggt aaatgatttt tctaccaaca gtatactcca ttcctcatgt aggtaagtac     360
agaaaaggtt tttaaatgta ttttttttagc cagttaaagt ctatgaatct atctgcaacc     420
ttatttaatc tgtcctataa aattttgtg gttatgctaa gaaccatgta tactttaggt     480
attcttat                                                              488

<210> SEQ ID NO 91
<211> LENGTH: 709
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(709)
<223> OTHER INFORMATION: n = a, t, c or g

<400> SEQUENCE: 91
tagattgtct ctatttgagc agtaacatga ttgcaagaga ccaagtttca cagcttgtaa      60
agttctgtat ttgggattct tgcttatttt tccgcctgtg ttttttctgag aacttattcc     120 tgatgatcaa ttgaatccag tagtttttct atgctatttg ttgntgtata agctactgta     180
agaaacttat cataaggaaa aatagaaagg aaaacttgaa tcaatactca ttgattaaaa     240
tggaataaag aaagagcagc tgccactttt aaacaacata aggaatatc ttttttttgtc     300 tccgtgtagg aaatcccata agttcttata tttgttccag ttcccatttc ctgccattga     360
ccagataaca tcattgactt tcaaatgact tttagaagtg ataactctta atttcctaat     420
agatactaga ttgtattgaa ttctgttttta attattctct aggtaagtat gttttaggat     480 taaataccttt ttacagatac tgaaagtgcc tccttttgtg gtgtaaaaaa caaattatgg     540
tgcaaaaagt aatcactaga ttgaaataca tgaaggtttt ttgcttttttg acatacgaaa     600 atgtcaagag aaaggccaaa gatttgtact tttttcactta caaagcactc cttttttccct     660 taaacttctt tctgcaaatt agatttaatg agagagtact attttttaan                 709

<210> SEQ ID NO 92
<211> LENGTH: 305
<212> TYPE: DNA
<213> ORGANISM: Homo sapiens
<220> FEATURE:
<223> OTHER INFORMATION: zinc carboyxpeptidases
<220> FEATURE:
<221> NAME/KEY: misc_feature
<222> LOCATION: (1)..(305)
<223> OTHER INFORMATION: n = a, t, c or g

<400> SEQUENCE: 92
aggncccntt taagcaaacc gggagcagca tcgactgggc gtatgacaac ggcatcaaat      60
ttgcattcac atttgagttg agagataccg ggacctatgg cttcctcctg ccanctnacc     120
acatcatccc cactgcagan gatacgtggc tggggctgaa gaccatcntg gagcangtgc     180
```

```
gggacaacct ctactaggcg atggctctgc tctgtctaca gttatttgta cccncacntg      240
cacncactga ggccatagtt aaaggagcnc tttcctacct gtgtgagtca nanccctctg      300 ggttn                                                                  305

<210> SEQ ID NO 93
<211> LENGTH: 673
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(673)
<223> OTHER INFORMATION: n = a, t, c or g

<400> SEQUENCE: 93
ccgggacccc cgggccggat actgttcatt ggggcccctta ttgggtccag catctgtggc      60
caagaaaaat ttttggggga ccaagttttt aggattaatg tcagaaatgg agacgagatc     120
agcaaattga gtcaactagt gaattcaaac aacttgaagc tcaatttctg gaaatctccc     180
tcctccttca atcggcctgt ggatgtcctg gtcccatctg tcagtctgca ggcatttaaa     240
tccttcctga gatcccaggg cttagagtac gcagtgacaa ttgaggacct gcaggccctt     300
ttagacaatg aagatgatga aatgcaacac aatgaaggc aagaacggag cagtaataac      360
ttcaactacg gggcttacca ttccctggaa gctatttacc acgagatgga caacattgcc     420
gcagactttc ctgacctggc gaggagggtg aagattggac attcgtttga aaaccggccg     480
atgtatgtac tgaagttcag cactgggaaa aggccgtgag gcggccggcc gtttgggctg     540
aaatgcaagc atcccattcc ccgaagagtn ggatctccca gggccactgc catcntggac     600
ggcaaaggaa gattggtntc ttgattacca gaagggatcc annctatcnc ctcccatctt     660
gggaaaaaat ggn                                                         673

<210> SEQ ID NO 94
<211> LENGTH: 1811
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(1811)
<223> OTHER INFORMATION: n = a, t, c or g

<400> SEQUENCE: 94
gaccncgcgt ccgcaatgac agtcggacct ggtggggaag ttggaaccac agcagtggga      60
tggacgcagt atttcctgcc aattcagacc cagaaactcc agtgctgaac ctcctgccgg     120
agccccaggt ggcccgcttc attcgcctgc tgccccagac ctggctccag ggaggcgcgc     180
cttgcctncg ggcagagatc ctggcctgcc cagtctcaga ccccaatgac ctattccttg     240
aggcccctgc gtcgggatcc tctgaccctc tagactttca gcatcacaat tacaaggcgt     300
ccgggaagct gatgaagcag gtacaagagc aatgccccaa catcacccgc atctacagca     360
ttgggaagag ctaccaggc ctgaagctgt atgtgatgga aatgtcggac aagcctgggg      420
agcatgagct gggggagcct gaggtgcgct acgtggctgg catgcatggg aacgaggccc     480
tggggcggga gttgcttctg ctcctgatgc agttcctgtg ccatgagttc ctgcgaggga     540
acccacgggt gacccggctg ctctctgaga tgcgcattca cctgctgccc tccatgaacc     600
```

-continued

```
ctgatggcta tgagatcgcc taccaccggg gttcagagct ggtgggctgg gccgagggcc    660
gctggaacaa ccagagcatc gatcttaacc ataattttgc tgacctcaac acaccactgt    720
gggaagcaca ggacgatggg aaggtgcccc acatcgtccc caaccatcac ctgccattgc    780
ccacttacta caccctgccc aatgccaccg tgactattta gtgggcggca gccgaactct    840
gtgggcggcc aaccttgtct cttgctcccg cccttcctga cccccaccac cccggtggct    900
cctgaaacgc gggcagtaat caagtggatg aagcggatcc cctttgtgct aagtgccaac    960
ctccacgggg gtgagctcgt ggtgtcctac ccattcgaca tgactcgcac cccgtgggct   1020
gcccgcgagc tcacgcccac accagatgat gctgtgtttc gctggctcag cactgtctat   1080
gctggcagta atctggccat gcaggacacc agccgccgac cctgcaacag ccaggacttc   1140
tccgttgaac ggcaacatca tcaaacgggg ctgactggca cacggtcccc ggggcatga    1200 atgacttcgg ctacctacac accaactgct ttgaggtcac tgtggagctt gtcctgtgac   1260
aagttccctt cacgagaatg aatttgcccc aggagtggga gaacaacaaa gacgccctcc   1320
tcacctacct ggagcaggtg cgcatgggca ttgcaggagt ggtgagggac aaggacacgg   1380
agcttgggat tgctgacgct gtcattgccg tggatgggat taaccatgac gtgaccacgg   1440
cgtggggcgg ggattattgg cgtctgctga ccccagggga ctacatgtg actgccagtg    1500 ccgagggcta ccattcagtg acacggaact gtcgggtcac ctttgaagag ggccccttcc   1560
cctgcaattt cgtgctcacc aagactccca acagagctg cgcgagctgc tggcagctgg    1620
ggccaaggtg cccccggacc ttcgcaggcg cctggagcgg ctaaggggac agaaggattg   1680
atactgcggt ttaagagccc tagggcaggc tggacctgtc aagacgggaa ggggaagagt   1740
agagagggag ggacaaagtg aggaaaaggt gctcattaaa gctaccgggc accttaaaaa   1800
aaaaaaaaaa n                                                       1811
```

<210> SEQ ID NO 95
<211> LENGTH: 65
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(65)
<223> OTHER INFORMATION: n = a, t, c or g

<400> SEQUENCE: 95

```
gaaaagggcg ccgngaggtg tccagtgcgg naangcgagc gatnccggag aaccggnggg    60 agncn                                                                65
```

<210> SEQ ID NO 96
<211> LENGTH: 537
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(537)
<223> OTHER INFORMATION: n = a, t, c or g

<400> SEQUENCE: 96

```
ncgcgtccgg gaagcacgtc cagcctgcca gctatgagca aagtccggcg gctacactat    60 gagggctaa ttttttaggtt caagttcctc atgcttatca ccttggcctg cgctgccatg   120
actgtcatct tcttcatcgt tagtcagcta ggatgcgtga cagcctagcc tcccctcctt    180
```

```
aatcacatac agaagagttc tctgtgttat gacagcaggt aacggaaggc cattggaaat      240
ggggcggcgt cacagtccaa gtgaacagtg ccttttttcac aggcatctat gggatgtgga     300
atctgtatgt ctttgctctg atgttcttgt atgcaccatc ccataaaaac tatggagaag     360
accagtccaa tggcgatctg ggtgtccata gtggggaaga actccagctc accaccacta     420
tcacccatgt ggacggaccc actgagatct acaagttgac ccgcaaggag gcccaggagt     480
aggaggctgc agcgcccggc tgggacggtc tctccatacc ccagcccctc taactag        537
```

```
<210> SEQ ID NO 97
<211> LENGTH: 179
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(179)
<223> OTHER INFORMATION: n = a, t, c or g

<400> SEQUENCE: 97
gtccgcntgc cgccganggt cccacgcggn aacgctggga ggangcaggc agggtagcaa      60
agcggcggcg ggcgcggcag ctctgtggca cctgtagggg tttactntnc nggccactta    120
agggacaact tttgtccaag caaggccaac tgcattttat tacacgccca ctgcgtgca     179
```

```
<210> SEQ ID NO 98
<211> LENGTH: 514
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(514)
<223> OTHER INFORMATION: n = a, t, c or g

<400> SEQUENCE: 98
gatcgacccc cgtccggtga tttaatcgct atagctaaaa tacgtcaaat atacgttgtc      60
atgtgcttga acatgatgct aaccctgaca ggatgaagga aagtaatatt ctttcagtgt    120
agttcaggag agcatttgtt ttcttttcta ccaattaacc catcattgct tttaaacaac    180
catctgaagg agcaganagg cagggtagaa gacagaaggg ggatctatgt ggtaactaaa    240
gaatgtttct gttttgttaa ttattgtgtg tgtgtggttt tattgtttgc ttaacagaat    300
caaaaactga aaaaaatgag aatacccggg aaatgngcgt ctctgtttat gacttcttgc    360
tgatgttcta cacctgtgtt aaatgctcta ctgtctttgt ttcaacagac atttgttcac    420
tgcccagctc gttttgtgtc ctgagcccta tgcccagccc accttataaa tcatgcctgt    480
ttagatgttt gattttgttc tgtttgctat tgtt                                514
```

```
<210> SEQ ID NO 99
<211> LENGTH: 616
<212> TYPE: DNA
<213> ORGANISM: Homo sapiens
<220> FEATURE:
<223> OTHER INFORMATION: trypsin-like serine  proteases

<400> SEQUENCE: 99
tttttacccc tgggGattta ttaatcatgc ggtttaattc caattaaatg gactccttgg      60
gagaaaagga ttggattgat ggggggggttc ccaatttaat ccatggtacg gcgaattaaa    120
```

-continued

| | |
|---|---|
| gggcattcct aaatggtggt tattcagtta aaattaattg cacctttgt ggtaacacat | 180 |
| gggaactcct ggttttcaca gttttttcccc caacttatca cagccccgac aatagttcca | 240 |
| tttgtggcat ccatacagac taaggggggcc tcagagtctc ccttacaggc atcgatggga | 300 |
| ccatcatatg tacccgcgca ttccattttc ttttcataga aacggatttc gtaaaactta | 360 |
| gagcagttgc ttattagttt tacttcaccc cactgcaagt gaaagactct ttcgctatct | 420 |
| atttctcgtc cccagccaga aacgatgcat gtatcatagg gttggatagg gtatggagac | 480 |
| aatgggacac aggcggggat ggaacgaggc aagtcacaat ctctttttgg tgtccggctt | 540 |
| ttttttccatt tcattcaagg cggatgtcca tttgggggaag tggcctgcca tgttggtttt | 600 |
| cttggaaaat aaatct | 616 |

<210> SEQ ID NO 100
<211> LENGTH: 220
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(220)
<223> OTHER INFORMATION: n = a, t, c or g

<400> SEQUENCE: 100

| | |
|---|---|
| gcttcaactg gctcctctcc tgtttctccc ttgtgggggc cgcctttggc tgcggggtcc | 60 |
| ccgccatcca ccctgtgctc agcggcctgt ccangatcgt gaatggggag gacgccgtcc | 120 |
| ccggctcctg gccctggcac gtgtccctgc aggacaaaac cggctcccac ttctgcgggg | 180 |
| gctccctcat cagcgatgac tgggtggtca ccgctgccca | 220 |

<210> SEQ ID NO 101
<211> LENGTH: 1856
<212> TYPE: DNA
<213> ORGANISM: Homo sapiens
<220> FEATURE:
<223> OTHER INFORMATION: trypsin-like serine proteases

<400> SEQUENCE: 101

| | |
|---|---|
| cgtccggttc tagatcgcga gcggccgccc tttttttttt tttttttga aataaaacta | 60 |
| taatataaat tctcctatta aataaaatta ttttaagttt tagtgtcaaa agtgagatgc | 120 |
| tgagagtagg tgataatgta tattttacag agtgggggtt ggcaggatgg tgacattgaa | 180 |
| catgattgct ctctgtctct ttttcagct tatgggtatt tatcttctat tagtatttgt | 240 |
| atcttcagtt cattccactt taggaaacag agctgccaat tgaaacagaa gaagaaaaaa | 300 |
| aaaaaagcag cagacaacac actgtagagt cttgcacaca cacaagtgcc caggcaaggt | 360 |
| gcttggcaga accgcagagt gggaagagag tactggcatc gggtttcctt gggatcaatt | 420 |
| tcattaccgt gtacctttcc cattgtggtc atgccatttg gcagggggag aatgggaggc | 480 |
| ttggccttct ttgtgaggca gtgtgagcag aagaagctga tgccagcatg tcactggttt | 540 |
| tgaagggatg agcccagact tgatgttttg ggattgtcct tattttaacc tcaaggtctc | 600 |
| gcatggtggg gccctgacc aacctacaca agttccctcc cacaagttgg acatcaagtg | 660 |
| tcttctctgt gaggcatcct ggccattccc actcccctgg tgttggtcca gcctctcctc | 720 |
| cacacaaaga aagaacttgg gtgaaggctg agtgtgaggc acctgaagtt tccctgcgga | 780 |
| gtcgataaat tagcagaacc acatcccccat ctgttaggcc ttggtgagga ggccctgggc | 840 |
| aaagaagggt ctttcgcaaa gcgatgtcag agggcggttt tgagctttct ataagctata | 900 |

```
gctttgttta tttcacccgt tcacttactg tataatttaa aatcatttat gtagctgaga      960
cacttctgta tttcaatcat atcatgaaca tttttattttg ctaaatcttg tgtcatgtgt    1020
aggctgtaat atgtgtacat tgtgtttaaa agaaaaatga aacccacatg ccgccatttt    1080
cctgaatcaa attctgcagt ggaatggaga ggaaaatact tctaggcaag cagctagact    1140
ggtgaattgg gggaaataga aggaactagt aactgagact cctccagcct cctccctatt    1200
ggaatcccaa tggctcctgg agtaggaaaa agtttaaac tacattcatg ttcttgttct    1260
gtgtcacttg gccctgggta gtctaccatt tacttcaccc caagtcctgc tgcccatcca    1320
gttgggaagc catgattttc ctaagaatcc agggccatgg gagatacaat tccaagttct    1380
cgcttcctcc tttgggcatc tcttctgcct cccaatcaag gaagctccac gctcaggctc    1440
tcagctctcg ggccagtgct ctgctctgtc cagggtaggt aatactggga gactcctgtc    1500
ttttacccct cccctcgttcc agacctgcct catggtggca acatggttct tgaacaatta   1560
aagaaacaaa tgacttttg gaatagccct gtctagggca aactgtggcc cccaggagac     1620
actacccttc catgccccag acctctgtct tgcatgtgac aattgacaat ctggactacc    1680
ccaagatggc acccaaagtg ttttggcttc tggctaccta aggttaacat gtcactagag    1740 tattttttatg aagagacaaa cattataaaa atctgatggc aaaagcaaaa caaaatggaa   1800
agtaggggag gtggatgtga caacaacttc caaattggct ctttggaggc gagggg        1856
```

<210> SEQ ID NO 102
<211> LENGTH: 161
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(161)
<223> OTHER INFORMATION: n = a, t, c or g

<400> SEQUENCE: 102

```
tcctgattct cccttgtngg ggccncctat ggctgcgggg tccccgccat ccaccctgtg      60
ctcaacggtc tgtccaagat cgtgantngg gaggacnccg tccccngctc ctgnccctgt    120
cnggtgtccc tgcatganaa naccggnttc cacttctgcg g                        161
```

<210> SEQ ID NO 103
<211> LENGTH: 371
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(371)
<223> OTHER INFORMATION: n = a, t, c or g

<400> SEQUENCE: 103

```
gaaaagctat cttctcngcc tcaatctttnt aggactgcat gcaagatgga agcacgcaca     60
gcacggttcc tctctccnct gcattgtttc actgggctca cctgcttctg aaaacggctc    120
cctgtcttgg gctctaatga ggatctgggg ttgggagagg ctgttggtct gagggcagta    180
atcacangct gcaggctaga gggggcagtt atgactgcct gaaagtgggt gagggattgc    240
acttcagaaa aacatctaaa aaacttagtc tatgtttgaa ttccccacct ccatcccatc    300
tatgggaaga ccgttcagtg tttanagaat ggggagatgg gtccctgcac ttggcctctc    360
```
cataagcctt g                                                                      371

<210> SEQ ID NO 104
<211> LENGTH: 2886
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(2886)
<223> OTHER INFORMATION: n = a, t, c or g

<400> SEQUENCE: 104

| | | | | | |
|---|---|---|---|---|---|
| gctggcgaag | ctgaaacccg | agctcccgct | cagctggggc | tcggggaggt | ccctgtaaaa | 60 |
| cccgcctgcc | cccggcctcc | ctgggtccct | cctctccctc | cccagtagac | gctcgggcac | 120 |
| cagccgcggc | aaggatggag | ctgggttgct | ggacgcacgt | tggggctcac | ttttcttcag | 180 |
| ctccttctca | tctcgtcctt | gccaagagag | tacacagtca | ttaatgaagc | ctgccctgga | 240 |
| gcagagtgga | atatcatgtg | tcgggagtgc | tgtgaatatg | atcagattga | gtgccgtctg | 300 |
| ccccggaaag | agggaagtcg | tgggttatac | catcccttgc | tgcaggaatg | aggagaatga | 360 |
| gtgtgactcc | tgcctgatcc | acccaggttg | taccatcttt | gaaaactgca | agagctgccg | 420 |
| aaatggctca | tggggggggt | taccttggat | gactttctat | gttgaagggg | ttctacttgt | 480 |
| gcagagtgcc | gagcaggctg | gtacggaang | gagactgcat | gccgatgttg | gccaggttct | 540 |
| gccgaacccc | aaagggtcag | atttttgtttg | gaaagctatc | cccttaaatg | ctcacttgtg | 600 |
| aatggaccat | tcatgctaaa | cctgggtttg | tcatccaact | aagatttgtc | atgttgagcc | 660 |
| tggagtttga | ctacatgtgc | cagtatgact | atgttgaggt | tcgtgatgga | gacaacccgc | 720 |
| gatggccaga | tcatcaagcg | tgtctgtggc | aacgagcggc | cagctcctat | ccagagcata | 780 |
| ggatcctcca | ctcccacgtc | cctcttccac | tccggatggc | tccaagaatt | ttgacggttt | 840 |
| ccatgccatt | tatgaggaga | tcacagcatg | ctcctcatcc | ccttgtttcc | atgacggcac | 900 |
| gtgcgtcctt | gacaaggctg | gatcttacaa | gtgtgcctgc | ttggcaggct | atactgggc | 960 |
| agcgctgtga | aaatctcctt | gaagaaagaa | actgctcaga | ccctgggggc | ccagtcaatg | 1020 |
| ggtaccagaa | aataacaggg | ggccctgggc | ttatcaacgg | acgccatgct | aaaattggca | 1080 |
| ccgtggtgtc | tttcttttgt | aacaactcct | atgttcttag | tggcaatgag | aaaagaactt | 1140 |
| gccagcagaa | tggagagtgg | tcagggaaac | agcccatctg | cataaaagcc | tgccgagaac | 1200 |
| caaagatttc | agacctggtg | agaaggagag | ttcttccgat | gcaggttcag | tcaagggaga | 1260 |
| cacccaattc | accagctata | tcagcgcgcc | ttcagcaagc | agaaacttgc | aagagtgccc | 1320 |
| ctaccaagaa | gccagcccct | ccctttggag | atcttgccca | tgggatacca | acatcttgca | 1380 |
| tacccagctc | cagtatgagt | gcatctcacc | cttctaccgc | cgcctgggca | gcagcacgga | 1440 |
| ggacatgttt | gaggactggg | aagtggagtg | ggcggggcac | catcctgcat | ccctatctgc | 1500 |
| gggaaaattg | agaacatcac | tgctccaaag | acccaagggt | tgcgctggcc | gtggcaggca | 1560 |
| gccatctaca | ggaggaccag | cggggtgcat | gacggcagcc | tacacaaggg | agcgtggttc | 1620 |
| ctagtctgca | gccggtgccc | tgtgaatga | gcgcacttgt | ggtggtggct | gcccactgtg | 1680 |
| ttactgacct | ggggaaggtc | accatgatca | agacagcaga | cctgaaagtt | gttttgggga | 1740 |
| aattctaccg | ggatgatgac | cggggatgag | aagaccatcc | agagcctaca | gatttctgct | 1800 |
| atcattctgc | atcccaacta | tgaccccatc | ctgcttgatg | ctgacatcgc | catcctgaag | 1860 |
| ctcctagaca | aggcccgtat | cagcacccga | gtccagccca | tctgcctcgc | tgccagtcgg | 1920 |

```
gatctcagca cttccttcca ggagtcccac atcgactgtg gctggctgga atgtcctggc    1980
agacgtgagg agccctggct tcaagaacga cacactgcgc tctggggtgg tcagtgtggt    2040
ggactcgctg ctgtgtgagg aagcaacatg agggaccatg catcccagt ggagtgtcac     2100 tgataacatg ttctgtgcca gctgggaacc cactgcccct tctgtatatct gcactgcaga   2160 gacaggaggc atcgcggctg tgtcctttcc gggacgagca tctcctgagc cacgctggca   2220
tttgatggga actggtcaag ctggagctta tgataaaaca tgcagccaca ggctctccac   2280
tgccttcacc aaggtgctgc cttttaaaag actggattga aagaaatatg aaatgaacca   2340
tgctcatgca ctccttgaga aagtgtttct gtatatccgt ctgtacgtgt gtcattgcgt   2400
gaagcagtgt gggcctgaag tgtgatttgg cctgtgaact tggctgtgcc agggcttctg   2460
acttcaggga caaaactcag tgaagggtga gtagacctcc attgctggta ggctgatgcc   2520
acgtccacta ctaggacagc caattggaag atgccaggc ttgcaagaag taagtttcgt    2580
tcaaagaaga ccatatacaa aacctctcca ctccactgac ctggtggtct tccccaactt   2640
tcagttatac gaatgccatc agcttgacca gggaagatct gggcttcatg aggccccttt   2700
tgaggctctc aagttctaga gacgctgcct gtgggacagc ccagggcagc agagctggga   2760
attgtggtgc atgcctttgt gtacatggcc acagtacaag tctggtcctt ttccttcccc   2820
atctcttgta cacattttaa taaataaag ggttggcttc tgactacaaa aaaaaaaaa    2880 aaaagg                                                              2886

<210> SEQ ID NO 105
<211> LENGTH: 407
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(407)
<223> OTHER INFORMATION: n = a, t, c or g

<400> SEQUENCE: 105
cccgcgtccg tttttttttt tttttttttt tcaagggttc tgcatctcgt ttattacgca      60
cagaaataac aggtttagag tatattacaa aaagagctca aactgttcag atacagcaac    120
tgggcttact aggggacaga agggaaata cgtcagacta ctgtacaggg acacaaagac     180
tcngtcatcc taaacaaagt attaaggtac atagacaagt ttnttgtaag acagaaaaca   240
gagaaatcca cagtaactnt aacacatccc ttaaggaata agcatgtatt tgtaggaagc   300
aaacaaagct ttccatagag aaaccacttt cacaggatga ttaggtggac ctgcaatgaa   360
gaaaatacat ttcaaaagat gggttcagac attacaccaa gttttca                  407

<210> SEQ ID NO 106
<211> LENGTH: 549
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(549)
<223> OTHER INFORMATION: n = a, t, c or g

<400> SEQUENCE: 106
aacccacgcg tccgnttgct gggtgggaag atgtgtgtgg cagccgggag gcacacgggc      60
```

| | |
|---|---|
| tggatgtgcc ggccgaaagg cagagggctg gtcagctcct gcacagccac gtcaaagtcg | 120 |
| gccgtgtccg cgttgtacag ggggtgcttg acgatctgga ccacctgggc ccgcacggtg | 180 |
| ctggcctccg agccgctgag gtaggtcgca cccacgtagg ccacccactt cgtcgggtct | 240 |
| tggaacctgc aggagcaaac cccagctcag aagccaccga gggtcagagc cgtcggggga | 300 |
| ggcagacggg acactcgcct tgggtgcaaa atgtaagggg tatcccccca cattaatatt | 360 |
| tatgaatagt atttataaaa atcaggccag acacagtggc tcatgcctgt aatcccacac | 420 |
| ttttggaggc tgaagcggna ggatcacctg agcccaggag ttaagaacga tcctgggcaa | 480 |
| catagcgaaa cacagtcttt aaaaacaaca acaaaaaaca ggccaggtgc ggtggctcat | 540 |
| gcctgtaat | 549 |

<210> SEQ ID NO 107
<211> LENGTH: 796
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(796)
<223> OTHER INFORMATION: n = a, t, c or g

<400> SEQUENCE: 107

| | |
|---|---|
| ggagtcgacc acgcgtccgg tgcaaagagg acagcacatg catctcactg cccaaggtct | 60 |
| gtgatgggca gcctgattgt ctcaacggca gcgacgaaga gcagtgccag gaagggggtgc | 120 |
| catgtgggac attcaccttc cagtgtgagg accggagctg cgtgaagaag cccaacccgc | 180 |
| agtgtgatgg gcggcccgac tgcagggacg gctcggatga ggagcactgt gactgtggcc | 240 |
| tccagggccc ctccagccgc attgttggtg gagctgtgtc ctccgagggt gagtggccat | 300 |
| ggcaggccag cctccaggtt cggggtcgac acatctgtgg gggggccctc atcgctgacc | 360 |
| gctgggtgat aacagctgcc cactgcttcc aggaggacag catggcctcc acggtgctgt | 420 |
| ggaccgtgtt cctgggcaag gtgtggcaga actcgcgctg gcctggagag gtgtccttca | 480 |
| aggtgagccg cctgctcctg cacccgtacc acgaagagga cagccatgac tacgacgtgg | 540 |
| cgctgctgca gctcgaccac ccggtggtgc gctcggccgc cgtgcgcccc gtctgcctgc | 600 |
| ccgcgcgctc ccacttcttc gagcccggcc tgcactgctg gattacgggc tggggcgcct | 660 |
| tgcgcgaggg cggcccccatc agcaacgctc tgcagaaagt ggatgtgcan ttgatcccac | 720 |
| aggacctgtg cagcgaggtc tatcgctacc aggtgacgcc acgcatgctt gtgtgccggc | 780 |
| taccgcaagg gcaagn | 796 |

<210> SEQ ID NO 108
<211> LENGTH: 1828
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(1828)
<223> OTHER INFORMATION: n = a, t, c or g

<400> SEQUENCE: 108

| | |
|---|---|
| gacgcgtggg tcaacatcca aaactacaac cacgatatag ctctggtgca gctgcaggag | 60 |
| cctgtgcccc tgggacccca cgttatgcct gtctgcctgc caaggcttga gcctgaaggc | 120 |
| ccggcccccc acatgctggg cctggtggcc ggctggggca tctccaatcc caatgtgaca | 180 |

-continued

```
gtggatgaga tcatcagcag tggcacacgg accttgtcag atgtcctgca gtatgtcaag      240
ttacccgtgg tgcctcacgc tgagtgcaaa actagctatg agtcccgctc gggcaattac      300
agcgtcacgg agaacatgtt ctgtgctggc tactacgagg gcggcaaaga cacgtgcctt      360
ggagatagcg gtgggccctt tgtcatcttt gatgacttga gccagcgctg ggtggtgcaa      420
ggcctggtgt cctggggggg acctgaagaa tgcggcagca agcaggtcta tggagtctac      480
acaaaggtct ccaattacgt ggactgggtg tgggagcaga tgggcttacc acaaagtgtt      540
gtggagcccc aggtggaacg tgagctgac  ttacttcctc ggggcctgcc tcccctgagc      600
gaagctacac cgcacttccg acagcacact ccacattact tatcagacca tatggaatgg      660
aacacactga cctagcggtg gcttctccta ccgagacagc ccccaggacc ctgaaaggca      720
gagtgtggta tagggaaaag gctccaggca ggagacctgt gttcctgagc ttgtccaagt      780
ctctttccct gtctgggcct cactctaccg agtaatacaa tgcaggagct caaccaaggc      840
ctctgtgcca atcccagcac tccttttccag gccatgcttc ttaccccagt ggcctttatt      900
cactcctgac cacttatcaa acccatcggg tcctactgtt ggtataactg agcttggacc      960
tgactattag aaaatggttt ctaacattga actgaatgct gcatctgtat attttcctgc     1020
tctgccttct gggactagcc ttggcctaat ccttcctcta ggagaagagc attcaggttt     1080
tgggagatgg ctcatagcca agccctctc  tcttagtgtg atcccttgga gcaccttcat     1140
gcctggggtt tctctcccaa aagcttcttg cagtctaagc cttatccctt atgttcccca     1200
ttaaaggaat ttcaaaagac atggagaaag ttgggaaggt ttgtgctgac tgctgggagc     1260
agaatagccg tgggaggccc accaagccct taaattccca ttgtcaactc agaacacatt     1320
tgggcccata tgccaccctg aacaccagc  tgacaccatg ggccgtccac acctgctgct     1380
ccagacaagc acaaagcaat ctttcagcct tgaaatgtat tatctgaaag gctacctgaa     1440
gcccaggcct gaatatgggg acttagtcga ttacctggaa aaagaaaaga cccacactgt     1500
gtcctgctgt gcttttgggc aggaaaatgg aagaaagagt ggggtgggca cattagaagt     1560
cacccaaatc ctgccaggct gcctggcatc cctggggcat gagctgggcg agaatccac      1620 cccgcaggat gttcagaggg acccactcct tcattttttca gagtcaaagg aatcagaggc     1680
tcacccatgg caggcagtga aaagagccag gagtcctggg ttctagtccc tgctctgccc     1740
ccaactggct gtataacctt tgaaaaatca ttttctttgt ctgagtctct ggttctccgt     1800
cagcaacagg ctggcataag gtcccctn                                         1828
```

<210> SEQ ID NO 109
<211> LENGTH: 488
<212> TYPE: DNA
<213> ORGANISM: Homo sapiens
<220> FEATURE:
<223> OTHER INFORMATION: trypsin-like serine proteases

<400> SEQUENCE: 109

```
ccgtccgggc tcgggttgag gggctgggga cgtcctctgc tgactgtggc caccgccctg       60
atgctgcccg tgaagccccc cggctcctgg ggggcccaga tcatcggggg ccacgaggtg      120 acccccccact ccaggcccta catggcatcc gtgcgcttcg ggggccaaca tcactgcgga      180
ggcttcctgc tgcgagcccg ctgggtggtc tcggccgccc actgcttcag ccacagagac      240
ctccgcactg gctggtggt  gctgggcgcc acgtcctga gtactgcgga gcccaccag       300 caggtgtttg gcatcgatgc tctcaccacg cacccccgact accacccccat gacccacgcc      360
```

| | |
|---|---|
| aacgacatct gcctgctgcg gctgaacggc tctgctgtcc tgggccctgc agtgggctg | 420 |
| ctgaggctgc cagggagaag ggccaggccc cccacagcgg ggacacggtg ccgggtggct | 480 |
| ggctgggc | 488 |

<210> SEQ ID NO 110
<211> LENGTH: 1872
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(1872)
<223> OTHER INFORMATION: n = a, t, c or g

<400> SEQUENCE: 110

| | |
|---|---|
| tggatcgccc ccgcgtccgg catgatttaa gattaaattc atgtattgaa aatattgttc | 60 |
| agaccccatg tgacataact ggagccagtg cagtgccatg aagaactacg agattagcct | 120 |
| ggatattaac ttgtcttcta gagaatagat ttcatgttcc attcttctgc aatggttaat | 180 |
| tcacacagaa aaccaatgtt taacattcac agaggatttt actgcttaac agccatcttg | 240 |
| ccccaaatat gcatttgttc tcagttctca gtgccatcta gttatcactt cactgaggat | 300 |
| cctggggctt tcccagtagc cactaatggg gaacgatttc cttggcagga gctaaggctc | 360 |
| cccagtgtgg tcattcctct ccattatgac ctctttgtcc accccaatct cacctctctg | 420 |
| gactttgttg catctgagaa gatccgaagt cttggtcagc aatgctaccc agtttatcat | 480 |
| cttgcacagc aaagatcttg aaatcacgaa tgccacccct tcagtcagag gaagattcaa | 540 |
| gatacatgaa accaggaaaa gaactgaaag ttttgagtta ccctgctcat gaacaaattg | 600 |
| cactgctggt tccagagaaa cttacgcctc acctgaaata ctatgtggct atggacttcc | 660 |
| aagccaagtt aggtgatggc tttgaagggt tttataaaag cacatacaga actcttggtg | 720 |
| gtgaaacaag aattcttgca gtaacagatt ttgagccaac ccaggcacgc atggctttcc | 780 |
| cttgctttga tgaaccgttg ttcaaagcca acttttcaat caagatacga agagagagca | 840 |
| ggcatattgc actatccaac atgccaaagg ttaagacaat tgaacttgaa ggaggtcttt | 900 |
| tggaagatca ctttgaaact actgtaaaaa tgagtacata ccttgtagcc tacatagttt | 960 |
| gtgatttcca ctctctgagt ggcttcactt catcaggggt caaggtgtcc atctatgcat | 1020 |
| ccccagacaa acggaatcaa acacattatg cttgcaggc atcactgaag ctacttgatt | 1080 |
| tttatgaaaa gtactttgat atctactatc cactctccaa actggattta attgctattc | 1140 |
| ctgactttgc acctggagcc atggaaaatt ggggcctcat tacatatagg gagacgtcac | 1200 |
| tgcttttga ccccaagacc tcttctgctt ccgataaact gtgggtcacc agagtcatag | 1260 |
| cccatgaact ggcgcaccag tggtttggca acctggtcac aatggaatgg tggaatgata | 1320 |
| tttggcttaa ggagggtttt gcaaaataca tggaacttat cgctgttaat gctacatatc | 1380 |
| cagagctgca atttgatgac tatttttga atgtgtgttt tgaagtaatt acaaaagatt | 1440 |
| cattgaattc atcccgccct atctccaaac cagcggaaac cccgactcaa atacaggaaa | 1500 |
| tgtttgatga agtttcctat aacaagggag cttgtatttt gaatatgctc aaggattttc | 1560 |
| tgggtgagga gaaattccag aaaggaataa ttcagtactt aaagaagttc agctatagaa | 1620 |
| atgctaagaa tgatgacttg tggagcagtc tgtcaaatag ttgtttagaa agtgattta | 1680 |
| catctggtgg agtttgtcat tcggatccca agatgacaag taacatgctc gcctttctgg | 1740 |
| gggaaaatgc agaggtcaaa gagatgatga ctacatggac tctccagaaa ggaatccccc | 1800 |

```
tgctggtggt taaacaagac gggtgttcac tccgactgca acaggagcgc ttnctncagg   1860
gggttttcca gn                                                      1872
```

<210> SEQ ID NO 111
<211> LENGTH: 606
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(606)
<223> OTHER INFORMATION: n = a, t, c or g

<400> SEQUENCE: 111

```
cgtccggggc agtgcaggaa cacctccttc tttgaaactg aaggctgtgg gaagaagtgc     60
aatggccatg gggtctgtaa caacaaccag aactgccact gcctgccggg ctgggccccg    120
cccttctgca acacaccggg ccacggggggc agtatcgaca gtgggcctat gcccctgag    180 agtgtgggtc ctgtggtagc tggagtgttg gtggccatct tggtgctggc ggtcctcatg    240
ctgatgtact actgctgcag acagaacaac aaactaggcc aactcaagcc ctcagctctc    300
ccttccaagc tgaggcaaca gttcagttgt cccttcaggg tttctcagaa cagcgggact    360
ggtcatgcca acccaacttt caagctgcag acgccccagg gcaagcgaaa ggtgatcaac    420
actccggaaa tcctgcggaa gccctcccag cttctncccg gcccctcag attatctgcg     480 tggtgggtcc cacctgcacc actgccagct nacctgacag ggctgctagg aacttcccan    540
ggccgggtct caaatagaga ngacgggtcg tccaagaagc ctctcaagcc ggcaattncc    600
cccccc                                                              606
```

<210> SEQ ID NO 112
<211> LENGTH: 153
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(153)
<223> OTHER INFORMATION: n = a, t, c or g

<400> SEQUENCE: 112

```
ggagattttc ncatcatcct gaacccatct gcctccttcc catcctanaa agcagctgtg     60
acaacattca gggcttcatc gangagttcc ttnacatctt cagctccttg ctgcaggaga    120
agaggttcct ccgggactat gatgcactct tcc                                 153
```

<210> SEQ ID NO 113
<211> LENGTH: 512
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(512)
<223> OTHER INFORMATION: n = a, t, c or g

<400> SEQUENCE: 113

```
cgaaatccac atggtccgaa accttncctg caanttttc agggnatana tggaagatat      60
taaataccag gtatggganaa ccnttgttta tgatttccaa actcatcant ggtgtcacag    120
```

-continued

| | |
|---|---|
| aatttcttaa tactganggt gaactcnaag agctcaagaa cttcatgaaa aactatgatg | 180 |
| gggtagctgc tgcttctttc tcacganctg tggaaactgt cnaagccaat gtgcgctgga | 240 |
| aaatgcttta ccaagacgag cttttccaat ggttaggaaa agctctaaga cactaatata | 300 |
| tgtatcttat aaacaancna ttcanctcag aagtttatga agagcacgc tttttgtgga | 360 |
| atgagganta tgtnctacct anaaaanggc cagattttca gtgttaacnt gtgggaggaa | 420 |
| ttttttttnt agttcntanc ttttggtttt ggggdatatt ttttatttgt ttcattcatt | 480 |
| cctgttctgt ttctctactg ggtgttcctc tc | 512 |

<210> SEQ ID NO 114
<211> LENGTH: 789
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(789)
<223> OTHER INFORMATION: n = a, t, c or g

<400> SEQUENCE: 114

| | |
|---|---|
| aagggcaagg accgggtcta agatgttgac ccaggantga gccaacgtgt tctctggaag | 60 |
| aggaggagag gggctaagag gaggctggag acagtctctg cccttatcgg acctctagta | 120 |
| acggccgcca gtgtgctnta aagccaggag gtgggcaggg atgggccccc tcaggtcgat | 180 |
| gagctcgggc ccatagtggc ggtggagggc cctgcgcacg taggtgtgcg ggttcaggta | 240 |
| gagtggccgc agctcctgga atagccgctc caggtcttgc tccagggtat ccgactcata | 300 |
| cttggagtgc cacaaggccc ccatgtcttt gtaacctagg acaggagaga ggactcacca | 360 |
| ggagctcacc atctcaccct ttagccatgg cctagctgac aggatacccca gacgccttct | 420 |
| agggaagcca ctcaacctcg ctgaccgtct gggtcttctt tggcaaaacg gggagaatac | 480 |
| ctgcccattt cagaaaggca ctgagcaaag tccatgatcc gagctcccca ccatgcctgc | 540 |
| aaggcctgag tccctctta tcccacctca tccttagccc tgtggccacc tgggcttctt | 600 |
| tcaggtcttc cagagcaccg gctctcctgc cgcggagctc tgcctaggct gctcttttn | 660 |
| acatttgctt ccgtcttttg ccatctttca ggtcttggat aaatgtcaga gtcttccctg | 720 |
| tcattgttgc agcagctctt ctcatttctt tctcagaagc tcttctatcc gcananccag | 780 |
| atggtagtn | 789 |

<210> SEQ ID NO 115
<211> LENGTH: 617
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(617)
<223> OTHER INFORMATION: n = a, t, c or g

<400> SEQUENCE: 115

| | |
|---|---|
| ttaaattgcc aagtgatttt acttcaagat gacatcagaa ttgctaaaag gtgatgtaac | 60 |
| cgtcagagtg actattgatt ataactccca gtaagtgtca acgtgatttt ctccattgtg | 120 |
| tgggcttcca ttagtatttta ctcattaggt tcagtagttt tcattatttt ctcttccata | 180 |
| aattctattg cttgtgaaaa gccaccaaag agaagtgaaa ccagaaaaag gatgcaacga | 240 |
| gtaaatatta aagtagtgc tcagtttata ttcgcaagtg tgctggctgt aatacgatat | 300 |

```
tgtttgtcag gtggagggcc actatctata ctacctcctt ttcctctcag ttcacatgtt      360
ggtggttgcc acccatgcag acagtgacaa tgttttttgt tgttacatac tcctttgtaa      420
ttgcatgttt taagatcaca ctcaaaatgc aggtcttgat aagaagtaca attgtgttta      480
agacagtagc tccctgggcc acaggtttgc accatccact accagcccca tttctgggaa      540
gtctgtcccc tggtgttgct tcatagccaa agcatttttc ttcttttatg tcgtgtacta      600
atatattacg aaatgtn                                                     617

<210> SEQ ID NO 116
<211> LENGTH: 756
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(756)
<223> OTHER INFORMATION: n = a, t, c or g

<400> SEQUENCE: 116
acgcccgtct ggttttttt gtttgtttnn cngagggttt tctttgcatg agagttgtat       60
gtaaccagtg atatgattat tcctgaatgt acagacagaa gtaagcctgg acattgttaa     120
atagtccctg ctttaaggga ctacgataat gtgtactatg acaaacgtgc tttattcttc     180
taacgcagta agaattaggt ggaatttttt ccttcaacca agtgcaggaa agccctgtgt     240
gtcttggttt agttatggtt tcatttctag ccatacaatt gatgaattgt gtacaacttt     300
tgttagtacc aaaataatct gttatatgaa cagacttcta aaataacgtc tgtatatttt     360
atatatagat acatatatga aagaaggctt ttattgaaca gcttatcttc cacttgcagg     420
tttatggaaa cagcagtatt tgaaaataaa taaaaagttg ggagaattcc ttgctgttag     480
aaagaatgtg gccattattt tgatttttg aatgagatat ataatccaaa gtactgctga     540
acttgtgagt tgcagttatt cctaaacatt tcagctagga gaataccact tgatttaga     600 aaaccaaact gttttgtctct ggtttccttg aatttaaatg tttgggatta cctgttttaa     660
tctgtccttg gggantttaa aaataattct gtaatgtnng ttgcaatatn tcntgcnccc     720
ccccgaattt gggttccctg gttcccgaat tcccnn                               756

<210> SEQ ID NO 117
<211> LENGTH: 667
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(667)
<223> OTHER INFORMATION: n = a, t, c or g

<400> SEQUENCE: 117 ttaagggag ttttctggga aaaggaacct ttaatattgc ttaagacact gtagagtaag       60
taagaatagg ctaggaatcc tttgctgtga tagctaatgc ttgcaatcct gacatgaaat     120
gtccatgaag ttttatttaa acagtgagac atggcttcat attttctat taaaaattg      180 gatattaaaa atgaagtata aagtttagtc tccttctttt tcccatttct cttatccttc     240
ttcatcttct ttactttttg tgcgtttctt aaaaagcaca tgtaagcaaa ataataaaaa     300
agcaaccaaa ggaagaaggc acaatagtga caggtaacgc aactttccca tcacatttaa     360
```

```
tccttccatg ttgttcttag gaggtgggcc actatcagca ctacctccat agcctttgtc      420
cttgcagtat gggggtgcca ttcatggttg cagtgacagt gttgtttgtt gttgcagatt      480
cccctcatgt tgcaggtctt aggctgacag gcttgtgaca agatgaacca tactggcaca      540
cttcttacgg atgcagatct tttctggacc acatactggg ccatctttca cctcaccaat      600
atcaggtata gccatcccta aatgataatc agtgcccag caggtggcac ccttgatatg       660 agtgtgn                                                                667
```

<210> SEQ ID NO 118
<211> LENGTH: 127
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(127)
<223> OTHER INFORMATION: n = a, t, c or g

<400> SEQUENCE: 118

```
ggatcatttc agattggaga acaaggagtn gattgcctga acacctgaac atccgtttat      60
gggggccaga tagaatttgt tttcanatan gcttaacagg cntcattaaa atttcattct     120
gtgtgtt                                                              127
```

<210> SEQ ID NO 119
<211> LENGTH: 400
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(400)
<223> OTHER INFORMATION: n = a, t, c or g

<400> SEQUENCE: 119

```
ggtgttcacc tacagaaagg gctactgctt cgtgtactac ctgtcccagc tctgcggaga      60
cccacagcgc tttgatgact ttctccgagc ctatgtggag aagtacaagt tcaccagcgt     120 ggtgcccag gacctgctgg actccttcct gagcttcttc ccggagctga aggagcagag     180
cgtggactgc cgggcaggcc gccggctggc tgagccggac cttgttcagg gagtcagcct     240
gacccggccc gtggaggccc ttttccagct gtggaccgca gaacctctgg accacgcag     300 ctgcctcggc agcgccattg acatctccaa gtggaggacc ttccagacag cactcttcct     360
ggaccggctc ctggatgggt ccccgctgcc gcaggaggtn                            400
```

<210> SEQ ID NO 120
<211> LENGTH: 1366
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(1366)
<223> OTHER INFORMATION: n = a, t, c or g

<400> SEQUENCE: 120

```
cacgagcgcg tgtgggccga gccatgcctc ctgcccacgg ccaccagcaa gctgtcgggc      60
gcagtggagc agtggctgag tgcagctgag cggctgtatg ggccctacat gtggggcagg     120
tacgacattg tcttcctgcc accctccttc cccatcgtgg ccatggagaa cccctgcctc     180
```

```
accttcatca tctcctccat cctggagagc gatgagttcc tggtcatcga tgtcatccac    240
gaggtggccc acagttggtt cggcaacgct gtcaccaacg ccacgtggga agagatgtgg    300
ctgagcgagg gcctggccac ctatggaccn cgcgtccgca ccaccgagac ctacggtgct    360
gccttcacct gcctggagac tgccttccgc ctggacgccc tgcaccggcn gatgaagctn    420
ctgggagagg acagcccggt cagcaaactg caggtcaagc tggagccagg agtgaatccc    480
agccacctga tgaacctgtt cacctacgag aagggctact gcttcgtgta ctacctgtcc    540
cagctctgcg gagacccaca gcgctttgat gactttctcc gagcctatgt ggagaagtac    600
aagttcacca gccgtggtgg cccaggacct gctggactcc ttcctgagct tcttcccgga    660
gctgaaggag cagagcgtgg actgccgggc agggctggaa ttcgagcgct ggctcaatgc    720
cacaggcccg ccgctggctg agccggacct gtctcagggg atccagcctg accggcccg    780 tggaggccct tttccagctg tggaccgcag aacctctgga ccaggcagct gcctcggcca    840
gcgccattga catctccaag tggaggacct tccagacagc actcttcctg gaccggctcc    900
tggatgggtc cccgctgccg aaggaggtgg tgatgagcc gtccaagtgc tactcctccc    960
tgctggactc gatgaacgct gagatccgca tccgctggct gcagattgtg gtccgcaacg   1020
actactatcc tgacctccac agggtgcggc gcttcctgga gagccagatg tcacgcatgt   1080
acaccatccc gctgtacgag gacctctgca ccggtgccct caagtccttc gcgctggagg   1140
tcttctacca gacgcagggc cggctgcacc ccaacctgcg cagagccatc cagcagatcc   1200
tgtcccaggg cctggggttc cagcacagag cccggcctta ggagcccagc acgggagctt   1260
ggnaaagggt tgaaggcagg acacaggatt ngggacgcac agggccttgt tngttttggg   1320
ggacgagggn ccccagcagt tgccnttttt tttnagggg acgttn                   1366
```

<210> SEQ ID NO 121
<211> LENGTH: 606
<212> TYPE: DNA
<213> ORGANISM: Homo sapiens
<220> FEATURE:
<223> OTHER INFORMATION: neprilysin family of proteases
<220> FEATURE:
<221> NAME/KEY: misc_feature
<222> LOCATION: (1)..(606)
<223> OTHER INFORMATION: n = a, t, c or g

<400> SEQUENCE: 121

```
gtcggctacc cggacttcct gctgaaaccc gatgctgtgg acaaggagta tgagtttgag     60
gtccatgaga agacctactt caagaacatc ttgaacagca tccgcttcag catccagctc    120
tcagttaaga agattcggca ggaggtggac aagtccacgt ggctgctccc cccacaggcg    180
ctcaatgcct actatctacc caacaagaac cagatggtgt tccccgccgg gatcctgcag    240
cccaccctgt acgaccctga cttcccacag tctctcaact acggggcat cggcaccatc    300 attggacatg agctgaccca cggctacgac ggactggggg ggccagtatg accgctcagg    360
gaacctgctt gcactggtgg gacgaggct tccttacagc cgntttcctg cgaaaggctg    420
agtgcatcgt tccctnttt atggacaact ttcaatgtnt tacaaccagg cggtgaacgg    480
gaaacacang tttgggagaa catcgcagta tggggcggnc ttaagttggc ttaccacgct    540
attagagttg gttncgggan ggccccagga gcaccatttc ccggttaaat acanactgaa    600 ccagtn                                                              606
```

<210> SEQ ID NO 122

<211> LENGTH: 1507
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(1507)
<223> OTHER INFORMATION: n = a, t, c or g

<400> SEQUENCE: 122

```
cgctgcgccc tcacctgggc ccttcttgcc tttctggtcc caggagtgcc gcgacctctg      60
ctgctttgct cacaactgct cgctgcgccc gggggcccag tgcgcccacg gggactgctg     120
cgtgcgctgc ctgctgaagc cggctggagc gctgtgccgc caggccatgg gtgactgtga     180
cctccctgag ttttgcacgg gcacctcctc ccactgtccc ccagacgttt acctactgga     240
cggctcaccc tgtgctgctg gcattggcta ctgccgcgat gccctagggc ccccgttgcg     300
cccacggggc ctgctgcgtg cgctgcctgg ctcccaccca gctcccgagg cctgtttcca     360
ggtggtgaac tctgcgggag atgctcatgg aaactgcggc caggacagcg agggccactt     420
cctgccctgt gcagggaggg atgccctgtg tgggaagctg cagtgccagg gtggaaagcc     480
cagcctgctc gcaccgcaca tggtgccagt ggactctacc gttcacctag atggccagga     540
agtgacttgt cggggagcct tggcactccc cagtgcccag ctggacctgc ttggcctggg     600
cctggtagag ccaggcaccc agtgtggacc tagaatggtg tgccagagca ggcgctgcag     660
gaagaatgcc ttccaggagc ttcagcgctg cctgactgcc tgccacagcc acggggtttg     720
caatagcaac cataactgcc actgtgctcc aggctgggct ccaccttct gtgacaagcc     780
aggctttggt ggcagcatgg acagtggccc tgtgcaggct gaaaaccatg acaccttcct     840
gctggccatg ctcctcagcg tcctgctgcc tctgctccca ggggccggcc tggcctggtg     900
ttgctaccga ctcccaggag cccatctgca gcgatgcagc tggggctgca gaagggaccc     960
tgcgtgcagt ggccccaaag atgcccacca cagggaccac ccctgggcg cgttcacccc    1020
catggagttg ggcccacag ccactggaca gccctggccc ctggaccctg agaactctca    1080
tgagcccagc agccaccctg agaagcctct gccagcagtc tcgcctgacc cccaagcaga    1140
tcaagtccag atgccaagat cctgcctctg gtgagggta gctcctaaaa tgaacagatt    1200
taaagacagg tggccactga cagccactcc aggaacttga actgcagggg cagagccagt    1260
gaatcaccgg acctccagca cctgcaggca gcttggaagt ttcttcccg agtggagctt    1320
cgacccaccc actccaggaa cccagagcca cattagaagt tcctgagggc tggagaacac    1380
tgctgggcac actcttccag ctcaataaac catcagtccc agaaagcaaa ggtcacacag    1440
cccctgacct ccctcaccag tggaggctgg ggtagtgctg gccatcccaa aagggctctg    1500
tcctggn                                                              1507
```

<210> SEQ ID NO 123
<211> LENGTH: 531
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(531)
<223> OTHER INFORMATION: n = a, t, c or g

<400> SEQUENCE: 123

```
ccgcatgatt ctgttggttg ttattgtttt cgacgaacca actgtctcat gaccctgttc      60
```

-continued

```
ctgatcttaa tgatatgatg agcaattgtt cttatgagat aattcaacgc aagtttaatc      120
aatgggatcc ttgtttgagt gctccaaatg ttccatacac taattttcca tacgtagctc      180
ctcgttgtgg agacaagatc aaaaatcaga gggaagaatg tgactgtggc tcccttaaag      240
attgtgccag tgatagatgt tgtgagacct cttgtaccct ttctcttggc agtgtttgca      300
atacagcgac tttgctgcca taagtgtaaa tatgctgccc ctggagtggt ttgcagagac      360
ttgggtggta tatgtgatct accggaatac tgtgatggga aaaaggaaga gtgtccaaat      420
gacatctaca tccaggatgg aaccccatgt tcagcagtat ctgtttgtat aagaggaaac      480
tgcagtgacc gtgatatgca gtgtcaagcc cttttttggct accaagtgaa n             531
```

<210> SEQ ID NO 124
<211> LENGTH: 54
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(54)
<223> OTHER INFORMATION: n = a, t, c or g

<400> SEQUENCE: 124

```
caaatccccc gtgccaggcg gccctaaata ttcctaaaaa aaaccncccc nccn            54
```

<210> SEQ ID NO 125
<211> LENGTH: 387
<212> TYPE: DNA
<213> ORGANISM: Homo sapiens
<220> FEATURE:
<223> OTHER INFORMATION: calpain
<220> FEATURE:
<221> NAME/KEY: misc_feature
<222> LOCATION: (1)..(387)
<223> OTHER INFORMATION: n = a, t, c or g

<400> SEQUENCE: 125

```
ttcttattcc aacaacaaaa gtgaattatg ggtttccctc atagaaaaag catacatgaa      60
agtcatggga ggtatatgatt ttccaggatc caactccaat attgatcttc atgcactgac    120
tggcatggat accagaaaga attgctatgc attcagatag ccaaactttc agtaaggata    180 attcttttcag aatgctttat caaagatttc acaaaggaga tgtcctcatc actgcgtcaa    240
ctggaatgat gacagaagct gaaggagaga agtgggggtct ggttcccaca cacgcatatg   300 ctgtttttgga tattagagag ttcaaggttt tgccttaaat cttttncttt natnnttctt    360
gttggataag acatttcagg gatccca                                        387
```

<210> SEQ ID NO 126
<211> LENGTH: 349
<212> TYPE: DNA
<213> ORGANISM: Homo sapiens
<220> FEATURE:
<223> OTHER INFORMATION: calpain

<400> SEQUENCE: 126

```
tccgtttcaa ttttttattat gggaaaattt caaacatata caaaagtata gagaatagta    60
taatgaactc tcaaacatcc atcacacagc ttcagcaatt accaatttat ggccaatctt    120
gtttcatcta tgtactcaat taccccacac tcagatgatt ttgaagcgaa taccagtaac   180
atatcatttc acctgtacat ttttcagtat acttctctaa aagataatca ttttttaaaa    240
```

```
caacataacc acagtaccat atcacatctt aaaaaacaat aaatcaagaa gttatatttt    300
tatttcaaat tatgtaacaa ctggggacac aatcaataca tttcactgg              349
```

<210> SEQ ID NO 127
<211> LENGTH: 441
<212> TYPE: DNA
<213> ORGANISM: Homo sapiens
<220> FEATURE:
<223> OTHER INFORMATION: calpain

<400> SEQUENCE: 127

```
cacgcgtccg cccacgcgtc cggcagcggt atgcatctga gctcctgtcc cagctccagg    60
aaggggagtt ctgggtggag gaggaggagt tcctcaggga gtttgacgag ctcaccgttg   120
gctaccgggt cacggaggcc ggccacctgc agagcctcta cacagagagg ctgctctgcc   180
atacgcgggc gctgcctggg gcctgggtca agggccagtc agcaggaggc tgccggaaca   240
acagcggctt tcccagcaac cccaaattct ggctgcgggt ctcagaaccg agtgaggtgt   300
acattgccgt cctgcagaga tccaggctgc acgcggcgga ctgggcaggc cgggcccggg   360
cactggtggg tgacagtcat acttcgtgga gcccagcgag catcccgggc aagcactacc   420
aggctgtggg tctgcacctc t                                             441
```

<210> SEQ ID NO 128
<211> LENGTH: 722
<212> TYPE: DNA
<213> ORGANISM: Homo sapiens
<220> FEATURE:
<223> OTHER INFORMATION: calpain

<400> SEQUENCE: 128

```
ctggcaccca tacctttaca ttagtggttt ctcaatatga aaaacagaac acaatccatt    60
acacggttcg ggtatattca gcatgcagct ttacttttc aaagattcct tcaccataca   120
ccttatcaaa acggattaat ggaaagtgga gtggtcagag tgctggaagg atgtggaaat   180
ttccaagaga ctcacaaaaa taccccatc taccaattcc atatagaaaa gactgggccg    240
ttactgattg agctacgagg accaaggcaa tatagccgtt ggatttgagg gtgtaacagt   300
ttctactcta ggagatcctg gcccccatgg ctttctgagg aaatctagtg gtgactatag   360
gtgtgggttt tgctacctgg aattaagaaa atataccttc tgggatcttc aatatcattc   420
ctagtacctt tttgcctaaa caagaaggac cttttttctt ggactttaat agtattatcc   480
ccatcaagat cacacaactt cagtgatgga gaaatctcaa gttactggct tttatactta   540
ccaaacatca gttcttcaaa taaggacgca atcttcagg acagtaagca gaacaatcag    600
aatggaatta aatctctaaa aaccgtgtta cagtggaatc tggtgcttgt cagggtgttt   660
ggtaagaact gtatatagtc agaattacct aaatcaccta gaggtacctc ggccgcgacc   720
ac                                                                  722
```

<210> SEQ ID NO 129
<211> LENGTH: 290
<212> TYPE: DNA
<213> ORGANISM: Homo sapiens
<220> FEATURE:
<223> OTHER INFORMATION: calpain
<220> FEATURE:
<221> NAME/KEY: misc_feature
<222> LOCATION: (1)..(290)
<223> OTHER INFORMATION: n = a, t, c or g

<400> SEQUENCE: 129

```
tagagcacnt ccatatttta gggctactct aagtaacagn gagacagctg ttttttaacc    60
ctcttctgca agtttgttga cctacatggg ctaatatgga tactaaaaat actacattga   120
tctaagaaga aactagcctt gtggagtata tagatgcttt ncattataca cacaaaaatc   180
cctgagggac attttgaggc atgaatataa aacatttttta tttcagtaac ttttcccct   240 gtgtaagtta ctatggttnn gtgggnacaa ctncattcta tanaatatta             290
```

<210> SEQ ID NO 130
<211> LENGTH: 607
<212> TYPE: DNA
<213> ORGANISM: Homo sapiens
<220> FEATURE:
<223> OTHER INFORMATION: serine carboxypeptidases
<220> FEATURE:
<221> NAME/KEY: misc_feature
<222> LOCATION: (1)..(607)
<223> OTHER INFORMATION: n = a, t, c or g

<400> SEQUENCE: 130

```
ggatcgaccc cggcttccgg cctgttgctg atgctgccgt gcggtacttg tcatggagct    60
ggcactgcgg cgctctcccg tcccgcggtg gttgctgctg ctgccgctgc tgctgggcct   120
gaacgcagga gctgtcattg actggcccac agaggagggc aaggaagtat gggattatgt   180
gacggtccgc aaggatgcct acatgttctg gtggctctat tatgccacca actcctgcaa   240
gaacttctca naactgcccc tggtcatgtg gcttcagggc ggtccaggcg gttctagcac   300
tggatttgga aactttgagg aaattgggcc ccttgacagt gatctcaaac cacggaaaac   360
cacctggctc caggctgcca gtctcctatt tgtggataat cccgtgggca ctgggttcan   420
ttatgtgaat ggtggcttca ganatgatgg ttctcctgaa gaactcttca ntggcncaaa   480
aaaatccaaa agttccattc tacatttnct caaaatccta tggangaaaa aatggcanct   540
gggcattggt ctnaactttn taagggcatc nancaaagga catcaattgc aacttttgcg   600
ggggttg                                                             607
```

<210> SEQ ID NO 131
<211> LENGTH: 357
<212> TYPE: DNA
<213> ORGANISM: Homo sapiens
<220> FEATURE:
<223> OTHER INFORMATION: serine carboxypeptidases

<400> SEQUENCE: 131

```
ggaaggtgat tgtttcgctg gtcctgttga tgcctggccc ctgtgatggg ctgtttcgct    60
ccctatacag aagtgtttcc atgccaccta agggagactc aggacagcca ttatttctca   120
ccccttacat tgaagctggg aagatccaaa aaggaagaga attgagtttg gtcggcccttt  180 tcccaggact gaacatgaag agttatgccg gcttcctcac cgtgaataag acttacaaca   240
gcaacctctt cttctggttc ttcccagctc agatacagcc agaagatgcc ccagtagttc   300
tctggctaca gggtgggccg ggaggttcat ccatgtttgg actctttgtg gaacatg      357
```

<210> SEQ ID NO 132
<211> LENGTH: 674
<212> TYPE: DNA
<213> ORGANISM: Homo sapiens
<220> FEATURE:
<223> OTHER INFORMATION: serine carboxypeptidases

<400> SEQUENCE: 132

-continued

| | |
|---|---|
| ggctccaacg tctttgtgaa catggaggag gacttcatga agccagtcat tagcattgtg | 60 |
| gacgatgttg ctggaggcag ggatcaacgt gacggtgtat aatggacacg ctggatctca | 120 |
| tcgtagatac catgggtcag gaggcctggg tgcggaaact gaagtggcca gaactgccta | 180 |
| aattcagtca gctgaagtgg aaggccctgt acagtgaccc taaatctctg gaaacatctg | 240 |
| cttttgtcaa gtcctacaag aaccttgctt tctactggat tctgaaagct ggtcatatgg | 300 |
| ttccttctga ccaaggggac atggctctga agatgatgag actggtgact cagcaagaat | 360 |
| aggatggatg gggctggaga tgagctggtt tggccttggg gcacagagct gagctgaggc | 420 |
| cgctgaagct gtaggaagcg ccattcttcc ctgtatctaa ctggggctgt gatcaagaag | 480 |
| gttctgacca gcttctgcag aggataaaat cattgtctct ggaggcaatt tggaaattat | 540 |
| ttctgcttct taaaaaaaac ctaagatttt ttaaaaaaat tgatttgttt tgatccaaaa | 600 |
| taaaggatga taatagatat tatttttttct tatgacagaa gcaaatgatg tgatttatag | 660 |
| aaaaactggg aaat | 674 |

<210> SEQ ID NO 133
<211> LENGTH: 1960
<212> TYPE: DNA
<213> ORGANISM: Homo sapiens
<220> FEATURE:
<223> OTHER INFORMATION: serine carboxypeptidases

<400> SEQUENCE: 133

| | |
|---|---|
| cacgcgtccg gccgtgcggt acttgtcatg gagctggcac tgcggcgctc tcccgtcccg | 60 |
| cggaaggatg ctgctgctgc cgctgctgct gggcctgaac gcaggagctg tcattgactg | 120 |
| gcccacagag gagggcaagg gaacttatgg ggattatgtg acgtccgca aggatgccta | 180 |
| catgttctgg tggctctatt atgccaccaa ctcctgcaag aacttctcag aactgcccct | 240 |
| ggtcatgtgc cttcagggcg gtccaggcgg ttctagcact ggatttggaa actttgagga | 300 |
| aattgggccc cttgacagtg atctcaaacc acgggaaaac cacctggctc caggctgcca | 360 |
| gtctcctatt tgtggataat cccgtagggc actgggttca gttatgtgaa tggtaagtgg | 420 |
| tgcctatgcc aaggacctgg cttatggtgg cttcagacat ggatggttct cctgaagacc | 480 |
| ttcttcagtt gccacaaaga attccagaca gttccattct acattttttc agagtcctat | 540 |
| ggaggaaaaa tggcagctgg cattggtcta gagctttata aggccattca gcgagggacc | 600 |
| atcaagtgca actttgcggg ggttgccttg ggtgaatcct ggatctcccc tgttgattcg | 660 |
| gtgctctcct ggggaccatt acctgtacag catgtctctt ctcgaagaca aggtctggc | 720 |
| agaggtgtct aaggttgcag agcaagtctg aatgccgtaa ataagggct ctacagagag | 780 |
| gccacagagc tgtgggggaa agcagaaatg atcattgaac agaacacaga tggggtgaac | 840 |
| ttctattaac atcttaacta aaagcactcc cacgtctaca atggagtcga gtcttagaat | 900 |
| tcacacagag ccacctagtt tgtctttgtc agcgccacgt gaagacacct tacacgagat | 960 |
| gccttaagcc agctcatgaa tggccccatc agaaagaagc tcaaaattat tcctgaggat | 1020 |
| caatcctggg gaggccaggc taccaacgtc tttgtgaaca tggaggagga cttcatgaag | 1080 |
| ccagtcatta gcattgtgga ccaagttgct ggaggcaggg atcaaccgtg accggtgtat | 1140 |
| taatggacaa gcttggatct catcgtagat accatgggtc aggaggcctg ggtgcggaaa | 1200 |
| ctgaagtggc cagaactgcc taaattcagt cagctgaagt gggaaggccc tgtacagtga | 1260 |
| ccctaaatct ttggaaacat ctgcttttgt caagtcctac aagaaccttg cttttctactg | 1320 |
| gattctgaaa gctggtcata tggttccttc tgaccaaggg ggacatggct ctgaagatga | 1380 |

-continued

| | |
|---|---|
| tgagactggt gactcagcaa gaataggatg gatggggctg gagatgagct ggttatggcc | 1440 |
| ttggggcaca gagctgagct gaggccgctg aagctgtagg aagcgccatt cttccctgta | 1500 |
| tctaacttgg ggctgtgatc aagaaggttc tgaccagctt ctgcagagga taaaatcatt | 1560 |
| tgtctctgga ggcaatttgg aaattatttc tgcttcttaa aaaaacctaa gattttttaa | 1620 |
| aaaatttgat tcgtttcgat caaaataaag gatgataata gatattattt tttcttatga | 1680 |
| cagaagcaaa tgatgtgatt tatagaaaaa ctgggaaata caggtaccca aagagtaaat | 1740 |
| caacatctgt atacccccctt cccaggggta agcactgtta ccaatttagc atatgtcctt | 1800 |
| gcagaatttt tttttctata tatacatata tattttttac caaaatgaat cattactcta | 1860 |
| tgttgtttta ctatttggtt ggcatatcaa gtatatctga aacacctttt catgtcaata | 1920 |
| aatgttcttc tctaacattt ttaaaaaaaa aaaaaaaagg | 1960 |

<210> SEQ ID NO 134
<211> LENGTH: 1000
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(1000)
<223> OTHER INFORMATION: n = a, t, c or g

<400> SEQUENCE: 134

| | |
|---|---|
| cgcggacgcg tgggtgcgtc agaaggttct aacttttgtc atcactatta ccagcattgt | 60 |
| catcgttatc gttatcttcg tcatcatcat taccaccgtt ataccctgata ctgccataac | 120 |
| aatcagaaca ttatgtacag gcacggcata tcttcccaaa gatcttggcc actatggact | 180 |
| acgatcttta ttttttcttgg agtggcggca atcttgggag taaccattgg tcttcttgtt | 240 |
| cattttctgg cagttgagaa gacttactat tatcaaggtg attttcatat ttctggagtc | 300 |
| acatacaatg ataattgtga aaacgcagct tcacaagcca gcacaaatct aagcaaagat | 360 |
| attgagacta agatgttaaa tgcatttcaa aattccagta tatataagga atatgtcaaa | 420 |
| tctgaggtca tcaaacttct gcctaatgcc aatggttcaa atgtgcagtt acagctgaaa | 480 |
| ttcaagtttc ctccagcaga aggagttagc atgaggacta aaatcaaggc taaattacat | 540 |
| cagatgttga aaacaacat ggcatcctgg aatgcagttc ctgcttccat taaactcatg | 600 |
| gaaatcagca aggctgcttc tgaaatgctt accaacaact gttgtgggag acaagtagcc | 660 |
| aacagtatca taactggcaa caaaattgtg aatggaaaaa gctccctgga ggggcatgg | 720 |
| ccatggcagg ccagcatgca atggaaaggc cgtcactact gtggagcctc tctgatcagc | 780 |
| agcaggtggc tattatctgc agctcactgc tttgctaaga aaataattc aaaagattgg | 840 |
| actgtcaact ttggagttgt agtaaataaa ccatatatga cacggaaagt ccaaaacatt | 900 |
| attttttcatg aaaattatag cagtcctggg cttcgatgat ttgccttgtc agcttgttag | 960 |
| aagtttcttt tcagagtact tcgtaagatt gcttctgaan | 1000 |

<210> SEQ ID NO 135
<211> LENGTH: 69
<212> TYPE: DNA
<213> ORGANISM: Homo sapiens
<220> FEATURE:
<223> OTHER INFORMATION: trypsin-like serine proteases

<400> SEQUENCE: 135

```
aaagaaaaga atggtggaag cctttttgtga gaacaagccc catttgcagc catggtcacg      60
actcatttc                                                              69
```

<210> SEQ ID NO 136
<211> LENGTH: 472
<212> TYPE: DNA
<213> ORGANISM: Homo sapiens
<220> FEATURE:
<223> OTHER INFORMATION: trypsin-like serine proteases

<400> SEQUENCE: 136

```
ccgcaaacaa gctgggagaa gcacggaatc tgcgctcggg ttccgcagat gcacgaggtt     60
gaggtggctg cgggactgga agtcatcggg cagaggtctc acagcagcca aggaacctgg    120
ggcccgctcc tcccccctcc aggccatgag gattctgcag ttaatcctgc ttgctctggc    180
aacagggctt gtagagggag agaccaggat catcaagggg ttcgagtgca agcctcactc    240
ccagccctgg caggcagccc tgttcgagaa gacgcggcta ctctgtgggg cgacgctcat    300
cgcccccaga tggctcctga cagcagccca ctgcctcaag cccgctaca tagttcacct    360
ggggcagcac aacctccaga aggaggaggg ctgtgagcag accggacag ccactgagtc    420
cttcccccac cccggcttca acaacagcct cccaacaaa gaccaccgca at             472
```

<210> SEQ ID NO 137
<211> LENGTH: 532
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(532)
<223> OTHER INFORMATION: n = a, t, c or g

<400> SEQUENCE: 137

```
tgtccacccc cgcgtccgat aagccttaat ttctaagata atttaactt tgttatggga      60
cgggaggtaa gagtgtaaat tttatataca tgaaggtaag atctgagtgt aaactttaca    120
tacatgaagt atgaatggaa ggtagaaaaa aagtcccttt tcgcatgtaa tctctttatc    180
aaagaattt cttttgacac tttaccactg aagtattttt gtaagtccta aattcgcagc    240
atattgtttc atatttatat gccatcttgc aaatagttct tgctatttta ttcactgctg    300
ttacactttta naaaaattcc agcttgttta cttgcattta tcagtgatgc caaccaagct    360
ttgactgtta acttgaaagc ttgcttctga aatgtnggtg catttttcagg tgacctctta    420
tctctctgaa agttcatacc tattagcagg ctctgtanat attgacatac ttagctttta    480
atacattcta tangtaaatt tatagatttc agaataactt aaaaaattaa tg             532
```

<210> SEQ ID NO 138
<211> LENGTH: 591
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(591)
<223> OTHER INFORMATION: n = a, t, c or g

<400> SEQUENCE: 138

```
gcttggtgtt cagagtatgt taaagagaaa gggaggtctg gaaggctccc aataaaagac      60
actgagacac agaacattag ctggacatgc agacccagag acccgggacc cagagactcg    120
```

```
gagacccgag acctggacac ccagtgggag aagggctggg ctggttcgcc tcccctcccc      180
gtcctcctcc ccactcttcc ccttcctctg cttcctcatc ttcttcctct gtgaaatgcc      240
cctaacccct acaaatagga tttcaggatt tcaaccagtg ttcccaacaa attccatcag      300
ctttagtggt ttctgaaaag cagacagtga cggtgccccc caccacggcc ctggggctg       360 ttggtcactt acctaccctc accttgaatc tcttggcttg gtagagaaca gtgggctgcc      420
gtagggatgt agaactcgct cagaatagtt ccaccacaga aaccettcgt tttcctcatt      480 gatgagcagg gcctgtgacc aggacgtgac aggcttcant gtggctggcc aggtgacaag      540
gtgttgcctg acttgagaag ccagctcttt caggtggcac tgnccgggcc t              591
```

<210> SEQ ID NO 139
<211> LENGTH: 619
<212> TYPE: DNA
<213> ORGANISM: Homo sapiens
<220> FEATURE:
<223> OTHER INFORMATION: trypsin-like serine proteases

<400> SEQUENCE: 139

```
gatatgcaag cgacgcggac aggccaaaca gtgacagcca cgtagaggat ctggcagaca       60
aagagacaag actttggaag tgacccacca tggggctcag catcttttg ctcctgtgtg      120 ttcttgggct cagccaggca gccacaccga agattttcaa tggcactgag tgtgggcgta     180
actcacagcc gtgcaggtg gggctgtttg agggcaccag cctgcgctgc ggggtgtcc       240 ttattgacca caggtgggtc ctcacagcgg ctcactgcag cggcagcagg tactgggtgc     300
gcctggggga acacagcctc agccagctcg actggaccga gcagatccgg cacagcggct    360
tctctgtgac ccatcccggc tacctgggag cctcgacgag ccacgagcac gacctccggc    420
tgctgcggct gcgcctgccc gtccgcgtaa ccagcagcgt tcaaccctg cccctgccca     480 atgactgtgc aaccgctggc accgagtgcc acgtctcagg ctggggcatc accaaccacc    540
cacggaaccc attccggatc tgtccagtgc ctcaacctct catcgtctcc atgccacctg    600
catggtgtgt atccgggag                                                  619
```

<210> SEQ ID NO 140
<211> LENGTH: 460
<212> TYPE: DNA
<213> ORGANISM: Homo sapiens
<220> FEATURE:
<223> OTHER INFORMATION: trypsin-like serine proteases

<400> SEQUENCE: 140

```
cgcgtccggt gaacttctgt catctccttc tggcttggtt gcctctgaaa ggagggaaag       60
tctcttggta aattatctct tttgtgctgt ttgctgtttc tctgctgccg tctttgcagt      120
tctcctctca ctggttgcag gctttcatag taaggtttgg cgagaaatgt tccaaacatc      180
acattttgga ttctaggctg tcaccctca ttctgtgaaa cgtattagca tgtgttcgcc       240
caagatgact attccttgtg agccagttaa tgatgatatt ctacgccctt cccttctaag      300
ctgtagttca ggaatccagc ccacatagac agactcttgc tttccatggt gtagtcaatg      360
ccaagtgatg catctaggca ggaaaatcta ctctttgctt ttttggggc aattagtaca      420 tttgtgaagt gcagcatcca agaaacagcc tgttttttca                            460
```

<210> SEQ ID NO 141
<211> LENGTH: 372
<212> TYPE: DNA

<213> ORGANISM: Homo sapiens
<220> FEATURE:
<223> OTHER INFORMATION: trypsin-like serine proteases

<400> SEQUENCE: 141

```
ccgccactgt ggatgaagca gagaaagcaa ttgagctgcg tctggcaaaa attgaccata      60
ctgcaattca cccatttact tgacatgaag attggacaag ggaaatatga gccgggcttc     120
ttccctaagc tgcagtctga tgtactttcc actgggccag ccagcaacaa gtggacgaaa     180
aggaatgccc ctgcccagtg gaggcggaaa gatcggcaga agcagcacac agaacacctg     240
cgtttagata atgaccagag ggagaagtac atccaggaag ccaggactat gggcagcact     300
atccgccagc ccaaactgtc caacctctct ccatcagtga ttgcccagac caattggaag     360
tttgtagagg gc                                                         372
```

<210> SEQ ID NO 142
<211> LENGTH: 313
<212> TYPE: DNA
<213> ORGANISM: Homo sapiens
<220> FEATURE:
<223> OTHER INFORMATION: trypsin-like serine proteases

<400> SEQUENCE: 142

```
cgggggcctg tgctgtgcct cgagcctgac ggacactggg ttcaggctgg catcatcagc      60
tttgcatcaa gctgtgccca ggaggacgct cctgtgctgc tgaccaacac agctgctcac     120
agttcctggc tgcaggctcg agttcagggg gcagctttcc tggcccagag cccagagacc     180
ccggagatga gtgatgagga cagctgtgta gcctgtggat ccttgaggac agcaggtccc     240
caggcaggag caccctcccc atggccctgg gaggcagggc ttgatgcacc aggggacagc     300
tggcctgtgg cgg                                                        313
```

<210> SEQ ID NO 143
<211> LENGTH: 558
<212> TYPE: DNA
<213> ORGANISM: Homo sapiens
<220> FEATURE:
<223> OTHER INFORMATION: trypsin-like serine proteases

<400> SEQUENCE: 143

```
gcccagtgtt tcttttcctt gtcccttccc tcaccaacct ggagttattt tggttgacta      60
tgtcctggct ttggcttctc ctggcaggaa gtcatcaggc atcctctcca ggtgagccga     120
aattccaccc tcccaggttg gacatcatct tttaaaccca atggtctact cccctccttc     180
tttatgaaac agtgatttcc cgtgcagtaa ctctggttct gattttttgt accggcgctt     240
aaattctttc tgtagacatt ggaaagccac aaagaacgtg actgcagtga gcctcccact     300
ggagcagcct taaccaacac tttggccaaa gccccccac ctcccctgtg tactgtgtgt     360
gtgtttggtg gatacagtat tccttttcag tgtccctaaa gctgtgatgg ggagtcccca     420
cttacctaga aagcattacc agtcacctac tctgcattct ccagatgtta aaccttgttg     480
ttattgttct ttttttgcaat gacctattta tttaacctat ttaatattta tttaattttt     540
tactcctgaa atgttttcc                                                  558
```

<210> SEQ ID NO 144
<211> LENGTH: 246
<212> TYPE: DNA
<213> ORGANISM: Homo sapiens
<220> FEATURE:
<223> OTHER INFORMATION: trypsin-like serine proteases

<400> SEQUENCE: 144

```
accgcaacac ccgaggattg aacttccttt gaacagtcca atgcagagca cagggtctcc    60
ccaatgaccc aggaatgatt gcatgtctcc ctcaaggctg cctccacagt tcattttgct   120
gttaatctct actgggtagg aggcctgaca ctggatccgg gttcgcatca tgagcatgca   180
cgcactccag gtcctcgggg tcagtagttc ccaaaagtgc actgttgacc agcgagacat   240
gacgca                                                             246
```

<210> SEQ ID NO 145
<211> LENGTH: 154
<212> TYPE: DNA
<213> ORGANISM: Homo sapiens
<220> FEATURE:
<223> OTHER INFORMATION: trypsin-like serine proteases

<400> SEQUENCE: 145

```
tagcaaaggc ccccccaaac caaccgaaaa aggcggaaac ccgaggaaac cccgggggcc    60
cccaaaaaaa gttgccccca aacccaaaaa aaaagcgggc caccccgggg accggccacc   120
caccaccccc ggggggcaa taggggggcc cccc                                154
```

<210> SEQ ID NO 146
<211> LENGTH: 41
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(41)
<223> OTHER INFORMATION: n = a, t, c or g

<400> SEQUENCE: 146

```
gttnaaaaaa aaaaanantt tttgggggcc ccccctttt t                         41
```

<210> SEQ ID NO 147
<211> LENGTH: 462
<212> TYPE: DNA
<213> ORGANISM: Homo sapiens
<220> FEATURE:
<223> OTHER INFORMATION: trypsin-like serine proteases

<400> SEQUENCE: 147

```
cccccacatt ccgcccacgc gtccgggtaa aaatgctgaa atgtctgtaa cccagtaata    60
gagcaaacat tatttttacc aacccaaact ctgctggtcc taacatagta atgctatctc   120
acagataatc taatgatatt ctattactgg gttacagaca tttcagcatt tttaggttgg   180
ttttaaatca ctaaaaatat ttattcggat ttgaaggatt taagtgctaa aaatcaatcc   240
atttcttgcc cttcaataat tgtccatgcc tgccttttgt tgtttacatg ctcttctgcc   300
cagactgtta gtaatctagg gaccccctttt ggagctgata agtacagttc aacctttct   360
cctcaaatat ataatgactt taacattcct aagaatatag gtatttctga atgatttaaa   420
tttgaagaat tttaatacat aaaatacaat gtacaaactt tc                      462
```

<210> SEQ ID NO 148
<211> LENGTH: 512
<212> TYPE: DNA
<213> ORGANISM: Homo sapiens
<220> FEATURE:
<223> OTHER INFORMATION: trypsin-like serine proteases
<220> FEATURE:

<221> NAME/KEY: misc_feature
<222> LOCATION: (1)..(512)
<223> OTHER INFORMATION: n = a, t, c or g

<400> SEQUENCE: 148

```
nttccccttg ccctctacca cgcgtccgcg ccacgcgtgg gttttttttt tgcctcatca      60
aaatttatta agttgtacat atacagtata ttatcagaac aacaccaaag tggctacact     120
tgacagattc tcctaaagtg gacataattt tcctagagat tattattccc cttgataaaa     180
gttgtaatga ttgtgaaagc tttgaaagac aagcttgaag gccacagca ttgactatca      240
gggcaaggag ctatanatgc catgcacgca gggcccagaa ggcagcagag ccgcaggagg     300
ctgtggcagc cccgtttctg ctgtgagcaa acagtgctat gangagacca acncaaagaa     360
gaaggtgctc ctctccangg gtagggtctt tgggttcacn tccaaaacnc aaaaccccc     420
cccngaaaaa aaaaggaaac aaaccccta cagggtctng gccccncc aaaaaanggg       480
ccnntnttgg ccnaaaaagg cccaattnaa at                                   512
```

<210> SEQ ID NO 149
<211> LENGTH: 397
<212> TYPE: DNA
<213> ORGANISM: Homo sapiens
<220> FEATURE:
<223> OTHER INFORMATION: trypsin-like serine proteases

<400> SEQUENCE: 149

```
cgggactcct gcccacttgg gggaaacctt atacccagag gaaaatacac acctggggag      60
tacatttgac aaatttccct taggatttcg ttatctcacc ttgaccctca gccaagattg     120
gtaaagctgc gtcctggcga ttccaggaga cccagctgga aacctggctt ctccatgtga     180
ggggatggga aaggaaagaa gagaatgaag actacttagt aattcccatc aggaaatgct     240
gaccttttac ataaaatcaa ggagactgct gaaaatctct aagggacagg attttccaga     300
tcctaattgg aaatttagca ataaggagag gagtccaagg ggacaaataa aggcagagag     360
aagagacaga ctaaaaatac gaggaaagga gagtggg                              397
```

<210> SEQ ID NO 150
<211> LENGTH: 169
<212> TYPE: DNA
<213> ORGANISM: Homo sapiens
<220> FEATURE:
<223> OTHER INFORMATION: trypsin-like serine proteases

<400> SEQUENCE: 150

```
ttggtgtgga aaccagggtt tcctctctgg gcacaccata accccggaa aaaacacccc      60
ggggttgtcc attggagact aaggggccac caaagtcacc cggggaggag tcctttccgc     120
cctccaggaa gcccagacag aacatgtttt tagtgatctt gcctgggta                169
```

<210> SEQ ID NO 151
<211> LENGTH: 726
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(726)
<223> OTHER INFORMATION: n = a, t, c or g

<400> SEQUENCE: 151

```
cccnttttta aaacctgctt cnccttttnta atntgtaaag ggnncctct ntcgaaagnn      60
```

```
gcacgacntt tgatgagtna acatgtnccg cacaanctgc tgncncnccn gctancnnaa      120
aagantgaag acaaancatc tgaggacana ganaaaactt gangantatn aangaaagaa      180
aggaaatatc tggttctttg atgactttgt tcttgattgt aactcacctg aanccacccc      240
anctatanac atntgttgtg accnacaatc atttccttat ttttanancc agtttganat      300
ggccanaggc atatataaat ncaaatgtca ttataatnaa ttataatnat atntgaaatg      360
caatgtntac tgttatattt ataatgctat gattanatag canaatttta gggtttgtta      420
ttaactcccg attctccnca ganaccnact cnttggncac cacngggaga atcncatnt       480 attagnaaga nttggctcat atgattatna aagcttgana atcccatgg tctgccatct       540 gccacctgga aaccccgga aaaaacactt tccttaaatc catcnnaatc caantggcct       600
gcaaaacccc ttccancttc nnttgtctta attantantt gaacnaggac ctccnnngta     660
tccnaagaaa attttcttan cttccgggcc gnngcgaccc acaaanccaa nnggngggaa     720
tttctt                                                                 726

<210> SEQ ID NO 152
<211> LENGTH: 246
<212> TYPE: DNA
<213> ORGANISM: Homo sapiens
<220> FEATURE:
<223> OTHER INFORMATION: trypsin-like serine proteases

<400> SEQUENCE: 152
agggtggagg gggtcagggt gcgttttcgg gcaacagttc ggttccgggt gagctacaga      60
gacatgtagg ggcatttgga gcgtttggaa ctcacacgtc gaagcagtgc gccgccgaca     120
gcagccacct ctctgccacc agcacggccc cgcaacggtg ttcccggcgc cgcagccaca     180
ggtctacctg ccacggccac tccccacggc ccgctgcgct gccgcccaca atcctggtga     240
gcgcgg                                                                 246

<210> SEQ ID NO 153
<211> LENGTH: 495
<212> TYPE: DNA
<213> ORGANISM: Homo sapiens
<220> FEATURE:
<223> OTHER INFORMATION: trypsin-like serine proteases

<400> SEQUENCE: 153
cgcgtccggt cccgcacagt ggtcatggga cgtgcggctg atcatgcgcc aagaccggct      60
atggagtgga agagttgatc tctgcccttc agcgctcctg gcgctaccgt ggggacgtct     120
acttagtggg cgccaccaac gccggcaaat ccactctctt taacacgctc ctggagtccg     180
attactgcac tgccaagggc tccgaggcca tcgacagagc caccatctcc ccttggccag     240
gtactacatt aaaccttctg aagtttccta tttgcaaccc aactccttac agaatgttta     300
aaaggcatca aagacttaaa aaagattcaa ctcaagctga agaagatctt agtgagcaag     360
aacaaaatca gcttaatgtc ctcaaaaagc atggttattg tcgtaggaag agttggaagg     420
acattcttgt attcagaaga acagaaggat aacattccct ttgagtttga tgctgattca     480
cttgcctttg acatg                                                      495

<210> SEQ ID NO 154
<211> LENGTH: 525
<212> TYPE: DNA
<213> ORGANISM: Homo sapiens
<220> FEATURE:
```

<223> OTHER INFORMATION: trypsin-like serine proteases

<400> SEQUENCE: 154

| | | | | | |
|---|---|---|---|---|---|
| gtccggtttt | acgtctccat | ggtaactgtg | ccctgcaccc | ctcggtagcc | gccctgttag | 60 |
| ttttcagtct | cctttctttt | ctcaccattt | atcacttccc | tcactgccct | acccaggctt | 120 |
| tctctcccac | ttccctgact | ctgggaataa | ctaatattta | agcaaggtaa | gatgagaagc | 180 |
| aagggtctc | agttctagga | atacagtgct | agttgattgt | caggtatgtt | gtaaatagac | 240 |
| cctctttggc | catacactcc | atgcctagat | gcctcggaga | gcatcattct | ctgcctaggc | 300 |
| aaggccctgc | atcccttgcc | tcaggccggg | ctgagtgtga | ctgcagctcc | tgaggatggg | 360 |
| cctgccctgt | ctggggtatg | ccgtgatccc | tagatacatg | ttcccacaag | aggtgcctgc | 420 |
| tccgtcttcg | ctcaccagac | actcaggcag | gctggcttag | tctttgtgcg | tggcgatttt | 480 |
| gtgctctggg | ccctttctct | ttttccagcc | agtttccatt | cactt | | 525 |

<210> SEQ ID NO 155
<211> LENGTH: 481
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(481)
<223> OTHER INFORMATION: n = a, t, c or g

<400> SEQUENCE: 155

| | | | | | |
|---|---|---|---|---|---|
| ccgggacagc | tgtgtagcct | gtggatcctt | gaggacagca | nggtcccag | gcaggagca | 60 |
| ccctccccat | ggccctggga | ggccaggctg | atgcaccagg | acagctggc | ctgtggcgga | 120 |
| gccctggtgt | cagaggaggc | ggtgctaact | gctgcccact | gcttcattgg | gtgagtcttg | 180 |
| gatccctctc | tgctgtgccc | cctgccctgc | cggcagccct | gtcacctggt | gccggtccac | 240 |
| actgcctctg | cacaggcgcc | aggccccaga | ggaatggagc | gtagggctgg | ggaccagacc | 300 |
| ggaggagtgg | ggcctgaagc | agctcatcct | gcatggagcc | tacacccacc | ctgagggggg | 360 |
| ctacgacatg | gccctcctgc | tgctggccca | gcctgtgaca | ctgggagcca | gcctgcggcc | 420 |
| cctctgcctg | ccctatcctg | accaccacct | gcctgatggg | gagcgtggct | gggttcttgg | 480 |
| g | | | | | | 481 |

<210> SEQ ID NO 156
<211> LENGTH: 268
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(268)
<223> OTHER INFORMATION: n = a, t, c or g

<400> SEQUENCE: 156

| | | | | | |
|---|---|---|---|---|---|
| ccacgcgtcc | gccatgaaaa | tgcctccaaa | ctgagatgct | ttcagctgag | aacagatttg | 60 |
| actcacagac | attaccaaag | aggagcttgt | gaatccagga | aaagctccag | ggggctagct | 120 |
| gatctgagca | gagagctttc | agtgacccat | tttcctgtct | agactctgcc | ttaagctagt | 180 |
| ggcaactgct | ggggcccag | gtacttggga | catggaaact | cgttggatgg | ctgggcagat | 240 |
| gtnaccctgt | ccatgcngtc | ngccgacc | | | | 268 |

<210> SEQ ID NO 157
<211> LENGTH: 519
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(519)
<223> OTHER INFORMATION: n = a, t, c or g

<400> SEQUENCE: 157

```
cccgttntct acccgtctct tcatctgtcc attcacacat ccttccacac accaacactt    60
cgacctttac tacaggacag gcattctgtt aggtactagg gctccattag tgcagataca   120
gtttctgctt tcagtgggcc cacagctgga tggggcaggc aggggtgaaa tcaacacttc   180
taccttccca tcccccatac ttaggaccag gaataagaaa ggagagctgt ccacactggc   240
tctctggggc ttagcactgg gccacgcttc ctgagagtta ggaccatgct gacactcacc   300
tctctctctc tttctatctc acccatctct gttggcagag tgtggagcga ggccctggc    360 ttcccggata gttggtgggc agtctgtggc tcctgggcgc tggccgtggc aggccagcgt   420
ggccctgggc ttccggcaca cgtgtggggg ctctgtgcta gcgccacgct gggtggtgac   480
tgctgcacat tgtatgcaca gggcagagag tgtaatccc                          519
```

<210> SEQ ID NO 158
<211> LENGTH: 26
<212> TYPE: DNA
<213> ORGANISM: Homo sapiens
<220> FEATURE:
<223> OTHER INFORMATION: trypsin-like serine proteases

<400> SEQUENCE: 158

```
agacccggcc accggcctgg ggcgcc                                          26
```

<210> SEQ ID NO 159
<211> LENGTH: 424
<212> TYPE: DNA
<213> ORGANISM: Homo sapiens
<220> FEATURE:
<223> OTHER INFORMATION: Lon family of ATP-dependent proteases

<400> SEQUENCE: 159

```
tttttttttt ttttttttgt cagtttttct tttatttgat caaaatttta aaatatgaat    60
tagttacagg cataaaaata taatatatac ttaaaaccaa ggttttcata gaaagaaggc   120
aaacccgtat ttaaaaataa tattaatttt caaaaattaa ataaaaaata accatataaa   180
ttgttttttc atacttactg gaagaacaag acctctcagt gtaatttctc cagtcatggc   240
tacatctgaa cgtaccagcc gcccactaaa aagtgaggcg agacaggtta ctatggtaac   300
tccagcagat ggtccatctt ttgtgacagc tccagctggg aagtgcagat ggatgtctgt   360
gttgtcaaga agatcaaaac ttccaaagct ttaaaaagga aaagggact ttaatgtaga    420 aaaa                                                                 424
```

<210> SEQ ID NO 160
<211> LENGTH: 958
<212> TYPE: DNA
<213> ORGANISM: Homo sapiens
<220> FEATURE:
<223> OTHER INFORMATION: Lon family of ATP-dependent proteases

<400> SEQUENCE: 160

-continued

```
gcaatcctat gctttgttgg ccctcctgga gttggtaaaa caagtgtggg aagatcagtg      60
gccaagactc taggtcgaga gttccacagg attgcacttg gaggagtatg tgatcagtct     120
gacattcgag gacacaggcg cacctatgtt gggcagcatg cctgggtcgc atcatcaacg     180
gcttgaagac tgtgggagtg aacaacccag tgttcctatt agatgaaggt tgacaaactg     240
ggaaaaagtc tacagggtga tccagcagca gctctgcttt gaaggtgttg gatcctgaac     300
aaaaccataa cttcacagat cattatctaa atgtggcctt tgacctttct caagttcttt     360
ttatagctac tgccaacacc acttgctacc attccagctg ccttgttgga cagaatggga     420
gatcattcag gttccaggtt atacacagga ggagaagata gagattgccc ataggcactt     480
gatccccaag cagctggaac aacatgggct gactccacag cagattcaga taccccaggt     540
caccactctt gacatcatca ccaggtatac cagagaggca ggggttcgtt ctctggatag     600
aaaacttggg gccatttgcc gagctgtggc cgtgaaggtg gcagaaggac agcataagga     660
agccaagttg gaccgttctg atgtgactga gagagaaggt tgcagagaac acatcttaga     720
agatgaaaaa cctgaatcta tcagtgacac tactgacttg gctctaccac ctgaaatgcc     780
gattttgatt gatttccatg ctctgaaaga catccttggg cccccgatgt atgaatggag     840
gtatctcagc gtttgagtca gccaggagta gcaataggtt tggcttggac tcccttaggt     900
ggagaaatca ttttcgtgga ggcgagtcga ttggatggcg aggccaatta actctgac       958
```

<210> SEQ ID NO 161
<211> LENGTH: 1402
<212> TYPE: DNA
<213> ORGANISM: Homo sapiens
<220> FEATURE:
<223> OTHER INFORMATION: Lon family of ATP-dependent proteases
<400> SEQUENCE: 161

```
ttttttcgat tttatcagt ttactaaatc aacatcctta aattcctata ctaaacatta       60
gccactactt gaggttaatt actgttgtga ttatgtttat aaaacaggga catcttgcat     120 accectaatg tgtgaataa atcaaactg tgtcagaccc tttggagcac ttcaatactt      180
aaaaattctt aaaaaattga gatttggacc tacagtttgc tatttaacag accaggtctg     240
gtcttgacag taaagccacc atccaaaagc tgcattaaga acctcaatcc aggcagcttg     300
ctgtgacaaa acttaaatcc tgtcgtacgt tgcctgggat tccctcaagg tcttttttcat    360 ttctccgagg aataatgact tggcttcagt cccgctctgt gtgccgccag cactttgtct     420
ttaattccac ccactggaag aacaaagccc tctcagcgta atttccccag tcaatggcta    480
catcttgagc gcaacaagcc gcccactgaa aagtgaggcg agacaagtta ctatggtaac     540
accagcagat gggtccatct tttgtgacag gctccagctg ggaagtgcaa gatggatgtc    600
tgtgttgtca agaagatcaa aacttccaaa agctttaaaa aggaaaaagg gacttttaat     660
gtagaaaaat taaacctgtt ttcttttttct cctaaaaaaa aagtcacaac caaaaatgaa     720
tgttttgggt aaatgaattc ttcaaaatat tggtggacag tacaatttgg gtgagggtgt     780
ggaagaacag ttccattcta ctctaagtcg tattaaaaca aaataaacct tttgaattag     840
tttctagttc aggcactagt caaatagtcc tgaaatggga actaggattt ccacaggggt     900
tcaaaacggt gtgtactttg ctagatgtgt aactggcagt ctcgagctca tgccagtctc     960
cgccatggaa ggtaccgcct ccctgggtca aggcctgcct tggccggttg caaggctccc    1020
taccattggt cagctgggta cttctttgcg ttgctgcgga gcccagctga atagcgaggt    1080
gggcggactc cttcatcacg tccccgagct ggccggtcag agttaactgg ccctcgccat    1140
```

```
ccattcgact cgcctccacg aacatgattt ctccacctaa gggagtccaa gccaaaccta   1200
ttgctactcc tggctgactc aaacgctgag ataccttgaa agaagaagaa tgatcagagt   1260
tgggttggca aatgctaaag gtgactgata ccacacaatc ctgcaagagt cggctgactc   1320
cacagaagac ttcagccact tacctcaaag tccttgttac ctaacatgat tctgcgtcac   1380
attcagcact tactctctgg ct                                            1402

<210> SEQ ID NO 162
<211> LENGTH: 536
<212> TYPE: DNA
<213> ORGANISM: Homo sapiens
<220> FEATURE:
<223> OTHER INFORMATION: cathepsin

<400> SEQUENCE: 162 ccggttttc  taaatagacc cttatgggag tttgaaaata aatactcaca tatttcacta     60
cttaaattat tcccaagatt tgaatttatt ttaaaatttt aatagccacc aagaatgtgg    120
acatatgaaa attcaagaac ctaaaaaata ccagttttga atgagttttt gtggttttgg    180
tttttttttt aattattaca aatctatgtg taaaatctag atatttgaag tttgagatct    240
gatgagaatg gttgttataa actttatttt aaaaccaaat ttaggtgttc ttacatattt    300
aaatactgga aagtcattat aatagttttg gttctttgaa ttggtagaca attagtagag    360
tataattggt taggaggcag ggcttattaa gtggttatta accgctgaca tcagacaaac    420
ccaaatctgt agaattctaa ccttctaaca cctgtgacag tattaccctc ttcttggatt    480
atagatttag aactgattta ctcaattgca ctcttaacta atggtaaaag cttact        536

<210> SEQ ID NO 163
<211> LENGTH: 908
<212> TYPE: DNA
<213> ORGANISM: Homo sapiens
<220> FEATURE:
<223> OTHER INFORMATION: cathepsin
<220> FEATURE:
<221> NAME/KEY: misc_feature
<222> LOCATION: (1)..(908)
<223> OTHER INFORMATION: n = a, t, c or g

<400> SEQUENCE: 163
tccgatagta caataaatat ttgtgttaat gagaactaat attctgacta attatctaaa     60
gtgtttcact agtacaccag gaaactacag attgagatta gggggtggga ggaaagaaac    120
ctgggctaga gattaaaaca ttcctaaatt tagcanaatt tcagaaatga ttttgcaga     180 ttcattagaa aagaaaaatt gtcatttaat cttaagtttt ggatgtagct cacatgtcac    240
caccaccaga tagtgttaca gcatgtatcc atcatgttgc attgacacat caaacttgtg    300
tgtgtttgtt ttgattgcca aaagggctta atatcagttg tacaatcttt ctgaacttta    360
tagttcctgg ctccaggaaa gatggccttt gctattgaag ccaacttctt ccccatgctg    420 tttatctttta ccagaactta agagatcttt gtttcctatt agcaggtttt ccattgataa    480
ggaaaaagaa caagtagtgt gttgtcttta ttcttgatac aacaccacct ccggtgcttt    540
gcaacctgga accaaaacca taccatgaga gagaggggga aaaaaatcta tgcacttaac    600
ctacaaaatc tctggtgatg acagttgtat tgttgctatt acatggcata acggtctatt    660
atgtggtagg aaaatatagc ctgctaaatc ctacttaagt tgatccactt taaactgagt    720
aactgtataa aacatctatt gaaaattctt ttccttttga cttagattct gccttacatc    780
```

```
aatttttgca ttttggtaa aaaaaaaacc ctactacgtt tgactctaac ctgatacttg      840
ctctctaatg gctcttaata tatcctttga aatcngctat ttccatttta tcagactttt      900 accanaan                                                               908
```

<210> SEQ ID NO 164
<211> LENGTH: 442
<212> TYPE: DNA
<213> ORGANISM: Homo sapiens
<220> FEATURE:
<223> OTHER INFORMATION: cathepsin
<220> FEATURE:
<221> NAME/KEY: misc_feature
<222> LOCATION: (1)..(442)
<223> OTHER INFORMATION: n = a, t, c or g

<400> SEQUENCE: 164

```
acatttaggg actctgctgt cctttattgg tgttgttaat gctcagtaat atgaaggaag       60
cagaagcata gaccagaggg gaaaataaga aaatagatag attatgttaa cacggtgaag      120
agacaaagat tccactgtca ccaagaatgt catattgcta aacttcaatt taggggtta       180 cttaaaggca tgaccttatg gaaatttaat gatatgttat ggttcatcag aactcgtcag      240
ttggccccaa gctgcgataa tcaacttttc aatgtcggac tcatttactc ctcgaagaat      300
cctgaaatag ccattctctc cccatgactt tccccaggaa ttggcagcaa tccaaaattt      360
ttctttctgc ccttgtgctc ctctcagtgt gccccatcca gtgagtttga ctgcatgtgt      420
ctgaagcttt cgatattttt cn                                               442
```

<210> SEQ ID NO 165
<211> LENGTH: 492
<212> TYPE: DNA
<213> ORGANISM: Homo sapiens
<220> FEATURE:
<223> OTHER INFORMATION: cathepsin
<220> FEATURE:
<221> NAME/KEY: misc_feature
<222> LOCATION: (1)..(492)
<223> OTHER INFORMATION: n = a, t, c or g

<400> SEQUENCE: 165

```
cccgggacaa caaatgatg gtttctatct gtgaacagaa gctgcagcac ttcagtattg        60
gacaacaact tgtctatgtt ttgggaaccc aaatagtgct gtcttcctgc tcatcctctg      120
cttgggaatg atgtcagctg ctccaccccc tgatccaagt ttggataatg agtgaaaga       180 atggaagacg aaatttgcaa agcctacaa tctgaatgaa gaaagacaca gaagactcgt      240
gtgggaggag aataagaaga aaattgaggc acacaatgca gactatgagc agggcaagac      300
cagcttctac atgggcctga tcaattttta gtgacttgac tccagaagaa ttcaagacaa      360
attgctatgg aaactcactg aatagaggaa gaaatggctc ctgatttgcc tgaatatgaa      420
gatttgggaa agaacagcta tctgacacct ggaagggctc agccagagta acagctgtgg      480
cttgactggt an                                                          492
```

<210> SEQ ID NO 166
<211> LENGTH: 493
<212> TYPE: DNA
<213> ORGANISM: Homo sapiens
<220> FEATURE:
<223> OTHER INFORMATION: trypsin-like serine proteases

<400> SEQUENCE: 166

```
gccccgcgga cgcgtgggcg gacgcgtggg gatgatattg cccttgtgca gcttgctgaa        60
```

```
gaagtttctt ttacagagta cattcgtaag atttgtcttc ctgaagccaa aatgaagctc        120
tcagaaaatg acaatgttgt agttacaggt tggggaacac tttatatgaa tggttcattt        180
ccagtgatac ttcaagaagc ctttttgaag attattgaca acaaaatttg caatgcctca        240
tatgcatact ctggctttgt gactgattca atgttatgtg ctggatttat gtcaggagaa        300
gctgatgcat gtcagaatga ttctggtgga ccactagctt accctgattc cagaaatatc        360
tggcatcttg ttggaataag taagctgggg tgatgggatg tggtaaaaaa gaataagcca        420
ggtgtctatc ttcgagtgac ttcttatcgc aattggatta cattcaagac tggactctga        480
aaaaaaaaaa aaa                                                            493

<210> SEQ ID NO 167
<211> LENGTH: 56
<212> TYPE: DNA
<213> ORGANISM: Homo sapiens
<220> FEATURE:
<223> OTHER INFORMATION: trypsin-like serine proteases
<220> FEATURE:
<221> NAME/KEY: misc_feature
<222> LOCATION: (1)..(56)
<223> OTHER INFORMATION: n = a, t, c or g

<400> SEQUENCE: 167
cccgcgancg aggacgcgtg ggcggacncg tgggtcgngg gctcagctgg tccggc           56

<210> SEQ ID NO 168
<211> LENGTH: 418
<212> TYPE: DNA
<213> ORGANISM: Homo sapiens
<220> FEATURE:
<223> OTHER INFORMATION: caspase family of apoptosis regulating
      proteases

<400> SEQUENCE: 168
ccgctgggcc ctgggctttg agaccaccgt gagaacggac cctacagccc aggctttcca        60
ggaggagctg gcccagttcc gggagcaact ggacacctgc aggggccctg tgagctgtgc       120
ccttgtggcc ctgatggccc atgggggacc acggggtcag ctgctggggg ctgacgggca       180
agaggtgcag cccgaggcac tcatgcagga gctgagccgc tgccaggtgc tgcagggccg       240
ccccaagatc ttcctgttgc aggcctgccg tgggggaaac agggatgctg gtgtgggggcc     300 cacagctctc ccctggtact ggagctggct gcgggcacct ccatctgtcc cctcccatgc      360
agatgtcctg cagatctacg ctgaggccca aggcagctcc tgcagggca cccctcca         418

<210> SEQ ID NO 169
<211> LENGTH: 493
<212> TYPE: DNA
<213> ORGANISM: Homo sapiens
<220> FEATURE:
<223> OTHER INFORMATION: caspase family of apoptosis regulating
      proteases

<400> SEQUENCE: 169
ccgggctaga ggtgttttgt acaaattata tataagccag cctgatctac aacatgcca        60 cagagaatca caatcaacag tgtggggaaa gtcaggcag tggaagtgga tgcactcttt       120 ttatttgaa ggcttaaacc aaattgtctt ggaattaaag ctgtatttct gcagctttcg       180
gtacagagaa aaagaggaaa gtgaagctgt gtcagttta acattagcta tatcaacatg       240
tttaagaaag atagatgaag tcatttgcat aaaggtacag cattgaaata ctatgttgtg     300
```

-continued

| | |
|---|---|
| tttgttttta cattttttgca ttaaaaaaaa acatgccgta aaagccaagt taaatttcat | 360 |
| attaaagcaa gttctagtgt atgtgttgag ttcctggtaa tcacatactt gttcacatct | 420 |
| acaccgtact tcatagtatg atttgtcagg ggagggattg tggggtgaca gttttacatt | 480 |
| tactttttct tct | 493 |

<210> SEQ ID NO 170
<211> LENGTH: 187
<212> TYPE: DNA
<213> ORGANISM: Homo sapiens
<220> FEATURE:
<223> OTHER INFORMATION: caspase family of apoptosis regulating
      proteases

<400> SEQUENCE: 170

| | |
|---|---|
| ttaaaatcca gcccaccgtg ctgcctctcc aagacacgtc acagggaact tgaccacaga | 60 |
| acccaaggag atgcttctcc acaggtgctt tgctgacaac atcaccctgc accttctgat | 120 |
| atcacagcca agaggacact gtcaaggatg cgtgacagtc tctgaaccac agttacccac | 180 |
| ggtgtgc | 187 |

<210> SEQ ID NO 171
<211> LENGTH: 823
<212> TYPE: DNA
<213> ORGANISM: Homo sapiens
<220> FEATURE:
<223> OTHER INFORMATION: prolyl oligopeptidases

<400> SEQUENCE: 171

| | |
|---|---|
| gtcaaataga aattgacgat caggtggaag gacatccaat atctagcttc tcgatatgat | 60 |
| ttcattgact tagatcgtgt gggcatccac ggctggtcct atggaggata cctctccctg | 120 |
| atggcattaa tgcagaggtc agatatcttc agggttgcta ttgctgggtc cccagtcact | 180 |
| ctgtggatct tctatgatac aggatacacg gaacgttata tgggtcaccc tgaccagaat | 240 |
| gaacagggct attacttagg atctgtggcc atgcaagcag aaaagttccc ctctgaacca | 300 |
| aatcgtttac tgctcttaca tggtttcctg gatgagaatg tccattttgc ataccagt | 360 |
| atattactga gttttttagt gagggctgga aagcagtatg atttacagta tctttatttt | 420 |
| ttgttgttgg taagatctat cctcagggag agacaccggc ataagagttc cctgaatcgg | 480 |
| ggagaacatt atgaactgca tcttttggca ctaccttcaa gaaaaacctt ggatcacctt | 540 |
| attgctgctc ctaaaattga tataattttg acctgtgtag aactctctgg gtatacactg | 600 |
| gctatttaac caaatgagga ggtttaatca acagaaaaca cagaattgat catcacattt | 660 |
| tgatacctgc catgtaacat ctactcctga aaataaatgt ggtgccatgc agggggtctac | 720 |
| ggtttgtggt agtaatctaa taccttaacc ccacatgctc aaaatcaaat gatacatatt | 780 |
| cctgagagac ccagcaatac cataagaatt actaaaaaaa aaa | 823 |

<210> SEQ ID NO 172
<211> LENGTH: 502
<212> TYPE: DNA
<213> ORGANISM: Homo sapiens
<220> FEATURE:
<223> OTHER INFORMATION: prolyl oligopeptidases

<400> SEQUENCE: 172

| | |
|---|---|
| ggtggctata ttgcatcaat gatcttaaaa tcagatgaaa agcttttttaa ttgtggatcc | 60 |
| gtggttgcac ctatcacaga cttgaaattg tatgcctcag cttttctctga aagataccct | 120 |

-continued

| | |
|---|---|
| gggatgccat ctaaggaaga aagcacttac caggcagcca gtgtgctaca taatgttcat | 180 |
| ggcttgaaag aagaaaatat attaataatt catggaactg ctgacacaaa agttcatttc | 240 |
| caacactcag cagaattaat caagcaccta ataaaagctg gagtgaatta tactatgcag | 300 |
| gtctacccag atgaaggtca taaccgtatc tgagaagagc aagtatcatc tctacagcac | 360 |
| aatcctcaaa ttcttcaagt gattgtttga agggaggaat atctgtggct accacaggaa | 420 |
| ccagaaggaa gatggaataa tgggaccgta tttattacag aactggaagg gaatattgga | 480 |
| ggcttcatgg aaacctgaca ag | 502 |

<210> SEQ ID NO 173
<211> LENGTH: 706
<212> TYPE: DNA
<213> ORGANISM: Homo sapiens
<220> FEATURE:
<223> OTHER INFORMATION: lysosomal Pro-X carboxypeptidase
<220> FEATURE:
<221> NAME/KEY: misc_feature
<222> LOCATION: (1)..(706)
<223> OTHER INFORMATION: n = a, t, c or g

<400> SEQUENCE: 173

| | |
|---|---|
| ctgctgctgg cgctcgggct gcgcggcctc caggcggggg cccgcacggc ccccggggct | 60 |
| ccgctccctg ggccccggtc ctgctgctgg cgctcgggct gcgcggcctc caggcggggg | 120 |
| cccgcagggc cccggacccc ggcttccagg agcgcttctt ccagcagcgt ctggaccact | 180 |
| tcaacttcga gcgcttcggc aacaagacct cccctcagcc cttcctggtg tcggacaggt | 240 |
| tctgggtccg gggcgagggg cccatcttct tctacactgg gaacgagggc gacgtgtggg | 300 |
| ccttcgccaa caactcgggc ttcgtcgcgg agctggcggc cgagcggggg gctctactgg | 360 |
| tcttcgcgga gcaccgctac tacggggaag tcgctgccgt tcggtgcgca gtccacgcag | 420 |
| cgcgggcaca cggagctgct gacggtggag caggccctgg ccgacttcgc agagctgctc | 480 |
| cgcgcgctac gacgcgacct cggggcccag gatgcccccg ccatcgcctt cggtggaagt | 540 |
| tatgggggg atgctcagtg cctacctgag gatgaagtat cccacctggt ggcggggcgc | 600 |
| tggcggcaaa cgcgcccgtt ctagctgtgg aaggcttggc gacttcaaca gtctttncng | 660 |
| acgtacggcg gactttaggg caaatcccaa tgcccccagg ggggn | 706 |

<210> SEQ ID NO 174
<211> LENGTH: 478
<212> TYPE: DNA
<213> ORGANISM: Homo sapiens
<220> FEATURE:
<223> OTHER INFORMATION: lysosomal Pro-X carboxypeptidase
<220> FEATURE:
<221> NAME/KEY: misc_feature
<222> LOCATION: (1)..(478)
<223> OTHER INFORMATION: n = a, t, c or g

<400> SEQUENCE: 174

| | |
|---|---|
| tttacatggc caggcctcca ggcgtttatt cagccccttc cctctgccgc cagctgcttg | 60 |
| agtgaagccc ccactccatg aggagccttg agaccctcc agtcctgtgc tcagaggctg | 120 |
| agtctgggcc cccccacgca gagctggctg ctgctcacgc ctggctgcct ttacccactc | 180 |
| gccgatgatg gtggcctcca gcttccgcgc ctcaaccacg gaagcaggat cttctgggtg | 240 |
| ggaggctctg aggtcgaggt ggtgcgctcc ccctggatg gtgacggcga tgactgaggc | 300 |
| actcaggttc ctccgaatcc cgcccctgc ccaggggtcc aggttcccgt tggagaagat | 360 |
| gatgttgctg gcggctctaa gatcgctggc ggagctcgtc agtgaagggc aggtcggnga | 420 |

| acatatcngt cacatttgtg ctggcgaagg tcanngtgat ctcngtgcan ggcctgta | 478 |

<210> SEQ ID NO 175
<211> LENGTH: 703
<212> TYPE: DNA
<213> ORGANISM: Homo sapiens
<220> FEATURE:
<223> OTHER INFORMATION: lysosomal Pro-X carboxypeptidase

<400> SEQUENCE: 175

| ggtccgctgg gagttcggca cctgccagcc gctgtcagac gagaaggacc tgacccagct | 60 |
| cttcatgttc gcccggaatg ccttcaccgt gctggccatg atggactacc cctaccccac | 120 |
| tgacttcctg gtcccctcc ctgccaaccc cgtcaaggtg ggctgtgatc ggctgctgag | 180 |
| tgaggcccag aggatcacgg ggctgcgagc actggcaggt gccctttccc ccggccccag | 240 |
| atgggcaagt gtggagaccc caggcttggc ttgggtcctg gggccgggtg gggcgaggat | 300 |
| ccgcagcccg gccaggggct ttgcctcctg ccccagggct gtggtggggt ggacagcacg | 360 |
| accttcccag aaaccctggg ggaggcaggg ccgtccctg ggaccctct cagcactggc | 420 |
| tgtagccagg cccagcttgg gtgggtgctg cccaaggggc cccttggggt ccccagcatg | 480 |
| gagggcaaca gagggcagca ggccccaccc tgccccgtgg agagccgggg ggccctcaac | 540 |
| agtcaggccc ggggctggca gcacagacac cgccgacctc caagcaggta gcctggaggg | 600 |
| ccttcctcac tgggacctac agatcccaga gccccagatc ccctgcagga ccattccgag | 660 |
| ggggggacagg ttggtggccc ggagcccgcg gtgtgtctgt gtg | 703 |

<210> SEQ ID NO 176
<211> LENGTH: 1049
<212> TYPE: DNA
<213> ORGANISM: Homo sapiens
<220> FEATURE:
<223> OTHER INFORMATION: lysosomal Pro-X carboxypeptidase

<400> SEQUENCE: 176

| tttttttttt ttttttttgcc aggcctccag gcgtttattc agcccctccc ctctgccgcc | 60 |
| agctgcttga gtgaagcccc cactccatga ggagccttga ccccctcca gtcctgtgct | 120 |
| cagaggctga gtctgggccc cccacgcaga gctggctgct gctcacgcct ggctgccttt | 180 |
| acccactcgc cgatgatggt ggcctccagc ttccgcgcct caaccacgga agcaggatct | 240 |
| tctgggtggg aggctctgag gtcgaggtgg tgcgctcccc cctgggatgg tgacggcgat | 300 |
| gactgaggca ctcagggttc ctccgaatcc cgccccctgc ccagggggtt ccagggttcc | 360 |
| cgttgggaga agatgatgtt gctgggcggc tctgagatct ggtagtcccc aggccctggc | 420 |
| cgttcggggc cggtgccgca gcccagtggg gtcagcacag cttgtggtag agccggtaga | 480 |
| tgtcggtagc agtgctcgga agcccgaggc gttgtagacc agccctgcca gtgctcgcag | 540 |
| ccccgtgatc ctctgggcct cactcagcag ccgatcacag accaccttga cggggttggc | 600 |
| agggagggga cccaggaagt cagtgggta gggtagtcc atcatggcca gcacggtgaa | 660 |
| ggcattccgg gcgaacatga agagctgggt caggtccttc tcgtctgaca gcggctggca | 720 |
| ggtgccgaac tccagcggaa ccgtgtcgta ggctccctgt aggaacaagt ccttgatctg | 780 |
| tcggaacgct tcccgcacac cctgggtgca tttgggactc tggccctcaa agtccgccgt | 840 |
| gacgtccgcg aagaactggt tggagtcgcc gaggcctgcc acagctagaa cgggcgcgct | 900 |
| ggccgccagc gcccccgcca ccaggtgggg atacttcatc ctcaggtagg cactgagcat | 960 |

```
cccccccataa cttccaccga aggcgatggc gggggcatcc tgggccccga ggtcgcgtcg    1020
tagcgcgcgg agcagctctg cgaagtcgg                                      1049

<210> SEQ ID NO 177
<211> LENGTH: 279
<212> TYPE: DNA
<213> ORGANISM: Homo sapiens
<220> FEATURE:
<223> OTHER INFORMATION: zinc proteases
<220> FEATURE:
<221> NAME/KEY: misc_feature
<222> LOCATION: (1)..(279)
<223> OTHER INFORMATION: n = a, t, c or g

<400> SEQUENCE: 177
gacctgatgc tatcagaaga ggatccgggg actatgctct ccatataaca nagagattaa     60
tagaatntta tgaagactac tntaaagtgc cctataccct gccaaaacta gatcttttan    120
ctgtgcctaa gcatncgtat gctgctatgg agaactgggg actaagtntt tttgtggaac    180
aaagaatact gctggatccc aggtnacat ctatntntta ttngctggat gtcaccatgg     240
tcattgttca tgagatatgt caccagaggt ttggtgacc                           279

<210> SEQ ID NO 178
<211> LENGTH: 673
<212> TYPE: DNA
<213> ORGANISM: Homo sapiens
<220> FEATURE:
<223> OTHER INFORMATION: thimet oligopeptidase
<220> FEATURE:
<221> NAME/KEY: misc_feature
<222> LOCATION: (1)..(673)
<223> OTHER INFORMATION: n = a, t, c or g

<400> SEQUENCE: 178
cgagcagcaa gtacagaagc agacaaaaga ctttctcgtt ttgatattga gatgagcatg     60
agaggagata tatttgagag aattgttcat ttacaggaaa cctgtgatct ggggaagata    120
aaacctgagg ccagacgata cttggaaaag tcaattaaaa tggggaaaag aaatgggctc    180
catcttcctg aacaagtaca gaatgaaatc aaatcaatga gaaaagaat gagtgagcta    240 tgtattgatt taacaaaaa cctcaatgag gatgatacct tccttgtatt ttccaaggct    300
gaacttggtg ctcttcctga tgatttcatt gacagtttag aaaagacaga tgatgacaag    360
tataaaatta ccttaaaata tccacactat ttccctgtca tgaaganatg ttgtttccct    420
gaaaccagaa naaggatgga aatggctttt aataccaggt gcnaagagga aaaccacctn    480
gttttggngc agcttctccc nctgcgaaac canggtgggc aaacttctcc ggttttttcc    540
canattgctg aacttcccnt ccctggaaat tgaaacncng gcccaaganc ncaancccg    600 ggtttaccnc ccttcttgaa tnaattttag ccccnaaatt ttaaancccc tngggtttaa    660
nccaaaccaa aaa                                                       673

<210> SEQ ID NO 179
<211> LENGTH: 505
<212> TYPE: DNA
<213> ORGANISM: Homo sapiens
<220> FEATURE:
<223> OTHER INFORMATION: asticin/m 12a metalloproteases

<400> SEQUENCE: 179
gcttggatga cttctatgtg aagggttct actgtgcaga gtgccgagca gctggtacgg     60
aggagactgc atgcgatgtg gccaggttct gcgagcccca aagggtcaga ttttgttgga    120
```

```
aagctatccc ctaaatgctc actgtgaatg gaccattcat gctaaacctg ggtttgtcat      180
ccaactaaga tttgtcatgt tgagcctgga gtttgactac atgtgccagt atgactatgt      240
tgaggttcgt gatggagaca accgcgatgg ccagatcatc aagcgtgtct gtggcaacga      300
gcggccagct cctatccaga gcataggatc ctcactccac gtcctcttcc actccgatgg      360
ctccaagaat tttgacggtt tccatgccat ttatgaggag atcacagcat gctcctcatc      420
cccttgtttc catgacggca cgtgcgtcct tgacaaggct ggatcttaca aagtgtgcct      480
gcttggcagg ctatactggg cagcg                                            505

<210> SEQ ID NO 180
<211> LENGTH: 696
<212> TYPE: DNA
<213> ORGANISM: Homo sapiens
<220> FEATURE:
<223> OTHER INFORMATION: astacin/m 12a metalloproteases
<220> FEATURE:
<221> NAME/KEY: misc_feature
<222> LOCATION: (1)..(696)
<223> OTHER INFORMATION: n = a, t, c or g

<400> SEQUENCE: 180
cgtccgntcc gtctcctcct ctctctctcc atctgctgtg ttatggcct gtcgctggag        60 cacaaaagag tctccgcggt ggaggtctgc gttgctcttg cttttcctcg ctggggtgta     120
cgcttgtgga gagactccag agcaaatacg agcaccaagt ggcataatca aagcccagg      180 ctggccttct gaatatcctg caaaaatcaa ctgtagctgg ttcataaggg caaacccagg     240
cgaaatcatt actataagtt ttcaggattt tgatattcaa ggatccagaa ggtgcaattt     300
ggactggttg acaatagaaa catacaagaa tattgaaagt tacagagctt gtggttccac     360
aattccacct ccgtatatct cttcacaaga ccacatctgg attaggtttc attcggatga     420
caacatctct agaaagggtt tcagactggc atatttttca gggaaatctg aggaaccaaa     480
ttgtgcttgt gatcagtttc gttgtggtaa tggaaagtgt ataccagaag cctgaaaatg     540
taataacatg gatgaatgtg gagatagttc cgatgaagag atctgtgcca agaagcaaa     600 tcctccaact gctgctgctt ttcaaccctg tgcttacaac cagtccagtg tttatcccgt     660
ttaccaaagt tacacttgcc tcccgaatct ttaaan                               696

<210> SEQ ID NO 181
<211> LENGTH: 498
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(498)
<223> OTHER INFORMATION: n = a, t, c or g

<400> SEQUENCE: 181
ttatttttgt gttttttgaag atttatttca gagtgagcat cagcgaccta caagaacctg      60
ggacagaagc caatgcctcc cgtttccctg tgatgtgaaa caggaccctg tgcttcctgt     120
ggacttcaag aaatgtggac ttgagctttg ccatcccttc ccctgatcct gtttcataga     180
ttttgctgtt atattctctg tatctttaca gggatcggga ggctgaatta gtgttattca     240
gggttagtaa ctgtcccttc cttaacggtg gtggtcctga tagttcgcac attttttggct    300 gtcccaaaga gcagtgcaat tatgaaggcg taaatacgac caaagaccac tctcagatac     360
```

| | |
|---|---:|
| atcactgatt gctggctttg tttgacggaa cgtgttcttt ttggaggtgg cccgctgttg | 420 |
| acactcccac cagcacctct tcttaggcac agtggaggat cccagcctat atggcaatgg | 480 |
| cagttccttc tgttgtgn | 498 |

<210> SEQ ID NO 182
<211> LENGTH: 86
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(86)
<223> OTHER INFORMATION: n = a, t, c or g

<400> SEQUENCE: 182

| | |
|---|---:|
| gacgcgtntg gggcnncccc tcncnagaaa annnnnnncc cnnattnttc cccnnccccn | 60 |
| gcccccctatn tgcngaaagg gggggc | 86 |

<210> SEQ ID NO 183
<211> LENGTH: 86
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(86)
<223> OTHER INFORMATION: n = a, t, c or g

<400> SEQUENCE: 183

| | |
|---|---:|
| gacgcgtntg gggcnncccc tcncnagaaa annnnnnncc cnnattnttc cccnnccccn | 60 |
| gcccccctatn tgcngaaagg gggggc | 86 |

<210> SEQ ID NO 184
<211> LENGTH: 99
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(99)
<223> OTHER INFORMATION: n = a, t, c or g

<400> SEQUENCE: 184

| | |
|---|---:|
| ctgtgctcgc cttcagcgcn ngcccagccc nacgtccgcg ccccggtggt gggcccgacg | 60 |
| cccgcattcc gcccgtgtcc atgcgcagaa ctcccgccc | 99 |

<210> SEQ ID NO 185
<211> LENGTH: 558
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(558)
<223> OTHER INFORMATION: n = a, t, c or g

<400> SEQUENCE: 185

| | |
|---|---:|
| gggatcgacc cccgtctgcc cacgcgtccg tctacccccc ccctttttt tctttttttt | 60 |
| tttttttttt tttttttttt tttccgggca ccaacgttgg ttttaatggc atcaacaccc | 120 |
| agaaggtcac acgtcanttc tggttggcaa cgtctagggg tgagggctg tggcctccat | 180 |

```
tcggccccac agcctttgaa aactggctgc ccggtcccac ccgcttcccg ccccgcccca    240
ctgaaaaaac actaaacnat tgcactgaca gacanacccc aaaacgcccg gcctcccaca    300
cacccacggg gctgtcaaan tcaaccaggg ctttggcntc actcggcggt ggcccggggc    360
tgcccccaaa atantgttta tcaaatntga cacaggttca tttacaaact ggggctctgg    420
aaggtctact tctgtggctc taaaaaactt gtctctcatg gcttctctcg gaatnccngg    480
aanttgggcc ctggataacc ctgttgtagg ttggttgggt ttatttttntt aaggaaattn    540 ttaaggcatt ttggtaan                                                  558
```

<210> SEQ ID NO 186
<211> LENGTH: 506
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(506)
<223> OTHER INFORMATION: n = a, t, c or g

<400> SEQUENCE: 186

```
cgaaagccac ccctaggcca attgcctgga tctcctcccc tctcccttct ttaaacgagc     60
ttgcctccct cctgccaagt ttgagggcaa ggctaagaaa tgtcagccac ggaaacaact    120
ctattatctg gtgactttgg gtaatgtgaa tcagtgcctg aggacctttg ctgtgtcctt    180
ggtacagaac catccacttg acctaactac ctcccctggc cgcgctctcg ctcttctctt    240
ctttgttaag ccaacaacta tcaccctctc ctactcttct tctccctgcc ccctggaggg    300
cactgtgttt ggttgtgcaa atgtatttac tatgcgtgtt tccagcagtt ggcattaaag    360 tgccttttc taataaaatc aagtttatta tgacagtttc ctgatggttg aaagtaagca    420
tcttgataaa gggtcaccat taaaaaaaaa ttttgcataa aggtgctgca tgggttgggg    480
tagccccgcc cccacctgaa aactgn                                         506
```

<210> SEQ ID NO 187
<211> LENGTH: 669
<212> TYPE: DNA
<213> ORGANISM: Homo sapiens
<220> FEATURE:
<223> OTHER INFORMATION: ADAM family of matelloprotease
<220> FEATURE:
<221> NAME/KEY: misc_feature
<222> LOCATION: (1)..(669)
<223> OTHER INFORMATION: n = a, t, c or g

<400> SEQUENCE: 187

```
tttagtaggg cttttttattg tttttaggcc attgcctgct cagtcccgac agcattcccc     60
cttcttgaaa gtagggcttt ttattgtttt taggccattg cttgctcagt cccgacagca    120 ttccccttc ttgaaacttc actatagctg ctgacactct tctgaactttt tctgacttg    180 atactctgaa ttaaaccaag tataagtgtc attttcttct aagagaatat tagtgtcagc    240
atatttttct tcataaatct tgtgtataaa tcctgataac agcctccatc ggttcaattc    300
catatgagat gttttcagc tgcattgttc ccctgagtcc tgaacatacg ctgagagtca    360
caagagaatt tggaatatccc gcaacatatc cattataaat gcaatccatc tgaactagca    420
gaggtttgga atgacggatg tcattttcgt cataagaatt aataacagaa gctgaagata    480
aaattgatag tatgttgagg aggagttttt gcatccgatg atgaaatctt catgtaaata    540
```

```
acattatgtt ctggatctgt ttttgcatcc gatgaagaaa tcttctctgg aaatgtggtc    600
cgcaggaaga ttttatgagg attgaggtct gcatgcatcc caccaagtcc agtgagaagc    660 accagaagn                                                            669
```

<210> SEQ ID NO 188
<211> LENGTH: 930
<212> TYPE: DNA
<213> ORGANISM: Homo sapiens
<220> FEATURE:
<223> OTHER INFORMATION: thimet oligopeptidase
<220> FEATURE:
<221> NAME/KEY: misc_feature
<222> LOCATION: (1)..(930)
<223> OTHER INFORMATION: n = a, t, c or g

<400> SEQUENCE: 188

```
gcctccnaaa tgtggaaact gactttgtag aggtgccatc gcaaatgctt gaaaattggg     60
tgtgggacgt cgattccctc cgaagattgt caaaacatta taaagatgga agccctattg    120
cagacgatct gcttgaaaaa cttgttgctt ctaggctggt caacacaggt cttctgaccc    180
tgcgccagat tgttttgagc aaagttgatc agtctcttca taccaacaca tcgctggatg    240
ctgcaagtga atatgccaaa tactgctcag aaatattagg agttgcagct actccaggca    300
caaatatgcc agctaccttt ggacatttgg caggggata cgatggccaa tattatggat    360
atctttggag tgaagtattt tccatggata tgttttacag ctgttttaaa aagaaggga    420 taatgaatcc agaggttgga atgaaataca gaaacctaat cctgaaacct ggggatctc    480 tggacggcat ggacatgctc cacaatttct tgaaacgtga gccaaaccaa aaagcgttcc    540
taatgagtag aggcctgcat gctccgtgaa ctggggatct tggtagccg tccatgtctg    600 gaggacaagt cgacatcacc atgtgttact ggcctggaaa ctgaagggag ttttgcaagt    660
gaaaatttag atttctattg acatcctttt gttttctaat tttaaaaatt ataaagatgt    720
aaatggaatt ataaatactg tgacctaaga aaagacccac tagaaagtaa ttgtactata    780
aaatttcata aaactggatt tgatttcttt ttatgaaagt tcatatgaa tgtaacttgg    840 atttttttact attataatct aggataatat gatataagga gggcctaaga attttttaaat    900 tggaatccat atatatggta taatttgggn                                     930
```

<210> SEQ ID NO 189
<211> LENGTH: 507
<212> TYPE: DNA
<213> ORGANISM: Homo sapiens
<220> FEATURE:
<223> OTHER INFORMATION: asticin/m 12a metalloproteases
<220> FEATURE:
<221> NAME/KEY: misc_feature
<222> LOCATION: (1)..(507)
<223> OTHER INFORMATION: n = a, t, c or g

<400> SEQUENCE: 189

```
cggtttgatc acttggaagt tcgagatggg ccatttggtt tctctcctct tatagatcgt     60
tactgtggcg tgaaaagccc tccattaatt agatcaacag ggagattcat gtggattaag    120
tttagttctg atgaagagct tgaaggactg ggatttcgag caaaatattc atttattcca    180
gatccagact ttacttacct aggagattgt cagttcgagc tctcgggagc tgatggaata    240
gtgcgctcta gtcaggtaga acaagaggag aaaacaaaac caggncaagc cgtttgattg    300
catctngacc nttaaagcca ctccaaaagc taagatttat ttnaggttcc nagattatca    360
aatgggagca ctcaaatgaa tgcaagagaa actttcgttg ccagtctatg atgggaagca    420
```

```
gtttcttttt naaaacccga agggcccaag tttttncagc actgttggcc cattnatgtt    480
aattgntttt aaaanccggg aatttgn                                       507
```

<210> SEQ ID NO 190
<211> LENGTH: 512
<212> TYPE: DNA
<213> ORGANISM: Homo sapiens
<220> FEATURE:
<223> OTHER INFORMATION: astacin/m 12a metalloproteases
<220> FEATURE:
<221> NAME/KEY: misc_feature
<222> LOCATION: (1)..(512)
<223> OTHER INFORMATION: n = a, t, c or g

<400> SEQUENCE: 190

```
tcgagcggcc gcccgggcag gtactggtag tggaagggat tgccgtggcc caaaaaaacc    60
caagatggac aaaatattgg aatcaagcat attcctgcaa cccagtgtgg catttgggtt   120
cgaaccagca atggaggtca ttttgcttcg ccaaattatc ctgactcata tccaccaaac   180
aaggagtgta tctacatttt ggaagatcgt tactgtggcg tgaaaagccc tccattaatt   240
agatcaacag ggagattcat gtggattaag tttagttctg atgaagagct tgaaggactg   300
ggatttcgag caaaatattc atttattcca gatccagact ttacttacct aggaggtatt   360
ttaaatccca ttccagattg gtcagttcga gctctcggga gctgatggaa tagtgcgctc   420
tagtcaggta gaacaagagg agaaaacaaa accaggccaa gccgttgatt gcatctggac   480
cattaaagcc acttcaaaag ctaagattta tn                                 512
```

<210> SEQ ID NO 191
<211> LENGTH: 933
<212> TYPE: DNA
<213> ORGANISM: Homo sapiens
<220> FEATURE:
<223> OTHER INFORMATION: astacin/m 12a metalloproteases
<220> FEATURE:
<221> NAME/KEY: misc_feature
<222> LOCATION: (1)..(933)
<223> OTHER INFORMATION: n = a, t, c or g

<400> SEQUENCE: 191

```
cgtccgaagg gattgccgtg gcccaaaaaa cccaagatgg acaaaatatt ggaatcaagc    60
atattcctgc aacccagtgt ggcatttggg ttcgaaccag caatggaggt cattttgctt   120
cgccaaatta tcctgactca tatccaccaa acaaggagtg tatctacatt ttggaagctg   180
ctccacgtca aagaatagag ttgacctttg atgaacatta ttatatagaa ccatcatttg   240
agtgtcggtt tgatcacttg gaagttcgag atgggccatt tggtttctct cctcttatag   300
atcgttactg tggcgtgaaa agccctccat taattagatc aacagggaga ttcatgtgga   360
ttaagtttag ttctgatgaa gagcttgaag gactgggatt tcgagcaaaa tattcattta   420
ttccagatcc agactttact tacctaggag gtattttaaa tcccattcca gattgtcagt   480
tcgagctctc gggagctgat ggaatagtgc gctctagtca ggtagaacaa gaggagaaaa   540
caaaaccagg ccaagccttt gattgcatct ggaccattaa agccactcca aaagcttaag   600
atttatttga ggttcctaga ttatcaaatg gagcactcaa atgaatgcaa gagaaacttc   660
gttgcagtct atgatggaag cagttctatt gaaaacctga aggccaagtt ttgcagcact   720
gtggccaatg atgtaatgct taaaacagga attggagtga ttcgaatgtg ggcagatgaa   780
ggtagtcggc ttagcaggtt tcgaatgctc tttacttcct ttggtggagc ctcccctgca   840
```

```
caagcagcac tttcctttg ccatngcaac atgtgcatca ataattcctt aagtcngtaa    900
tggtgtccaa aattgtgcat accctgggg atn                                  933
```

<210> SEQ ID NO 192
<211> LENGTH: 455
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(455)
<223> OTHER INFORMATION: n = a, t, c or g

<400> SEQUENCE: 192

```
tttatgtcat caaatattta ttgagtgggc cttctggctg gcatgggcg acacaaatgc     60 cccctgccac catcagagag atcccaggcc ccagggtctt attgccacag tttctgcagt   120
ccattggggg gcggaagtgg ccaggggcat gtgggccggg gtccaggagc agactccagc   180
ctgagtcccc tgtgcccatg gtacccactc tgcccaccag gaaggtgctg caggctggct   240
cctccaggcc ctggcaggag gtgctgaagg acatggtcgg cttagatgcc ttgcatgctc   300
cagccggtgt ctcaagtact tccagccagt cacacattgt gtggaagagc agaaccatca   360
taacggcgag gttgtgctct ggcccgatta ccagttgtga ccgtcgctgc ctgacaacta   420
gccggagggc ataggtaaag ccctgagtga ggatn                              455
```

<210> SEQ ID NO 193
<211> LENGTH: 355
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(355)
<223> OTHER INFORMATION: n = a, t, c or g

<400> SEQUENCE: 193

```
cgcgtccgct cttacagata ttnacttggt aaatgtgcat gtggggaaga gggaatgcta    60
ngttgatagg gctggtggct tctgaatttg gtatttgaac tacgagtccc tatagagggg   120
ctgctttatg ggaagtnttt ctctgaccag gtacaacacc tgactttaaa ggcctgaaat   180
gctaccattt cttcctctgg ctcaaaattc ttccctgggg agagagttat attcccttat   240
ttattgatat ttagtccaga acaccagttc taacgaagca tgccgtgtct cttcatctac   300
aggatgcaat aggctgattg tatttaaaaa tcaaagtacc caaaactgag tcccn         355
```

<210> SEQ ID NO 194
<211> LENGTH: 461
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(461)
<223> OTHER INFORMATION: n = a, t, c or g

<400> SEQUENCE: 194

```
tggaggggac caaaaccttg aattttatan agaagtctaa agaaagggga acaagactca    60
taagattgga gaatcatatt tgaatactta aaacaaagct aatgctaaaa agaaactata   120
aatgtctctg gaggcacttc aaagctgtca gccctaatgg cactaagttg cttctataaa   180
```

```
atatgtgctt atgtaaaagc aggattttag ttatgggcta agtctaattt cttttctttg      240
gtaatacagt tctctctctc tctctctctc tttctctgtg tgtctgtttt atcaaagcaa      300
tataagcact tgttagaata atgtaatagt taagaagacc ttgccctgtc tttcccatcc      360
caatccccgt ttcttcctcc catcaggcaa ctgctcttaa tatttctatt tttaattttg      420
atagttatct ccacatataa ataatgagct tgtgttccta t                         461
```

<210> SEQ ID NO 195
<211> LENGTH: 570
<212> TYPE: DNA
<213> ORGANISM: Homo sapiens
<220> FEATURE:
<223> OTHER INFORMATION: angiotensin-converting enzyme

<400> SEQUENCE: 195

```
tttaccccgc gtccgaatat attgattatt cagaaataga caatacattt tttaattacc       60
caaggactga ctgttttgtg cattttactg ttggttgtct tcagtagaga atagtaatag      120
ggcagagaaa agtatatatt ttgcctcagt cagtcccacc accacaatgg actattggga      180
tattttctaa aaaaccaatc aatttgccca tgattacctc acaataatt agtgctacct       240 ggggtactct caaatataca gcttttgaaa ctgtagatga aaaaagctct actcagagtt      300
tttgtcaaga ctgtgcctgg gttgaatatc agtcaattgc ctacacttct aaacaataag      360
tgccaatgtc tcaattttct caccctgaat gatagaagct agctttatca aatgccaagg      420
ttagaaagcc tggaaataaa acttaagcac agacattcaa gttttttgaaa agcataagcc     480 taaattcaga taaatcacac tgatatattg tactatgcat agaaagttgt aggtggcgtt      540
cagggaagac tttgatttta ataaagcaat                                       570
```

<210> SEQ ID NO 196
<211> LENGTH: 1149
<212> TYPE: DNA
<213> ORGANISM: Homo sapiens
<220> FEATURE:
<223> OTHER INFORMATION: peptidase family m17
<220> FEATURE:
<221> NAME/KEY: misc_feature
<222> LOCATION: (1)..(1149)
<223> OTHER INFORMATION: n = a, t, c or g

<400> SEQUENCE: 196

```
gatgaacacc gacaccttcc tcgaggagat taacaaagtt ggaaaggagc tgggatcat       60 cccaaccatc atccgggatg aggaactgaa gacgagagga tttggaggaa tctatgggt      120 tggcaaagcc gccctgcatc ccccagccct ggccgtcctc agccacaccc cagatggagc     180
cacgcagacc atcgcctggg tgggcaaagg tcgcgtctat gacactggag gcctcagcat     240
caaagggaag actaccatgc cggggatgaa gcgagactgc ggggtgctg cggccgtcct     300 gggggccttc agagccgcaa tcaagcaggg tttcaaagac aacctccacg ctgtgttctg     360
cttggctgag aactcggtgg ggcccaatgc gacaaggcca gatgacatcc acctgctgta     420
ctcagggaag acgtggaaa tcaacaacac ggatgcccga gggcaggctg gtgctggcag     480
atggcgtgtc ctatgcttgc aaggacctgg gggccgacat catcctgaac atggccacct     540
tgaccggggc tcagggcatt gccacaggga agtaccacgc cgcggtgctc accaacagcg     600
ctgagtggga ggccgcctgt gtgaaggcgg caggaaagtg tggggacctg gtgcacccgc     660
tggtctactg ccccgagctg cacttcagcg agttcacctc agctgtggcg gacatgaaga     720
```

-continued

| | |
|---|---|
| actcagtggc ggaccgagac aacagcccca gctcctgtgc tggcctcttc atcgcctcac | 780 |
| acatcggctt cgactggccc ggagtctggg tccacctgga cattgctgca ccggtgcatg | 840 |
| ctggtgagcg agccacaggc ttcggtgtgg ccctccttct ggcgctcttc ggccgtgcct | 900 |
| ctgaggaccc tctgctgaac ctggtgtccc cactgggctg tgaggtggat gtcgaggagg | 960 |
| gggacgtggg gagggactcc aagagacgca ggcttgtgtg agcctcctgc ctcggccctg | 1020 |
| acaaacgggg atcttttacc tcactttgca ctgattaatt ttaagcaatt gaaagattgc | 1080 |
| ccttcaaaaa aaaaaaaaaa aaaaaaaaat tccgtgccca gtggtgacag gagtgagcca | 1140 |
| ttcttctcn | 1149 |

<210> SEQ ID NO 197
<211> LENGTH: 1361
<212> TYPE: DNA
<213> ORGANISM: Homo sapiens
<220> FEATURE:
<223> OTHER INFORMATION: ubiquitin carboxy-terminal hydrolases family 2
<220> FEATURE:
<221> NAME/KEY: misc_feature
<222> LOCATION: (1)..(1361)
<223> OTHER INFORMATION: n = a, t, c or g

<400> SEQUENCE: 197

| | |
|---|---|
| gaccccgtc cntancagcg gaggctggac gcttgcatgg cgcttgagag attccatcgt | 60 |
| gcctggctca cataagcgct tcctggaagt gaagtcgtgc tgtcctgaac gcgggccagg | 120 |
| cagctgcggc ctgggggttt tggagtgatc acgaatgagc aaggcgtttg ggctcctgag | 180 |
| gcaaatctgt cagtccatcc tggctgagtc ctcgcagtcc ccggcagatc ttgaagaaaa | 240 |
| gaaggaagaa gacagcaaca tgaagagaga gcagcccacg agagcgtccc agggcctggg | 300 |
| actaccctca tggcctggtt ggtttacaca acattggaca gacctgctgc cttaactcct | 360 |
| tgattcaggt gttcgtaatg aatgtggact tcaccaggat attgaagagg atcacggtgc | 420 |
| ccagggggag ctgacgagca gaggagaagc gtccctttcc agatgcttct gctgctggag | 480 |
| aagatgcagg acagccggca gaaagcagtg cggcccctgg agctggccta ctgcctgcag | 540 |
| aagtgcaacg tgcccttgtt tgtccaacat gatgctgccc aactgtacct caaactctgg | 600 |
| aacctgatta aggaccagat cactgatgtg cacttggtgg agagactgca ggccctgtat | 660 |
| acgatccggg tgaaggactc cttgatttgc gttgactgtg ccatggagag tagcagaaac | 720 |
| agcagcatgc tcaccctccc actttctctt tttgatgtgg actcaaagcc cctgaagaca | 780 |
| ctggaggacg ccctgcactg cttcttccag cccagggagt tatcaagcaa agcaagtgc | 840 |
| ttctgtgaga actgtgggaa gaagacccgt gggaaacagg tcttgaagct gacccatttg | 900 |
| ccccagaccc tgacaatcca cctcatgcga ttctccatca ggaattcaca gaccgagaaa | 960 |
| gatcttgcca ctcccttgta cttccccag agcttggatt tcaagccaag atccttccaa | 1020 |
| ttgaagcgag agtcttgttg atgcttgagg agcagtctgg agggcagtat gagcttttg | 1080 |
| ctgtgattgc gcacgtggga atggcagact ccggtcatta ctgtgtctac atccggaatg | 1140 |
| ctgtggatgg aaaatggggtt ctgcttccaa taccccaata cctgctcggt ntcctccgaa | 1200 |
| tacacccacc ctactacnna aacccactac cacaccccnc gaanctnnnn nnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn n | 1361 |

<210> SEQ ID NO 198
<211> LENGTH: 502

<210> SEQ ID NO 198 (continued)
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 198

```
cacccccgcg tccgctcaga tcaaggatgt tcaaacgtca agtaattgtg agagttccct      60
gtaatgtaac gaggccttgc aaagattcca atacaaggca gtttcatcct tttgaggcct     120
aacttgggga ggaaatggaa ggagtcatgt tgccctgtgc agagtcatgc atgtgatctg     180
tgttatgata gcaaatggcc agtgttagtt actcttgggg aaagtagtgg gattggatga     240
aggccattgg gggaggccag tgtagcttaa acctttatt taagtatgtg tctgtatggt     300
tttgaaattt ttatattatt ttttaactta gaaataaatg acttaaatat tccctcaaag     360
gcagtcatct gtagggctt taacaaatat ttgtagtttt taaatgtca agagatggc      420 ttcttactga gatattttcc tgtgtggtga ttttgtttag aaatggagca tctactgttg     480
tcacggctat attcggaggc at                                             502
```

<210> SEQ ID NO 199
<211> LENGTH: 1438
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(1438)
<223> OTHER INFORMATION: n = a, t, c or g

<400> SEQUENCE: 199

```
cgggcaggta cagaaagtca gagaacactt acagaacttg ggaaaaactc agctttcaca      60
gctgacaggc ataagaaaaa agaaaacttt tgggaanaac tccaacacta acaagcaaa      120 gttattaaaa gtaaatggaa acaaccactg cccatttgtt gccacagggc cttcggaatt     180
tggggaacac atgtttcatg aatgccatcc ttcagtcact cagtaacatt gagcagtttt     240
gctgttattt caagaactg cccgccgtgg agttaaggaa tgggaaaaca gcaggaaggc      300
ggacatacca caccaggagc caaggggata acaatgtgtc tttggtagaa gagtttagaa     360
agacactctg tgctttatgg caaggcagcc agactgcatt tagcccagag tccttatttt     420
atgttgtttg ggaagattat gccaaacttt agggggctat caacagcagg acgcccatgg     480
aatttcatgg cgctaccttt tgggaccacc tacacttggg aacttcaggg cggtttcaac     540
ggtgtttccc gctcaggcaa ttttttgcagg gagaatttct actctgtctg gcaagttaac     600
aagtgttgca taaatggagc atctactgtt ggtcacggct atattcgggg ggcattctcc     660
aaaatgaggt taactgcctc atatgtggga cagaatctag aaagtttgga tccattccta     720
gacctttcat tagatattcc aagtcagttc agaagtaagc gctctaagaa tcaagaaaat     780
ggaccagttt gttcgttacc gagattgtct tcgcagtttt accgacttag gaagaacttg     840
atgagacaga gttatataat gtgccataaa tgcaaaaaga aacaaaagtc cacaaaaaag     900
ttttggattc aaaaactacc caaggtngct atgcttacat ttgaaaagat ttcattggac     960
agcatattta aggaaataaa gttgatacat acgtaggaat ttccactgag aggcctagac    1020
atgaaatgct acttactaga tcctgagaac agtggcccgg agagctgcct gtatgacctc    1080
gccgctgtgg ttgtacacca tggttcccgg ggttggttct ggacattaca cagcatacgc    1140
aactcacgag gcccgctggg tttccacttc aaatgacagt acttgtaaca cttgacttga    1200
```

```
ccgaaggaga ctgtgggtga aaggcgaagg ctaaccatcc cttttctac gttggaacac    1260 caggccaaag ctggatcgga taaacttaa tacctgctgc aaatcatcat tcaccaacca    1320
taccagagaa acatttccag ttttccacaa atacttgata caagatttaa tttcattatg    1380
cacttttcaa tttccctatt tttggattta agttttgtca atggtagtga cttacctg     1438
```

<210> SEQ ID NO 200
<211> LENGTH: 778
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 200

```
accccgcgtc cgcccagttc ttcatctata aaattgattc atccaaccga gagcagcggc      60
tagaggacaa aggagacacc ccactggagc tgggtgacga ctgtatgcct ggctctcgtc     120
tggcggaaca atgagcgctt gcaggagttt gtgttggtag cctccaagga gctggaatgt     180
gctgaggatc caggctctgc cggtgaggct gcccgggccg ccacttcac cctgaccag      240 tgcctcaacc tcttcacacg gcctgaggtg ctggcacccg aggaggcctg gtactgccca     300
cagtgcaaac agcaccgtga ggcctccaag cagctgttgc tatggcgcct gccaaatgtt     360
ctcatcgtgc agctcaagcg cttctccttt cgtagtttta tcttggcgtg acaagatcaa     420
tgacttggtg gagttccctg ttaggaacct ggacctgaag caagttctgc attggtcaga     480
aagaggagca gctgcccagc tacgatctat atgctgtcat caaccactat ggaggcatga     540
ttggtggcca ctacactgcc tgtgcacgcc tgcccaatga atcgtagcag tcagcgcagt     600
gaccgtgggc tggcgcttgt ttgatgacag cacagtgaca acgtagacg agagccaagg     660 ttgtgacgcc gttatgccta tgtactcttc taccgccggc ggaactctcc tgtggagagg     720 cccccaggg caggtcactc tgagcaccac ccagacctag ccctgcagc tgaggctg        778
```

<210> SEQ ID NO 201
<211> LENGTH: 693
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(693)
<223> OTHER INFORMATION: n = a, t, c or g

<400> SEQUENCE: 201

```
ggtttaaaaa caggagacta tttaatccat ctaaaaatac aaatcaggaa aagggggaa      60 ccataggaaa atcctccacc tctaacagag cgaagttact ggctttctgc ttgctccaag    120
aatcccaagg cttgatgttt ggaaggaatt atctgttctt caactactcc cagatactca    180
agacataagt tacacacatc tggagaaggg ttctgccctg ctgaagctag atgggagctc    240
aatgcatggg agaaaggagc atcaatcatc atcagccaca gcccttggga gcaaagccct    300
agacgcctcc ttcaagcccc ctgctggttg gtttcatcat tatctcgcct cttccaaatc    360
tgaatgtaag cctctgacag tgtgatcatc tggggaagga tgtcagtcac ctggaggtct    420
tggtaattca taccatttgc ctgtcccatg atgaagcacg tggatccggt agagccctcg    480
gagggcttgc cgttcatgca cgatgttggc aatgaggtca taggtggtat tcttgtgtac    540
tgcttgtact tcttcagaca agtattctct cagntccaca tttgtaatan gggaattgac    600
aatagttgga tcttctcaca aagaagttgt cttagtgata tcttgataca aagattggnt    660
```

| | |
|---|---|
| tggaggcant tggtnagctg gaggcttcag aat | 693 |

<210> SEQ ID NO 202
<211> LENGTH: 2276
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 202

| | |
|---|---|
| gcgctcgagc gtgcttggcg cctgcgctgg acgactcggc cggtaggtgg agatgtccgg | 60 |
| ccggtctaag cgggagtctc gcggttccac tcgcgggaag cgagagtctg agtcgcgggg | 120 |
| cagctccggt cgccgtcaag cgggagcgag atcgggagcg ggagcctgag gcggcgagct | 180 |
| cccggggcag ccctgtgcgc gtgaagcggg agttcgagcc ggcgagcgcg cgcgaggccc | 240 |
| cggcttctgt tgtcccgttt gtgcgggtga agcgggagcg cgaggtcgat gaggactcgg | 300 |
| agcctgagcg ggaggtgccg agcccacat tggccgagtt ggattcctga ggacccggag | 360 |
| gagccgccac tgccccgtac cttgacaccc attaacagga attgttgctt ggacttttga | 420 |
| cttttgagaaa catgtgttcc tatctccctc tcacacatca atgcttatgc ctgtctggtg | 480 |
| tgtggcaagt actttcaagg ccgggggttg aaagtctcac gcctacattc acagtgtcca | 540 |
| gtttagccac catgtttttcc tcaacctcca caccctcaag ttttactgcc ttccagacaa | 600 |
| ctatgagatc atcgattcct cattggagga tatcacgtat gttttgaagc ccacttttcac | 660 |
| aaagcagcaa attgcaaact tggacaagca agccaaattg tcccgggcat atgatggtac | 720 |
| cacttacctg ccgggtattg tgggactgaa aacataaag gccaatgatt atgccaacgc | 780 |
| tgtccttcag gctctatcta atgttcctcc tctccggaac tactttctgg aagaagacaa | 840 |
| ttataagaac atcaaacgtc ctccaggggg atatcattgt tcttgttggt ccagcgtttt | 900 |
| ggagagctga tgagaaagct ctggaaccct cgaaatttca aggcacatgt gtctccccat | 960 |
| gagatgcttc aggcagttgt actttgcagt aagaagactt ttcagatcac caaacaagga | 1020 |
| gatgggcgtt gactttctgt cttggtttct gaatgctctg cactcagctc tgggggggcac | 1080 |
| aaagaagaaa aagaagacta ttgtgactga tgttttccag gggtccatga ggatcttcac | 1140 |
| taaaaagctt ccccatcctg atctgccagc agaagaaaaa gagcagttgc tccataatga | 1200 |
| cgagtaccag gagacaatgg tggagtccac ttttatgtac ctgacgctgg accttcctac | 1260 |
| tgcccccctc tacaaggacg agaaggaagc agctcatcat ttccccaagt gccactcttc | 1320 |
| aacatcctgg gctaagttca atgggcatca cttgagaagg aatataagac ttacaaggag | 1380 |
| aactttctga gcgcttcca gcttaccaag gttgccttcc atatctaaat cttttgtatc | 1440 |
| aagagattca ctaaggaaca acttctttgt tgaggaagga atccaactat ttgtcaattt | 1500 |
| ccctattaca aatgtggatc tgagagaata cttgtctgaa gaagtacaag cagtacacaa | 1560 |
| gaataccacc tatgacctca ttaccaacat cgtgcatgac ggcatgccct ccgaggttcg | 1620 |
| ctaccggtat ccacgttgct tcatcatggt tacaggcaaa tggttatgaa ttacaagacc | 1680 |
| ttccaggtga ctgacatcct tccccagatg atcacactgt cagaggctta catgtcagat | 1740 |
| ttggaagagg cgagataatg atgaaaccaa ccagcagggg gcttgaagga ggcgtctagg | 1800 |
| ggctttgctc ccaagggctg tggctgatgg atggtaaata agaacacaga agctgtagct | 1860 |
| gaacacaggt gggctggtgg gcttcctagg gccagcccag cttgtatggg gttctggcta | 1920 |
| caccagagca ccaagagccc acttgcctgg gatggcccca cactgtcact cagctgttct | 1980 |

-continued

```
ttgatcattt ttttctagat tgatgctcct ttctcccatg cattgagctc ccatctagct    2040
tcagcagggc agaacccttc tccagatgtg tgtaacttat gtctgagtat ctgggagtag    2100
ttgaagaaca gataattcct tccaaacatc aagccttggg attcttggag caagcagaaa    2160
gccagtaact tcgctctgtt agaggtggag gattttccta tggttccccc catttcctga    2220
tttgtatttt tagatggatt aaatagtctc ctgtttttaa aaaaaaaaaa aaaagg        2276
```

<210> SEQ ID NO 203
<211> LENGTH: 503
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 203

```
ttttttttt tttttttgta atcaaattta cttttattca caaattattt tttcaaacat      60
ttactacatt gaaataaaaa tttatcaaca aaatattaaa atctggttta taattttgat   120
ttttaaagtg aggaaaattc taccttggca gtgaagacag cctgtcttgc ctcaggtatc   180
atataaagtt gctgaatagt agaagctaag taacaagtag ctccaaggtt agtaaggcca   240
acaaatctac attcagcacg gacatcttca tgaggccagt aatcccattt ataaggtgca   300
tgggactgca tgtgttgtgc cataacccag ttgtgtatta gcctgtagtt ctcaacagac   360 cccttacca tctctactaa caaatcgtaa gcggcagctc ttgaagaatg tgatttgcac   420
tttggctgtt gtcggtcctt tagacttggc aacaaaaaca ggagattgaa gatatctctc   480
aaaaattcct gtcccggggc ggg                                            503
```

<210> SEQ ID NO 204
<211> LENGTH: 507
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 204

```
gaaagttgtt tacatcgctg gaggacagaa atagaaaatg acaccagaga tttgcaggaa     60
agcatatcca gaatccatcc gaacaattga attaatgtac tctgacaaat ctatgataca   120
agttccttat cgattacatg ccgttttagt tcacgaaggc caagctaatg ctgggcacta   180
ctgggcatat attttгgatc atcgtgaaag cagatggatg aaagtacaat gatattgctg   240
tgacaaaatc catcatggga agagctagtg agggactctt ttggtggtta taagaaatgc   300
cagtgcatac tgtttaatgt acataaatga taaggcacag ttcctaatac aagaggagtt   360
taataaagaa actgggcagc ccccttgttg gtatagaaac attaccaccg gatttgagag   420
attttgttga ggaagacaac caacgatttg aaaaagaact agaagaatgg gatgcacaac   480
ttgcccagaa agctttgcag gaaaagc                                        507
```

<210> SEQ ID NO 205
<211> LENGTH: 576
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 205

```
ccgcggacag tctcaacaat gacaacaagt attccctgtt tgctgttgtt aaccatcaag     60
ggaccttgga gagtggccac tacaccagct ttatccggca gcacaaagac cagtggttca   120
```

```
agtgtgacga tgccatcatc accaaggcca gcatcaagga cgtcctggac agcgaagggt    180
acttgctgtt ctatcacaaa cagttcctgg aatacgagta gccttatctg cagctggtca    240
gaaaaacaaa ggcaatgcat tggcaagcct cacagcacag agtgaccgct acctgctgta    300
agattatggg tccatgaaag cagtaagctg gacacagagg tgtagtgtgc gggacagagg    360
gccttgcaga tgcctttctg ttggtgtttt agtgttaaaa tacggagagt atggaactct    420
tcacctccat tttctcagcg gctgtgaagc agcctcctag cttcggaagt acggacacta    480
cgtcgcgttt tcaagcgtgt ctgttctgca ggtaacagca ttcaagctgc acgtggaagc    540
atttcgcggg ttttctagaa acaggcattt tcttat                              576
```

<210> SEQ ID NO 206
<211> LENGTH: 424
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 206

```
tccgcagaaa tttaggtaac ttctcccttta gtctcaagag cgagtcttgc ttttaatgg     60 gtgccgttta tgttgctgcc cgccctgtgt gcctggctcc tctgggtgcc ttggtgtctg    120
ctggtggctg gcagtgggcg cagcggagga gagttgtgct gcagctcata cggtgtgtct    180
gtcatctcag tctggagtaa atgcagtgtc tgccggtgtc tgatgggttc tgtccctcgt    240 atttctttg ccttctatcc ctgcctggca gccaagggtg ttggtcgcga agctggagtg    300
gcctctggtg gagcctgcat cttgtctcgt ctgcctctgc tttacatttg gtgtactttc    360
gggcgtggtg ggcagtaaaa tgacaccgtg attgagcttg tcagcagagc tgaaagagaa    420
agta                                                                 424
```

<210> SEQ ID NO 207
<211> LENGTH: 1465
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 207

```
ctagttact ctggacaccg gtcccctcac atcccgtata acgttgctgc acctggtgtg     60
gacccacgcg aggcacctag caggctacga gcagcaggac gcccacgagt tcctcatcgc    120
ggccctggac gtgctccacc gacactgcaa aggtgatgac aatgggaaga aggccaacaa    180
ccccaaccac tgcaactgca tcatagacca cgatcttcac aggcgggttg cagtcagacg    240
tcacctgcca agtctgccat ggagtctcca ccaccatcga cccttctgg gacatcagct    300 tggatctccc cggtcttcc acccattct ggccctgag cccagggagc gagggcaacc    360
gtggtaaacg gggaaagcca ccgtgtcggg aaccaccacg ctcacggact gcctgcgacg    420
attcaccaga ccagagcact tgggcagcag cgccaagatc aagtgcagcg gttgccatag    480
ctaccaggag tccacaaagc agctcactat gaagaaactg cccatagtag cctgttttca    540
tctcaaacga tttgaacact cagccaagct gcggcggaag atcaccacgt atgtgtcctt    600 cccctggag ctggacatga ccccttttcat ggcctccagc aaagagagca ggatgaatgg    660
acagtaccag cagcccacgg acagtctcaa caatgacaac aagtattccc tgtttgctgt    720
tgttaaccat caagggacct tggagagtgg ccactacacc agctttatcc ggcagcacaa    780
```

```
agaccagtgg ttcaagtgtg acgatgccat catcaccaag gccagtatta aggaccgtac    840
tggacagcga aagggtactt gctgttctat cacaaacagt tcctggaata cgagtagcct    900
tatctgcagc tggtcagaaa aacaaaggca atgcattggc aagcctcaca aagtgatcct    960
ccctggccac cccctcccc caagcctccc gccgcctccc cggcctggtg acaccacctc    1020
ccatgcagat gtggccccctc tgcacctggg acccatcggg tcgggatgga ccacacggac    1080
ggggaggctc ctggagcttg cttttgaagat ggatgagatg aggggtgtgc tctgggtggg    1140
aggagcaagc gtacaccccg tcaccagaac atctccttgt gtcatgacat gggggtgcaa    1200
cgggggcctc acagcacaga gtgaccgctg cctggcgttc cccagcactc ggtgtggaaa    1260
ggcccctacc tgctgtaaga ttatgggtcc atgaaagcag taagctggac acagaggtgt    1320
agtgtgcggg acaaaagggc cttgcagatg cctttctgtt ggtgttttag tgttaaaata    1380
cggagagtat ggaactcttc acctccattt tctcagcggc tgtgaagcag cctcctagct    1440
tcggaagtac ctcggccgcg accac                                           1465
```

<210> SEQ ID NO 208
<211> LENGTH: 492
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(492)
<223> OTHER INFORMATION: n = a, t, c or g

<400> SEQUENCE: 208

```
ggaaccacgc gtccgtcccg cgtccgcttt taattaggga acaaatctaa tggaaagacc    60
actcataggc caggtgcggt ggctcacgcc tataatccca gcnctttggg acgctgaggt    120
gggtggatcg cctgaggtca ggagtttgag acatggccaa acccaggcag ctgccagaaa    180
gccttctgca ctccgcaaga cacccccagta aactggggcg tcccaaggtg caagccttc    240 atgaaggcac tgcccagctc acaatcctgt gggccaactt cagtcaactc tcctttccat    300
tagatttgtt cctaattaaa agaccactca taggccaggt gcggtggctc acgcctataa    360
tcccagcact ttgggacgct tgaggtgggt ggatcgcctg aggtcaggag tttgagacat    420
ggtgaaaccc catctctact aaaaatacaa aaattagcct ggcgtggtgg cgcatgcctg    480
tagtcccagc ta                                                         492
```

<210> SEQ ID NO 209
<211> LENGTH: 470
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(470)
<223> OTHER INFORMATION: n = a, t, c or g

<400> SEQUENCE: 209

```
gctttgaaca caatctggcc ttcagatgca gttgagacat tacagtaatc atcaaaataa    60
tcccatctcc accatgctta ttttgcaaaa gcagtatagg gccttcctct catccctcca    120
tagtggttgg aaacagcaat caaattatag cagcgaggcc ctgcgcttgg attaatcaga    180
aattccaata cagccaagtc attgatagga aaatcaacta agttatctaa cttgtttctc    240
aaggatctac tgtaaggaaa aatcacttga ggatgcaaca gctactggga gggcagggat    300
```

| | | |
|---|---|---|
| catacatcca atttcttagt ggtggctgct tcttggacgg atttgggata ccnggggatc | 360 | |
| ttttatccac ttaggttttc cttttttgttt gnaaaagggg tcntgagggc cgtctttttt | 420 | |
| aattttcggc aaaaggtttt ttttttttttt tccagggggag gtttatattn | 470 | |

<210> SEQ ID NO 210
<211> LENGTH: 2786
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(2786)
<223> OTHER INFORMATION: n = a, t, c or g

<400> SEQUENCE: 210

| | |
|---|---|
| tttttttttt tagggtaagt cagtttattg atgtgttgtg atccatcacc cagatatatt | 60 |
| aaacacaaag tacttaagta attcaggatt tcctttccag aaacaaagca ggaataaaaa | 120 |
| ccactatgac aatataaaac ctttgtacat ttttaggtat ttttccttc aatatttaaa | 180 |
| taaacatgat ttcttctggc atgtatttaa tgttaagtga acatgatttt aattagtctt | 240 |
| tttttatcgt tatttcagcc attataaaag ccataaatgt gtttccagaa aaagtgctttt | 300 |
| tgatattatt acagtattct ctcataaaat aggaggtacg cttgtgagtt tagtacttta | 360 |
| gttgtaggca cagcttgcac atgtgtgtcg ctgatgtgaa accactggcc ttttgattc | 420 |
| catttcaaaa tcttgtggaa tatcaccgtg aaagaacaag attagagaga tgactatttg | 480 |
| cgggttcttg ccttggcata gggcagtgta atgccccgac tcatagtac cacgtgtgtt | 540 |
| caacaaactc catataagga atagagtacc cttgtatttt cttctgcaac attcttacat | 600 |
| ttaagggtgc aaaaaggagc caaatctaag atttccggaa aactttatgt gtttgttaac | 660 |
| cttgcgtagg taaaaaccag cctgctgaaa tctctttaaa tgaagagtaa gaacaggagg | 720 |
| agcaagagaa attagcatct gcttttttggc attggtgtaa acatgcttcc tttcacctttt | 780 |
| tatatttgcc tttggtccat tacactgtct ccgtgtgcat acttcacaaa gcagtttatt | 840 |
| cgcatctcga gtttctcat tacgggtgaa ctgatataaa caatgttgga ttgaacactc | 900 |
| atcagtattg aaaacttccc tgtttgcaag agtacagaaa gcagtttctg gatcttcatt | 960 |
| tacaacctca tacacctttg ttccaggagt atgactatca ttcagaatct ctatattat | 1020 |
| ttcatcagga tgaagagcag cattcaaatt taggttttttg aaaccattgg aaatgtccac | 1080 |
| ttctccattg ctcccttccg ttaggtaggc accatttaaa ttcctagtgg gagaagatgt | 1140 |
| taaaacctcc cagatcatta tccatgttga tatttttcat atctacttcc ctctgtggat | 1200 |
| ttttgattgt cagttacact ttcggatcat ttttgcttgg ccattcaaat ctttctggtt | 1260 |
| gacacaatat tctttatgca taacaccctc ttgtgaaata tggttggatt taatatttaa | 1320 |
| cttctccttg aagtgacatt tcagcttcat attcactgtc ttcaggatgg tcaatagtac | 1380 |
| aaatatcatt taaatgaaga acttttcctt gaatttttg ttgtcttcgt tggttcttgg | 1440 |
| cttgcttttt ggcttgtttc tttgcttttt tctgtaagtg cttacgttgt tccagaagga | 1500 |
| atatcacttc tctcttttat gtaactgtcg ttatcttttt cttcctcact atcttgatct | 1560 |
| tcatcctcca cgtgtctttt tcagattttt atcatttaca cttttcttac cactctgatc | 1620 |
| atctaaaact gggagggaca aatcaaggaa agattcatga accaaggaga cagttctgca | 1680 |
| ttgatcacac atgatcatac tagttagttc accaccaaag atgcggtcgg acaaaacttg | 1740 |

-continued

```
gcattgattt ttcttctca taatcgttta acgtttattt tttagttctt catccaactt    1800
ttcagtagaa ttaccaaatg ctttaagtat tcctttactc actctttggt gttcttctgc    1860
tctcatccca tccaataagt agcgaagcag ctcctggctg tcttgctgct gatagccttt    1920
aaaccgcact gcttttttac agacctgaga aaagagttct ttcggtgtca caccccctt    1980 tttggtctct tgcatctcat taagaaactg gctcatggct aaagtaagag ggcctggagg    2040
ctcaaggttt atttctaatg gttctgttaa tgccaaatca ggtggttcaa tttttacaat    2100
tgttccagac attttcactt cttttagtag ttctctaagc actggtgttt gtgacaagtt    2160
ctgcataact gcattgaaga aacatgtgtt tcccaaatta ctgagtcctt tcncggttat    2220
ttggcaagga gaattcatgg gaggattctc tttagccatg ttttccttct tttctctctc    2280
ttgttcattc ttactctctt tttctaattt tccattttca agttcaatat ttccattatc    2340
tttctctgct ggctttggag ttgtaatgct ggcttgtttt ctgacataat caaccacttg    2400
acccaactgg tttgaactac aatactggac ctcattatca catacgtaac accatacact    2460
ccagttgtcc aaactaagaa ccagacagtg aggttcagat cttggcgtca gatagtgctt    2520
caaggcatgc tgctcctgag aatttctgcc acagccctga tggccacatt taagacacag    2580
ccaaactgaa ggcttttctt ctgtttcttc ttcagcttta tctttcactt tattgtcagt    2640
cttacagtct tggcagatat tccattccac attcactaaa gccttttca aattaccttg    2700 ttccaatcct tttctaatgt gtctgcacac aggttctaaa gtttcagagg aatcatcgat    2760
tggaacagtt tttcccttg tccgtt                                          2786
```

<210> SEQ ID NO 211
<211> LENGTH: 805
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(805)
<223> OTHER INFORMATION: n = a, t, c or g

<400> SEQUENCE: 211

```
tttttaaagt taactatttt aattagaatt tgtattctaa caggataaaa taactacatt      60
tagcttgccc tttccagtgg acgcttttgc ccaaatgtca gctaacaagg agtccatctc     120
cttccccacc caagctgtct agcagccaga gtggtagctt tactgtaaca cacagtactt     180
tttgtaatca gactcaaagt cttcatccat actgcttgtg tctgccatct ttttgccatc     240
agtctttggc agaaattgtg catagtctat cccctgctgc tcatagaaaa agaatgtagg     300
cagagtcggt gtcaatttca tcccgggtga gttcctttac agctgctgtc attgtaacag     360
taccacttgc agtttggggt ttttgggcat aagtgacgta atgggccccc acccaggatt     420
ccccgaatgg gcacggaaat tggcatatag gttttaaat agggttaata cgggtatctt      480
ctctttgggg catcagtgct gtcttcttca ctgtgggttt ccaggttgac cattgctgta    540
gccattgcca catgcttcat gctcataaat gaatccattg ccaaagcct acctcatggt     600 cctgaggagt gaccaactct ggttggctgc ccccagcac atgccctcga ctcaagcgtc     660
agccagctca catatctgcc cagccccatt ttctttgctg gcatccaagt tctctttact     720
acttgacagt ttattttgc tgccaatctg gggcagccgg agcctccctt tgctcctcnc     780
caaagtccgt gggctgctaa ttagg                                            805
```

<210> SEQ ID NO 212
<211> LENGTH: 1072
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(1072)
<223> OTHER INFORMATION: n = a, t, c or g

<400> SEQUENCE: 212

```
caggaggcgg acccccgag ggcagcgctg cggggccgtt ttccggccct cctgacgcga      60
cactgcccct ctccgagagc tgagaaggaa aagaggagct tgcggaggtg cggctgcagg     120
ccgttgttgg tcgagctggc gggtcccgcg ggccaggccg tggaggtgtt acctcatttt     180
gaaagtcttg ggaaacagga aaaaattcct aacaaaatgt cagcttttcg aaatcattgt     240
ccacatttgg gattcaagtt gggtgaaata acaaagaag atttgataca aaatcccctt      300
ggtacttgtc agggattgta aagtccaagg accaaatctt tgggcatgtc tggagaatag     360
atgttcatat gttggctgtg gtgaatcaca agtagatcac agcaccatac attctcagga     420
gacaaagcat tatctaactg tgaaccttac cactcttcga gtatggtgtt atgcttgcag     480
caagaagta tttttggat aggaaattag gaactcagcc ttcattgcct catgtaagac      540
aacctcacca atacaagaa acagtgtcc aggatttaa atacccagt aatacaacat         600
taaaaactcc tctggttgcc gtatttgatg atctggatat agaagcggat gaagaagatg     660
aacttagggc aagaggtctt acaggtttga aaaatattgg aaatacttgt tacatgaatg     720
cagcttttgca ggctctttct aattgcccac ctttgacaca gttttttctt gattgtggag    780
gactagctcg aacagataag aaacctgcca tttgtaaaag ttatctcaaa ctaatgacag     840
agctgtggca taaaagcagg ccaggatctg ttgtgcctac tactctgttt caaggaatta    900
aaactgtaaa tccaacattt cggggtatt ctcagcagga tgctcaagaa ttccttcnat     960
gtttaatgga tttgcttcat gaagaattga aagagcaagt catggaagta aagaagatc    1020
cgcaaaccat aaccactgag gagacaatgg aagaagacaa gagccagtcg ga            1072
```

<210> SEQ ID NO 213
<211> LENGTH: 465
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 213

```
gtccgcactg tatgatgtat cattattctg gatttccaga tctctatgaa cctattctgg      60
aggcaataaa ggattttcct aagcccagtg aagagaagat taagttaatt ctcaatcaaa     120
gtgcctggac ttctcaatcc aattctttgg cgtcttgctt gtctagactt tctggaaaat     180
ctgaaactgg gaaaactggt cttattaacc taggaaatac catgttatat gaacagtgtt     240
atacaagcct tgtttatggc cacagatttc aggagacaag tattatcttt aaatctaaat     300
ggggtgcaat tcattaatga aaaaattaca gcatcttttt gcctttctgg cccatacaca     360
gagggaaagc catacgcacc tccggatatt cctttggagg cttccagac ctcccatggt      420
ttactcccca gattcaccag ccaagactgt tcctgaaata cctcc                     465
```

<210> SEQ ID NO 214
<211> LENGTH: 457
<212> TYPE: DNA

<213> ORGANISM: Homo sapiens
<220> FEATURE:
<223> OTHER INFORMATION: ubiquitin carboxyl-terminal hydrolases family 2

<400> SEQUENCE: 214

```
atggagcgag cgccgagccg ggtcagagtt gaacaatgac catagttgac aaagcttctg    60
aatcttcaga cccatcagcc ttatcatgaa tcagcctggc atctccgagg cagtctcacc   120
tggagacatg gatgcaggtt ctgccagctg gggtgctgtg tcttcattga atgatgtgtc   180
aaatcacaca ctttctttag gaccagtacc tggtgctgta gtttattcga gttcatctgt   240
acctgataaa tcaaaaccat caccacaaaa ggatcaagcc ctaggtgatg gcatcgctcc   300
tccacaggaa agtactttc ccatctgaga agatttgtct taagtggcaa caaactcata   360
gagttggagc tgggctccag aaatttgggg caatacctgg ttttgccaat gcagcactgc   420
agtgtttaac ctacacacca cctcttgcca attacat                             457
```

<210> SEQ ID NO 215
<211> LENGTH: 165
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 215

```
gtccgattac ctaaagcgct ttcggcacga ggtgatgtac tcattcaaga tcaacagcca    60
cgtctccttc cccctcgagg ggctcgacct gcgcccttc cttgccaagg agtgcacatc    120
ccagatcacc acctacgacc tcctctcggt catctgccac cacgg                    165
```

<210> SEQ ID NO 216
<211> LENGTH: 460
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 216

```
gcacaacttg accgtgaacc tgacccgttc cgactgtggt gttacgcctg tgagaaggag    60
gtattcctgg agcagcggct ggcagcccct ctgctgggcc cctcttccaa gttctctgaa   120
caggactccc cgccaccctc ccaccctctg aaagctgttc ctattgctgt ggctgatgaa   180
ggagagtctg agtcagagga cgatgacctg aaacctcgag gcctcacggg catgaagaac   240
ctcgggaact cctgctacat gaacgctgcc ctgcaggccc tgtccaattg cccgccgctg   300
actcagttct tcttggagtg tggcggcctg gtgcgcacag ataagaagcc agccctgtgc   360
aagagctacc agaagctggt ctctgaggtc tggcataaga acggccaag ctacgtggtc   420
cccaccagtc tgtctcatgg gatcaagttg gtcaacccaa                          460
```

<210> SEQ ID NO 217
<211> LENGTH: 672
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(672)
<223> OTHER INFORMATION: n = a, t, c or g

<400> SEQUENCE: 217

```
ggcgcgcccg cggagacgcc ggggctctga cgcccgctct gcggcttcgg tgtttgaaca    60
```

```
ggccacagtc caggagcgct acattcagg agctccgcgt agcacctgcc caaccaaact    120
cagccctccg ttaagatcct ggttccatgc cgcagtagga cagcaggccc aagtctgcac    180
atcccaggca gtgagcacac gtatgagagc tgtggtgacg gagtcccagc cccgcagaaa    240
gtgcttttcc ccacggagcg actgtctctg aggtgggagc gggtcttccg cgtgggcgca    300
ggactccaca accttggcaa cacctgcttt ctcaatgcca ccatccagtg cttgacctac    360
acaccacctc tagccaacta cctgctctcc aaggagcatg ctcgcagctg ccaccaggga    420
agcttctgca tgctgtgtgt catgcagaac acattgtcc aggccttcgc caacagcggc    480
aacgccatca gcccgtctc cttcatccga naactgaaaa agatcgcccg cacttccgc    540 tttgggaacc aagaagangc gcatgaattc ctgcggtaca ccatcgacnc catgcaaaaa    600
ncctgcctga atggctgtgc caagttggat cttcaaacnn agctactaac tttggtccat    660 caaattttg ga                                                        672

<210> SEQ ID NO 218
<211> LENGTH: 612
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 218
tccggcgtcg cggtgacacg tgtgtgaggc gccggaggcc cggatggtgc gcgtgctggg    60
ccgcgggccg aaggagtcgc cagggctgcg taggcttgtg gcgcgcccgc ggagaggccg    120
gggctctgac gcccgctctg cggcttcggt gtttgaacag gccacagtcc aggagcgctt    180
acattcagga gctccgcgta gcacctgccc aaccaaactc agccctccgt taagatcctg    240
gttccatgcc gcagtaggac agcaggccca agtctgcaca tcccagtgat gcaccatgcc    300
aatagtggat aagttgaagg aggctcctga aacccggccg caaggactcg gctgatgatg    360
gagaactggg gaagcttctt gcctcctctg ccaagaaggt cctttacag aaaatcgagt    420 tcgagccagc cagcaagagc ttctcctacc agctggaggc cttaaagagc aaatatgtgt    480
tgctcaaccc caaaacagag ggagctagtc gccaccaaga gtggagatga cccaccggcc    540
aggagacagg gcagtgagca cacgtatgag agcttgtggt gacggagtcc cagccccgca    600
gaaagtgctt tt                                                        612

<210> SEQ ID NO 219
<211> LENGTH: 917
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 219
ctgcccaggg aagcttctgc atgctgtgtg tcatgcagaa ccacattgtc caggccttcg    60
ccaacagcgc caacgccatc aagcccgtct ccttcatccg agacctgaaa agatcgccc    120 gacacttccg ctttgggaac caggaggacg cgcatgagtt cctgcggtac accatcgacg    180
ccatgcagaa agcctgcctg aatggctgtg ccaagttgga tcgtcaaacg caggctacta    240
ccttggtcca tcaaattttt ggagggtatc tcagatcacg cgtgaagtgc tccgtgtgca    300
agagcgtctc ggacacctac gaccctact tggacatcgc gctggagatc cggcaagctg    360
cgaatattgt gcgtgctctg gaactttttg tgaaagcaga tgtcctgagt ggagagaatg    420
```

-continued

```
cctacatgtg tgctaaatgc aagaagaagg gtccagccag caaagcgctt caccattcac      480
agaacattca acgtcttaac cctttccctc aagcgctttg ccaacttcag cggggggaag      540
atcaccaagg atgtaggcta tccggaattc ctcaacatac gtccgtatat gtcccagaat      600
aatggtgatc ctgtcatgta tggactctat gctgtcctgg tgcactcggg ctacagctgc      660
catgccgggc actattactg ctacgtgaag gcaagcaatg gacagtggta ccagatgaat      720
gattccttgg tccattccag caacgtcaag gtggttctga accagcaggc ctacgtgctg      780
ttctatctgc gaattccagg ctctaagaaa agtcccgagg gcctcatctc caggacaggc      840
tcctcctccc ttcccggccg ccgagtgtga ttccagatca ctccaagaag aacatcggca      900
atgggattat ttcctcc                                                    917
```

<210> SEQ ID NO 220
<211> LENGTH: 668
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 220

```
ccccgcgtcc gcggacgcgt gggcgaaact gcaaaggaaa tcccgaattg cttggttggt       60
attggtgagc atatttggtt aggagaaata gatgaaaata gttttcataa catcgatgat      120
cccaactgtg agaggagaaa aaagaactca tttgtgggcc tgactaacct tggagccact      180
tgttatgtca acacatttct tcaagtgtgg tttctcaact tggagcttcg gcaggcactc      240 tactatgtc caagcacttg tagtgactac atgctgggag acggcatcca agaagaaaaa       300
gattatgagc ctcaaacaat ttgtgagcat ctccagtact tgtttgcctt gttgcaaaac      360
agtaataggc gatacattga tccatcagga tttgttaaag ccttgggcct ggacactgga      420
caacagcagg atgctcaaga attttcaaag ctctttatgt ctctattgga agatactttg      480
tctaaacaaa agaatccaga tgtgcgcaat attgttcaac agcagttctg tggagaatat      540
gcctatgtaa ctgtttgcaa ccagtgtggc agagagtcta agcttttgtc aaaattttat      600
gagctggagt taaatatcca aggccacaaa cagttaacag attgtatctc ggaatttttg      660
aagggaga                                                              668
```

<210> SEQ ID NO 221
<211> LENGTH: 525
<212> TYPE: DNA
<213> ORGANISM: Homo sapiens
<220> FEATURE:
<223> OTHER INFORMATION: ubiquitin carboxyl-termianl hydrolases family 2

<400> SEQUENCE: 221

```
cgcgtccgcg gacgcgtggg cgccctcgcc aacatggcgg cgcccagttg gggcgggttc       60
gttcgcttcg cgttttggcc agggcggggg tctgggcttt aggcaggtag tatttagttt      120
cacaatgttt ggggacctgt ttgaagagga gtattccact gtgtctaata atcagtatgg      180
aaaagggaag aaattaaaga ctaaagcttt gtaagccacc tgctcctaga gaattcacca      240
atttaagcgg aatcaagaaa tcaggtggaa acctgttacc tcaattccct tcttcagact      300
cttcatttca cacctgaatt cagagaagct ctattttctc ttggcccaga agagcttggt      360
ttgtttgaag ataaggataa acccgatgca aaggttcgaa tcatcccttt acagttacag      420
cgcttgtttg ctcagcttct gctcttagac caggaagctg catccacagc agacctcact      480
gacagctttg ggtggaccag taatgaggaa atgaggcaac atgat                     525
```

<210> SEQ ID NO 222
<211> LENGTH: 1998
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(1998)
<223> OTHER INFORMATION: n = a, t, c or g

<400> SEQUENCE: 222

| | | | | |
|---|---|---|---|---|
| tttaccaagt | gcagtctctc | tttggacatt | taatggaaag caagctgcag tactatgtac | 60 |
| ctgagaattt | ttggaagatt | ttcaagatgt | ggaataaaga actttatgtg agagaacagc | 120 |
| aggatgcata | tgaattcttt | actagtctca | ttgatcagat ggatgaatac ctcaagaaaa | 180 |
| tggggagaga | ccaaattttt | aagaatacat | tcagggcat ctactctgat cagaagatct | 240 |
| gtaaagactg | tcctcacaga | tatgagcgtg | aagaagcttt catggctctc aatctaggag | 300 |
| tgacttcttg | tcagagtttg | gaaatttctt | tggaccaatt tgttagagga aagttctag | 360 |
| aaggaagtaa | tgcgtactac | tgtgaaaagt | gtaaagaaaa gagaataaca gtgaaaagga | 420 |
| cctgtattaa | atctttacct | agcgtcttgg | taattcacct aatgagattt gggtttgact | 480 |
| gggaaagcgg | acgctccatt | aaatatgatg | aacaaataag gtttccctgg atgctaaaca | 540 |
| tggagcctta | cacagtttca | ggaatggctc | gccaagattc ttcttctgaa gttggggaaa | 600 |
| atgggcgaag | tgtggatcag | ggcggtggag | gatccccacg aaaaaaggtt gccctcatag | 660 |
| aaaactatga | acttgtcggt | gtcatcgtac | acagtgggca ggcacacgca ggccactact | 720 |
| attccttcat | taaggacagg | cgagggtgtg | aaaaggaaa gtggtataaa tttaatgaca | 780 |
| cagttataga | agaatttgac | ctaaatgacg | agaccctgga gtatgaatgc tttgaggag | 840 |
| aatatagacc | aaaagtttat | gatcaaacaa | acccatacac tgatgtgcgc cgaagatact | 900 |
| ggaatgccta | tgctttttc | taccaaaggg | tgtctgatca gaactcccca gtattaccaa | 960 |
| agaaaagtcg | agtcagccgt | tgtacggcag | gaagctgagg atctctctct gtcagctcca | 1020 |
| tcttcaccag | aaatttcacc | tcagtcatcc | cctcggcccc ataggccgaa caatgaccgg | 1080 |
| ctgtctattc | ttaccaagct | ggttaaaaaa | ggcgagaaga aaggactgtt tgtggagaaa | 1140 |
| atgcctgctc | gaatatacca | gatggtgaga | gatgagaacc tcaagtttat gaagaataga | 1200 |
| gatgtataca | gtagtgatta | tttcagtttt | gttttgtctt tagcttcatt gaatgctact | 1260 |
| aaattaaagc | atccatatta | tccttgcatg | gcaaaggtga gcttacagct tgctattcaa | 1320 |
| ttcctttttc | aaacttatct | acggacaaag | aagaaactca agggttgata ctgaagaatg | 1380 |
| gattgctacc | attgaagcat | tgctttcaaa | aagttttgat gcttgtcagt ggttagttga | 1440 |
| atatttatt | agttctgaag | gaccgagaat | tgataaagat tttcttactg gagtgcaatg | 1500 |
| tgagagaagt | acgagttgct | gtggccacca | ttctggagaa aaccctagac agtgccttgt | 1560 |
| tttatcagga | taagttaaaa | agccttcatc | agttactgga ggtactactt gctctgttgg | 1620 |
| acaaagacgt | cccagaaaat | tgtaaaaact | gtgctcagta cttttcctg ttcaacactt | 1680 |
| ttgtacaaaa | gcaaggaatt | agggctggag | atcttcttct gaggcattca gctctgcggc | 1740 |
| acatgatcag | cttcctccta | ggggccagtc | ggcaaaacaa tcagataccg tcgatggagt | 1800 |
| tcagcacaag | cacgagaatt | tgggaatctt | cacaatacag tggcgttact tgttttgcat | 1860 |
| tcagatgtct | catcccaaag | gaatgttgct | cctggcatat ttaagcaacg accacccatt | 1920 |

```
agcattgctc cctcaagccc tctgttgccc tcatgaggag gtagaagcct tgtgttcatg    1980
tctgaaggga aaccttan                                                  1998
```

<210> SEQ ID NO 223
<211> LENGTH: 722
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(722)
<223> OTHER INFORMATION: n = a, t, c or g

<400> SEQUENCE: 223

```
ggtgttctgt gggtctcccc tcctgggaag ctctaagtac cctctacctg aatatgtgga     60
atgatctgtg ccctcggaaa tgtttctcct gtttccattt ccttctagga tgtgaaatac    120
cctgagtatc ttgatattcg gccatatatg tctcaaccca acggagagcc aattgtctac    180
gtcttgtatg cagtgctggt ccacactggt tttaattgcc atgctggcca ttacttctgc    240
tacataaaag ctagcaatgg cctctggtat caaatgaatg actccattgt atctaccagt    300
gatattagat cggtactcag ccaacaagcc tatgtgctct tttatatcag gtcccatgat    360
gtgaaaaatg gaggtgaact tactcatccc acccatagcc ccggccagtc ctctccccgc    420
cccgtcatca gtcagcgggt tgtcaccaac aaacaggctg cgcaggcttt atcggaccac    480
agcttccctc tcacatgata aagaatccac ctcacttaaa tgggacatgg accattgaaa    540
gacacgccaa gcagttccat gtcgagtcct aacgggaatt ccagtgtcaa cagggctagc    600
ctgttaatgt tcactntgtc caaatggtc agttaatagg tctcagtgat ccagaacatc     660
tangaaacaa aaaattcaan agtatnacaa caagttgctg tcgcagtgta gntacanacc    720
tt                                                                   722
```

<210> SEQ ID NO 224
<211> LENGTH: 576
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 224

```
ccgggtgaag ctcaggaatc tgattgagcc agagcagtgc accttctgtt tcacggcttc     60
tcgcatcgac atctgccttc gtaagaggca gagtcagcgc tgggggggcc tggaggcccc    120
ggctgcacga ggtgcagtgg gtggtgcaaa ggttgccgtg ccgacaggtc caacccctct    180
ggattcaacc ccaccaggag gtgctcccca cccctgaca ggccaggagg aggcccgggc     240
tgtggagaag gataaatcca aggcacgatc tgaggacaca tgggctagac agtgtggcaa    300
cccgcacacc catggagcat gtaacccccaa agccagagac acacctggcc tcgcccaagc    360
ctacatgcat ggtgcctccc atgccccaca gcccagttag tggagacagc gtggaggagg    420
aggaagagga agagaagaag gtgtgtctgc caggcttcac tggccttgtc aatttaggca    480
acacctgctt catgaacagc gtcattcagt ctctgtccaa cactcgggaa ctccgggact    540
tcttccatga ccgctccttt gaggctgaga tcaacc                              576
```

<210> SEQ ID NO 225
<211> LENGTH: 825
<212> TYPE: DNA
<213> ORGANISM: Homo sapiens

```
<220> FEATURE:
<223> OTHER INFORMATION: ubiquitin carboxyl-terminal hydrolases family 2

<400> SEQUENCE: 225
tggaaggtga taacatgtat acttgttctc attgtgggaa cgaaagtacg agctgaaaaa      60
agggcatgtt ttaagaaatt gcctcgcatt ttgagtttca atactatgag atacacattt     120
aatatggtca cgatgatgaa agagaaagtg aatacacact tttccttccc attaccgttt     180
ggacatgacg ccctatacag aagattttct tatgggaaag agtgagagga agaaggttt      240 taaagaagtc agtgatcatt caaaagactc agagagctat gaatatgact tgataggagt     300
gactgttcac acaggaacgg cagatggtgg acactattat agctttatca gagatatagt     360
aaatccccat gcttataaaa acaataaatg gtatcttttt aatgatgctg aggtaaaacc     420
ttttgattct gctcaacttg catctgaatg ttttggtgga gagatgaccg accaagacct     480
atgattctgt tacagataaa tttatggact tctcttttga aaagacacac agtgcatata     540
tgctgtttta caaacgcatg gaaccagagg aagaaaatgg cagagaatac aaatttgatg     600
tttcgtcaga gttactagag tggatttggc atgataacat gcagtttctt caagacaaaa     660 acattttga acatacatat tttggattta tgtggcaatt gtgtagttgt attcccagta      720
cattaccaga tcctaaagct gtgtccttaa tgacagcaaa gttaagcact tcctttgtcc     780
tagagacatt tattccattc taaagaaaag cccacgatgc ttcag                    825

<210> SEQ ID NO 226
<211> LENGTH: 147
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 226
atgaactcag cgcagtcctc atacacagag gagttgagta gcttattctg gccactacat      60
cgcccacgtg aaagatccac agtctggtga atggtataag tttaatgatg aagacataga    120
aaagatggag gggaagaaat tacaact                                         147

<210> SEQ ID NO 227
<211> LENGTH: 1719
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(1719)
<223> OTHER INFORMATION: n = a, t, c or g

<400> SEQUENCE: 227 cctttctga agataataat gaaacaacaa tgttaattca ggatgatgaa acaattcag        60 aaatgtcaaa ggattggcaa aagagaaga tgtgcaataa gattaataaa gtaaattctg     120
aaggcgaatt tgataaagat agagactcta tatctgaaac agtcgactta acaaccagg     180 aaactgtcaa agtgcaaata cacagcagag cttcagaata tatcactgat gtccattcga    240
atgacctgtc tacaccacag atccttccat caaatgaagg tgttaatcca cgtttatcgg    300
caagccctcc taaatcaggc aatttgtggc caggattggc accaccacac aaaaagctc     360 agtctgcatc tccaaagaga aaaaacagc acaagaaata cagaagtgtt atttcagaca    420
tatttgatgg aacaatcatt agttcagtgc agtgtctgac ttgtgacagg gtgtctgtaa    480
```

-continued

```
ccctcgagac ctttcaagat ctgtccttgc caattcctgg caaggaagac cttgctaagc      540
tgcattcatc aagtcatcca acttctatag tcaaagcagg atcatgtggc gaagcatatg      600
ctccacaagg gtggatagct tttttcatgg aaatatgtga agaggtttgt tgtctcatgt      660
gtccctagct ggttttgggg tccagtagta accttgcaag attgtcttgc tgccttcttt      720
gccagagatg aactaaaagg tgacaatatg tacagttgtg aaaaatgcaa aaagttgaga      780
aatggagtga agttttgtaa agtacaaaac tttcctgaga ttttgtgcat ccaccttaaa      840
agattcagac atgaactaat gttttccacc aaaatcagta cccatgtttc atttccgcta      900
gaaggcttgg atcttcagcc atttcttgct aaggatagtc cagctcaaat tgtgacatat      960
gatcttctgt cagtcatttg ccatcatgga actgcaagta gtgggacact atattagcct     1020
tactgccgaa acaatctaaa taatctctgg tatgaatttg atgatcagag tgtcactgaa     1080
gttttcgagt ctacggtaca aaatgcagaa gcttacgttc ttttctatag gaagagcagc     1140
gaagaggcac aaaaagagag gagaaggata tcaaatttat tgaacataat ggaaccaagc     1200
ctccttcagt tttatatttc tcgacagtgg cttaataaat ttaagacctt tgccgaacct     1260
ggccctattt caaataatga ctttctttgt attcatggag gtgttcctcc aagaaaagct     1320
ggttatattg aagacctggt tttgatgctg cctcagaaca tttgggataa cctatatagc     1380
aggtatggtg gaggaccagc tgtcaaccat ctgtacattt gtcatacttg ccaaattgag     1440
gcggagaaaa ttgaaaaaag aagaaaaact gaattgaaa tttaaattca gcataacaga     1500
gcgttccaaa aagaggactc tccagctact ttttattgca tcagtatgca gtggtttaga     1560
gaatgggaaa gttttgtgaa gggtaaagat ggagatcctc caggtcctat tgacaatact     1620
aagattgcag tcactaaatg tggtaatgtg atgcttaggc aaggagcana ttctggccng     1680
atttctgaag aaacatggaa ttttctgcag tctattta                             1719
```

<210> SEQ ID NO 228
<211> LENGTH: 629
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(629)
<223> OTHER INFORMATION: n = a, t, c or g

<400> SEQUENCE: 228

```
gtncggtttg aacnagagac naaagctgtt gccngcttca tagagagcaa gaaggatgat       60
attttgtgct tcctgaccat gcactcttat gggcagttaa ttctcacacc ttacggctac      120
accaaaaata aatcaagtaa ccacccagaa atgattcaag ttggacagaa ggcagcaaat      180
gcattgaaag caaagtatgg aaccaattat agagttggat cgagtgcaga tattttatat      240
gcctcatcag ggtcttcaag agattgggcc cgagacattg ggattccctt ctcatatacg      300
tttgagctga gggacagtgg aacgtatggg tttgttctgc cagaagctca gatccagccc      360
acctgtgagg agaccatgga ggctgtgctg tcagtcctga tgatgtgta tgcgaaacac      420 tggcactcgg acagtgctgg aagggtgaca tctgccacta tgctgctggg cctgctggtg      480
tctgcatgtc tcttctctaa gtgcattctg gccaggcctg ctcaacccca gtggcatgag      540
tgtggctgga ggaacgggt ntatggttgt aaagaaacca ataattaac taaaaatact      600 tctatttaat aaggaaaaaa aaaaaaaaa                                         629
```

<210> SEQ ID NO 229
<211> LENGTH: 653
<212> TYPE: DNA
<213> ORGANISM: Homo sapiens
<220> FEATURE:
<223> OTHER INFORMATION: zinc carboxypeptidases
<220> FEATURE:
<221> NAME/KEY: misc_feature
<222> LOCATION: (1)..(653)
<223> OTHER INFORMATION: n = a, t, c or g

<400> SEQUENCE: 229

| | | | | |
|---|---|---|---|---|
| caagttattt | ggataaatgg | gaacaaagaa | aagaaaacag | cctcagcctc cagccttccc | 60 |
| ttttgggacc | tgcctcacaa | tgcaccctct | cttccaggca | cttcttgatt tccaaaagga | 120 |
| aaccaccagt | gagtgagtcc | actatgaagc | ttactaccag | gttggtttaa tttgcatggg | 180 |
| tcccagacga | agtctcaagg | gcccagaagg | gtcacccacg | ctgtcgtctc ttccgccccc | 240 |
| gcagcttcag | ccgcctggct | ggcaggctga | cgggctgctt | cccaaacttc tccatgatct | 300 |
| ctcggatcct | ggccatgttg | gttttgctaa | gtgtgaagtc | acaccttgtg gccccatgt | 360 |
| catagccaac | catacagttc | ttggtggatg | cagtgaaacc | ttcggccttt gctgtgacca | 420 |
| catactctcc | agggttcagg | aggcgccagt | aatccccatc | gttggctgtt cggatgtcat | 480 |
| ggttaatgcc | ttctacggag | ataatggcgt | ttgggattcc | gttttccatg tgaatctctc | 540 |
| accaagcctt | taatgccacg | atgaacctgc | tgcatgaaca | cgatcagaga gtacctgtta | 600 |
| ttatctcact | cctncggcag | ctgcctctca | tgtgggtatt | tatcacagcc cac | 653 |

<210> SEQ ID NO 230
<211> LENGTH: 796
<212> TYPE: DNA
<213> ORGANISM: Homo sapiens
<220> FEATURE:
<223> OTHER INFORMATION: cathepsin

<400> SEQUENCE: 230

| | | | | |
|---|---|---|---|---|
| gtccggggag | aggccaggag | cggctccgtt | tggcttggtg | gctgcaggcc caggctgtcg | 60 |
| cgctcgctc | ggtgagtgca | ggatccagca | tccaggatgt | ggtggtcctt gatccttctt | 120 |
| tcttgcctgc | tggcactgac | cagtgcccat | gacaagcctt | ccttccaccc gctgtcggat | 180 |
| gacctgatta | actatatcaa | caaacagaat | acaacatggc | aggctggacg caacttctac | 240 |
| aatgttgaca | taagctatct | gaagaagctg | tgtggcactg | tcctgggtgg acccaaactg | 300 |
| ccaggaaggg | ttgcgttcgg | tgaggacata | gatctacctg | aaacctttga tgcacgggaa | 360 |
| caatggtcca | actgcccgac | cattggacag | attagagacc | agggctcctg cggctcttgt | 420 |
| tgggcatttg | gggcagtgga | agccatttct | gaccgaacct | gcattcacac caatggccga | 480 |
| gtcaacgtgg | aggtgtctgc | tgaagacctg | cttacttgct | gtggtatcca gtgtggggac | 540 |
| ggctttaatg | tggctatcc | ctctggagca | tggagcttct | ggacaaaaaa aggcctggtt | 600 |
| tcaggtggag | tctacaattc | tcatgtaggc | tgcttaccat | acaccatccc tcctgcgag | 660 |
| caccatgtca | atggctcccg | tccccatgc | actggagaag | gagatactcc caggtgcaac | 720 |
| aagagctgtg | aagctggcta | ctccccatcc | tacaaagagg | ataagcactt tgggtacact | 780 |
| tcctacagcg | tgtcta | | | | 796 |

<210> SEQ ID NO 231
<211> LENGTH: 586
<212> TYPE: DNA
<213> ORGANISM: Homo sapiens
<220> FEATURE:

```
<223> OTHER INFORMATION: ADAM family of metalloprotease
<220> FEATURE:
<221> NAME/KEY: misc_feature
<222> LOCATION: (1)..(586)
<223> OTHER INFORMATION: n = a, t, c or g

<400> SEQUENCE: 231
gacaagtgaa agggtttata caagcaaaaa gaatgtacac tttctggcaa gagaatacag      60
aagagatttg aatgtcatga agatattaaa aaaaaaagaa tacagaggag ataagagact     120
tgagtaagaa taggtcatgt tttaataaaa ctaccaaaag aacaaaacag attcttcaac     180
ccaggaggac atgtgagtca caataccctt taatccacag gttggctcct tggtttctgg     240
aactttctgc ctcctgtaaa cgatgtgcgg gtggtaccct ccctcaacca gtggatgctt     300
cttcacgggt tcaatgaaaa agtctccatg tggtagttgg aaaaatccag tcagtccatg     360
gcaggcactg agggctgccg tcccaactct ggtgccctgc tgtagaaccg tgccactgag     420
atggcagagg ggggcagagg aagccatcat cttaacatgg agaggttcc catatctctt      480 ctccatgatg tagctattgg aaagaaatcc ttcattgacc gtcaagttaa aaaacaggtc     540
cttctcctcg tgagaaattc tgtagtacac ccagtcctct gagccn                    586

<210> SEQ ID NO 232
<211> LENGTH: 644
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(644)
<223> OTHER INFORMATION: n = a, t, c or g

<400> SEQUENCE: 232
tggtcgcggc cgaggtacct ttattgttcc atgttatagt gtaatatttc agtagttctt      60
ttcatggtta gttaaatcct aagccaatga caaaagaaa atggtaacca gatgtgaaac      120
tccgcttcct ctcctctgta tcataacaca acncattcat cctggctctt tggcggttca     180 cttttcttgtc ctcatcagga agtggagtca ttggataggg gtattttatg ctggaggcaa    240
tagacccagt tgatgaagaa ggagacttgg caggagataa agtctcagtt gaattagacc     300
cgaggtctaa atcttttgcc tctgattntc tttttgttgc ctcccaggtt accttgccaa     360
gagttacttc gaggtcgccc attttcacaa gatgtctgaa atatgttttg tgtctggaat     420
cctttcactc caagaatgag agagcccatt tgacctctgt tctcgatagg ttttatancc     480
ccacgcagtt attcctaata tnagggccag cnctaaaatg gtgccagcaa ttatgcctat     540
tatgatattg gtgccagcaa caccattgcc agacagagtg ataccagtct ttgcatcatc     600
attgtgaggg aagtaagtgt tgcaatcaga acctatccag tgtn                      644

<210> SEQ ID NO 233
<211> LENGTH: 430
<212> TYPE: DNA
<213> ORGANISM: Homo sapiens
<220> FEATURE:
<223> OTHER INFORMATION: ADAM family of metalloprotease
<220> FEATURE:
<221> NAME/KEY: misc_feature
<222> LOCATION: (1)..(430)
<223> OTHER INFORMATION: n = a, t, c or g

<400> SEQUENCE: 233
cgtccggcat tatgccccaa caacaggcat aangcaagat ggctcaaaat gtcatacaat      60
```

```
ttacgagtgc cttaaagttc attgtatgga ccctaataat cagtgcttac aattatatgg    120
atatggtgca aaatcagcct cacaagagtg ttacaattca atgaacagca aaggggacca    180
atttggaaac tgtggcattt ctaccagtcc tgggtcacaa tatgttcggt gttcagatgg    240
taatatattt tgtgggaaac ttatatgttc aggtattaca ggcttaccaa aaatcaatct    300
ccaacataca atgattcagg tccctcaggg agatggctca tgttggagca tggatgccta    360
tatgagtact gacattcctg atgaaggaga tgtgcacaat ggcacttact gtgcaccaaa    420
caaagtctgc                                                           430
```

`<210>` SEQ ID NO 234
`<211>` LENGTH: 491
`<212>` TYPE: DNA
`<213>` ORGANISM: Homo sapiens
`<220>` FEATURE:
`<223>` OTHER INFORMATION: ubiquitin carboxyl-terminal hydrolases family 2

`<400>` SEQUENCE: 234

```
tcggcggccg cccgggcagg tacatttctc tttgtcatga attgcatact ttgttccaag     60
tcatgtggtc tggaaagtgg gcgttggtct caccatttgc tatgctacac tcagtgtgga    120
gactcattcc tgcctttcgt ggttacgccc aacaagacgc tcaggaattt ctttgtgaac    180
ttttagataa aatacaacgt gaattagaga caactggtac ctgatcctaa tccagttccg    240
gattgacctc cgcttgtaga tgaaccagat cctggttgtt gtgatttatc tgtattagtt    300
tgtccacatg aaatagctat tagaggtatt aaagctagtg ccacaagcga accaaaacta    360
actaataatt tctttgaaaa tatcgatttt ttcactttc ctcaattctt tattttctta    420
aataaattaa taaataaaag caaaaataaa agaagtgtgc attatttgtg tgtgacctcg    480
gccgcgacca c                                                         491
```

`<210>` SEQ ID NO 235
`<211>` LENGTH: 237
`<212>` TYPE: DNA
`<213>` ORGANISM: Homo sapiens
`<220>` FEATURE:
`<223>` OTHER INFORMATION: ubiquitin carboxyl-terminal hydrolases family 2
`<220>` FEATURE:
`<221>` NAME/KEY: misc_feature
`<222>` LOCATION: (1)..(237)
`<223>` OTHER INFORMATION: n = a, t, c or g

`<400>` SEQUENCE: 235

```
agnggccgcn cgngcaggna cagaccccat aacacagatt aaccaagtta ctcatgatca     60
agcagtgntg ctacaaagtg ccnttnagag cattcctaat ccctcatccg nntgcatgct    120
tagaaatgtg tnanttcgtc ttgctcanca gatatctgat gaggctnnaa gatatatgcc    180
tgatatttgt gtaattagag ctntacaaaa aatnatctgg gcatcaggat gtgggtc        237
```

`<210>` SEQ ID NO 236
`<211>` LENGTH: 384
`<212>` TYPE: DNA
`<213>` ORGANISM: Homo sapiens
`<220>` FEATURE:
`<223>` OTHER INFORMATION: ubiquitin carboxyl-terminal hydrolases family 2

`<400>` SEQUENCE: 236

```
cgtccggtga cccgcggctg ggcgcctcgg ccatgactgc ggagctgcag caggacgacg     60
cggccggcgc ggcagacggc cacggctcga agttatagac cttactcatg ataacaaaga    120
```

```
tgatcttcag gctgccattg ctttgagtct actggagtct cccaaaattc aagctgatgg    180
aagagatctt aacaggatgc atgaagcaac ctctgcagaa actaaacgct caaagagaaa    240
acgctgtgaa gtctggggag aaaacccccaa tcccaatgac tggaggagag ttgatggttg    300
gccagttggg ctgaaaaatg ttggcaatac atgttggttt agtgctgtat tcagtctctc    360
tttcaattgc ctgaatttcg aaga                                            384
```

<210> SEQ ID NO 237
<211> LENGTH: 931
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(931)
<223> OTHER INFORMATION: n = a, t, c or g

<400> SEQUENCE: 237

```
cgcgtccgcc cacgcgtccg gtttgctttg cgggagctga caggctcgct cttggcactc     60
attgagatgg tagtgtactg ctgtttctgt aatgagcatt tttccttcac aatgctgcat    120
ttcattaaga accaactaga aacggctcca cctcatgagt taaagaatac gttccaacta    180
cttcatgaaa tattggttat tgaagatcct atacaagcag agcgagtcaa atttgtgttt    240
gagacagaaa atggattact agctttgatg caccacagta atcatgtgga cagtagtcgc    300
tgctaccagt gtgtcaaatt tcttgtcact cttgctcaaa gtaagtatt gaattaaaat    360 gcagggagga aatggtgttt taattacaag tcacatatga gcagaagggg aacatgtgcc    420
cggttttgat acctggagaa tctgactcag tcagggcctg cttgcttgga aggtacagaa    480
acctatttgc atgatctcaa aaaatatga ggggaagtat taaaagagtg acagatcttt    540
atagaatccc agaaaagctc acccatcagg ccttatgtca gaaggcagg aatcagggca    600 gatatggagg ctttaagagc aagagttcat gagctttcac tcaaggtttc tcattaatgt    660
aacccagcta ccagctcttc aggctctagg tccctaacct cagaatagcc tttcaaatca    720
tgtcacctgt agctcctgag cacttgtgaa cccaggcacc ngtgtcaaga accttgcctg    780
tattatctta tttcatcttt gtaacaactt catgaggtta gtacagttgt gagtcatata    840
tcatgggtag tntaagtgac atgcctagaa tcatagaatg aaaacttgaa cacaggctga    900
ttgactgcaa aatgaangtt cttttttttt n                                    931
```

<210> SEQ ID NO 238
<211> LENGTH: 809
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(809)
<223> OTHER INFORMATION: n = a, t, c or g

<400> SEQUENCE: 238

```
tggattacta gctttgatgc accacagtaa tcatgtggac agtagtcgct gctaccagtg     60
tgtcaaattt cttgtcactc ttgctcaaaa gtgtcctgca gctaaggagt acttcaagga    120
gaattcccac cactgagct gggctgtgca gtggctacag aagaagatgt cagaacatta    180
ctggacacca cagagtaatg tctctaatga aacatcaact ggaaaaacct ttcagcgaac    240
catttcagct caggacacgt tagcgtatgc cacagctttg ttgaatgaaa aagagcaatc    300
```

```
aggaagcagt aatgggtcgg agagtagtcc tgccaatgag aacggagaca ggcatctaca    360
gcagggttca gaatctccca tgatgattgg tgagttgaga agtgaccttg atgatgttga    420
tccctagagg aacatgccca gcctgagagg agtcaagaca caatactgga tgctcagcac    480
cttcttggaa tcagaatctc gaacccttg gaagagcctg gagattggac tgggaaagct     540
tgctgtgact tgggccggat cgtgtatttc tcaaggaaag catttttaag ccctagaagg    600
tttgggagct gttttggcagt gggagaactc cggcatgtgg atcagctgtc ccgggagcgt   660
ggtctatatg tggattcaca tttctgtgga gatttcggaa tagagccagt ggcagacttt    720
tttgttcacg aacataccaa gagtgacata agctggtgct ttctctccga tgctacaaaa    780
gaaattcctt tggnntttat attttaagn                                      809
```

`<210>` SEQ ID NO 239
`<211>` LENGTH: 859
`<212>` TYPE: DNA
`<213>` ORGANISM: Homo sapiens
`<220>` FEATURE:
`<223>` OTHER INFORMATION: ubiquitin carboxyl-terminal hydrolases family 2
`<220>` FEATURE:
`<221>` NAME/KEY: misc_feature
`<222>` LOCATION: (1)..(859)
`<223>` OTHER INFORMATION: n = a, t, c or g

`<400>` SEQUENCE: 239

```
aaaacgacag gcccttgcct tcccggtccc ggaaagatgg gaactcctgt gcttcgtgcc    60
catggtatac gattttgcag aggctgtaaa attgattgtg gggaagacag agctttcatt    120
ggaaatgcct atatcgctgt ggattgggat cccacagccc ttcaccttcg ctatcaaaca    180
tcccaggaaa gggttgtaga tgagcatgag agtgtggagc agagtcggcg agcgcaagcc    240
gagcccatca acctggacag ctgtctccgt gctttcacca gtgaggaaga gctaggggaa    300
aatgagatgt actactgttc caagtgtaag acccactgct tagcaacaaa gaagctggat    360
ctctggaggc ttccacccat cctgattatt caccttaagc gatttcaatt tgtaaatggt    420
cggtggataa aatcacagaa aattgtcaaa tttcctcggg aaagttttga tccaagtgct    480
tttttggtac caagagaccc ggctctctgc cagcataaac cactcacacc ccaggggggat   540 gagctctctg agcccaggat tctggcaagg gaggtgaaga agtggatgt gcagagtttg     600 gctggggaat aggacatgct cctgagcaaa agcccatcct cactcagcgc taacatcatc    660
agcagcccaa aaggttctcc ttcttcatca agaaaaagtg gaaccagctg tccctccagc    720
aaaaacagca gccctaatag cagcccacgg actttggggg gaggagcaaa gggggctct     780 ggctgcccca nattggcngc aaaataaac tgtcaagtng taagaagaac ttggatgcca     840
gcaaagagaa tggggctgn                                                  859
```

`<210>` SEQ ID NO 240
`<211>` LENGTH: 594
`<212>` TYPE: DNA
`<213>` ORGANISM: Homo sapiens
`<220>` FEATURE:
`<223>` OTHER INFORMATION: ubiquitin carboxyl-terminal hydrolases family 2
`<220>` FEATURE:
`<221>` NAME/KEY: misc_feature
`<222>` LOCATION: (1)..(594)
`<223>` OTHER INFORMATION: n = a, t, c or g

`<400>` SEQUENCE: 240

```
nccccgcgtc cgcactgcac tgcagcctgg gcaacagagt gagaccctgt ctgaaaataa    60
```

-continued

```
ataaataaat aaatattata aataaataag tgtgaacatt gattaccacc attttattga    120
tgggaaaacc aaaaccagaa ggttaaattt tctcagtttc ctgttttatt aatacctacc    180
tctacctacg attatatatg ccagttttta ctagtaacaa gcttatatcc atgttctagg    240
tggtctggcc gtaatcatcg agagaagatt ggggtccatg tcgtctttga ccaggtatta    300
accatggaac cttactgctg cagggacatg ctctcctctc ttgacaaaga gacctttgcc    360
tatgatctct ccgcagtggt catgcatcac gggaaagggt ttggctcagg acactacaca    420
gcctattgct acaacacaga ggggaggtgc gtgcgcttta ctctgtgggg tgggggacac    480
ggaaaggggt tgatttgcca cattttattg gtttcctttt atttccatcc catggattac    540
ctagagggaa attacataca tcaaaaatnc agtggaaaga attgtgaaaa ttgg          594
```

<210> SEQ ID NO 241
<211> LENGTH: 199
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(199)
<223> OTHER INFORMATION: n = a, t, c or g

<400> SEQUENCE: 241

```
gggggggaagc agcgngcgca gccggaggat cgcggagtcc caatgaaacg ggcanccatg     60
gccctccaca gcccgnagta tatntnnggn gatgnnagcc ctgatgaatt naatnaattn    120
tttgtgactc ctngatcttc aggtgagctt nctccataca gnggnacant tctgtgnggc    180
acacangctg tggataaac                                                  199
```

<210> SEQ ID NO 242
<211> LENGTH: 389
<212> TYPE: DNA
<213> ORGANISM: Homo sapiens
<220> FEATURE:
<223> OTHER INFORMATION: ubiquitin carboxyl-terminal hydrolses family 2
<220> FEATURE:
<221> NAME/KEY: misc_feature
<222> LOCATION: (1)..(389)
<223> OTHER INFORMATION: n = a, t, c or g

<400> SEQUENCE: 242

```
gaaagtacct tttcttctcc tgaagattct ttacccaagt ctaaaccact gacatcttct     60
cggtcttcca tggaaatgcc ttcacagcca gctccacgaa cagtcacaga tgaggagata    120
aattttgtta agacctgtct tcagagatgg aggagtgaga ttgaacaaga tatacaagat    180
ttaaagactt gcattgcaag tactactcag actattgaac anatgtactg ngatcctntc    240
cttcgtcagg tgccttatcg cttgcatgca gttcttgttc atgaaggaca agcaaatgct    300
ggacactatt gggcctatat ctataatcaa ccccgacaga gctggctcaa gtacaatgac    360
atctctgtta ctgaatcttc ctgggaaga                                      389
```

<210> SEQ ID NO 243
<211> LENGTH: 1094
<212> TYPE: DNA
<213> ORGANISM: Homo sapiens
<220> FEATURE:
<223> OTHER INFORMATION: ubiquitin carboxyl-terminal hydrolases family 2
<220> FEATURE:
<221> NAME/KEY: misc_feature
<222> LOCATION: (1)..(1094)
<223> OTHER INFORMATION: n = a, t, c or g ―continued

```
<400> SEQUENCE: 243
ccncgcntcc ggacccgtgg gaaacaggtc ttgaagctga cccatttgcc ccagaccctg       60
acaatccacc tcatgcgatt ctccatcagg aattcacaga cgagaaagat ctgccactcc      120
ctgtacttcc cccagagctt ggatttcagc cagatccttc caatgaagcg agagtcttgt      180
gatgctgagg agcagtctgg agggcagtat gagcttttg ctgtgattgc gcacgtggga      240
atggcagact ccggtcatta ctgtgtctac atccggaatg ctgtggatgg aaaatggttc      300
tgcttcaatg actccaatat ttgcttggtg tcctgggaag acatccagtg tacctacgga      360
aatcctaact accactggca ggaaactgca tatcttctgg tttacatgaa gatggagtgc      420
taatggaaat gcccaaaacc ttcagagatt gacacgctgt cattttccat ttccgttcct      480
ggatctacgg agtcttctaa gagattttgc aatgaggaga agcattgttt tcaaactata      540
taactgagcc ttatttataa ttagggatat tatcaaaata tgtaaccatg aggcccctca      600
ggtcctgatc agtcagaatg gatgctttca ccagcagacc cggccatgtg gctgctcggt      660
cctgggtgct cgctgctgtg caagacatta gccctttagt tatgagcctg tgggaacttc      720
aggggttccc agtggggaga gcagtggcag tgggaggcat ctgggggcca aaggtcagtg      780
gcagggggta tttcagtatt atacaactgc tgtgaccaga cttgtatact ggctgaatat      840
cagtgctgtt tgtaattttt cactttgaga accaacatta attccatatg aatcaaagtg      900
ttttgtaact gctattcatt tattcagcaa atatttattg atcatctctt ctccataaga      960
atagtgtgat aaacacagtc atgaataaag ttattttcca caaaaaaaa aaaaannnnn     1020 nnnnnnnnnn nnnnnnnnnn nnnnnnnnnn nacacctncc cntnaacctn nacataaatg     1080
aatgcaattg gttn                                                       1094

<210> SEQ ID NO 244
<211> LENGTH: 466
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 244
cgtctgtctg gccattggct ttgccgtgct gcttcgggcg ctgtggaagg gcacccacca       60
tgccttccag ccttccaagt tgaaggccat tgtggcgagt aaggccagcc agttcacagg      120
ctatgcacag catgatgccc aggagttcat ggctttcctg ctggatgggc tgcacgagga      180
cctgaatcgc attcagaaca agccctacac agagaccgtg gattcagatg gcggccccga      240
tgaggtggta gctgaggaag catggcagcg gcacaagatg aggaatgact ctttcatcgt      300
ggacctattt caggggcagt acaagtcgaa gctggtgtgc cctgtgtgtg ccaaggtctc      360
catcactttt gacccgtttc tttatctgcc gggtgcccct gccacaaaag caaaaggttc      420
tccctgtctt ttattttgcc cgagagcccc acagcaagcc catcaa                    466

<210> SEQ ID NO 245
<211> LENGTH: 518
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 245
cgcaagatgc cttccaatga aagctgaaga ggagacggat gaagagaagc caaagaaccc       60
```

```
catggtagag ttgttctatg gcagattcct ggctgtggga gtacttgaag gtaaaaatt     120 tgaaaacact gaaatgtttg gtcagtaccc acttcaggtc aatgggttca agatctgca     180 tgagtgccta gaagctgcaa tgattgaagg agaaattgag tctttacatt cagagaattc    240
aggaaaatca ggccaagagc attggtttac tgaattacca cctgtgttaa catttgaatt    300
gtcaagattt gaatttaatc aggcattggg aagaccagaa aaaattcaca acaaattaga    360
atttccccaa gttttatatt tggacagata catgcacaga aacagagaaa taacaagaat    420
taagagggaa gagatcaaga gactgaaaga ttacctcacg gtattacaac aaaggctaga    480
aagatattta agctatggtt ccggtcccaa acgattcc                            518
```

<210> SEQ ID NO 246
<211> LENGTH: 1102
<212> TYPE: DNA
<213> ORGANISM: Homo sapiens
<220> FEATURE:
<223> OTHER INFORMATION: ubiquitin carboxyl-terminal hydrolases family 2

<400> SEQUENCE: 246

```
agatccagca tcatcaccca gtatacaaga tggtggtcta atgcaagcct ctgtacccgg    60
tccttcagaa gaaccagtag tttataatcc aacaacagct gccttcatct gtgactcact    120
tgtgaatgaa aaaaccatag gcagtcctcc taatgagttt tactgttctg aaaacacttc    180
tgtccctaac gaatctaaca agattcttgt taataaagat gtacctcaga accaggagg    240 tgaaaccaca ccttcagtaa ctgacttact aaattatttt ttggctccag agattcttac    300
tggtgataac caatattatt gtgaaaactg tgcctctctg caaaatgctg agaaaactat    360
gcaaatcacg gaggaacctg aataccttat tcttactctc ctgagatttt catatgatca    420
gaagtatcat gtgagaagga aaatttaga caatgtatca ctgccactgg ttttggagtt    480
gccagttcca aagaattact tctttctctt cattgtcaga agttggtct gtagatgttg    540 acttcactga tcttagtgag aaccttgcta aaaattaaa gccttcaggg actgatgaag    600
cttcctgcac aaaattggtg ccctatctat taagttccgt tgtggttcac tctggtatat    660
cctctgaaag tgggcattac tattcttatg ccagaaatat cacaagtaca gactcttcat    720
atcagatgta ccaccagtct gaggctctgg cattagcatc ctcccagagt catttactag    780
ggagagatag tcccagtgca gttttttgaac aggatttgga aaataaggaa atgtcaaaag    840
aatggttttt atttaatgac agtagagtga catttacttc atttcagtca gtccagaaaa    900
ttacgagcag gtttccaaag gacacagctt atgtgctttt gtataaaaaa cagcatagta    960
ctaatggttt aagtggtaat aacccaacca gtggactctg gataaatgga gacccacctc   1020
tacagaaaga acttatggat gctataacaa aagacaataa actatattta caggaacaag   1080
agttgaattg ctctgcccca gc                                             1102
```

<210> SEQ ID NO 247
<211> LENGTH: 544
<212> TYPE: DNA
<213> ORGANISM: Homo sapiens
<220> FEATURE:
<223> OTHER INFORMATION: hemoglobinase
<220> FEATURE:
<221> NAME/KEY: misc_feature
<222> LOCATION: (1)..(544)
<223> OTHER INFORMATION: n = a, t, c or g

<400> SEQUENCE: 247

```
ccgcttagaa ctccaaattg gcctcccagg caaggatcta aaacttcacc aaatcatttc    60
```

```
tcccaggcag acgcgtgcca tgcctaccag atcattcacc gcaatgggat tcctgacgaa    120
cagatcgttg tgatgatgta cgatgacatt gcttactctg aagagtaagt ggggaacact    180
tggaacttgg tggggaagga cttcagggta tttaaaaaaa ggtcacatag actcacagga    240
atcctagtgg cctaatgtta aaatatataa gagactccca gacagaagat cacagggata    300
cctcatgtta agcttttttt tttttattat tatttatttg agacagtctt gctccagcct    360
gagtgacaga gtgagactct gtctcaaaca cacacacaca cacacacaca cccncaccct    420
gaccaacagt gtgaatcccc gtctctacta aaaatacaaa aattaaccag gcgtggtggc    480
gtgtgcctat aatcccagct actcgggagg ctgaggcagg agaactgctt taacctggga    540
ggcg                                                                 544
```

<210> SEQ ID NO 248
<211> LENGTH: 554
<212> TYPE: DNA
<213> ORGANISM: Homo sapiens
<220> FEATURE:
<223> OTHER INFORMATION: prolyl oligopeptidases

<400> SEQUENCE: 248

```
gtccggtcaa aatggtcact ttatattgtt atgtagttaa tatattttag agcaaatatt     60
ccaaattttg taatttgctc cttttaaaaa acaagcataa gataggcatc taacctagaa    120
tttcctttat tttagatgaa ctcacaaatt cgtcagaaac cagattgtct ttggaagacc    180
tctttaggaa agactttgtg cttcacgatc cagaggctcg gtggatcaat gatacagatg    240
tggtgtataa aagcgagaat ggacatgtca ttaaactgaa tatagaaaca aatgctacca    300
cattattatt ggaaaacaca acttttgtaa ccttcaaagc atcaagacat tcagtttcac    360
cagatttaaa atatgtcctt ctggcatatg atgtcaaaca ggtaaaggag tgatcttctt    420
tgagaatact tttctttgtg atgcattggg gtgacaatgc ataattttac tcagctataa    480
ctcacctaag caaaatctgg catgtctagt aactaccgga ggacagtaat gactactttg    540
cacaaaagat gttt                                                      554
```

<210> SEQ ID NO 249
<211> LENGTH: 547
<212> TYPE: DNA
<213> ORGANISM: Homo sapiens
<220> FEATURE:
<223> OTHER INFORMATION: prolyl oligopeptidases
<220> FEATURE:
<221> NAME/KEY: misc_feature
<222> LOCATION: (1)..(547)
<223> OTHER INFORMATION: n = a, t, c or g

<400> SEQUENCE: 249

```
acaaatgcta ccacattatt attggaaaac acaacttttg taaccttcaa agcatcaaga     60
cattcagttt caccagattt aaaatatgtc cttctggcat atgatgtcaa acagattttt    120
cattattcgt atactacttc atatgtgatt tacaacatac acactaggga gtttgggag    180 ttaaatcctc cagaagtaga ggactccgtc ttgcagtacg cggcctgggg tgtccaaggg    240
cagcagctga tttatatttt tgaaaataat atctactatc aacctgatat aaagagcagt    300
tcattgcgac tgacatcttc tggaaaagaa gaaataattt ttaatgggat tgctgactgg    360
ttatatgaag aggaactcct gcattctcac atcgcccact ggtggtcacc agatggagaa    420
agacttgcct tcctgatgat aaatgactct ttggtaccca ccatggttat ccctcggttt    480
```

```
actggagcgt tgtatcccaa aggaaagcan gtatccgtat cctaaggcag gtcaagtgaa    540
cccaaca                                                              547
```

<210> SEQ ID NO 250
<211> LENGTH: 821
<212> TYPE: DNA
<213> ORGANISM: Homo sapiens
<220> FEATURE:
<223> OTHER INFORMATION: methionine aminopeptidases
<220> FEATURE:
<221> NAME/KEY: misc_feature
<222> LOCATION: (1)..(821)
<223> OTHER INFORMATION: n = a, t, c or g

<400> SEQUENCE: 250

```
tggtcgcggc cgaggtacgt ggccagtcaa tggcaggttc accgcacctc aggcagaact     60
ctatgaagcc gttctagaga tccaaagaga ttgtttggcc ctctgcttcc ctgggacaag    120
cttggagaac atctacagca tgatgctgac cctgatagga cagaagctta agacttggg    180 gatcatgaag aacattaagg aaaataatgc cttcaaggct gctcgaaaat actgtcctca    240
tcatgttggc cactacctcg ggatggatgt ccatgacact ccagacatgc cccgttccct    300
ccctctgcag cctgggatgg taatcacaat tgagcccggc atttatattc cagaggatga    360
caaagatgcc ccagagaaag tttcggggtc ttggtgtacg aattgaggat gatgtagtgg    420
tgactcagga ctcacctctc atcctttctg cagactgtcc caaagagatg aatgacattg    480
aacagatatg cagccaggct tcttgacctt cactgcggcc cacatgcacc tcaggttcaa    540
aatgggtgtc ttctggcagc cctgcacgtg tgctttctga gtgtctctgt gtgtgcatta    600
atatatgcat tccatttggg agcatagcag ctgtgtgaat gtatgtaatt gtgtgtgggg    660
ggttttttgt tttaagtagt tagaagtctg ggaaaatgaa ttttttgaata gtatgttact    720 gcagctttgg taacattaat tctatagaat taatgatcag agcaagttta attttttaanc    780 ataaaggtct tggttacaca tgtccatgca ttccagttaa n                        821
```

<210> SEQ ID NO 251
<211> LENGTH: 449
<212> TYPE: DNA
<213> ORGANISM: Homo sapiens
<220> FEATURE:
<223> OTHER INFORMATION: methionine aminopeptidases
<220> FEATURE:
<221> NAME/KEY: misc_feature
<222> LOCATION: (1)..(449)
<223> OTHER INFORMATION: n = a, t, c or g

<400> SEQUENCE: 251

```
agccaagagc aagaacaagg ttcggggtgt tcagcagctg atacagcgcc tccggctgat     60
caagtctcct gcagaaattg aacgaatgca gattgctggg aagctgacat cacaggcttt    120
catagaaacc atgttcacca gtaaagcccc tgtggaagaa gcctttcttt atgctaagtt    180
tgaatttgaa tgccgggctc gtggcgcaga cattttagcc tatccacctg tggtggctgg    240
tggtaatcgg tcaaacactt tgcactatgt gaaaaataat caactcatca aggatgggga    300
aatggtgctt ctggatggag gttgtgagtc ttcctgctat gtgagtgaca tcacacgtac    360
ctcggccgcg accaccagct ttcacaaatt agctgacatt ttaaaagtat tttattgctt    420
attaaaatgg ttttttacaga cattatctn                                    449
```

<210> SEQ ID NO 252
<211> LENGTH: 496

<212> TYPE: DNA
<213> ORGANISM: Homo sapiens
<220> FEATURE:
<223> OTHER INFORMATION: methionine aminopeptidases

<400> SEQUENCE: 252

| | | | | | |
|---|---|---|---|---|---|
| gtggtcgcgg | cgaggtacga | cctattccat | gaccagaaaa | ttctttaggc | gtgtataaat | 60 |
| tattttgttt | gattacttta | aaaattgcat | tagcaatgtc | taaagttgta | gcatcttttt | 120 |
| taatagcgtt | gaatcctgct | caaaatgcac | tttcagcaac | atcaatgatt | ttttgatctt | 180 |
| gataagatac | tttacctact | gcttttgtaa | aggcactatc | agcgtgaaat | ccttcaaaag | 240 |
| caagacccca | aatcaatgga | gacaacatca | gattcttgaa | ttacataatc | cgttggtata | 300 |
| ccatgaatta | atacattatt | aacactagcg | caaattgttg | ctggaaaacc | ttgatagttt | 360 |
| aaaaatggaa | gggttagcat | ttctttttc | gatctcttta | aaagcgatgg | catctaattc | 420 |
| ttttaaagaa | acacctggtc | ttacaaggtc | ataaataatt | tgttttacct | ctgccaggag | 480 |
| ctgaccagct | ttaatt | | | | | 496 |

<210> SEQ ID NO 253
<211> LENGTH: 363
<212> TYPE: DNA
<213> ORGANISM: Homo sapiens
<220> FEATURE:
<223> OTHER INFORMATION: methionine aminopeptidases
<220> FEATURE:
<221> NAME/KEY: misc_feature
<222> LOCATION: (1)..(363)
<223> OTHER INFORMATION: n = a, t, c or g

<400> SEQUENCE: 253

| | | | | | |
|---|---|---|---|---|---|
| tcgccagcga | ngctnaccgt | gcctttnata | tgcaccgcgc | cggccactgg | ctgggcatgg | 60 |
| atgtgcacga | tgtgggcgaa | tacaaagtgg | gcggtgaatg | gcgagtgctg | gaagtgggca | 120 |
| tggccttgac | cgtggagccg | gggatttata | tttcgccgga | caaccagaac | gtggcaaaga | 180 |
| aatggcgtgg | cattggcgta | cgcatcgagg | atgacgtggt | agtgaccaag | caaggctgtg | 240 |
| aaattctgac | cggtggtgtg | cctaaaactg | tcgctgagnt | cgaagcgctg | atggcggctg | 300 |
| cccgatgagc | cgggtcaacc | tgggcgatta | tcgtggtgg | cctgggtngg | cgccactggg | 360 |
| cgt | | | | | | 363 |

<210> SEQ ID NO 254
<211> LENGTH: 438
<212> TYPE: DNA
<213> ORGANISM: Homo sapiens
<220> FEATURE:
<223> OTHER INFORMATION: c15 thiol protease family
<220> FEATURE:
<221> NAME/KEY: misc_feature
<222> LOCATION: (1)..(438)
<223> OTHER INFORMATION: n = a, t, c or g

<400> SEQUENCE: 254

| | | | | | |
|---|---|---|---|---|---|
| ccncgcgtcc | gccggccgct | gggccgctgc | ctgagccagg | gaggcgcagc | gcgagctccc | 60 |
| acttcgtctt | catggattcc | cagcccagct | gcgtggtggt | gactggtttt | gggcccttcc | 120 |
| ggcagcactt | ggtgaattcc | agctgggaag | cagtgaagga | gctctccaag | ctgggcctgg | 180 |
| ggaatgaaac | agtggtgcag | ctgcggactc | tggagctgcc | tgtagattac | agggaggcta | 240 |
| agcggagggt | caccggaatc | tggaagatc | atcagccgca | actcgtcgtg | catgtgggca | 300 |
| tggacaccgc | cgccaaggcg | atcattctgg | aacagtctgg | caagaaccaa | ggctaccggg | 360 |

| | | |
|---|---|---|
| acgccgacat ccgcagcttc tggcccgagg gcggcgtgtg cctacctggc agcccagacg | 420 | |
| tgctggagtc agggtct | 438 | |

<210> SEQ ID NO 255
<211> LENGTH: 642
<212> TYPE: DNA
<213> ORGANISM: Homo sapiens
<220> FEATURE:
<223> OTHER INFORMATION: neprilysin family of protease

<400> SEQUENCE: 255

| | |
|---|---|
| ttttttttt tttcaacaga gacaggttta ttttgggaat aaacctgaga ggggcttctg | 60 |
| gccgatttcg gtcagggaca ttctcttaca gactaagggc atttaagggt ttaggaaggg | 120 |
| ggagcctacc gcagcctgcg aatgtttttt gtgtgaagga gagttttatt gcagagttgg | 180 |
| aatatctctg gctggagggg aggttattct caggattggc atgtttctgg tcagatgggg | 240 |
| gtttatctca tggttgaaat gtttctgctc atactgacat gagccattag gctgatgttt | 300 |
| tgggctggtt tttaatcacg gagaacttaa aatggccatg tttgtccaag atggcaatgc | 360 |
| tcctgctgtc acacccaccc acccacaggg tactcggggt cgctgcagaa cctggccgcc | 420 |
| ttcgcagaca cgttccactg tgcccggggc accccatgc accccaagga gcgatgccgc | 480 |
| gtgtggtagc caaggccctg ccgcgctgtg cggcccacgc ccacccgctg ctcggaggca | 540 |
| tctgtgcgaa ggtgcagcta gcggcgacca gtgtagtccg cccggccaac atgcaacctg | 600 |
| ctgccagctc tggctggcta gggtcagcac ctgctgaacc ag | 642 |

<210> SEQ ID NO 256
<211> LENGTH: 400
<212> TYPE: DNA
<213> ORGANISM: Homo sapiens
<220> FEATURE:
<223> OTHER INFORMATION: cathepsin

<400> SEQUENCE: 256

| | |
|---|---|
| cagggatca ttgcaaggtg gctcctctag tgtggcttcc agggagaaca gagagccctg | 60 |
| gccggcccgg cggacgcgtc cgcgcaccgc tcctagcacg gcccttgtcc ccgcagcacg | 120 |
| gccgtaattg tacatgtcca gcgcgaagcg ggcgggggcc agcagctcct gggacgacaa | 180 |
| gttccaggcc tgctcgtcat ctgcccaggg cttggcgggg acggggctca gagccacagt | 240 |
| cgagagcagt gtcagcagcc acagaagctg cagtaggggc gccatagcga ggtcgaagct | 300 |
| gctcgcccgg attcactgac ccacaaacac acggatcaag agacccgagg cggagcctgc | 360 |
| tgtcagaggc cacagagagc ggacgcggct cgatccctaa | 400 |

<210> SEQ ID NO 257
<211> LENGTH: 546
<212> TYPE: DNA
<213> ORGANISM: Homo sapiens
<220> FEATURE:
<223> OTHER INFORMATION: calpain

<400> SEQUENCE: 257

| | |
|---|---|
| aactgaaaca gttggctcga caggcactag acagagcaga agcgctgagt gagcctttga | 60 |
| ccaagccagt tggcaaaatc agttcaacaa gtgttaagcc aaagccacct ccagtgagag | 120 |
| cacattttcc actgggcgct aatcccttcc ttgaaagacc tcagtcattt ataagtcctc | 180 |
| agtcatgtga tgcacaagga cagagataca cagcagaaga aatagaagta ctcaggacaa | 240 |
| catcaaaaat aaatggtata gaatatgttc ctttcatgaa tgttgacctg agagaacgtt | 300 |

```
ttgcctatcc aatgcctttc tgtgatagat ggggcaagct accattatca cctaaacaaa    360
aaactacatt ttccaagtgg gtaccgacca gaagacctca ccaacaatcc tacaatgata    420
tatactgtgt ccagttttag cataaagcag acaatagtat cggattgctc ctttgtggca    480
tcactggcca tcagtgcagc ttatgaaaga cgttttaata agaagttaat tcccggcata    540
atttac                                                              546

<210> SEQ ID NO 258
<211> LENGTH: 555
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(555)
<223> OTHER INFORMATION: n = a, t, c or g

<400> SEQUENCE: 258
ccgccagtgt gctttaaagg ctggcctcac ccagctctgc tgctctgttg gtcatgggag     60
caaggtggac ttgccctgga ccttccctac ttgtgctcct ctgttatggg cagctcttgc    120
cttggctcag gatcaagggt gaacacagtt taggtgtggc tgggacccca agaagcatgg    180
gaccagacaa agggactggg tgcggacagg accttctcag cacatgatgc ccatatcctt    240
ccctgcagat gacttctaca atgagaccga gaccaagatc ttcctgcagg ttttatgacc    300
aaacaggtga agttgtgttg aacaagttca tggaggccac ttggaactat gtcaccaata    360
tcaccaggaa aaatcaggag gagatgatgt gataccacct ccaccccagc ctctcctctc    420
tttgctcttt ttagggattt gggaccatgg ggcaccacac ctcctgcccc catcccaagc    480
aagaggaaca agggaagccc cagtgtacat gtcaaagagg gctgcaantc tgggcctcct    540
ggaagcccta atctt                                                    555

<210> SEQ ID NO 259
<211> LENGTH: 831
<212> TYPE: DNA
<213> ORGANISM: Homo sapiens
<220> FEATURE:
<223> OTHER INFORMATION: angiotensin-converting enzyme
<220> FEATURE:
<221> NAME/KEY: misc_feature
<222> LOCATION: (1)..(831)
<223> OTHER INFORMATION: n = a, t, c or g

<400> SEQUENCE: 259
taacggccgc cagtgtgctc taaaggcaaa cacacaatta caatatcaca tgtacccaga     60
tctgccacag ctgaacccaa ttataattgg gcactatgca tgcaggctgt cccctcctct    120
gccccccaac tctctggctc agcctccctc ctcctgcccc ccagcctcac cagttcactg    180
gtgtctagtc ccaacttcac cattcagctc ttacccttgg aggctttcct ggctttactg    240
tgtgaaaatc cagatggcca ggctgattga gcacagcatc aggacaaggc agaggccag     300 cagcatccac tgtccttag cagcctggca gggttccatg gctatgccca ggaagcaggc    360
attgggcagt gggctgaata tctcagtgtc ttgagtcagt gactgttttt ccagggactg    420
cagcctgcag gccacgcccc agcaccacca gagacatgac aaagcccagg gccaacagca    480
cccagtaccc aaatttagcc tggttggggt ccagcttcag actcaggaat gtcactttgt    540
ctgtgtcttt ttctgtggaa gacataggag tctcataggg tgggtagaac tggagaggga    600
```

-continued

```
ccctggggt  ctcctgtggc  tgtcagagga  gatctgattg  gactacatgc  ccctgcatgc   660
aagggaccag  aggcaagatg  ctgatccttt  gctcagatgt  cagcctggca  acctagctgg   720
acagtgtgca  aggaagcaac  tgagccaggg  ntgtggtggg  agcggtggtc  ttggctgaag   780
ctgcatcagg  nctggtacag  acagggtccc  acagcagcag  tgctgttgat  t             831
```

<210> SEQ ID NO 260
<211> LENGTH: 152
<212> TYPE: DNA
<213> ORGANISM: Homo sapiens
<220> FEATURE:
<223> OTHER INFORMATION: angiotensin-converting enzyme

<400> SEQUENCE: 260

```
ccagcagaaa  agtggaactt  ggcacctgga  tcaaagtctt  cctctgagtg  aggaatagcg    60
gggcacaagc  ctggtatttc  aacctggcag  ggaaaaggca  gagggcttgg  tggtggtgtc   120
tggcaggttc  tcagagcctc  tttcttttcc  tt                                   152
```

<210> SEQ ID NO 261
<211> LENGTH: 340
<212> TYPE: DNA
<213> ORGANISM: Homo sapiens
<220> FEATURE:
<223> OTHER INFORMATION: methionine aminopeptidases

<400> SEQUENCE: 261

```
aacatggcgg  cgcccagtgg  cgtccacctg  ctcgtccgca  gaggttctca  tagaattttc    60 tcttccaccac  tcaatcatat  ctacttacac  aagcagtcaa  gcagtcaaca  aagaagaaat  120 ttctttttc  ggagacaaag  agatatttca  cacagtatag  ttttgccggc  tgcagtttct    180
tcagctcatc  cggttcctaa  gcacataaag  aagccagact  atgtgacgac  aggcattgta   240
ccagactggg  gagacagcat  agaagttaag  aatgaagatc  agattcaagg  gcttcatcag   300
gcttgtcagc  tggcccgcca  cgtcctcctc  ttggctggga                           340
```

<210> SEQ ID NO 262
<211> LENGTH: 245
<212> TYPE: DNA
<213> ORGANISM: Homo sapiens
<220> FEATURE:
<223> OTHER INFORMATION: methionine aminopeptidases
<220> FEATURE:
<221> NAME/KEY: misc_feature
<222> LOCATION: (1)..(245)
<223> OTHER INFORMATION: n = a, t, c or g

<400> SEQUENCE: 262

```
gtccggcggc  ggccaccgga  ccctgcgttn  nggctgggga  atgaaaccct  gaaggtgccg    60
ctggcgctct  ttgccttgaa  ccggnagcag  cctgtgtgag  cggctgcgga  agaaccctgc   120
tgtgcangcc  ggctccatcg  tggtcctgca  gggcgggag  gagactcagc  gctactgcac   180
cgacaccggg  gtcctattcc  gncaggagtc  cttctttcac  tgggcgttcg  gngtcactga   240
gccag                                                                    245
```

<210> SEQ ID NO 263
<211> LENGTH: 527
<212> TYPE: DNA
<213> ORGANISM: Homo sapiens
<220> FEATURE:
<223> OTHER INFORMATION: matrix metalloproteases
<220> FEATURE:
<221> NAME/KEY: misc_feature

```
<222> LOCATION: (1)..(527)
<223> OTHER INFORMATION: n = a, t, c or g

<400> SEQUENCE: 263
cgcgtccgcc cacgcgtncg cccctcaaa   cttctgtgca caaagtgctc ccttcccaga        60 ggagggccc  catcggtgtg taaggnggcc  tattcctctg tgngtnctct ggatcttttc       120
agccctgtgg tccaatngtc catcacagcc  atgctgacta gtgactgga  gacagggatg       180 atggagagtt caggaagggc tgggcagagg  aggctggggc cacctctgga gggtgtcctg       240
ctgttcctgn tggcccagc  tgcactcct   anccccaac  tccattatga ggcccttcta       300
ccagggtccg gtgggcgacc ctgacangtn  ccgcgctgtc tcaggatgac cgcgatggcc       360
tgcagcaact ctatgggaag cgccccaaa   ccccatntng acaagcccac aaggaaaccc       420
ctggctcctn cgccccagtc  ccggccttc  caccacacac agcccatcct ttncccatcc       480
tgatcgatnt gagggcaatt ttngacgcct  cgccaacatt cgagggg                     527

<210> SEQ ID NO 264
<211> LENGTH: 511
<212> TYPE: DNA
<213> ORGANISM: Homo sapiens
<220> FEATURE:
<223> OTHER INFORMATION: calpain

<400> SEQUENCE: 264
ccgcccacgc gtccgcttgc ccaggcgctt  aaagaagcaa atctcttgt  gcaggagcag        60 cagagactcc tcaggaagac tcactggact  gtacccacca cctgccatgt ctctgtggcc       120
acctttccga tgcagatgga agctggcgca  aaggtactct aggagggcgt ctccacagca       180
accccaacag gactttgagg ccctgctggc  agagtgcctg aggaatggct gcctctttga       240
agacaccagc ttcccggcca ccctgagctc  catcggcagt ggctccctgc tgcagaagct       300 gccacccgc  ctgcagtgga gaggccccc   ggagctgcac agcaatcccc agttttattt       360
tgccaaggcc aaaaggctgg atctgtgcca  ggggatagta ggagactgct ggttcttggc       420
tgctttgcaa gctctggcct tgcaccagga  catcctgagc cgggttgttc ccctgaatca       480
gagtttcact gagaagtatg ctggcatctt  c                                      511

<210> SEQ ID NO 265
<211> LENGTH: 663
<212> TYPE: DNA
<213> ORGANISM: Homo sapiens
<220> FEATURE:
<223> OTHER INFORMATION: aspartyl proteases
<220> FEATURE:
<221> NAME/KEY: misc_feature
<222> LOCATION: (1)..(663)
<223> OTHER INFORMATION: n = a, t, c or g

<400> SEQUENCE: 265
cggtctccac cactgctgct gctacccttg  ctgctgctgc tgcctctgct gaatgtggag        60
cctgctgggg ccacactgat ccggatccct  cttcgtcaag tccaccctgg acgcaggacc       120
ctgaacctac tgaggggatg gggaaaacca  gcagagctcc ccagttgggg gccccatcc        180 cctggggaca agcctgcctc ggtacctctc  tccaaattcc tggatgccca gtattttggg       240
gaaattgggc tgggaacgcc tccacaaaac  ttcactgttg cctttgacac tggctcctcc       300
aatctctggg tcccgtccag gagatgccac  ttcttcaagt gtgccctgct ggttccacca       360
ccgcttcaat cccaatgcct ccagctcctt  caagcccagt gggaccaagt ttgccattca       420
```

```
gtatgggaac tgggccgggt agatggaatc ctgagtgagg acaagctgac tattggtgga      480
atcaaagggt gcatcccgtg attttcgggg aagctctgtg ggaatccagc ctgggcttca      540 atgnttccog cccgatggga tattgggcct cgggttttncc attctgnctg tggaaggagt     600
ttcggccccg cttggatgna ctggttggac aaggggctnt ttggtaacct gcttctcctt     660
tta                                                                    663

<210> SEQ ID NO 266
<211> LENGTH: 186
<212> TYPE: DNA
<213> ORGANISM: Homo sapiens
<220> FEATURE:
<223> OTHER INFORMATION: Lon family of ATP-dependent proteases

<400> SEQUENCE: 266
ccccgcgtcc gcagacatcc atctgcactt cccagctgga gctgtcacaa aagatggacc      60
atctgctgga gttaccatag taacctgtct cgcctcactt tttagtgggc ggctggtacc     120
gttcagatgt agccatgact ggagaaatta cactgagagg tcttgttctt ccagtgggtg     180
gaatta                                                                186

<210> SEQ ID NO 267
<211> LENGTH: 543
<212> TYPE: DNA
<213> ORGANISM: Homo sapiens
<220> FEATURE:
<223> OTHER INFORMATION: ubiquitin carboxyl-terminal hydrolases family 1
<220> FEATURE:
<221> NAME/KEY: misc_feature
<222> LOCATION: (1)..(543)
<223> OTHER INFORMATION: n = a, t, c or g

<400> SEQUENCE: 267
aggcctccga cctcaaatcc ggaccgattg atttaggtgc atgcaatcaa gatgattgga      60
tcagtgcagt aaggcctgtc atagaaaaaa ggatacaaaa gtacagtgaa ggtgaaattc     120
gatttaattt aatggccatt gtgtctgaca gaaaaatgat atatgagcag aagatagcag     180
agttacaaag acaacttgca gaggaggaac ccatggatac agatcaaggt aatagtatgt     240
taagtgctat tcagtcagaa gttgccaaaa atcagatgct tattgaagaa gaagtacaga     300
aattaaaaag atacaagatt gagaatatca gaaggaagca taattatctg cctttcatta     360
tggaattgtt aaagacttta gcagaacacc agcagttaat accactagta gaaaaggcaa     420
aagaaaaaca gaacgcaaag aaagctcagg aaaccaaatg aagatgtttt cagatatgta     480
cacatttctg cttctgcaca tattttcatg ggaaccatta tgtataaagg ncttngggga     540 can                                                                    543

<210> SEQ ID NO 268
<211> LENGTH: 781
<212> TYPE: DNA
<213> ORGANISM: Homo sapiens
<220> FEATURE:
<223> OTHER INFORMATION: ubiquitin carboxyl-terminal hydrolases family 1
<220> FEATURE:
<221> NAME/KEY: misc_feature
<222> LOCATION: (1)..(781)
<223> OTHER INFORMATION: n = a, t, c or g

<400> SEQUENCE: 268
gtggttgacg agctcggcgg cgggtttgct gagatctgtg gccggcggca gctggtgcgg      60
ggggcacgct gagagcgaga ggtggatcgg ggcggtgtgt ggccagggcc atgacgggca     120
```

```
atgccggga  gtggtgcctc  atggaaagcg  accccggggt  cttcaccgag  ctcattaaag    180
gattcggttg  ccgaggagcc  caagtagaag  aaatatggag  tttagagcct  gagaattttg    240
aaaaattaaa  gccagttcat  gggttaattt  ttcttttcaa  gtggcagcca  ggagaagaac    300
cagcaggctc  tgtggttcag  gactcccgac  ttgacacgat  atttttgct  aagcaggtaa     360
ttaataatgc  ttgtgctact  caagccatag  tgagtgtgtt  actgaactgt  acccaccagg    420
atgtccattt  aggcgagaca  ttatcagagt  ttaaagaatt  ttcacaaagt  tttgatgcag    480
ctatgaaagg  cttggcactg  agcaattcag  atgtgattcg  accaagtaca  caacagtttc    540
gccagacagc  aaatgtttga  atttgatacg  aagacatcag  caaaagaaga  agatgctttt    600
cactttgtca  gttatgttcc  tgttaatggg  agactgtatg  aattagatgg  attaagagaa    660
ggacccgatt  gatttaggtg  catgcaatca  agatgattgg  atcagtgcgg  taaggcctgt    720
catagaaaaa  aggatacaaa  agtacctcgg  ccgcgaccac  gctaaaaatt  taatggccat    780
n                                                                         781
```

PROTEASE HOMOLOGS

FIELD OF THE INVENTION

The invention relates to newly identified polynucleotides having homology to various protease families. The invention also relates to protease polypeptides. The invention further relates to methods using the protease polypeptides and polynucleotides as a target for diagnosis and treatment in protease-mediated disorders. The invention further relates to drug-screening methods using the protease polypeptides and polynucleotides to identify agonists and antagonists for diagnosis and treatment. The invention further encompasses agonists and antagonists based on the protease polypeptides and polynucleotides. The invention further relates to procedures for producing the protease polypeptides and polynucleotides.

BACKGROUND OF THE INVENTION

Proteases are a major target for drug action and development. Accordingly, it is valuable to the field of pharmaceutical development to identify and characterize previously unknown protease nucleic acids and polypeptides. The present invention advances the state of the art by providing previously unidentified human protease sequences.

SUMMARY OF THE INVENTION

It is an object of the invention to identify novel proteases.

It is a further object of the invention to provide novel protease polypeptides that are useful as reagents or targets in protease assays applicable to treatment and diagnosis of protease-mediated disorders.

It is a further object of the invention to provide polynucleotides corresponding to the novel protease polypeptides that are useful as targets and reagents in protease assays applicable to treatment and diagnosis of protease-mediated disorders and useful for producing novel protease polypeptides by recombinant methods.

A specific object of the invention is to identify compounds that act as agonists and antagonists and modulate the expression of the novel proteases.

A further specific object of the invention is to provide compounds that modulate expression of the proteases for treatment and diagnosis of protease-related disorders.

The present invention is based on the discovery of novel nucleic acid molecules that are homologous to protease sequences.

Thus, in one aspect, the invention provides an isolated nucleic acid molecule that comprises a nucleotide sequence selected from the group consisting of SEQ ID NOS: 1–268 and the complements of SEQ ID NOS: 1–268.

In another aspect, the invention provides isolated proteins and polypeptides encoded by nucleic acid molecules of the invention.

In another embodiment, the invention provides an isolated nucleic acid molecule that comprises a nucleotide sequence that is at least about 60% identical, preferably at least about 80% identical, preferably at least about 85% identical, more preferably at least about 90% identical, and even more preferably at least about 95% identical, and most preferably about 98% or more identical to a nucleotide sequence selected from the group consisting of SEQ ID NOS: 1–268 and the complements of SEQ ID NOS: 1–268.

The invention also provides isolated variant polypeptides.

The invention also provides an isolated fragment or portion of any of SEQ ID NOS: 1–268 and the complement of SEQ ID NOS: 1–268. In preferred embodiments, the fragment is useful as a probe or primer, and/or is at least 15, more preferably at least 18, even more preferably 20–25, 30, 50, 100, 200 or more nucleotides in length.

The invention also provides isolated fragments of the polypeptides.

In another embodiment, the invention provides an isolated nucleic acid molecule that hybridizes under high stringency conditions to a nucleotide sequence selected from the group consisting of SEQ ID NOS: 1–268 and the complements of SEQ ID NOS: 1–268.

The invention further provides nucleic acid constructs comprising the nucleic acid molecules described above. In a preferred embodiment, the nucleic acid molecules of the invention are operatively linked to a regulatory sequence.

The invention also provides vectors and host cells for expressing the protease nucleic acid molecules and polypeptides and particularly recombinant vectors and host cells.

The invention also provides methods of making the vectors and host cells and methods for using them to produce the protease nucleic acid molecules and polypeptides.

The invention also provides antibodies or antigen-binding fragments thereof that selectively bind the protease polypeptides and fragments.

The invention also provides methods of screening for compounds that modulate expression or activity of the protease polypeptides or nucleic acid (RNA or DNA).

The invention also provides a process for modulating protease polypeptide or nucleic acid expression or activity, especially using the screened compounds. Modulation may be used to treat conditions related to aberrant activity or expression of the protease polypeptides or nucleic acids.

The invention also provides assays for determining the presence or absence of and level of the protease polypeptides or nucleic acid molecules in a biological sample, including for disease diagnosis.

The invention also provides assays for determining the presence of a mutation in the protease polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

Eucaryotic and Viral Aspartyl Active Sites

Aspartyl proteases, also known as acid proteases, (EC 3.4.23.-), are a widely distributed family of proteolytic enzymes (Foltman (1981) *Essays Biochem* 17:52–84; Davis (1990) *Annu. Rev. Biophys. Chem.* 19: 189–215; Rao et al. (1991) *Biochemistry* 30: 4663–4671) that exist in vertebrates, fungi, plants, retroviruses and some plant viruses. Aspartate proteases of eukaryotes are monomeric enzymes which consist of two domains. Each domain contains an active site centered on a catalytic aspartyl residue. The two domains most probably evolved from the duplication of an ancestral gene encoding a primordial domain. Currently known eukaryotic aspartyl proteases include, but are not limited to:

Vertebrate gastric pepsins A and C (also known as gastricsin).

Vertebrate chymosin (rennin), involved in digestion and used for making cheese.

Vertebrate lysosomal cathepsins D (EC 3.4.23.5) and E (EC 3.4.23.34).

Mammalian renin (EC 3.4.23.15) whose function is to generate angiotensin I from angiotensinogen in the plasma.

Fungal proteases such as aspergillopepsin A (EC 3.4.23.18), candidapepsin (EC 3.4.23.24), mucoropepsin (EC 3.4.23.23) (mucor rennin), endothiapepsin (EC 3.4.23.22), polyporopepsin (EC 3.4.23.29), and rhizopuspepsin (EC 3.4.23.21).

Yeast saccharopepsin (EC 3.4.23.25) (proteinase A) (gene PEP4). PEP4 is implicated in posttranslational regulation of vacuolar hydrolases.

Yeast barrierpepsin (EC 3.4.23.35) (gene BAR1), a protease that cleaves alpha-factor and thus acts as an antagonist of the mating pheromone.

Fission yeast sxa1 which is involved in degrading or processing the mating pheromones.

Most retroviruses and some plant viruses, such as badnaviruses, encode an aspartyl protease which is an homodimer of a chain of about 95 to 125 amino acids. In most retroviruses, the protease is encoded as a segment of a polyprotein which is cleaved during the maturation process of the virus. It is generally part of the pol polyprotein and, more rarely, of the gag polyprotein.

Family Active Sites

Interleukin-1 beta converting enzyme (EC 3.4.22.36) (ICE) (Thornberry et al. (1995) *Protein Sci.* 4:3–12; Kumar (1995) *Trends Biochem. Sci.* 20:198–202) is responsible for the cleavage of the IL-1 beta precursor at an Asp-Ala bond to generate the mature biologically active cytokine. ICE a thiol protease composed of two subunits of 10 (p10) and 20 Kd (p20), both derived by the autocleavage of a 45 Kd precursor (p45). Two residues are implicated in the catalytic mechanism: a cysteine and an histidine. ICE belongs to a family of peptidases (Nicholson et al. (1997) *Trends Biochem Sci.* 22:299–306) which is implicated in programmed cell death (apoptosis) and which has been termed 'caspase' for cysteine aspase. ICE is known as Caspase-1 and the other members of this family (Alnemri et al. (1996) *Cell* 87:171–171) include, but are not limited to:

Caspase-2 (ICH-1, NEDD-2).
Caspase-3 (also known as apopain, CPP32, Yama), a protease which, at the onset of apoptosis, proteolytically cleaves poly(ADP-ribose) polymerase (see) at an Asp-Gly bond.
Caspase-4 (ICH-2, TX, ICErel-II).
Caspase-5 (ICH-3, TY, ICErel-III).
Caspase-6 (MCH-2).
Caspase-7 (MCH-3, ICE-LAP3, CMH-1, SCA-2, LICE2).
Caspase-8 (MCH-5, MACH, FLICE).
Caspase-9 (MCH-6, ICE-LAP6).
Caspase-10 (MCH-4, FLICE2).
Caspase-11.
Caspase-12.
Caenorhabditis elegans ced-3 involved in the initiation of apoptosis.
Drosophila Ice.
Eukaryotic Thiol (Cysteine) Proteases Active Sites Eukaryotic thiol proteases (EC 3.4.22.-) (Dufour (1988) *Biochimie* 70:1335–1342) are a family of proteolytic enzymes which contain an active site cysteine. Catalysis proceeds through a thioester intermediate and is facilitated by a nearby histidine side chain; an asparagine completes the essential catalytic triad. Proteases that belong to this family include, but are limited to:

Vertebrate lysosomal cathepsins B (EC 3.4.22.1), H (EC 3.4.22.16), L (EC 3.4.22.15), and S (EC 3.4.22.27) (Kirschke et al. (1995) *Protein Prof.* 2:1587–1643).

Vertebrate lysosomal dipeptidyl peptidase I (EC 3.4.14.1) (also known as cathepsin C) (Kirschke et al. (1995) *Protein Prof.* 2:1587–1643).

Vertebrate calpains (EC 3.4.22.17). Calpains are intracellular calcium-activated thiol protease that contain both N-terminal catalytic domain and a C-terminal calcium-binding domain.

Mammalian cathepsin K, which seems involved in osteoclastic bone resorption (Shi et al. (1995) *FEBS Lett.* 357:129–134).

Human cathepsin O (Velasco et al. (1994) *J. Biol. Chem.* 269:27136–27142).

Bleomycin hydrolase. An enzyme that catalyzes the inactivation of the antitumor drug BLM (a glycopeptide).

Plant enzymes: barley aleurain (EC 3.4.22.16), EP-B1/B4; kidney bean EP-C1, rice bean SH-EP; kiwi fruit actinidin (EC 3.4.22.14); papaya latex papain (EC 3.4.22.2), chymopapain (EC 3.4.22.6), caricain (EC 3.4.22.30), and proteinase IV (EC 3.4.22.25); pea turgor-responsive protein 15A; pineapple stem bromelain (EC 3.4.22.32); rape COT44; ice oryzain Ipha, beta, and gamma; tomato low-temperature induced, *Arabidopsis thaliana* A494, RD19A and RD21 A.

House-dust mites allergens DerP1 and EurM1.

Cathepsin B-like proteinases from the worms *Caenorhabditis elegans* (genes gcp-1, cpr-3, cpr-4, cpr-5 and cpr-6), *Schistosoma mansoni* (antigen SM31) and Japonica (antigen SJ31), *Haemonchus contortus* (genes AC-1 and AC-2), and *Ostertagia ostertagi* (CP-1 and CP-3).

Slime mold cysteine proteinases CP1 and CP2.

Cruzipain from *Trypanosoma cruzi* and *brucei*.

Throphozoite cysteine proteinase (TCP) from various Plasmodium species.

Proteases from *Leishmania mexicana, Theileria annulata* and *Theileria parva*.

Baculoviruses cathepsin-like enzyme (v-cath).

Drosophila small optic lobes protein (gene sol), a neuronal protein that contains a calpain-like domain.

Yeast thiol protease BLH1/YCP1/LAP3.

*Caenorhabditis elegans* hypothetical protein C06G4.2, a calpain-like protein.

Two bacterial peptidases are also part of this family:

Aminopeptidase C from *Lactococcus lactis* (gene pepC) (Chapot-Chartier et al. (1993) *Appl. Environ. Microbiol* 59:330–333).

Thiol protease tpr from *Porphyromonas gingivalis*.

Three other proteins are structurally related to this family, but may have lost their proteolytic activity.

Soybean oil body protein P34. This protein has its active site cysteine replaced by a glycine.

Rat testin, a sertoli cell secretory protein highly similar to cathepsin L but with the active site cysteine is replaced by a serine. Rat testin should not be confused with mouse testin which is a LIM-domain protein (see).

Plasmodium falciparum serine-repeat protein (SERA), the ajor blood stage antigen. This protein of 111 Kd possesses a C-terminal thiol-protease-like domain Higgins et al. (1989) *Nature* 340:604–604), but the active site cysteine is replaced by a serine.

The sequences around the three active site residues are well conserved and can be used as signature patterns.

Cytosol Aminopeptidase Signature

Cytosol aminopeptidase is a eukaryotic cytosolic zinc-dependent exopeptidase that catalyzes the removal of unsubstituted amino-acid residues from the N-terminus of proteins. This enzyme is often known as leucine aminopeptidase (EC 3.4.11.1) (LAP) but has been shown (Matsushima et al. (1991) *Biochem. Biophys. Res. Commun.* 178:1459–1464) to be identical with prolyl aminopeptidase (EC 3.4.11.5). Cytosol aminopeptidase is a hexamer of identical chains, each of which binds two zinc ions.

Cytosol aminopeptidase is highly similar to *Escherichia coli* pepA, a manganese dependent aminopeptidase. Residues involved in zinc ion-binding (Burley et al. (1992) *J. Mol. Biol.* 224:113–140) in the mammalian enzyme are absolutely conserved in pepA where they presumably bind manganese.

A cytosol aminopeptidase from *Rickettsia prowazekii* (Wood et al. (1993) *J. Bacteriol.* 175:159–165) and one from *Arabidopsis thaliana* also belong to this family.

Neutral Zinc Metallopeptidases, Zinc-Binding Region Signature

The majority of zinc-dependent metallopeptidases (with the notable exception of the carboxypeptidases) share a common pattern of primary structure (Jongeneel et al. (1989) *FEBS Lett.* 242:211–214; Murphy et al.((991) *FEBS Lett.* 289:4–7) in the part of their sequence involved in the binding of zinc, and can be grouped together as a superfamily on the basis of this sequence similarity. They can be classified into a number of distinct families (Rawlings et al. (1995) *Meth. Enzymol.* 248:183–228) listed below along with some proteases that belong to these families:

Family M1
Bacterial aminopeptidase N (EC 3.4.11.2) (gene pepN).
Mammalian aminopeptidase N (EC 3.4.11.2).
Mammalian glutamyl aminopeptidase (EC 3.4.11.7) (aminopeptidase A). It may play a role in regulating growth and differentiation of early B-lineage cells.
Yeast aminopeptidase yscII (gene APE2).
Yeast alanine/arginine aminopeptidase (gene AAP1).
Yeast hypothetical protein YIL137c.
Leukotriene A-4 hydrolase (EC 3.3.2.6). This enzyme is responsible or the hydrolysis of an epoxide moiety of LTA-4 to form LTB-4; it has been shown (Medina et al.I (1991) *Proc. Natl. Acad. Sci. U.S.A.* 88:7620–7624) that it binds zinc and is capable of peptidase activity.
Family M2
Angiotensin-converting enzyme (EC 3.4.15.1) (dipeptidyl carboxypeptidase I) (ACE) the enzyme responsible for hydrolyzing angiotensin I to angiotensin II. There are two forms of ACE: a testis-specific isozyme and a somatic isozyme which has two active centers (Ehlers et al. (1991) *Biochemistry* 30:7118–7126).
Family M3
Thimet oligopeptidase (EC 3.4.24.15), a mammalian enzyme involved in the cytoplasmic degradation of small peptides.
Neurolysin (EC 3.4.24.16) (also known as mitochondrial oligopeptidase M or microsomal endopeptidase).
Mitochondrial intermediate peptidase precursor (EC 3.4.24.59) (MIP). It is involved the second stage of processing of some proteins imported in the mitochondrion.
Yeast saccharolysin (EC 3.4.24.37) (proteinase yscD) (Buchler et al. (1994) *Eur. J. Biochem.* 219:627–639).
*Escherichia coli* and related bacteria dipeptidyl carboxypeptidase (EC 3.4.15.5) (gene dcp).
*Escherichia coli* and related bacteria oligopeptidase A (EC 3.4.24.70) (gene opdA or prlC).
Yeast hypothetical protein YKL134c.
Family M4
Thermostable thermolysins (EC 3.4.24.27), and related thermolabile neutral proteases (bacillolysins) (EC 3.4.24.28) from various species of Bacillus.
Pseudolysin (EC 3.4.24.26) from *Pseudomonas aeruginosa* (gene lasB).
Extracellular elastase from *Staphylococcus epidermidis*.
Extracellular protease prt1 from *Erwinia carotovora*.
Extracellular minor protease smp from *Serratia marcescens*.
Vibriolysin (EC 3.4.24.25) from various species of Vibrio.
Protease prtA from *Listeria monocytogenes*.
Extracellular proteinase proA from *Legionella pneumophila*.
Family M5
Mycolysin (EC 3.4.24.31) from *Streptomyces cacaoi*.
Family M6
Immune inhibitor A from *Bacillus thuringiensis* (gene ina). Ina degrades two classes of insect antibacterial proteins, attacins and cecropins.
Family M7
Streptomyces extracellular small neutral proteases
Family M8
Leishmanolysin (EC 3.4.24.36) (surface glycoprotein gp63), a cell surface protease from various species of Leishmania.
Family M9
Microbial collagenase (EC 3.4.24.3) from *Clostridium perfringens* and *Vibrio alginolyticus*.
Family M10A
Serralysin (EC 3.4.24.40), an extracellular metalloprotease from Serratia.
Alkaline metalloproteinase from *Pseudomonas aeruginosa* (gene aprA).
Secreted proteases A, B, C and G from Erwinia chrysanthemi.
Yeast hypothetical protein YIL108w.
Family M10B
Mammalian extracellular matrix metalloproteinases (known as matrixins) (Woessner (1991) *FASEB J.* f:2145–2154): MMP-1 (EC 3.4.24.7) (interstitial collagenase), MMP-2 (EC 3.4.24.24) (72 Kd gelatinase), MMP-9 (EC 3.4.24.35) (92 Kd gelatinase), MMP-7 (EC 3.4.24.23) (matrylisin), MMP-8 (EC 3.4.24.34) (neutrophil collagenase), MMP-3 (EC 3.4.24.17) (stromelysin-1), MMP-10 (EC 3.4.24.22) (stromelysin-2), and MMP-11 (stromelysin-3), MMP-12 (EC 3.4.24.65) (macrophage metalloelastase).
Sea urchin hatching enzyme (envelysin) (EC 3.4.24.12), a protease that allows the embryo to digest the protective envelope derived from the egg extracellular matrix.
Soybean metalloendoproteinase 1.
Family M11
*Chlamydomonas reinhardtii* gamete lytic enzyme (GLE).
Family M12A
Astacin (EC 3.4.24.21), a crayfish endoprotease.
Meprin A (EC 3.4.24.18), a mammalian kidney and intestinal brush border metalloendopeptidase.
Bone morphogenic protein 1 (BMP-1), a protein which induces cartilage and bone formation and which expresses metalloendopeptidase activity. The Drosophila homolog of BMP-1 is the dorsal-ventral patterning protein tolloid.
Blastula protease 10 (BP10) from *Paracentrotus lividus* and the related protein SpAN from *Strongylocentrotus purpuratus*.
*Caenorhabditis elegans* hypothetical proteins F42A10.8 and R151.5.
Choriolysins L and H (EC 3.4.24.67) (also known as embryonic hatching proteins LCE and HCE) from the fish *Oryzias lapides*. These proteases participates in the breakdown of the egg envelope, which is derived from the egg extracellular matrix, at the time of hatching.

Family M12B
Snake venom metalloproteinases (Hite et al. (1992) *Bio. Chem. Hoppe-Seyler* 373:381–385). This subfamily mostly groups proteases that act in hemorrhage. Examples are: adamalysin II (EC 3.4.24.46), atrolysin C/D (EC 3.4.24.42), atrolysin E (EC 3.4.24.44), fibrolase (EC 3.4.24.72), trimerelysin I (EC 3.4.25.52) and II (EC 3.4.25.53).
Mouse cell surface antigen MS2.
Family M13
Mammalian neprilysin (EC 3.4.24.11) (neutral endopeptidase) (NEP).
Endothelin-converting enzyme 1 (EC 3.4.24.71) (ECE-1), which process the precursor of endothelin to release the active peptide.
Kell blood group glycoprotein, a major antigenic protein of erythrocytes.
The Kell protein is very probably a zinc endopeptidase.
Peptidase O from *Lactococcus lactis* (gene pepO).
Family M27
Clostridial neurotoxins, including tetanus toxin (TeTx) and the various botulinum toxins (BoNT). These toxins are zinc proteases that block neurotransmitter release by proteolytic cleavage of synaptic proteins such as synaptobrevins, syntaxin and SNAP-25 (Montecucco et al. (1993) *Trends Biochem. Sci.* 18:324–327; Niemann et a. (1994) *Trends Cell Biol.* 4:179–185).
Family M30
*Staphylococcus hyicus* neutral metalloprotease.
Family M32
Thermostable carboxypeptidase 1 (EC 3.4.17.19) (carboxypeptidase Taq), an enzyme from *Thermus aquaticus* which is most active at high tempertature.
Family M34
Lethal factor (LF) from *Bacillus anthracis*, one of the three proteins composing the anthrax toxin.
Family M35
Deuterolysin (EC 3.4.24.39) from *Penicillium citrinum* and related proteases from various species of Aspergillus.
Family M36
Extracellular elastinolytic metalloproteinases from Aspergillus.

From the tertiary structure of thermolysin, the position of the residues acting as zinc ligands and those involved in the catalytic activity are known. Two of the zinc ligands are histidines which are very close together in the sequence; C-terminal to the first histidine is a glutamic acid residue which acts as a nucleophile and promotes the attack of a water molecule on thecarbonyl carbon of the substrate.
Aminopeptidase P and Proline Dipeptidase Signature Aminopeptidase P (EC 3.4.11.9) is the enzyme responsible for the release of any N-terminal amino acid adjacent to a proline residue. Proline dipeptidase (EC 3.4.13.9) (prolidase) splits dipeptides with a prolyl residue in the carboxyl terminal position.

Bacterial aminopeptidase P II (gene pepP) (Yoshimoto et al. (1989) *J. Biochem.* 105:412–416), proline dipeptidase (gene pepQ) (Nakahigashi et al. (1990) *Nucleic Acids Res.* 18:6439–6439), and human proline dipeptidase (gene PEPD) (Endo et al. (1989) *J. Biol chem.* 264: 4476–4481) are evolutionary related. These proteins are manganese metalloenzymes.

Yeast hypothetical proteins YER078c and YFR006w and *Mycobacterium tuberculosis* hypothetical protein MtCY49.29c also belong to this family.
Methionine Aminopeptidase Signatures Methionine aminopeptidase (EC 3.4.11.18) (MAP) is responsible for the removal of the amino-terminal (initiator) methionine from nascent eukaryotic cytosolic and cytoplasmic prokaryotic proteins if the penultimate amino acid is small and uncharged. All MAP studied to date are monomeric proteins that require cobalt ions for activity.

Two subfamilies of MAP enzymes are known to exist (Arfin et al. (1995) *Proc. Natl. Acad. Sci. U.S.A.* 92:7714–1128; Keeling et al. (1996) *Trends Biochem. Sci.* 21:285–286). While being evolutionary related, they only share a limited amount of sequence similarity mostly clustered around the residues shown, in the *Escherichia coli* MAP (Roderick et al. (1993) *Biochemistry* 32:3907–3912), to be involved in cobalt-binding.

The first family consists of enzymes from prokaryotes as well as eukaryotic MAP-1, while the second group is made up of archebacterial MAP and eukaryotic MAP-2. The second subfamily also includes proteins which do not seem to be MAP, but that are clearly evolutionary related such as mouse proliferation-associated protein 1 and fission yeast curved DNA-binding protein.
Matrixins Cysteine Switch Mammalian extracellular matrix metalloproteinases (EC 3.4.24.-), also known as matrixins (Woessner (1991) *FASEB J.* 5:2145–2154) (see ), are zinc-dependent enzymes. They are secreted by cells in an inactive form (zymogen) that differs from the mature enzyme by the presence of an N-terminal propeptide. A highly conserved octapeptide is found two residues downstream of the C-terminal end of the propeptide. This region has been shown to be involved in autoinhibition of matrixins (Sanchez-Lopez et al. (1988) *J. Biol. Chem.* 266:11892–11899; Parks et al. (1991) *J. Biol. Chem.* 266:1584–1590); a cysteine within the octapeptide chelates the active site zinc ion, thus inhibiting the enzyme. This region has been called the "cysteine switch" or "autoinhibitor region".

A cysteine switch has been found in the following zinc proteases:
MMP-1 (EC 3.4.24.7) (interstitial collagenase).
MMP-2 (EC 3.4.24.24) (72 Kd gelatinase).
MMP-3 (EC 3.4.24.17) (stromelysin-1).
MMP-7 (EC 3.4.24.23) (matrilysin).
MMP-8 (EC 3.4.24.34) (neutrophil collagenase).
MMP-9 (EC 3.4.24.35) (92 Kd gelatinase).
MMP-10 (EC 3.4.24.22) (stromelysin-2).
MMP-11 (EC 3.4.24.-) (stromelysin-3).
MMP-12 (EC 3.4.24.65) (macrophage metalloelastase).
MMP-13 (EC 3.4.24.-) (collagenase 3).
MMP-14 (EC 3.4.24.-) (membrane-type matrix metalliproteinase 1).
MMP-15 (EC 3.4.24.-) (membrane-type matrix metalliproteinase 2).
MMP-16 (EC 3.4.24.-) (membrane-type matrix metalliproteinase 3).
Sea urchin hatching enzyme (EC 3.4.24.12) (envelysin) (Lepage et al. (1990) *EMBO J.* 93003–3012).
*Chlamydomonas reinhardtii* gamete lytic enzyme (GLE) (Kinshita et al. (1992) *Proc. Natl. Acad. Sci. U.S.A.* 89:4693–4697).
Serine Carboxypeidases, Active Sites All known carboxypeptidases are either metallo carboxypeptidases or serine carboxypeptidases (EC 3.4.16.5 and EC 3.4.16.6). The catalytic activity of the serine carboxypeptidases, like that of the trypsin family serine proteases, is provided by a charge relay system involving an aspartic acid residue hydrogen-bonded to a histidine, which is itself hydrogen-bonded to aserine (Liao et al. (1990) *J. Biol. Chem.* 265:6528–6531). Proteins known to be serine carboxypeptidases include, but are not limited to:

Barley and wheat serine carboxypeptidases I, II, and III (Sorenson et al. (1989) *Carlsberg Res. Commun.* 54:193–202).

Yeast carboxypeptidase Y (YSCY) (gene PRC1), a vacuolar protease involved in degrading small peptides.

Yeast KEX1 protease, involved in killer toxin and alpha-factor precursor processing.

Fission yeast sxa2, a probable carboxypeptidase involved in degrading or processing mating pheromones (Imai et al. (1992) *Mol. Cell. Biol.* 12:1827–1834).

*Penicillium janthinellum* carboxypeptidase S1 (Svendsen et al. (1993) *FEBS Lett.* 333:39043).

*Aspergullus niger* carboxypeptidase pepF.

*Aspergullus satoi* carboxypeptidase cpdS.

Vertebrate protective protein/cathepsin A (Galjart et al. (1991) *J. Biol. Chem* 266:14754–14762), a lysosomal protein which is not only a carboxypeptidase but also essential for the activity of both beta-galactosidase and neuraminidase.

Mosquito vitellogenic carboxypeptidase (VCP) (Cho et al. (1991) *Proc. Natl. Acad. Sci. U.S.A.* 88:10821–10824).

*Naegleria fowleri* virulence-related protein Nf314 (Hu et al. (1992) *Infect. Immun.* 60:2418–2424).

Yeast hypothetical protein YBR139w.

*Caenorhabditis elegans* hypothetical proteins C08H9.1, F13D12.6, F32A5.3, F41C3.5 and K10B2.2.

This family also includes:

Sorghum (s)-hydroxymandelonitrile lyase (EC 4.1.2.11) (hydroxynitrile lyase) (HNL) (Wajant et al. (1994) *Plant Mol. Biol.* 26:735–746), an enzyme involved in plant cyanogenesis.

The sequences surrounding the active site serine and histidine residues are highly conserved in all these serine carboxypeptidases.

Proteasome A-type Subunits Signature

The proteasome (or macropain) (EC 3.4.99.46) (Rivett (1993) *Biochem. J.* 29:1–10; Rivett (1989) *Arch. Biochem Biophys.* 268:1–8; Goldbert et al. (1992) *Nature* 357:375–379; Wilk (1993) *Enzyme Protein* 47:187–188; Hilt et al. (1996) *Trends Biochem. Sci.* 21:96–102) is an eukaryotic and archaebacterial multicatalytic proteinase complex that seems to be involved in an ATP/ubiquitin-dependent nonlysosomal proteolytic pathway. In eukaryotes the proteasome is composed of about 28 distinct subunits which form a highly ordered ring-shaped structure (20S ring) of about 700 Kd.

Most proteasome subunits can be classified, on the basis on sequence similarities into two groups, A and B. Subunits that belong to the A-type group are proteins of from 210 to 290 amino acids that share a number of conserved sequence regions. Subunits that are known to belong to this family include, but are not limited to:

Vertebrate subunits C2 (nu), C3, C8, C9, iota and zeta.

Drosophila PROS-25, PROS-28.1, PROS-29 and PROS-35.

Yeast C1 (PRS1), C5 (PRS3), C7-alpha (Y8) (PRS2), Y7, Y13, PRE5, PRE6 and PUP2.

*Arabidopsis thaliana* subunits alpha and PSM30.

*Thermoplasma acidophilum* alpha-subunit. In this archaebacteria the proteasome is composed of only two different subunits.

Proteasome B-type Subunits Signature

The proteasome (or macropain) (EC 3.4.99.46) (Rivett (1993) *Biochem. J.* 29:1–10; Rivett (1989) *Arch. Biochem Biophys.* 268:1–8; Goldbert et al. (1992) *Nature* 357:375–379; Wilk (1993) *Enzyme Protein* 47:187–188; Hilt et al. (1996) *Trends Biochem. Sci.* 21:96–102) is an eukaryotic and archaebacterial multicatalytic proteinase complex that seems to be involved in an ATP/ubiquitin-dependent nonlysosomal proteolytic pathway. In eukaryotes the proteasome is composed of about 28 distinct subunits which form a highly ordered ring-shaped structure (20S ring) of about 700 Kd.

Most proteasome subunits can be classified, on the basis on sequence similarities into two groups, A and B. Subunits that belong to the B-type group are proteins of from 190 to 290 amino acids that share a number of conserved sequence regions. Subunits that belong to this family include, but are not limited to:

Vertebrate subunits C5, beta, delta, epsilon, theta (C10II), LMP2/RING12, C13 (LMP7/RING10), C7-I and MECL-1.

Yeast PRE1, PRE2 (PRG1), PRE3, PRE4, PRS3, PUPI and PUP3.

Drosophila L(3)73AI.

Fission yeast pts1.

*Thermoplasma acidophilum* beta-subunit. In this archaebacteria the proteasome is composed of only two different subunits.

Serine Proteases, Trypsin Family, Active Sites

The catalytic activity of the serine proteases from the trypsin family is provided by a charge relay system involving an aspartic acid residue hydrogen-bonded to a histidine, which itself is hydrogen-bonded to a serine. The sequences in the vicinity of the active site serine and histidine residues are well conserved in this family of proteases (Brenner (1988) *Nature* 334:528–530). Proteases that belong to the trypsin family include, but are not limited to:

Acrosin.

Blood coagulation factors VII, IX, X, XI and XII, thrombin, plasminogen, and protein C.

Cathepsin G.

Chymotrypsins.

Complement components C1r, C1s, C2, and complement factors B, D and I.

Complement-activating component of RA-reactive factor.

Cytotoxic cell proteases (granzymes A to H).

Duodenase I.

Elastases 1, 2, 3A, 3B (protease E), leukocyte (medullasin).

Enterokinase (EC 3.4.21.9) (enteropeptidase).

Hepatocyte growth factor activator.

Hepsin.

Glandular (tissue) kallikreins (including EGF-binding protein types A, B, and C, NGF-gamma chain, gamma-renin, prostate specific antigen (PSA) and tonin).

Plasma kallikrein.

Mast cell proteases (MCP) 1 (chymase) to 8.

Myeloblastin (proteinase 3) (Wegener's autoantigen).

Plasminogen activators (urokinase-type, and tissue-type).

Trypsins I, II, III, and IV.

Tryptases.

Snake venom proteases such as ancrod, batroxobin, cerastobin, flavoxobin,and protein C activator.

Collagenase from common cattle grub and collagenolytic protease from Atlantic sand fiddler crab.

Apolipoprotein(a).

Blood fluke cercarial protease.

Drosophila trypsin like proteases: alpha, easter, snake-locus.

Drosophila protease stubble (gene sb).

Major mite fecal allergen Der p III.

All the above proteins belong to family S1 in the classification of peptidases (Rawlings et al. (1994) *Meth. Enzymol.* 244:19–61) and originate from eukaryotic species. It should be noted that bacterial proteases that belong to family S2A are similar enough in the regions of the active site residues that they can be picked up by the same patterns. These proteases include, but are not limited to:

*Achromobacter lyticus* protease I.

Lysobacter alpha-lytic protease.

Streptogrisin A and B (Streptomyces proteases A and B).

*Streptomyces griseus* glutamyl endopeptidase II.

*Streptomyces fradiae* proteases 1 and 2.

Ubiquitin Carboxyl-Terminal Hydrolases Family 1 Cysteine Active Sites

Ubiquitin carboxyl-terminal hydrolases (EC 3.1.2.15) (UCH) (deubiquitinating enzymes) (Jentsch et al. (1991) *Biochim. Biophys. Acta* 1089:127–139) are thiol proteases that recognize and hydrolyze the peptide bond at the C-terminal glycine of ubiquitin. These enzymes are involved in the processing of poly-ubiquitin precursors as well as that of ubiquinated proteins.

There are two distinct families of UCH. The first class consist of enzymes of about 25 Kd and is currently represented by:

Mammalian isozymes L1 and L3.

Yeast YUH1.

Drosophila Uch.

One of the active site residues of class-I UCH (Johnston et al. (1997) *EMBO J.* 16:3787–3796) is a cysteine.

Ubiquitin Carboxyl-Terminal Hydrolases Family 2 Signatures

Ubiquitin carboxyl-terminal hydrolases (EC 3.1.2.15) (UCH) (deubiquitinating enzymes) (Jentsch et al. (1991) *Biochim. Biophysi. Acta* 1089:127–139) are thiol proteases that recognize and hydrolyze the peptide bond at the C-terminal glycine of ubiquitin. These enzymes are involved in the processing of poly-ubiquitin precursors as well as that of ubiquinated proteins.

There are two distinct families of UCH. The second class (Papa et al. (1993) *Nature* 366:313–319) consist of large proteins (800 to 2000 residues) and is represented by:

Yeast UBP1, UBP2, UBP3, UBP4 (or DOA4/SSV7), UBP5, UBP7, UBP9, UBP11, UBP12 and UBP13.

Yeast hypothetical protein YBR058c.

Yeast hypothetical protein YFR010w.

Yeast hypothetical protein YMR304w.

Yeast hypothetical protein YMR223w.

Yeast hypothetical protein YNL186w.

Human tre-2.

Human isopeptidase T.

Human isopeptidase T-3.

Mammalian Ode-1.

Mammalian Unp.

Mouse Dub-1.

Drosophila fat facets protein (gene faf).

Mammalian faf homolog.

*Caenorhabditis elegans* hypothetical protein R10E11.3.

*Caenorhabditis elegans* hypothetical protein K02C4.3.

These proteins only share two regions of similarity. The first region contains a conserved cysteine which is probably implicated in the catalytic mechanism. The second region contains two conserved histidines residues, one of which is also probably implicated in the catalytic mechanism.

The identification and characterization of the genes encoding the human proteases is described. The invention is based, at least in part, on the discovery of human genes encoding members of protease families, including but not limited to those described herein. The human protease family members were isolated based on a specific consensus motif or protein domain characteristic of a protease family of proteins. The search of the nucleic acid sequence database (usually derived from random cDNA library sequencing) was performed with one or more HMM motifs, a TBLASTN set, or both.

The TBLASTN set included a set of protein sequence probes which correspond to amino acid sequence motifs that are conserved in the protease family of proteins.

The HMM motif included a consensus sequence for a protein domain. Such consensus sequences can be found in a database of Hidden Markov Models (HMMs), e.g., the Pfam database, release 2.1, (http://www.sanger.ac.uk/Software/Pfam/HMM search). A description of the Pfam database can be found in Sonhammer et al. (1997) *Proteins* 23(3):405–420 and detailed description of HMMs can be found in, for example, Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

The sequences of the positive clones were determined and are set forth herein as SEQ ID NOS:1–268.

Polynucleotides

Accordingly, the invention provides isolated nucleic acid molecules comprising a nucleotide sequence selected from the group consisting of SEQ ID NOS: 1–268 and the complements thereof. The Sequence Listing shows the relationship between each nucleotide sequence and protease family.

In one embodiment, the isolated nucleic acid molecule has the formula:

$$5'(R_1)_n-(R_2)-(R_3)_m3'$$

wherein, at the 5' end of the molecule $R_1$ is either hydrogen or any nucleotide residue when n=1, and is any nucleotide residue when n>1; at the 3' end of the molecule $R_3$ is either hydrogen, a metal or any nucleotide residue when m=1, and is any nucleotide residue when m>1; n and m are integers between about 1 and 5000; and $R_2$ is a nucleic acid having a nucleotide sequence selected from the group consisting of SEQ ID NOS: 1–268 and the complements of SEQ ID NOS: 1–268. The $R_2$ nucleic acid is oriented so that its 5' residue is bound to the 3' molecule of $R_1$, and its 3' residue is bound to the 5' molecule of $R_3$. Any stretch of nucleic acid residues denoted by either $R_1$ or $R_3$, which is greater than 1, is preferably a heteropolymer, but can also be a homopolymer. In certain embodimentss, n and m are integers between about 1 and 2000, preferably between about 1 and 1000, and preferably between about 1 and 500. In other embodiments, the isolated nucleic acid molecule is at least about 50 nucleotides, preferably at least about 100 nucleotides, more preferably at least about 150 nucleotides, and even more preferably at least about 200 or more nucleotides in length. In still another embodiment, $R_1$ and $R_3$ are both hydrogen.

The term "protease polynucleotide" or "protease nucleic acid" refers to nucleic acid having the sequences shown in SEQ ID NO: 1–268 as well as variants and fragments of the polynucleotides of SEQ ID NO: 1–268.

An "isolated" protease nucleic acid is one that is separated from other nucleic acid present in the natural source of the protease nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the nucleic acid is isolated from flanking sequences such that it can be subjected to the specific manipulations described herein such as recombinant expression, preparation of probes and primers, and other uses specific to the protease nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector or other construct (i.e., as part of a larger constructed nucleic acid) are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The invention provides isolated polynucleotides encoding protease polypeptides.

The nucleic acid molecule can include all or a portion of the coding sequence. In one embodiment, the protease nucleic acid comprises only the coding region. The polynucleotides include, but are not limited to, the sequence encoding the mature polypeptide alone or the sequence encoding the mature polypeptide and additional coding sequences, such as a leader or secretory sequence (e.g., a pre-pro or pro-protein sequence). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes. The nucleic acid molecule can include the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification, such as those described herein.

Protease polynucleotides can be in the form of RNA, such as mRNA, or in the form of DNA, including cDNA and genomic DNA, obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

Protease nucleic acids comprise the nucleotide sequences shown in SEQ ID NOS: 1–268, corresponding to human protease cDNAs.

The invention further provides variant protease polynucleotides, and fragments thereof, that differ from the nucleotide sequence shown in SEQ ID NOS: 1–268 due to degeneracy of the genetic code and thus encode the same protein as that encoded by the nucleotide sequences shown in SEQ ID NOS: 1–268.

The invention also provides protease nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, the variants can contain nucleotide substitutions, deletions, inversions and insertions.

Variation can occur in either or both the coding and non-coding regions. The variations can produce both conservative and non-conservative amino acid substitutions.

Typically, variants have a substantial identity with a nucleic acid molecule selected from the group consisting of SEQ ID NOS: 1–268 and the complements thereof.

Orthologs, homologs, and allelic variants can be identified using methods well known in the art. These variants comprise a nucleotide sequence encoding a protease that is 50–55% at least about 55%, typically at least about 70–75%, more typically at least about 80–85%, and most typically at least about 90–95% or more homologous to the nucleotide sequence shown herein or a fragment of these sequences. Such nucleic acid molecules can be readily identified as being able to hybridize under stringent conditions to a nucleotide sequence or fragments thereof selected from the group consisting of SEQ ID NOS: 1–268 and the complements thereof. In one embodiment, the variants hybridize under high stringency hybridization conditions (e.g., for selective hybridization) to a nucleotide sequence selected from SEQ ID NOS: 1–268. It is understood that stringent hybridization does not indicate substantial homology where it is due to general homology, such as poly A sequences, or sequences common to all or most proteins, sequences common to all or most proteases, or sequences common to all or most members of the protease family to which the specific protease belongs. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a protease at least 50–55%, 55% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current *Protocols in Molecular Biology*, John Wiley & Sons, N.Y. (1989), 6.3.1–6.3.6, incorporated by reference. One example of stringent hybridization conditions are hybridization in 6×sodium chloride/sodium citrate (SSC) at about 45° C., followed by one or more washes in 0.2×SSC, 0.1% SDS at 50–65° C. In another non-limiting example, nucleic acid molecules are allowed to hybridize in 6×sodium chloride/sodium citrate (SSC) at about 45° C., followed by one or more low stringency washes in 0.2× SSC/0.1% SDS at room temperature, or by one or more moderate stringency washes in 0.2×SSC/0. 1% SDS at 42° C., or washed in 0.2×SSC/0.1% SDS at 65° C. for high stringency. In one embodiment, an isolated protease nucleic acid molecule that hybridizes under stringent conditions to the sequence of SEQ ID NOS: 1–268 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to a nucleotide sequence selected from the group consisting of SEQ ID NOS: 1–268 and the complements of SEQ ID NOS: 1–268. In one embodiment, the nucleic acid consists of a portion of a nucleotide sequence selected from the group consisting of SEQ ID NOS: 1–268 and the complements SEQ ID NOS: 1–268. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic proteins or polypeptides described herein are useful. Additionally, nucleotide sequences described herein can also be contigged to produce longer sequences (see, for example, http://bozeman.mbt.washington.edu/phrap.docs/phrap.html).

In a related aspect, the nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al., *Science* 254, 1497–1500 (1991). Typically, a probe comprises a region of nucleotide sequence that hybridizes under highly stringent conditions to at least about 15, typically about 20–25, and more typically about 40, 50 or 75 consecutive nucleotides of a nucleic acid selected from the group consisting of SEQ ID NOS: 1–268 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Fragments include nucleic acid sequences corresponding to specific amino acid sequences described herein. Further fragments can include subfragments of specific domains or sites, such as proteolytic cleavage sites, sites of interaction with a protein that modifies or activates the protease (an "effector" protein), or substrate binding sites. Nucleic acid fragments, according to the present invention, are not to be construed as encompassing those fragments that may have been disclosed prior to the invention.

Protease nucleic acid fragments include sequences corresponding to any domain described herein, subregions also described, and specific functional sites, such as binding and cleavage sites. Protease nucleic acid fragments also include combinations of the domains, regions, segments, and other functional sites described herein. A person of ordinary skill in the art would be aware of the many permutations that are possible.

It is understood that a protease fragment includes any nucleic acid sequence that does not include the entire gene.

Where the location of the domains or sites have been predicted by computer analysis, one of ordinary skill would appreciate that the amino acid residues constituting these domains can vary depending on the criteria used to define the domains.

The invention also provides protease nucleic acid fragments that encode epitope bearing regions of the protease proteins encoded by the cDNAs of the invention.

For example, the coding region of a protease gene can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of protease genes.

The nucleic acid molecules of the invention such as those described above can be identified and isolated using standard molecular biology techniques and the sequence information provided in SEQ ID NOS: 1–268. For example, nucleic acid molecules can be amplified and isolated by the polymerase chain reaction using synthetic oligonucleotide primers designed based on one or more of the sequences provided in SEQ ID NOS: 1–268 and the complements thereof. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Polynucleotide Uses

The nucleic acid sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The protease polynucleotides are useful for probes, primers, and in biological assays. Where the polynucleotides are used to assess protease properties or functions, such as in the assays described herein, all or less than all of the entire cDNA can be useful. In this case, even fragments that may have been known prior to the invention are encompassed. Thus, for example, assays specifically directed to protease functions, such as assessing agonist or antagonist activity, encompass the use of known fragments. Further, diagnostic methods for assessing protease function can also be practiced with any fragment, including those fragments that may have been known prior to the invention. Similarly, in methods involving treatment of protease dysfunction, all fragments are encompassed including those which may have been known in the art.

The protease polynucleotides are useful as a hybridization probe for cDNA and genomic DNA to isolate a full-length cDNA and genomic clones encoding the protease polypeptides and to isolate cDNA and genomic clones that correspond to variants producing the same protease polypeptides or the other types of variants described herein. Variants can be isolated from the same tissue and organism from which the polypeptides were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the protease. Accordingly, it could be derived from 5' noncoding regions, the coding region, and 3' noncoding regions.

The nucleic acid probe can be, for example, the full-length cDNA sequence of SEQ ID NOS: 1–268, or fragments thereof, such as an oligonucleotide of at least 12, 15, 30, 50, 100, 250 or 500 nucleotides in length and sufficient to specifically hybridize under stringent conditions to mRNA or DNA. For example, the nucleic acid probe can be all or a portion of SEQ ID NOS: 1–268, or the complement of SEQ ID NOS: 1–268, or a portion thereof. Other suitable probes for use in the diagnostic assays of the invention are described herein.

Fragments of the polynucleotides described herein are also useful to synthesize larger fragments or full-length polynucleotides described herein. For example, a fragment can be hybridized to any portion of an mRNA and a larger or full-length cDNA can be produced.

Antisense nucleic acids of the invention can be designed using the nucleotide sequences of SEQ ID NOS: 1–268, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid) will be of an antisense orientation to a target nucleic acid of interest.

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell proteases in vivo), or agents facilitating transport across the cell membrane (see, e.g., Letsinger et al. (1989) *Proc. Natl. Acad. Sci USA* 86:6553–6556; Lemaitre et al. (1987) *Proc. Natl. Acad. Sci. USA* 84:648–652; PCT Publication No. WO88/0918) or the blood brain barrier (see, e.g., PCT Publication No. Wo89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The protease polynucleotides are also useful as primers for PCR to amplify any given region of a protease polynucleotide.

The protease polynucleotides are also useful for constructing recombinant vectors. Such vectors include expression vectors that express a portion of, or all of, the protease polypeptides. Vectors also include insertion vectors, used to integrate into another polynucleotide sequence, such as into the cellular genome, to alter in situ expression of protease genes and gene products. For example, an endogenous protease coding sequence can be replaced via homologous recombination with all or part of the coding region containing one or more specifically introduced mutations.

The protease polynucleotides are also useful for expressing antigenic portions of the proteases.

The protease polynucleotides are also useful as probes for determining the chromosomal positions of the proteases by means of in situ hybridization methods.

Once the nucleic acid (or a portion of the sequence) has been isolated, it can be used to map the location of the gene on a chromosome. The mapping of the sequences to chromosomes is an important first step in correlating these sequences with genes associated with disease. Briefly, genes can be mapped to chromosomes by preparing PCR primers (preferably 15–25 bp in length) from the nucleic acid molecules described herein. Computer analysis of the sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the appropriate nucleotide sequences will yield an amplified fragment.

PCR mapping of somatic cell hybrids is a rapid procedure for assigning a particular sequence to a particular chromosome. Three or more sequences can be assigned per day using a single thermal cycle. Using the nucleic acid molecules of the invention to design oligonucleotide primers, sublocalization can be achieved with panels of fragments from specific chromosomes. Other mapping strategies which can similarly be used to map a specified sequence to its chromosome include in situ hybridization (described in Fan, Y et al. (1990) *PNAS,* 97:6223–27), pre-screening with labeled flow-sorted chromosomes, and pre-selection by hybridization to chromosome specific cDNA libraries.

Fluorescence in situ hybridization (FISH) of a nucleotide sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a nucleotide sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. for a review of this technique, see Verma et al., *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man,* available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible form chromosome spreads or detectable using PCR based on that DNA sequence. Ultimately, complete sequencing of genes from several individuals can be performed to confirm the presence of a mutation and to distinguish mutations from polymorphisms.

The polynucleotide probes are also useful to determine patterns of the presence of the gene encoding the proteases and their variants with respect to tissue distribution, for example, whether gene duplication has occurred and whether the duplication occurs in all or only a subset of tissues. The genes can be naturally-occurring or can have been introduced into a cell, tissue, or organism exogenously.

The polynucleotides are also useful for designing ribozymes corresponding to all, or a part, of the mRNA produced from genes encoding the polynucleotides described herein.

The polynucleotides are also useful for constructing host cells expressing a part, or all, of the protease polynucleotides and polypeptides.

The polynucleotides are also useful for constructing transgenic animals expressing all, or a part, of the protease polynucleotides and polypeptides.

The polynucleotides are also useful as hybridization probes for determining the level of protease nucleic acid expression. Accordingly, the probes can be used to detect the presence of, or to determine levels of, protease nucleic acid in cells, tissues, and in organisms. The nucleic acid whose level is determined can be DNA or RNA, including mRNA. Accordingly, probes corresponding to the polypeptides described herein can be used to assess gene copy number in a given cell, tissue, or organism. This is particularly relevant in cases in which there has been an amplification of the protease genes.

Alternatively, the probe can be used in an in situ hybridization context to assess the position of extra copies of the protease genes, as on extrachromosomal elements or as integrated into chromosomes in which the protease gene is not normally found, for example as a homogeneously staining region.

These uses are relevant for diagnosis of disorders involving an increase or decrease in protease expression relative to normal, such as a proliferative disorder, a differentiative or developmental disorder, or a hematopoietic disorder.

Thus, the present invention provides a method for identifying a disease or disorder associated with aberrant expression or activity of protease nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease, such as by measuring a level of a protease-encoding nucleic acid in a sample of cells from a subject e.g., mRNA or genomic DNA, or determining if a protease gene has been mutated.

Nucleic acid expression assays are useful for drug screening to identify compounds that modulate protease nucleic acid expression (e.g., antisense, polypeptides, peptidomimetics, small molecules or other drugs). A cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. The modulator may bind to the nucleic acid or indirectly modulate expression, such as by interacting with other cellular components that affect nucleic acid expression.

The invention thus provides a method for identifying a compound that can be used to treat a disorder associated with nucleic acid expression of the protease gene. The method typically includes assaying the ability of the compound to modulate the expression of the protease nucleic acid and thus identifying a compound that can be used to treat a disorder characterized by undesired protease nucleic acid expression.

The assays can be performed in cell-based and cell-free systems. Cell-based assays include cells naturally expressing the protease nucleic acid or recombinant cells genetically engineered to express specific nucleic acid sequences.

Modulatory methods can be performed in vitro (e.g., by culturing the cell with the agent) or, alternatively, in vivo (e.g., by administering the agent to a subject) in patients or in transgenic animals.

The assay for protease nucleic acid expression can involve direct assay of nucleic acid levels, such as mRNA levels, or on collateral compounds involved in the pathway in which the protease is found. Further, the expression of genes that are up- or down-regulated in response to the protease function in the pathway can also be assayed. In this embodiment the regulatory regions of these genes can be operably linked to a reporter gene such as luciferase.

Accordingly, the invention provides methods of treatment, with the nucleic acid as a target, using a compound identified through drug screening as a gene modulator to modulate protease nucleic acid expression. Modulation includes both up-regulation (i.e. activation or agonization) or down-regulation (suppression or antagonization) or effects on nucleic acid activity (e.g. when nucleic acid is mutated or improperly modified) Treatment is of disorders characterized by aberrant expression or activity of nucleic acid.

One aspect of the invention relates to diagnostic assays for determining nucleic acid expression as well as activity in the context of a biological sample (e.g., blood, serum, cells, tissue) to thereby determine whether an individual has a disease or disorder, or is at risk of developing a disease or disorder, associated with aberrant expression or activity. Such assays can be used for prognostic or predictive purpose to thereby prophylactically treat an individual prior to the onset of a disorder characterized by or associated with expression or activity of the nucleic acid molecules.

The protease polynucleotides are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The protease polynucleotides are also useful in diagnostic assays for qualitative changes in protease nucleic acid, and particularly in qualitative changes that lead to pathology. The polynucleotides can be used to detect mutations in protease genes and gene expression products such as mRNA. The polynucleotides can be used as hybridization probes to detect naturally-occurring genetic mutations in a protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of a protease gene associated with a dysfunction provides a diagnostic tool for an active disease or susceptibility to disease when the disease results from overexpression, underexpression, or altered expression of a protease.

Individuals carrying mutations in the protease gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA,* 87:1874–1878), transcriptional amplification system (Kwoh, D. Y. et al., (1989) *Proc. Natl. Acad. Sci. USA,* 86:1173–1177), Q-Beta Replicase (Lizardi, P. M. et al.,(1988) *Bio/Technology,* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant protease gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)).

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis,* 15:1657–1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039. In other embodiments, electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.,* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin, M. T. et al. (1996) *Human Mutation,* 7:244–255; Kozal, M. J. et al. (1996) *Nature Medicine,* 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market.

Pharmacogenomics deal with clinically significant hereditary variations in the response to drugs due to altered drug disposition and abnormal action in affected persons. See, e.g., Eichelbaum, M., *Clin. Exp. Pharmacol. Physiol.* 23(10–11):983–985 (1996), and Linder, M. W., *Clin. Chem.* 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease in which one or more of the protease functions in one population is different from those in another population.

The protease polynucleotides are thus useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in a protease gene that results in altered affinity for substrate or effector could result in an excessive or decreased drug effect with standard concentrations of effector that activates the protease or substrate cleaved by the protease. Accordingly, the protease polynucleotides described herein can be used to assess the mutation content of the protease gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The protease polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The protease polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the protease sequence can be used to provide an alternative technique which determines the actual DNA sequence of selected fragments in the genome of an individual. Thus, the protease sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The protease sequences can be used to obtain such identification sequences from individuals and from tissue. The sequences represent unique fragments of the human genome. Each of the sequences described herein can, to some degree, be used as a standard against which DNA from an individual can be compared for identification purposes. The noncoding sequences of these sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The protease polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The protease polynucleofides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique. Examples of polynucleotide reagents include the nucleic acid molecules or the invention, or portions thereof, e.g., fragments having a length of at least 20 bases, preferably at least 30 bases.

The protease polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of protease probes can be used to identify tissue by species and/or by organ type.

In a similar fashion, these primers and probes can be used to screen tissue culture for contamination (i.e. screen for the presence of a mixture of different types of cells in a culture).

Alternatively, the protease polynucleotides can be used directly to block transcription or translation of protease gene sequences by means of antisense or ribozyme constructs. Thus, in a disorder characterized by abnormally high or undesirable protease gene expression, nucleic acids can be directly used for treatment.

The protease polynucleotides are thus useful as antisense constructs to control protease gene expression in cells, tissues, and organisms. A DNA antisense polynucleotide is designed to be complementary to a region of the gene involved in transcription, preventing transcription and hence production of protease protein. An antisense RNA or DNA polynucleotide would hybridize to the mRNA and thus block translation of mRNA into protease protein.

Examples of antisense molecules useful to inhibit nucleic acid expression include antisense molecules complementary to a fragment of any 5' untranslated regions present in SEQ ID NOS: 1–268 which also includes the start codon and antisense molecules which are complementary to a fragment of any 3' untranslated region present in SEQ ID NOS: 1–268.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding and cleavage site.

The protease polynucleotides also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. For example, the kit can comprise reagents such as a labeled or labelable nucleic acid (probe or primer) or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease mRNA or DNA.

Polypeptides

The invention thus relates to novel proteases having the deduced amino acid sequences encoded by the open reading frames present in the nucleic acid molecules of SEQ ID NOS: 1–268.

The term "protease polypeptide" or "protease" refers to a protein sequence encoded by the nucleic acid sequences represented by SEQ ID NOS: 1–268. The term "protease" or "protease polypeptide", however, further includes the numerous variants described herein, as well as fragments derived from the polypeptides and variants.

The present invention thus provides an isolated or purified protease polypeptides and variants and fragments thereof.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

In some instances, the protease will be associated with cellular membranes. This could include intracellular membranes or the outer cellular membrane. In either case, a protease is considered isolated if it is part of a purified membrane preparation or if it is purified and then reconstituted into membrane vesicles or liposomes.

The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid comprising a nucleotide sequence selected from the group consisting of SEQ ID NOS: 1–268 and the complements thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide encoded by a nucleic acid comprising a nucleotide sequence selected from the group consisting of SEQ ID NOS: 1–268 and the complements thereof. Variants also include proteins substantially homologous to the protease but derived from another organism, i.e., an ortholog. Variants also include proteins that are substantially homologous to the protease that are produced by chemical synthesis. Variants also include proteins that are substantially homologous to the protease that are produced by recombinant methods. It is understood, however, that variants exclude any amino acid sequences disclosed prior to the invention.

As used herein, two proteins (or a region of the proteins) are substantially homologous when the amino acid sequences are at least about 50–55%, 55–60%, typically at least about 70–75%, more typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of a nucleic acid sequence selected from the group consisting of SEQ ID NOS: 1–268, or portion thereof under stringent conditions as more described above.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptide. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |

TABLE 1-continued

Conservative Amino Acid Substitutions.

| | |
|---|---|
| Small | Alanine |
| | Serine |
| | Threonine |
| | Methionine |
| | Glycine |

The comparison of sequences and determination of percent identity and similarity between two sequences can be accomplished by well-known methods such as using a mathematical algorithm. (*Computational Molecular Biology*, Lesk, A.M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al., *Proc. Natl. Acad. Sci. USA* 90:5873–5877 (1993). Such an algorithm is incorporated into the NBLAST and XBLAST programs (version 2.0) as described in Altschul et al., *Nucleic Acids Res.,* 25:3389–3402 (1997). When utilizing BLAST and Gapped BLAST programs, the default parameters of the respective programs (e.g., NBLAST) can be used. See http://www.ncbi.nlm.nih.gov. In one embodiment, parameters for sequence comparison can be set at score=100, wordlength=12, or can be varied (e.g., W=5 or W=20).

In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.* 10:3–5; and FASTA described in Pearson and Lipman (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to substrate binding, subcellular localization, such as membrane association, and proteolytic cleavage, effector binding, effector modification of the protease, other modification sites, or site of interaction with any other protein.

Fully functional variants typically contain only conservative variation or variation in non-critical residues or in non-critical regions. Functional variants can also contain substitution of similar amino acids which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the protease. This includes preventing immunogenicity from pharmaceutical formulations by preventing protein aggregation.

Useful variations further include alteration of substrate binding and cleavage characteristics. For example, one embodiment involves a variation at the binding site that results in binding but not release, or slower release, of substrate. A further useful variation at the same sites can result in a higher affinity for substrate. Useful variations also include changes that provide for affinity for another substrate. Another useful variation includes one that allows binding but which prevents proteolysis of the substrate. Another useful variation includes variation in the domain that provides for reduced or increased binding by the appropriate activator (effector) or for binding by a different activator than the one with which the protease is normally associated. Another useful variation provides a fusion protein in which one or more domains or subregions is operationally fused to one or more domains or subregions from another protease.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as protease binding, cleavage, or in vitro, or in vitro proliferative activity. Sites that are critical for protease binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

Substantial homology can be to the entire nucleic acid or amino acid sequence or to fragments of these sequences.

The invention also includes polypeptide fragments of the polypeptides of the invention Fragments can be derived from a polypeptide encoded by a nucleic acid comprising a nucleotide sequence selected from the group consisting of SEQ ID NOS: 1–268 and the complements thereof. However, the invention also encompasses fragments of the variants of the polypeptides encoded by the nucleic acid described herein.

In one embodiment, the fragment is or includes an open reading frame. Open reading frames can be determined by routine computerized homology search procedures.

The fragments to which the invention pertains, however, are not to be construed as encompassing fragments that may be disclosed prior to the present invention.

As used herein, a fragment comprises at least 10 contiguous amino acids. Fragments can retain one or more of the biological activities of the protein, for example the ability to bind to a substrate or activator, as well as fragments that can be used as an immunogen to generate protease antibodies.

Biologically active fragments (peptides which are, for example, 10, 12, 15, 20, 30, 35, 36, 37, 38, 39,40, 50, 100 or more amino acids in length) can comprise a domain or region, as indicated, identified by analysis of the polypeptide sequence by well-known methods, e.g., cleavage sites, substrate binding sites, glycosylation sites, cAMP and cGMP-dependent phosphorylation sites, N-myristoylation sites, activator binding sites, casein kinase II phosphorylation sites, palmitoylation sites, amidation sites, or parts of any of these. Such domains or sites can be identified by means of routine procedures for computerized homology or motif analysis.

Fragments further include combinations of the various functional regions described herein. Other fragments include the mature protein. Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

Accordingly, possible fragments include but are not limited to fragments defining a substrate-binding site, fragments defining a phosphorylation site, fragments defining membrane association, fragments defining glycosylation sites, fragments defining interaction with activators and fragments defining myristoylation sites. By this is intended a discrete fragment that provides the relevant function or allows the relevant function to be identified. In a preferred embodiment, the fragment contains the substrate or activator-binding site.

The invention also provides fragments with immunogenic properties. These contain an epitope-bearing portion of the protease and variants. These epitope-bearing peptides are useful to raise antibodies that bind specifically to a protease polypeptide or region or fragment. These peptides can contain at least 10, 12, at least 14, or between at least about 15 to about 30 amino acids.

Non-limiting examples of antigenic polypeptides that can be used to generate antibodies include peptides derived from the amino terminal extracellular domain or any of the extracellular loops. Regions having a high antigenicity index can be determined by routine computerized amino acid sequence analysis. However, intracellularly-made antibodies ("intrabodies") are also encompassed, which would recognize intracellular peptide regions.

The polypeptides (including variants and fragments which may have been disclosed prior to the present invention) are useful for biological assays related to proteases. Such assays involve any of the known protease functions or activities or properties useful for diagnosis and treatment of protease-related conditions.

The epitope-bearing protease and polypeptides may be produced by any conventional means (Houghten, R. A., *Proc. Natl. Acad. Sci. USA* 82:5131–5135 (1985)). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the protease fragment and an additional region fused to the carboxyl terminus of the fragment.

The invention thus provides chimeric or fusion proteins. These comprise a protease amino acid sequence operatively linked to a heterologous protein having an amino acid sequence not substantially homologous to the protease. "Operatively linked" indicates that the protease sequence and the heterologous protein are fused in-frame. The heterologous protein can be fused to the N-terminus or C-terminus of the protease sequence.

In one embodiment the fusion protein does not affect protease function per se. For example, the fusion protein can be a GST-fusion protein in which the protease sequences are fused to the C-terminus of the GST sequences or an influenza HA marker. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant protease. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al. (J. Mol. Recog. 8:52–58 (1995)) and Johanson et al. (J. Biol. Chem. 270, 16:9459–9471 (1995)). Thus, this invention also encompasses soluble fusion proteins containing a protease polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease encoding nucleic acid can be cloned into such an expression vector such that the fusion moiety is linked in-frame to the protease sequence.

Another form of fusion protein is one that directly affects protease functions. Accordingly, a polypeptide is encompassed by the present invention in which one or more of the protease domains (or parts thereof) has been replaced by homologous domains (or parts thereof) from another protease or other type of protease. Accordingly, various permutations are possible. The substrate binding, or subregion thereof, can be replaced, for example, with the corresponding domain or subregion from another substrate for the protease. Thus, chimeric proteases can be formed in which one or more of the native domains or subregions has been replaced.

The isolated protease sequence can be purified from cells that naturally express it, purified from cells that have been altered to express it (recombinant), or synthesized using known protein synthesis methods.

In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

As is also well known, polypeptides are not always entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al, (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The protease polypeptides are useful for producing antibodies specific for the protease, regions, or fragments.

The polypeptides (including variants and fragments which may have been disclosed prior to the present invention) are useful for biological assays related to proteases. Such assays involve any of the known protease functions or activities or properties useful for diagnosis and treatment of protease-related conditions.

The polypeptides are also useful in drug screening assays, in cell-based or cell-free systems. Cell-based systems can be native, i.e., cells that normally express the protease protein, as a biopsy or expanded in cell culture. In one embodiment, however, cell-based assays involve recombinant host cells expressing the protease protein.

The polypeptides can be used to identify compounds that modulate protease activity. Such compounds can increase or decrease affinity or rate of binding to a known substrate or activator, compete with substrate or activator for binding to the protease, or displace substrate or activator bound to the protease. Both protease protein and appropriate variants and fragments can be used in high-throughput screens to assay candidate compounds for the ability to bind to the protease. These compounds can be further screened against a functional protease to determine the effect of the compound on the protease activity. Compounds can be identified that activate (agonist) or inactivate (antagonist) the protease to a desired degree. Modulatory methods can be performed in vitro (e.g., by culturing the cell with the agent) or, alternatively, in vivo (e.g., by administering the agent to a subject).

The protease polypeptides can be used to screen a compound for the ability to stimulate or inhibit interaction between the protease protein and a target molecule that normally interacts with the protease protein. The target can be a component of the pathway with which the protease normally interacts. The assay includes the steps of combining the protease with a candidate compound under conditions that allow the protease or fragment to interact with the target molecule, and to detect the formation of a complex between the protein and the target or to detect the biochemical consequence of the interaction with the protease and the target, such as any of the associated effects of proteolytic cleavage, such as detecting the induction of a reporter gene (comprising a target-responsive regulatory element operatively linked to a nucleic acid encoding a detectable marker, e.g., luciferase), detecting a cellular response, for example, development, differentiation or rate of proliferation detection of activation of the substrate, or change in substrate levels (i.e., level of end product).

Determining the ability of the protein to bind to a target molecule can also be accomplished using a technology such as real-time Bimolecular Interaction Analysis (BIA). Sjolander, S. and Urbaniczky, C. (1991) *Anal. Chem.*, 63:2338–2345 and Szabo et al. (1995) *Curr. Opin. Struct. Biol.*, 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. U.S.A.*, 90:6909; Erb et al. (1994) *Proc. Natl Acad. Sci. U.S.A.*, 91:11422; Zuckermann et al. (1994). *J. Med. Chem.*, 37:2678; Cho et al.(1993) *Science*, 261:1303; Carell et al. (1994) *Angew. Chem. Int. Ed. Engl.*, 33:2059; Carell et al. (1994) *Angew. Chem. Int. Ed. Engl.*, 33:2061; and in Gallop et al. (1994) *J. Med. Chem.*, 37:1233.

Libraries of compounds may be presented in solution (e.g., Houghten (1992) *Biotechniques*, 13:412–421), or on beads (Lam(1991) *Nature*, 354:82–84), chips (Fodor (1993) *Nature*, 364;555–556), bacteria(Ladner U.S. Pat. No. 5,223, 409), spores (Ladner U.S. Pat. No. '409), plasmids (Cull et al. (1992) *Proc. Natl. Acad. Sci. U.S.A.,* 89:1865–1869) or on phage (Scott and Smith (1990) *Science,* 249:386–390); (Devlin (1990) *Science,* 249:404–406); (Cwirla et al. (1990) *Proc. Natl. Acad. Sci.,* 97:6378–6382); (Felici (1991) *J. Mol. Biol.,* 222:301–310); (Ladner supra).

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length protease or fragment that competes for substrate or activator binding. Other candidate compounds include mutant proteases or appropriate fragments containing mutations that affect protease function and thus compete for substrate, activator or other protein that interacts with the protease. Accordingly, a fragment that competes for substrate or activator, for example with a higher affinity, or a fragment that binds substrate or activator but does not allow release, is encompassed by the invention.

The invention provides other end points to identify compounds that modulate (stimulate or inhibit) protease activity. The assays typically involve an assay of events in the pathway in which the protease is found that indicate protease activity. Thus, the expression of genes that are up- or down-regulated in response to the protease protein dependent cascade can be assayed. In one embodiment, the regulatory region of such genes can be operably linked to a marker that is easily detectable, such as luciferase. Alternatively, modification of the protease protein, or a protease protein target, could also be measured.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric proteases in which a domain, or parts thereof, are replaced by heterologous domains or subregions. For example, a substrate-binding region can be used that interacts with a different substrate than that which is recognized by the native protease. Accordingly, a different set of pathway components is available as an end-point assay for activation. Alternatively, a portion or subregions can be replaced with a portion or subregions specific to a host cell that is different from the host cell from which the domain is derived. This allows for assays to be performed in other than the specific host cell from which the protease is derived. Alternatively, the substrate or activator could be replaced by a domain (and/or other binding region) binding a different substrate or activator, thus providing an assay for test compounds that interact with the heterologous domain (or region) but still cause the events in the pathway. Finally, activation can be detected by a reporter gene containing an easily detectable coding region operably linked to a transcriptional regulatory sequence that is part of the native signal transduction pathway.

The protease polypeptides are also useful in competition binding assays in methods designed to discover compounds that interact with the protease. Thus, a compound is exposed to a protease polypeptide under conditions that allow the compound to bind or to otherwise interact with the polypeptide. Soluble polypeptide is also added to the mixture. If the test compound interacts with the soluble polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

Determining the ability of the test compound to interact with the polypeptide can also comprise determining the ability of the test compound to preferentially bind to the polypeptide as compared to the ability of the native counterpart, such as activator or substrate, or a biologically active portion thereof, to bind to the polypeptide.

To perform cell free drug screening assays, it is desirable to immobilize either the protease, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/protease fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule; as well as enzyme-linked assays which rely on detecting an enzymatic activity associated with the target molecule.

Modulators of protease activity identified according to these drug screening assays can be used to treat a subject with a disorder mediated by the protease pathway, by treating cells that express the protease. These methods of treatment include the steps of administering the modulators of protein activity in a pharmaceutical composition as described herein, to a subject in need of such treatment. The compounds may be tested first in an animal model to determine safety and efficacy.

The protease polypeptides are thus useful for treating a protease-associated disorder characterized by aberrant expression or activity of a protease. In one embodiment, the method involves administering an agent (e.g., an agent identified by a screening assay described herein), or combination of agents that modulates (e.g., upregulates or downregulates) expression or activity of the protein. In another embodiment, the method involves administering a protein as therapy to compensate for reduced or aberrant expression or activity of the protein. Accordingly, methods for treatment include the use of soluble protease or fragments of the protease protein that compete, for example, with activator or substrate binding. These proteases or fragments can have a higher affinity for the activator or substrate so as to provide effective competition.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. Another example of such a situation is where the subject has a proliferative disease (e.g., cancer) or a disorder characterized by an aberrant hematopoietic response. Yet another example of such a situation is where it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell*, 72:223–232; Madura et al. (1993) *J. Biol. Chem.*, 268:12046–12054; Bartel et al. (1993) *Biotechniques*, 14:920–924; Iwabuchi et al. (1993) *Oncogene*, 8:1693–1696; and Brent WO94/10300), to identify other proteins (captured proteins) which bind to or interact with the proteins of the invention and modulate their activity. Such captured proteins are also likely to be involved in the pathway that includes by the proteins of the invention as, for example, downstream elements of a protease-mediated pathway.

The protease polypeptides also are useful to provide a target for diagnosing a disease or predisposition to disease mediated by the protease, such as a proliferative disorder, a differentiative or developmental disorder, or a hematopoietic disorder. Accordingly, methods are provided for detecting the presence, or levels of the protease in a cell, tissue, or organism. The method can involve contacting a biological sample with a compound capable of interacting with the protease such that the interaction can be detected.

One agent for detecting a protease is an antibody capable of selectively binding to the protease. A biological sample includes tissues, cells and biological fluids isolated from a subject, as well as tissues, cells and fluids present within a subject.

The protease also provides a target for diagnosing active disease, or predisposition to disease, in a patient having a variant protease. Thus, protease can be isolated from a biological sample, assayed for the presence of a genetic mutation that results in aberrant protease. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in activator, substrate, or antibody-binding pattern, altered isoelectric point, direct amino acid sequencing, and any other of the known assay techniques useful for detecting mutations in a protein.

In vitro techniques for detection of protease include enzyme linked immunosorbent assays (ELISAs), Western blots, immunoprecipitations and immunofluorescence. Alternatively, the protein can be detected in vivo in a subject by introducing into the subject a labeled anti-protease antibody. For example, the antibody can be labeled with a radioactive marker whose presence and location in a subject can be detected by standard imaging techniques. Particularly useful are methods which detect the allelic variant of a protease expressed in a subject and methods which detect fragments of a protease in a sample.

It is also within the scope of this invention to determine the ability of a test compound to interact with the polypeptide without the labeling of any of the interactants. For example, a microphysiometer can be used to detect the interaction of a test compound with the polypeptide without the labeling of either the test compound or the polypeptide. McConnell, H. M. et al. (1992) *Science*, 257:1906–1912.

The present invention provides for both prophylactic and therapeutic methods of treating a subject at risk of (or susceptible to) a disorder or having a disorder associated with aberrant expression or activity of proteins of the invention. Administration of a prophylactic agent can occur prior to the manifestation of symptoms characteristic of the aberrancy, such that a disease or disorder is prevented or, alternatively, delayed in its progression.

With regard to both prophylactic and therapeutic methods of treatment, such treatments may be specifically tailored or modified, based on knowledge obtained from the field of pharmacogenomics. The polypeptides thus provide a target to ascertain a genetic predisposition that can affect treatment modality. Thus, in a substrate-based treatment, polymorphism may give rise to substrate or activator-binding regions that are more or less active in substrate or activator binding, and protease activation or proteolysis. Accordingly, activator or substrate dosage would necessarily be modified to maximize the therapeutic effect within a given population containing a polymorphism. As an alternative to genotyping, specific polymorphic polypeptides could be identified.

The protease polypeptides are also useful for monitoring therapeutic effects during clinical trials and other treatment. Thus, the therapeutic effectiveness of an agent that is designed to increase or decrease gene expression, protein levels or protease activity can be monitored over the course of treatment using the polypeptides as an end-point target. The monitoring can be, for example, as follows: (i) obtaining a pre-administration sample from a subject prior to administration of the agent; (ii) detecting the level of expression of a specified protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

The invention also comprises kits for detecting a protease protein. The kit can comprise a labeled compound or agent capable of detecting protein in a biological sample, such as an antibody or other binding compound; means for determining the amount of in the sample; and means for comparing the amount of in the sample with a standard. The compound or agent can be packaged in a suitable container. The kit can further comprise instructions for using the kit to detect the protein.

Antibodies

In another aspect, the invention provides antibodies to the polypeptides and polypeptide fragments of the invention, e.g., having an amino acid encoded by a nucleic acid comprising all or a portion of a nucleotide sequence selected from the group consisting of SEQ ID NOS: 1–268. Antibodies selectively bind to the protease and its variants and fragments. An antibody is considered to selectively bind, even if it also binds to other proteins that are not substantially homologous with the protease. These other proteins share homology with a fragment or domain of the protease. This conservation in specific regions gives rise to antibodies that bind to both proteins by virtue of the homologous sequence. In this case, it would be understood that antibody binding to the protease is still selective.

To generate antibodies, an isolated protease polypeptide is used as an immunogen to generate antibodies using standard techniques for polyclonal and monoclonal antibody preparation. Either the full-length protein or an antigenic peptide fragment can be used.

Antibodies are preferably prepared from these regions or from discrete fragments in antigenic regions. However, antibodies can be prepared from any region of the peptide as described herein. A preferred fragment produces an antibody that diminishes or completely prevents substrate or activator-binding. Antibodies can be developed against the entire protease or portions of the protease, for example, specific segments or any portions thereof. Antibodies may also be developed against specific functional sites, such as the site of substrate or activator-binding, or sites that are phosphorylated, glycosylated, myristoylated, or otherwise modified, such as amidated.

An antigenic fragment will typically comprise at least 10 contiguous amino acid residues. The antigenic peptide can comprise, however, at least 12, at least 14 amino acid residues, at least 15 amino acid residues, at least 20 amino acid residues, or at least 30 amino acid residues. In one embodiment, fragments correspond to regions that are located on the surface of the protein, e.g., hydrophilic regions. These fragments are not to be construed, however, as encompassing any fragments which may be disclosed prior to the invention.

Antibodies can be polyclonal or monoclonal. An intact antibody, or a fragment thereof (e.g. Fab or F(ab')$_2$) can be used.

Any of the many well known protocols used for fusing lymphocytes and immortalized cell lines can be applied for the purpose of generating a monoclonal antibody to a polypeptide of the invention.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, protein or chemically synthesized peptides.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." This technology is described, for example, in Jespers et al. (1994, *Bio/technology* 12:899–903).

Antibody Uses

The antibodies can be used to isolate a protease by standard techniques, such as affinity chromatography or immunoprecipitation. The antibodies can facilitate the purification of the natural protease from cells and recombinantly produced protease expressed in host cells.

The antibodies are useful to detect the presence of a protease in cells or tissues to determine the pattern of expression of the protease among various tissues in an organism and over the course of normal development.

The antibodies can be used to detect a protease in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length protease can be used to identify protease turnover.

Further, the antibodies can be used to assess protease expression in disease states such as in active stages of the disease or in an individual with a predisposition toward disease related to protease function. When a disorder is caused by an inappropriate tissue distribution, developmental expression, or level of expression of the protease protein, the antibody can be prepared against the normal protease. If a disorder is characterized by a specific mutation in the protease, antibodies specific for this mutant protein can be used to assay for the presence of the specific mutant protease. However, intracellularly-made antibodies ("intrabodies") are also encompassed, which would recognize intracellular protease peptide regions.

The antibodies can also be used to assess normal and aberrant subcellular localization of cells in the various tissues in an organism. Antibodies can be developed against the whole protease or portions of the protease, such as those described herein.

The diagnostic uses can be applied, not only in genetic testing, but also in monitoring a treatment modality. Accordingly, where treatment is ultimately aimed at correcting protease expression level or the presence of aberrant proteases and aberrant tissue distribution or developmental expression, antibodies directed against the protease or relevant fragments can be used to monitor therapeutic efficacy.

Antibodies accordingly can be used diagnostically to monitor levels in tissue as part of a clinical testing procedure, e.g., to, for example, determine the efficacy of a given treatment regimen.

Additionally, antibodies are useful in pharmacogenomic analysis. Thus, antibodies prepared against polymorphic proteases can be used to identify individuals that require modified treatment modalities.

The antibodies are also useful as diagnostic tools as an immunological marker for aberrant protease analyzed by electrophoretic mobility, isoelectric point, tryptic peptide digest, and other physical assays known to those in the art.

The antibodies are also useful for tissue typing. Thus, where a specific protease has been correlated with expression in a specific tissue, antibodies that are specific for this protease can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting protease function, for example, blocking substrate or activator binding.

These uses can also be applied in a therapeutic context in which treatment involves inhibiting protease function. An antibody can be used, for example, to block activator or substrate binding. Antibodies can be prepared against specific fragments containing sites required for function or against intact protease associated with a cell.

The invention also encompasses kits for using antibodies to detect the presence of a protease in a biological sample. The kit can comprise antibodies such as a labeled or labelable antibody and a compound or agent for detecting protease in a biological sample; means for determining the amount of protease in the sample; and means for comparing the amount of protease in the sample with a standard. The compound or agent can be packaged in a suitable container. The kit can further comprise instructions for using the kit to detect protease.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention thus provides vectors containing the protease polynucleotides. Another aspect of the invention pertains to nucleic acid constructs containing a nucleic acid selected from the group consisting of SEQ ID NOS: 1–268 (or a portion thereof). The term "vector" refers to a vehicle, preferably a nucleic acid molecule, that can transport the protease polynucleotides. When the vector is a nucleic acid molecule, the protease polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the protease polynucleotides. Alternatively, the vector may integrate into the host cell genome and produce additional copies of the protease polynucleotides when the host cell replicates.

The invention provides vectors for the maintenance (cloning vectors) or vectors for expression (expression vectors) of the protease polynucleotides. The vectors can function in procaryotic or eukaryotic cells or in both (shuttle vectors).

Expression vectors contain cis-acting regulatory regions that are operably linked in the vector to the protease polynucleotides such that transcription of the polynucleotides is allowed in a host cell. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The polynucleotides can be introduced into the host cell with a separate polynucleotide capable of affecting transcription. Thus, the second polynucleotide may provide a trans-acting factor interacting with the cis-regulatory control region to allow transcription of the protease polynucleotides from the vector. Alternatively, a trans-acting factor may be supplied by the host cell. Finally, a trans-acting factor can be produced from the vector itself.

It is understood, however, that in some embodiments, transcription and/or translation of the protease polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989), and such regulatory sequences are described, for example, in Goeddel, *Gene Expression Technology: Methods in Enzymology* 185, Academic Press, San Diego, Calif. (1990).

A variety of expression vectors can be used to express a protease polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, adeno-associated virus, poxviruses, pseudorabies viruses, and retroviruses. Vectors may also be derived from combinations of these sources such as those derived from plasmid and bacteriophage genetic elements, e.g,. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The protease polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the protease polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the polynucleotide of interest can be altered to provide preferential codon usage for a specific host cell, for example *E. coli*. (Wada et al., *Nucleic Acids Res.* 20:2111–2118 (1992)).

The protease polynucleotides can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The protease polynucleotides can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the polynucleotides described herein are expressed in mammalian cells using mammalian expression vectors. Examples of mammalian expression vectors include pCDM8 (Seed, B. *Nature* 329:840 (1987)) and pMT2PC (Kaufman et al., *EMBO J.* 6:187–195 (1987)). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al, supra.

Suitable host cells are discussed further in Goeddel, supra. Alternatively, the recombinant expression vector can be transcribed and translated in vitro, for example using T7 promoter regulatory sequences and T7 polymerase.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The expression vectors listed herein are provided by way of example only of the well-known vectors available to those of ordinary skill in the art that would be useful to express the protease polynucleotides. The person of ordinary skill in the art would be aware of other vectors suitable for maintenance propagation or expression of the polynucleotides described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as plant, fungal, and insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the protease polynucleotides can be introduced either alone or with other polynucleotides that are not related to the protease polynucleotides such as those providing trans-acting factors for expression vectors. When more than one vector is introduced into a cell, the vectors can be introduced independently, co-introduced or joined to the protease polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the protease polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

The host cells expressing the polypeptides described herein, and particularly recombinant host cells, have a variety of uses. First, the cells are useful for producing protease polypeptides that can be further purified to produce desired amounts of these. Thus, host cells containing expression vectors are useful for polypeptide production.

Host cells are also useful for conducting cell-based assays involving the protease or protease fragments. Thus, a recombinant host cell expressing a native protease is useful to assay for compounds that stimulate or inhibit protease function. This includes activator binding, gene expression at the level of transcription or translation, substrate interaction, and components of the pathway in which the protease is a member.

Host cells are also useful for identifying protease mutants in which these functions are affected. If the mutants naturally occur and give rise to a pathology, host cells containing the mutations are useful to assay compounds that have a desired effect on the mutant protease (for example, stimulating or inhibiting function) which may not be indicated by their effect on the native protease.

Recombinant host cells are also useful for expressing the chimeric polypeptides described herein to assess compounds that activate or suppress activation by means of a heterologous activator binding domain. Alternatively, a heterologous proteolytic region can be used to assess the effect of a desired proteolytic domain on any given host cell. In this embodiment, a proteolytic region (or parts thereof) compatible with the specific host cell is used to make the chimeric vector. Alternatively, a heterologous substrate binding domain can be introduced into the host cell.

Further, mutant proteases can be designed in which one or more of the various functions is engineered to be increased or decreased (e.g., activator binding or substrate binding) and used to augment or replace proteases in an individual. Thus, host cells can provide a therapeutic benefit by replacing an aberrant protease or providing an aberrant protease that provides a therapeutic result. In one embodiment, the cells provide proteases that are abnormally active.

In another embodiment, the cells provide proteases that are abnormally inactive. These proteases can compete with endogenous proteases in the individual.

In another embodiment, cells expressing proteases that cannot be activated, are introduced into an individual in order to compete with endogenous proteases for activator. For example, in the case in which excessive activator is part of a treatment modality, it may be necessary to inactivate this activator at a specific point in treatment. Providing cells that compete for the activator, but which cannot be affected by protease activation would be beneficial.

Homologously recombinant host cells can also be produced that allow the in situ alteration of endogenous protease polynucleotide sequences in a host cell genome. This technology is more fully described in WO 93/09222, WO 91/12650 and U.S. Pat. No. 5,641,670. Briefly, specific polynucleotide sequences corresponding to the protease polynucleotides or sequences proximal or distal to a protease gene are allowed to integrate into a host cell genome by homologous recombination where expression of the gene can be affected. In one embodiment, regulatory sequences are introduced that either increase or decrease expression of an endogenous sequence. Accordingly, a protease can be produced in a cell not normally producing it, or increased expression of protease can result in a cell normally producing the protein at a specific level. Alternatively, the entire gene can be deleted. Still further, specific mutations can be introduced into any desired region of the gene to produce mutant proteases. Such mutations could be introduced, for example, into the specific functional regions.

In one embodiment, the host cell can be a fertilized oocyte or embryonic stem cell that can be used to produce a transgenic animal containing the altered protease gene. Alternatively, the host cell can be a stem cell or other early tissue precursor that gives rise to a specific subset of cells and can be used to produce transgenic tissues in an animal. See also Thomas et al., Cell 51:503 (1987) for a description of homologous recombination vectors. The vector is introduced into an embryonic stem cell line (e.g., by electroporation) and cells in which the introduced gene has homologously recombined with the endogenous protease gene is selected (see e.g., Li, E. et al., Cell 69:915 (1992)).

The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity.

Other examples of transgenic animals include non-human primates, sheep, dogs, cows, goats, chickens, and amphibians.

In one embodiment, a host cell is a fertilized oocyte or an embryonic stem cell into which protease polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding, protease activation, and the pathway events may not be evident from in vitro cell-free or cell-based assays. Accordingly, it is useful to provide non-human transgenic animals to assay in vivo protease function, including substrate or activator interaction, the effect of specific mutant proteases on protease function and interaction with other components, and the effect of chimeric proteases. It is also possible to assess the effect of null mutations, that is mutations that substantially or completely eliminate one or more protease functions.

Pharmaceutical Compositions

The protease nucleic acid molecules, protein (particularly fragments that comprise an extracellular domain), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a protease or anti-protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al., *PNAS* 91:3054–3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. A method for producing an isolated polypeptide comprising an amino acid sequence encoded by the nucleotide sequence shown in SEQ ID NO:257 said method comprising introducing a nucleotide sequence encoding said amino acid sequence into a host cell and culturing the host cell under conditions in which the polypeptide is expressed from the nucleotide sequence.

2. A method for detecting the presence in a sample of a polypeptide comprising the amino acid sequence encoded by the nucleotide sequence shown in SEQ ID NO:257 said method comprising contacting said sample with an antibody that specifically allows detection or the presence of the polypeptide in the sample and then detecting the presence of the polypeptide.

3. A kit comprising reagents used for a method for detecting the presence in a sample of a polypeptide comprising the amino acid sequence encoded by the nucleotide sequence shown in SEQ ID NO:257 wherein the reagents comprise an agent that specifically binds to said polypeptide.

4. A method for identifying an agent that binds to a polypeptide comprising the amino acid sequence encoded by the nucleotide sequence shown in SEQ ID NO:257 said method comprising contacting the polypeptide with an agent that binds to the polypeptide and assaying the complex formed with the agent bound to the polypeptide.

5. A method for modulating the proteolytic activity of an isolated polypeptide comprising the amino acid sequence encoded by the nucleotide sequence shown in SEQ ID NO:257 the method comprising contacting said polypeptide with an antibody under conditions that allow the antibody to modulate the proteolytic activity of the polypeptide.

6. An isolated nucleic acid molecule comprising the nucleotide sequence shown in SEQ ID NO:257, or a complement thereof.

7. A method for identifying a polynucleotide agent that modulates the expression of a nucleic acid molecule, wherein said nucleic acid molecule comprises the nucleotide sequence shown in SEQ ID NO:257, or the complement thereof, said method comprising contacting said nucleic acid molecule with the polynucleotide agent under conditions that allow the polynucleotide agent to modulate the expression or activity of said nucleic acid molecule.

* * * * *